United States Patent
Wesche et al.

(10) Patent No.: US 12,195,544 B2
(45) Date of Patent: Jan. 14, 2025

(54) EGFR BINDING PROTEINS AND METHODS OF USE

(71) Applicant: Harpoon Therapeutics, Inc., South San Francisco, CA (US)

(72) Inventors: Holger Wesche, San Francisco, CA (US); Richard J. Austin, San Francisco, CA (US)

(73) Assignee: Harpoon Therapeutics, Inc., South San Francisco, CA (US)

( * ) Notice: Subject to any disclaimer, the term of this patent is extended or adjusted under 35 U.S.C. 154(b) by 904 days.

(21) Appl. No.: 17/276,779

(22) PCT Filed: Sep. 20, 2019

(86) PCT No.: PCT/US2019/052206
§ 371 (c)(1),
(2) Date: Mar. 16, 2021

(87) PCT Pub. No.: WO2020/061482
PCT Pub. Date: Mar. 26, 2020

(65) Prior Publication Data
US 2022/0017626 A1    Jan. 20, 2022

Related U.S. Application Data

(60) Provisional application No. 62/734,908, filed on Sep. 21, 2018, provisional application No. 62/734,892, filed on Sep. 21, 2018.

(51) Int. Cl.
*C07K 16/28* (2006.01)
*A61K 39/00* (2006.01)

(52) U.S. Cl.
CPC .... *C07K 16/2863* (2013.01); *A61K 2039/505* (2013.01); *C07K 2317/24* (2013.01); *C07K 2317/565* (2013.01); *C07K 2317/569* (2013.01); *C07K 2317/73* (2013.01); *C07K 2317/92* (2013.01)

(58) Field of Classification Search
CPC ............ C07K 16/2863; C07K 2317/24; C07K 2317/565; C07K 2317/569; C07K 2317/73; C07K 2317/92; A61K 2039/505
See application file for complete search history.

(56) References Cited

U.S. PATENT DOCUMENTS

| | | |
|---|---|---|
| 4,816,567 A | 3/1989 | Cabilly et al. |
| 4,943,533 A | 7/1990 | Mendelsohn et al. |
| 5,061,620 A | 10/1991 | Tsukamoto et al. |
| 5,199,942 A | 4/1993 | Gillis |
| 5,225,539 A | 7/1993 | Winter |
| 5,350,674 A | 9/1994 | Boenisch et al. |
| 5,399,346 A | 3/1995 | Anderson et al. |
| 5,530,101 A | 6/1996 | Queen et al. |
| 5,565,332 A | 10/1996 | Hoogenboom et al. |
| 5,580,859 A | 12/1996 | Felgner et al. |
| 5,585,089 A | 12/1996 | Queen et al. |
| 5,585,362 A | 12/1996 | Wilson et al. |
| 5,589,466 A | 12/1996 | Felgner et al. |
| 5,759,808 A | 6/1998 | Casterman et al. |
| 5,766,886 A | 6/1998 | Studnicka et al. |
| 5,773,292 A | 6/1998 | Bander |
| 5,800,988 A | 9/1998 | Casterman et al. |
| 5,811,097 A | 9/1998 | Allison et al. |
| 5,840,526 A | 11/1998 | Casterman et al. |
| 5,843,439 A | 12/1998 | Anderson et al. |
| 5,844,093 A | 12/1998 | Kettleborough et al. |
| 5,858,358 A | 1/1999 | June et al. |
| 5,859,205 A | 1/1999 | Adair et al. |
| 5,874,541 A | 2/1999 | Casterman et al. |
| 5,883,223 A | 3/1999 | Gray |
| 5,977,318 A | 11/1999 | Linsley et al. |
| 6,005,079 A | 12/1999 | Casterman et al. |
| 6,015,695 A | 1/2000 | Casterman et al. |
| 6,051,227 A | 4/2000 | Allison et al. |
| 6,107,090 A | 8/2000 | Bander |
| 6,120,766 A | 9/2000 | Hale et al. |
| 6,136,311 A | 10/2000 | Bander |

(Continued)

FOREIGN PATENT DOCUMENTS

| | | |
|---|---|---|
| CA | 2992797 A1 | 2/2017 |
| CA | 2994579 A1 | 2/2017 |

(Continued)

OTHER PUBLICATIONS

Winkler et al. (2000) Journal of Immunology 165(8): 4505-4514. (Year: 2000).*
Holt et al. (2003) Trends in Biotechnology 21(11): 484-490. (Year: 2003).*
Schroeder and Cavacini. (2010) Journal of Allergy and Clinical Immunology 125(2, Suppl.2): S41-S52. (Year: 2010).*
Sela-Culang et al. (2013) Frontiers in Immunology 4: 302. (Year: 2013).*
Bannas et al. (2017) Frontiers in Immunology 8: 1603 (Year: 2017).*
Jovevska and Muyldermans. (2020) BioDrugs 34:11-16. (Year: 2020).*

(Continued)

*Primary Examiner* — Brad Duffy
*Assistant Examiner* — Elizabeth A Shupe
(74) *Attorney, Agent, or Firm* — Benjamin D. Atkins; Anna L. Cocuzzo

(57) ABSTRACT

Provided herein are EGFR binding proteins and EGFR targeting trispecific proteins comprising a domain binding to CD3, a half-life extension domain, and a domain binding to EGFR. Also provided are pharmaceutical compositions thereof, as well as nucleic acids, recombinant expression vectors and host cells for making such EGFR binding proteins, EGFR targeting trispecific proteins. Also disclosed are methods of using the disclosed EGFR binding proteins, EGFR targeting trispecific proteins in the prevention, and/or treatment diseases, conditions and disorders.

29 Claims, 5 Drawing Sheets
Specification includes a Sequence Listing.

(56) References Cited

U.S. PATENT DOCUMENTS

| | | |
|---|---|---|
| 6,210,669 B1 | 4/2001 | Aruffo et al. |
| 6,303,121 B1 | 10/2001 | Kwon |
| 6,326,193 B1 | 12/2001 | Liu et al. |
| 6,331,415 B1 | 12/2001 | Cabilly et al. |
| 6,352,694 B1 | 3/2002 | June et al. |
| 6,355,476 B1 | 3/2002 | Kwon et al. |
| 6,362,325 B1 | 3/2002 | Kwon |
| 6,407,213 B1 | 6/2002 | Carter et al. |
| 6,534,055 B1 | 3/2003 | June et al. |
| 6,548,640 B1 | 4/2003 | Winter |
| 6,569,997 B1 | 5/2003 | Kwon |
| 6,670,453 B2 | 12/2003 | Frenken et al. |
| 6,682,736 B1 | 1/2004 | Hanson et al. |
| 6,692,964 B1 | 2/2004 | June et al. |
| 6,759,518 B1 | 7/2004 | Kontermann et al. |
| 6,767,711 B2 | 7/2004 | Bander |
| 6,797,514 B2 | 9/2004 | Berenson et al. |
| 6,808,710 B1 | 10/2004 | Wood et al. |
| 6,867,041 B2 | 3/2005 | Berenson et al. |
| 6,887,466 B2 | 5/2005 | June et al. |
| 6,887,673 B2 | 5/2005 | Kunkel et al. |
| 6,905,680 B2 | 6/2005 | June et al. |
| 6,905,681 B1 | 6/2005 | June et al. |
| 6,905,685 B2 | 6/2005 | Kwon |
| 6,905,874 B2 | 6/2005 | Berenson et al. |
| 6,974,863 B2 | 12/2005 | Kwon |
| 6,984,720 B1 | 1/2006 | Korman et al. |
| 7,034,121 B2 | 4/2006 | Carreno et al. |
| 7,060,808 B1 | 6/2006 | Goldstein et al. |
| 7,067,318 B2 | 6/2006 | June et al. |
| 7,144,575 B2 | 12/2006 | June et al. |
| 7,163,680 B2 | 1/2007 | Bander |
| 7,172,869 B2 | 2/2007 | June et al. |
| 7,175,843 B2 | 2/2007 | June et al. |
| 7,214,493 B2 | 5/2007 | Kunkel et al. |
| 7,232,566 B2 | 6/2007 | June et al. |
| 7,247,301 B2 | 7/2007 | Van De Winkel et al. |
| 7,262,276 B2 | 8/2007 | Huang et al. |
| 7,288,638 B2 | 10/2007 | Jure-Kunkel et al. |
| 7,371,849 B2 | 5/2008 | Honda et al. |
| 7,488,802 B2 | 2/2009 | Collins et al. |
| 7,595,378 B2 | 9/2009 | Van De Winkel et al. |
| 7,605,238 B2 | 10/2009 | Korman et al. |
| 7,666,414 B2 | 2/2010 | Bander |
| 7,723,484 B2 | 5/2010 | Beidler et al. |
| 7,807,162 B2 | 10/2010 | Silence |
| 7,812,135 B2 | 10/2010 | Smith et al. |
| 7,850,971 B2 | 12/2010 | Maddon et al. |
| 7,939,072 B2 | 5/2011 | Yarden et al. |
| 7,943,743 B2 | 5/2011 | Korman et al. |
| 8,008,449 B2 | 8/2011 | Korman et al. |
| 8,114,965 B2 | 2/2012 | Maddon et al. |
| 8,153,768 B2 | 4/2012 | Kunz et al. |
| 8,168,757 B2 | 5/2012 | Finnefrock et al. |
| 8,188,223 B2 | 5/2012 | Beirnaert et al. |
| 8,236,308 B2 | 8/2012 | Kischel et al. |
| 8,354,509 B2 | 1/2013 | Carven et al. |
| 8,388,967 B2 | 3/2013 | Smith et al. |
| 8,470,330 B2 | 6/2013 | Schuelke et al. |
| 8,552,156 B2 | 10/2013 | Takayanagi et al. |
| 8,609,089 B2 | 12/2013 | Langermann et al. |
| 8,623,356 B2 | 1/2014 | Christopherson et al. |
| 8,629,244 B2 | 1/2014 | Kolkman et al. |
| 8,703,135 B2 | 4/2014 | Beste et al. |
| 8,709,424 B2 | 4/2014 | Schebye et al. |
| 8,779,105 B2 | 7/2014 | Korman et al. |
| 8,784,821 B1 | 7/2014 | Kufer et al. |
| 8,846,042 B2 | 9/2014 | Zhou |
| 8,900,587 B2 | 12/2014 | Carven et al. |
| 8,907,071 B2 | 12/2014 | Sullivan et al. |
| 8,937,164 B2 | 1/2015 | Descamps et al. |
| 8,986,972 B2 | 3/2015 | Stull et al. |
| 9,089,615 B2 | 7/2015 | Stull et al. |
| 9,089,616 B2 | 7/2015 | Stull et al. |
| 9,089,617 B2 | 7/2015 | Stull et al. |
| 9,090,683 B2 | 7/2015 | Stull et al. |
| 9,107,961 B2 | 8/2015 | Stull et al. |
| 9,126,984 B2 | 9/2015 | Crosignani et al. |
| 9,127,071 B2 | 9/2015 | Yoshida et al. |
| 9,133,271 B1 | 9/2015 | Stull et al. |
| 9,155,803 B1 | 10/2015 | Stull et al. |
| 9,169,316 B1 | 10/2015 | Baty et al. |
| 9,309,327 B2 | 4/2016 | Humphreys et al. |
| 9,327,022 B2 | 5/2016 | Zhang et al. |
| 9,334,318 B1 | 5/2016 | Stull et al. |
| 9,340,621 B2 | 5/2016 | Kufer et al. |
| 9,345,787 B2 | 5/2016 | Hemminki et al. |
| 9,352,051 B1 | 5/2016 | Stull et al. |
| 9,353,182 B2 | 5/2016 | Stull et al. |
| 9,358,304 B1 | 6/2016 | Stull et al. |
| 9,359,442 B2 | 6/2016 | Hoffee et al. |
| 9,422,368 B2 | 8/2016 | Spee et al. |
| 9,480,757 B2 | 11/2016 | Stull et al. |
| 9,481,724 B2 | 11/2016 | Ravetch et al. |
| 9,486,537 B2 | 11/2016 | Stull et al. |
| 9,624,185 B1 | 4/2017 | Xu |
| 9,642,918 B2 | 5/2017 | Bruederle et al. |
| 9,708,412 B2 | 7/2017 | Baeuerle et al. |
| 9,764,042 B1 | 9/2017 | Stull et al. |
| 9,770,518 B1 | 9/2017 | Stull et al. |
| 9,775,916 B1 | 10/2017 | Stull et al. |
| 9,855,343 B2 | 1/2018 | Stull et al. |
| 9,861,708 B2 | 1/2018 | Stull et al. |
| 9,867,887 B1 | 1/2018 | Stull et al. |
| 9,878,053 B1 | 1/2018 | Stull et al. |
| 9,920,115 B2 | 3/2018 | Dubridge et al. |
| 9,931,420 B2 | 4/2018 | Stull et al. |
| 9,931,421 B2 | 4/2018 | Stull et al. |
| 9,937,268 B2 | 4/2018 | Stull et al. |
| 10,066,016 B2 | 9/2018 | Dubridge et al. |
| 10,100,106 B2 | 10/2018 | Dubridge et al. |
| 10,137,204 B2 | 11/2018 | Stull et al. |
| 10,428,120 B2 | 10/2019 | Kontermann et al. |
| 10,543,271 B2 | 1/2020 | Wesche et al. |
| 10,544,221 B2 | 1/2020 | Dubridge et al. |
| 10,696,723 B2 | 6/2020 | Winston et al. |
| 10,730,954 B2 | 8/2020 | Wesche et al. |
| 10,815,311 B2 | 10/2020 | Wesche et al. |
| 10,844,134 B2 | 11/2020 | Baeuerle et al. |
| 10,849,973 B2 | 12/2020 | Dubridge et al. |
| 10,927,180 B2 | 2/2021 | Wesche et al. |
| 10,954,311 B2 | 3/2021 | Baeuerle et al. |
| 11,111,311 B2 | 9/2021 | Yoshida et al. |
| 11,180,563 B2 | 11/2021 | Wesche et al. |
| 11,186,641 B2 * | 11/2021 | Tveita .................... C07K 16/28 |
| 11,400,157 B2 | 8/2022 | Igawa et al. |
| 2002/0015704 A1 | 2/2002 | Bander |
| 2002/0051780 A1 | 5/2002 | Lindhofer et al. |
| 2002/0081296 A1 | 6/2002 | Theill et al. |
| 2003/0031673 A1 | 2/2003 | Bander |
| 2003/0092892 A1 | 5/2003 | Frenken et al. |
| 2004/0101519 A1 | 5/2004 | June et al. |
| 2005/0042664 A1 | 2/2005 | Wu et al. |
| 2005/0048617 A1 | 3/2005 | Wu et al. |
| 2005/0095244 A1 | 5/2005 | Jure-Kunkel et al. |
| 2005/0100543 A1 | 5/2005 | Hansen et al. |
| 2005/0175606 A1 | 8/2005 | Huang et al. |
| 2006/0034810 A1 | 2/2006 | Riley et al. |
| 2006/0046971 A1 | 3/2006 | Stuhler et al. |
| 2006/0121005 A1 | 6/2006 | Berenson et al. |
| 2006/0228364 A1 | 10/2006 | Dennis et al. |
| 2006/0252096 A1 | 11/2006 | Zha et al. |
| 2007/0014794 A1 | 1/2007 | Carter et al. |
| 2007/0178082 A1 | 8/2007 | Silence et al. |
| 2007/0269422 A1 | 11/2007 | Beirnaert et al. |
| 2008/0069772 A1 | 3/2008 | Stuhler et al. |
| 2008/0260757 A1 | 10/2008 | Holt et al. |
| 2009/0041789 A1 | 2/2009 | Elsaesser-Beile et al. |
| 2009/0117108 A1 | 5/2009 | Wang et al. |
| 2009/0136485 A1 | 5/2009 | Chu et al. |
| 2009/0136494 A1 | 5/2009 | Ponath et al. |
| 2009/0252683 A1 | 10/2009 | Kischel et al. |
| 2009/0259026 A1 | 10/2009 | Tomlinson et al. |
| 2009/0297529 A1 | 12/2009 | Li et al. |

(56) References Cited

U.S. PATENT DOCUMENTS

| | | |
|---|---|---|
| 2010/0022452 A1 | 1/2010 | Silence |
| 2010/0028330 A1 | 2/2010 | Collins et al. |
| 2010/0122358 A1 | 5/2010 | Bruggemann et al. |
| 2010/0150918 A1 | 6/2010 | Kufer et al. |
| 2010/0166734 A1 | 7/2010 | Dolk |
| 2010/0189651 A1 | 7/2010 | Stagliano et al. |
| 2010/0189727 A1 | 7/2010 | Rodeck et al. |
| 2010/0266531 A1 | 10/2010 | Hsieh et al. |
| 2010/0291112 A1 | 11/2010 | Kellner et al. |
| 2010/0311119 A1 | 12/2010 | Hermans et al. |
| 2011/0129458 A1 | 6/2011 | Dolk et al. |
| 2011/0150892 A1 | 6/2011 | Thudium et al. |
| 2011/0165621 A1 | 7/2011 | Dreier et al. |
| 2011/0262439 A1 | 10/2011 | Kufer et al. |
| 2011/0275787 A1 | 11/2011 | Kufer et al. |
| 2011/0313135 A1 | 12/2011 | Vanhove et al. |
| 2012/0039899 A1 | 2/2012 | Olsen et al. |
| 2012/0039906 A1 | 2/2012 | Olive |
| 2012/0114649 A1 | 5/2012 | Langermann et al. |
| 2012/0231024 A1 | 9/2012 | Elsaesser-Beile et al. |
| 2012/0237977 A1 | 9/2012 | Daugherty et al. |
| 2012/0263677 A1 | 10/2012 | Eagle et al. |
| 2012/0328619 A1 | 12/2012 | Fey et al. |
| 2013/0017199 A1 | 1/2013 | Langermann |
| 2013/0017200 A1 | 1/2013 | Scheer et al. |
| 2013/0136744 A1 | 5/2013 | Bouche et al. |
| 2013/0183321 A1 | 7/2013 | Smith et al. |
| 2013/0197201 A1 | 8/2013 | Vasquez et al. |
| 2013/0266568 A1 | 10/2013 | Brinkmann et al. |
| 2013/0267686 A1 | 10/2013 | Brinkmann et al. |
| 2013/0273055 A1 | 10/2013 | Borges et al. |
| 2013/0315906 A1 | 11/2013 | Lowman et al. |
| 2013/0330335 A1 | 12/2013 | Bremel et al. |
| 2014/0004121 A1 | 1/2014 | Fanslow, III et al. |
| 2014/0004575 A1 | 1/2014 | Ito et al. |
| 2014/0023664 A1 | 1/2014 | Lowman et al. |
| 2014/0044728 A1 | 2/2014 | Takayanagi et al. |
| 2014/0045195 A1 | 2/2014 | Daugherty et al. |
| 2014/0065152 A1 | 3/2014 | Kwon |
| 2014/0072565 A1 | 3/2014 | Kwon |
| 2014/0072566 A1 | 3/2014 | Kwon |
| 2014/0073767 A1 | 3/2014 | Lee et al. |
| 2014/0088295 A1 | 3/2014 | Smith et al. |
| 2014/0093511 A1 | 4/2014 | Lonberg et al. |
| 2014/0161828 A1 | 6/2014 | Armitage et al. |
| 2014/0205601 A1 | 7/2014 | Beirnaert et al. |
| 2014/0220002 A1 | 8/2014 | Ponte et al. |
| 2014/0242075 A1 | 8/2014 | Parren et al. |
| 2014/0302037 A1 | 10/2014 | Borges et al. |
| 2014/0308285 A1 | 10/2014 | Yan et al. |
| 2014/0322218 A1 | 10/2014 | Xiao et al. |
| 2014/0348841 A1 | 11/2014 | Schebye et al. |
| 2015/0037334 A1 | 2/2015 | Kufer et al. |
| 2015/0056206 A1 | 2/2015 | Zhou |
| 2015/0064169 A1 | 3/2015 | Wang et al. |
| 2015/0079088 A1 | 3/2015 | Lowman et al. |
| 2015/0079093 A1 | 3/2015 | Stuhler |
| 2015/0079109 A1 | 3/2015 | Li et al. |
| 2015/0093336 A1 | 4/2015 | Van Ginderachter et al. |
| 2015/0174268 A1 | 6/2015 | Li et al. |
| 2015/0175697 A1 | 6/2015 | Bonvini et al. |
| 2015/0183875 A1 | 7/2015 | Cobbold et al. |
| 2015/0225367 A1 | 8/2015 | Crosignani et al. |
| 2015/0232557 A1 | 8/2015 | Tan et al. |
| 2015/0274836 A1 | 10/2015 | Ho et al. |
| 2015/0274844 A1 | 10/2015 | Blankenship et al. |
| 2015/0328332 A1 | 11/2015 | Stull et al. |
| 2016/0009817 A1 | 1/2016 | Wang et al. |
| 2016/0017058 A1 | 1/2016 | Kim et al. |
| 2016/0024174 A1 | 1/2016 | Odunsi et al. |
| 2016/0032011 A1 | 2/2016 | Zhang et al. |
| 2016/0032019 A1 | 2/2016 | Xiao et al. |
| 2016/0039942 A1 | 2/2016 | Cobbold et al. |
| 2016/0046724 A1 | 2/2016 | Brogdon et al. |
| 2016/0068605 A1 | 3/2016 | Nemeth et al. |
| 2016/0068609 A1 | 3/2016 | Goletz et al. |
| 2016/0115241 A1 | 4/2016 | Yan et al. |
| 2016/0130331 A1 | 5/2016 | Stull et al. |
| 2016/0185875 A1 | 6/2016 | Cheng et al. |
| 2016/0194399 A1 | 7/2016 | Irving et al. |
| 2016/0215063 A1 | 7/2016 | Bernett et al. |
| 2016/0229913 A1 | 8/2016 | Bosques et al. |
| 2016/0251438 A1 | 9/2016 | Lucas et al. |
| 2016/0251440 A1 | 9/2016 | Roobrouck et al. |
| 2016/0257721 A1 | 9/2016 | Lieber et al. |
| 2016/0263087 A1 | 9/2016 | Crosignani et al. |
| 2016/0319040 A1 | 11/2016 | Dreier et al. |
| 2016/0340444 A1 | 11/2016 | Baeuerle et al. |
| 2016/0355842 A1 | 12/2016 | Parks et al. |
| 2017/0029502 A1 | 2/2017 | Raum et al. |
| 2017/0037130 A1 | 2/2017 | Raum et al. |
| 2017/0037149 A1 | 2/2017 | Raum et al. |
| 2017/0051068 A1 | 2/2017 | Pillarisetti et al. |
| 2017/0152316 A1 | 6/2017 | Cobbold et al. |
| 2017/0158771 A1 | 6/2017 | Glennie et al. |
| 2017/0204164 A1 | 7/2017 | Himmler et al. |
| 2017/0218085 A1 | 8/2017 | Geierstanger et al. |
| 2017/0274094 A1 | 9/2017 | Stull et al. |
| 2017/0275373 A1 | 9/2017 | Kufer et al. |
| 2017/0306014 A1 | 10/2017 | Cornen et al. |
| 2017/0334979 A1 | 11/2017 | Dubridge et al. |
| 2017/0334997 A1 | 11/2017 | Dubridge et al. |
| 2017/0349660 A1 | 12/2017 | Saville et al. |
| 2017/0362310 A1 | 12/2017 | Shoemaker |
| 2017/0369563 A1 | 12/2017 | Dubridge et al. |
| 2018/0016323 A1 | 1/2018 | Brandenburg et al. |
| 2018/0036306 A1 | 2/2018 | Jones et al. |
| 2018/0134789 A1 | 5/2018 | Baeuerle et al. |
| 2018/0148508 A1 | 5/2018 | Wang et al. |
| 2018/0318417 A1 | 11/2018 | Schuetz et al. |
| 2018/0326060 A1 | 11/2018 | Wesche et al. |
| 2018/0327511 A1 | 11/2018 | Satoh et al. |
| 2018/0346601 A1 | 12/2018 | Dettling et al. |
| 2019/0016811 A1 | 1/2019 | Lucas et al. |
| 2019/0023786 A1 | 1/2019 | Broderick et al. |
| 2019/0031749 A1 | 1/2019 | Dubridge et al. |
| 2019/0046656 A1 | 2/2019 | Stull et al. |
| 2019/0062427 A1 | 2/2019 | Rosenthal et al. |
| 2019/0092862 A1 | 3/2019 | Cui et al. |
| 2019/0112381 A1 | 4/2019 | Wesche et al. |
| 2019/0127483 A1 | 5/2019 | Li |
| 2019/0225702 A1 | 7/2019 | Baeuerle et al. |
| 2019/0247510 A1 | 8/2019 | Stull et al. |
| 2019/0359726 A1 | 11/2019 | Wang et al. |
| 2020/0115461 A1 | 4/2020 | Evnin et al. |
| 2020/0148771 A1 | 5/2020 | Paeuerle et al. |
| 2020/0155520 A1 | 5/2020 | Colburn et al. |
| 2020/0231672 A1 | 7/2020 | Dubridge et al. |
| 2020/0270362 A1 | 8/2020 | Wesche et al. |
| 2020/0270366 A1 | 8/2020 | Neijssen et al. |
| 2020/0289646 A1 | 9/2020 | Wesche et al. |
| 2020/0352998 A1 | 11/2020 | Albertson et al. |
| 2021/0047439 A1 | 2/2021 | Wesche et al. |
| 2021/0095047 A1 | 4/2021 | Baeuerle et al. |
| 2021/0100902 A1 | 4/2021 | Dubridge et al. |
| 2021/0130459 A1 | 5/2021 | Mandelboim et al. |
| 2021/0147541 A1 | 5/2021 | Takahashi et al. |
| 2021/0171649 A1 | 6/2021 | Wesche et al. |
| 2021/0179735 A1 | 6/2021 | Baeuerle et al. |
| 2021/0261671 A1 | 8/2021 | Wesche et al. |
| 2021/0269530 A1 | 9/2021 | Lin et al. |
| 2021/0284728 A1 | 9/2021 | Lin et al. |
| 2021/0292421 A1 | 9/2021 | Lin et al. |
| 2021/0317212 A1 | 10/2021 | Ng et al. |
| 2021/0355219 A1 | 11/2021 | Lin et al. |
| 2021/0380715 A1 | 12/2021 | Yoshida et al. |
| 2022/0054544 A1 | 2/2022 | Lin et al. |
| 2022/0098311 A1 | 3/2022 | Wesche et al. |
| 2022/0112297 A1 | 4/2022 | Wesche et al. |
| 2022/0267462 A1 | 8/2022 | Wesche et al. |
| 2022/0403024 A1 | 12/2022 | Short et al. |
| 2023/0257451 A1 | 8/2023 | Dubridge et al. |
| 2024/0084009 A1 | 3/2024 | Dubridge et al. |

(56) References Cited

U.S. PATENT DOCUMENTS

| | | |
|---|---|---|
| 2024/0084035 A1 | 3/2024 | Molloy et al. |
| 2024/0100157 A1 | 3/2024 | Wesche et al. |
| 2024/0141072 A1 | 5/2024 | Wesche et al. |

FOREIGN PATENT DOCUMENTS

| | | |
|---|---|---|
| CA | 3040823 A1 | 4/2018 |
| CN | 1563092 A | 1/2005 |
| CN | 101557817 A | 10/2009 |
| CN | 101646689 A | 2/2010 |
| CN | 104288765 A | 1/2015 |
| CN | 104520324 A | 4/2015 |
| CN | 105968201 A | 9/2016 |
| CN | 105968204 A | 9/2016 |
| CN | 108026174 A | 5/2018 |
| CN | 108137706 A | 6/2018 |
| CN | 108251442 A | 7/2018 |
| CN | 109593786 A | 4/2019 |
| CN | 112321708 A | 2/2021 |
| EP | 0239400 A2 | 9/1987 |
| EP | 0519596 A1 | 12/1992 |
| EP | 0592106 A1 | 4/1994 |
| EP | 1378520 A1 | 1/2004 |
| EP | 1736484 A1 | 12/2006 |
| EP | 2336179 A1 | 6/2011 |
| EP | 2581113 A1 | 4/2013 |
| EP | 2817338 A2 | 12/2014 |
| EP | 3093293 A1 | 11/2016 |
| EP | 3093294 A1 | 11/2016 |
| EP | 3095797 A1 | 11/2016 |
| EP | 3146979 A1 | 3/2017 |
| EP | 3337517 A2 | 6/2018 |
| EP | 3193929 B1 | 6/2019 |
| EP | 3556400 A1 | 10/2019 |
| FR | 901228 A | 7/1945 |
| JP | 2005501517 A | 1/2005 |
| JP | 2005518789 A | 6/2005 |
| JP | 2008278814 A | 11/2008 |
| JP | 2016500655 A | 1/2016 |
| JP | 2019052750 A | 4/2019 |
| WO | WO-9109967 A1 | 7/1991 |
| WO | WO-9307105 A1 | 4/1993 |
| WO | WO-9404678 A1 | 3/1994 |
| WO | WO-9937681 A2 | 7/1999 |
| WO | WO-0043507 A1 | 7/2000 |
| WO | WO-0130381 A2 | 5/2001 |
| WO | WO-0190190 A2 | 11/2001 |
| WO | WO-0196584 A2 | 12/2001 |
| WO | WO-0222685 A2 | 3/2002 |
| WO | WO-02055082 A1 | 7/2002 |
| WO | WO-02085945 A2 | 10/2002 |
| WO | WO-03025020 A1 | 3/2003 |
| WO | WO-03035694 A2 | 5/2003 |
| WO | WO-03064606 A2 | 8/2003 |
| WO | WO-2004003019 A2 | 1/2004 |
| WO | WO-2004035607 A2 | 4/2004 |
| WO | WO-2004041867 A2 | 5/2004 |
| WO | WO-2004042404 A1 | 5/2004 |
| WO | WO-2004049794 A2 | 6/2004 |
| WO | WO-2004056312 A2 | 7/2004 |
| WO | WO-2004099249 A2 | 11/2004 |
| WO | WO-2005003168 A2 | 1/2005 |
| WO | WO-2005009465 A1 | 2/2005 |
| WO | WO-2005040220 A1 | 5/2005 |
| WO | WO-2005095456 A1 | 10/2005 |
| WO | WO-2006020258 A2 | 2/2006 |
| WO | WO-2006072625 A2 | 7/2006 |
| WO | WO-2006072626 A1 | 7/2006 |
| WO | WO-2006105021 A2 | 10/2006 |
| WO | WO-2006121168 A1 | 11/2006 |
| WO | WO-2006122786 A2 | 11/2006 |
| WO | WO-2006122787 A1 | 11/2006 |
| WO | WO-2007005874 A2 | 1/2007 |
| WO | WO-2007024715 A2 | 3/2007 |
| WO | WO-2007042261 A2 | 4/2007 |
| WO | WO-2007042573 A2 | 4/2007 |
| WO | WO-2007062466 A1 | 6/2007 |
| WO | WO-2007113648 A2 | 10/2007 |
| WO | WO-2007115230 A2 | 10/2007 |
| WO | WO-2008028977 A2 | 3/2008 |
| WO | WO-2008084106 A1 | 7/2008 |
| WO | WO-2009009116 A2 | 1/2009 |
| WO | WO-2009021754 A2 | 2/2009 |
| WO | WO-2009025846 A2 | 2/2009 |
| WO | WO-2009030285 A1 | 3/2009 |
| WO | WO-2009035577 A1 | 3/2009 |
| WO | WO-2009101611 A1 | 8/2009 |
| WO | WO-2009114335 A2 | 9/2009 |
| WO | WO-2009147248 A2 | 12/2009 |
| WO | WO-2010003118 A1 | 1/2010 |
| WO | WO-2010012557 A1 | 2/2010 |
| WO | WO-2010019570 A2 | 2/2010 |
| WO | WO-2010027827 A2 | 3/2010 |
| WO | WO-2010037836 A2 | 4/2010 |
| WO | WO-2010037837 A2 | 4/2010 |
| WO | WO-2010065939 A1 | 6/2010 |
| WO | WO-2010077634 A1 | 7/2010 |
| WO | WO-2010081173 A2 | 7/2010 |
| WO | WO-2011028683 A1 | 3/2011 |
| WO | WO-2011039368 A2 | 4/2011 |
| WO | WO-2011051327 A2 | 5/2011 |
| WO | WO-2011066342 A2 | 6/2011 |
| WO | WO-2011070024 A1 | 6/2011 |
| WO | WO-2011076922 A1 | 6/2011 |
| WO | WO-2011079283 A1 | 6/2011 |
| WO | WO-2011107553 A1 | 9/2011 |
| WO | WO-2011117423 A1 | 9/2011 |
| WO | WO-2011131407 A1 | 10/2011 |
| WO | WO-2011140249 A2 | 11/2011 |
| WO | WO-2011155607 A2 | 12/2011 |
| WO | WO-2011161260 A1 | 12/2011 |
| WO | WO-2012071411 A2 | 5/2012 |
| WO | WO-2012122444 A1 | 9/2012 |
| WO | WO-2012131053 A2 | 10/2012 |
| WO | WO-2012138475 A1 | 10/2012 |
| WO | WO-2012145493 A1 | 10/2012 |
| WO | WO-2012158818 A2 | 11/2012 |
| WO | WO-2012160448 A2 | 11/2012 |
| WO | WO-2012163805 A1 | 12/2012 |
| WO | WO-2012175400 A1 | 12/2012 |
| WO | WO-2013006490 A2 | 1/2013 |
| WO | WO-2013036130 A1 | 3/2013 |
| WO | WO-2013039954 A1 | 3/2013 |
| WO | WO-2013045707 A2 | 4/2013 |
| WO | WO-2013053725 A1 | 4/2013 |
| WO | WO-2013072406 A1 | 5/2013 |
| WO | WO-2013072415 A1 | 5/2013 |
| WO | WO-2013079174 A1 | 6/2013 |
| WO | WO-2013087699 A1 | 6/2013 |
| WO | WO-2013104804 A2 | 7/2013 |
| WO | WO-2013110531 A1 | 8/2013 |
| WO | WO-2013119716 A1 | 8/2013 |
| WO | WO-2013126712 A1 | 8/2013 |
| WO | WO-2013128027 A1 | 9/2013 |
| WO | WO-2013128194 A1 | 9/2013 |
| WO | WO-2013132044 A1 | 9/2013 |
| WO | WO-2013158856 A2 | 10/2013 |
| WO | WO-2013169264 A1 | 11/2013 |
| WO | WO-2013173223 A1 | 11/2013 |
| WO | WO-2014008218 A1 | 1/2014 |
| WO | WO-2014012085 A2 | 1/2014 |
| WO | WO-2014033304 A2 | 3/2014 |
| WO | WO-2014036357 A1 | 3/2014 |
| WO | WO-2014047231 A1 | 3/2014 |
| WO | WO-2014052064 A1 | 4/2014 |
| WO | WO-2014055648 A1 | 4/2014 |
| WO | WO-2014094122 A1 | 6/2014 |
| WO | WO-2014125273 A1 | 8/2014 |
| WO | WO-2014132072 A1 | 9/2014 |
| WO | WO-2014138306 A1 | 9/2014 |
| WO | WO-2014140358 A1 | 9/2014 |
| WO | WO-2014144689 A1 | 9/2014 |
| WO | WO-2014151910 A1 | 9/2014 |
| WO | WO-2014153270 A1 | 9/2014 |

(56) References Cited

FOREIGN PATENT DOCUMENTS

| | | |
|---|---|---|
| WO | WO-2015026684 A1 | 2/2015 |
| WO | WO-2015031667 A2 | 3/2015 |
| WO | WO-2015031693 A1 | 3/2015 |
| WO | WO-2015042246 A1 | 3/2015 |
| WO | WO-2015082499 A2 | 6/2015 |
| WO | WO-2015103072 A1 | 7/2015 |
| WO | WO-2015121812 A1 | 8/2015 |
| WO | WO-2015127407 A1 | 8/2015 |
| WO | WO-2015140717 A1 | 9/2015 |
| WO | WO-2015142675 A2 | 9/2015 |
| WO | WO-2015146437 A1 | 10/2015 |
| WO | WO-2015150097 A1 | 10/2015 |
| WO | WO-2015150327 A1 | 10/2015 |
| WO | WO-2015150447 A1 | 10/2015 |
| WO | WO-2015173764 A1 | 11/2015 |
| WO | WO-2015184099 A1 | 12/2015 |
| WO | WO-2015184207 A1 | 12/2015 |
| WO | WO-2015187835 A2 | 12/2015 |
| WO | WO-2016009029 A1 | 1/2016 |
| WO | WO-2016026772 A1 | 2/2016 |
| WO | WO-2016032334 A1 | 3/2016 |
| WO | WO-2016046778 A2 | 3/2016 |
| WO | WO-2016055551 A1 | 4/2016 |
| WO | WO-2016071283 A1 | 5/2016 |
| WO | WO-2016071293 A2 | 5/2016 |
| WO | WO-2016075099 A1 | 5/2016 |
| WO | WO-2016087531 A1 | 6/2016 |
| WO | WO-2016105450 A2 | 6/2016 |
| WO | WO-2016125017 A1 | 8/2016 |
| WO | WO-2016130819 A2 | 8/2016 |
| WO | WO-2016134333 A1 | 8/2016 |
| WO | WO-2016134335 A2 | 8/2016 |
| WO | WO-2016138038 A1 | 9/2016 |
| WO | WO-2016147144 A1 | 9/2016 |
| WO | WO-2016171999 A2 | 10/2016 |
| WO | WO-2016179003 A1 | 11/2016 |
| WO | WO-2016179518 A2 | 11/2016 |
| WO | WO-2016180982 A1 | 11/2016 |
| WO | WO-2016181348 A1 | 11/2016 |
| WO | WO-2016182064 A1 | 11/2016 |
| WO | WO-2016187101 A2 | 11/2016 |
| WO | WO-2016187594 A1 | 11/2016 |
| WO | WO-2016210447 A1 | 12/2016 |
| WO | WO-2017007700 A1 | 1/2017 |
| WO | WO-2017021349 A1 | 2/2017 |
| WO | WO-2017021356 A1 | 2/2017 |
| WO | WO-2017021362 A1 | 2/2017 |
| WO | WO-2017025038 A1 | 2/2017 |
| WO | WO-2017025698 A1 | 2/2017 |
| WO | WO-2017025868 A1 | 2/2017 |
| WO | WO-2017027392 A1 | 2/2017 |
| WO | WO-2017031104 A1 | 2/2017 |
| WO | WO-2017041749 A1 | 3/2017 |
| WO | WO-2017079528 A1 | 5/2017 |
| WO | WO-2017093969 A1 | 6/2017 |
| WO | WO-2017134134 A1 | 8/2017 |
| WO | WO-2017136549 A1 | 8/2017 |
| WO | WO-2017156178 A1 | 9/2017 |
| WO | WO-2017157305 A1 | 9/2017 |
| WO | WO-2017161206 A1 | 9/2017 |
| WO | WO-2017162587 A1 | 9/2017 |
| WO | WO-2017201442 A1 | 11/2017 |
| WO | WO-2017201488 A1 | 11/2017 |
| WO | WO-2017201493 A1 | 11/2017 |
| WO | WO-2017220988 A1 | 12/2017 |
| WO | WO-2018017863 A1 | 1/2018 |
| WO | WO-2018017864 A2 | 1/2018 |
| WO | WO-2018026953 A1 | 2/2018 |
| WO | WO-2018027203 A1 | 2/2018 |
| WO | WO-2018033798 A1 | 2/2018 |
| WO | WO-2018048975 A1 | 3/2018 |
| WO | WO-2018067993 A1 | 4/2018 |
| WO | WO-2018071777 A1 | 4/2018 |
| WO | WO-2018075359 A1 | 4/2018 |
| WO | WO-2018083204 A1 | 5/2018 |
| WO | WO-2018085469 A2 | 5/2018 |
| WO | WO-2018098354 A1 | 5/2018 |
| WO | WO-2018098356 A1 | 5/2018 |
| WO | WO-2018106529 A1 | 6/2018 |
| WO | WO-2018106588 A1 | 6/2018 |
| WO | WO-2018110555 A1 | 6/2018 |
| WO | WO-2018115859 A1 | 6/2018 |
| WO | WO-2018119183 A2 | 6/2018 |
| WO | WO-2018133877 A1 | 7/2018 |
| WO | WO-2018136725 A1 | 7/2018 |
| WO | WO-2018160671 A1 | 9/2018 |
| WO | WO-2018160754 A2 | 9/2018 |
| WO | WO-2018165619 A1 | 9/2018 |
| WO | WO-2018183366 A1 | 10/2018 |
| WO | WO-2018204717 A1 | 11/2018 |
| WO | WO-2018209298 A1 | 11/2018 |
| WO | WO-2018209304 A1 | 11/2018 |
| WO | WO-2018220584 A1 | 12/2018 |
| WO | WO-2018232020 A1 | 12/2018 |
| WO | WO-2019011852 A1 | 1/2019 |
| WO | WO-2019011855 A1 | 1/2019 |
| WO | WO-2019025983 A1 | 2/2019 |
| WO | WO-2019075359 A1 | 4/2019 |
| WO | WO-2019075378 A1 | 4/2019 |
| WO | WO-2019136305 A1 | 7/2019 |
| WO | WO-2019222278 A1 | 11/2019 |
| WO | WO-2019222282 A1 | 11/2019 |
| WO | WO-2019222283 A1 | 11/2019 |
| WO | WO-2019229701 A2 | 12/2019 |
| WO | WO-2019246004 A1 | 12/2019 |
| WO | WO-2020053263 A1 | 3/2020 |
| WO | WO-2020060593 A1 | 3/2020 |
| WO | WO-2020061482 A1 | 3/2020 |
| WO | WO-2020061526 A1 | 3/2020 |
| WO | WO-2020069028 A1 | 4/2020 |
| WO | WO-2020092792 A2 | 5/2020 |
| WO | WO-2020097403 A1 | 5/2020 |
| WO | WO-2019166650 A9 | 8/2020 |
| WO | WO-2020181145 A1 | 9/2020 |
| WO | WO-2020232303 A1 | 11/2020 |
| WO | WO-2020252349 A1 | 12/2020 |
| WO | WO-2020261093 A1 | 12/2020 |
| WO | WO-2020263830 A1 | 12/2020 |
| WO | WO-2021097060 A1 | 5/2021 |
| WO | WO-2021168303 A1 | 8/2021 |
| WO | WO-2021231434 A1 | 11/2021 |
| WO | WO-2022031884 A2 | 2/2022 |
| WO | WO-2022032006 A2 | 2/2022 |
| WO | WO-2022098909 A1 | 5/2022 |
| WO | WO-2022192225 A1 | 9/2022 |
| WO | WO-2022212732 A1 | 10/2022 |
| WO | WO-2022256498 A1 | 12/2022 |
| WO | WO-2022256499 A2 | 12/2022 |
| WO | WO-2022256500 A2 | 12/2022 |
| WO | WO-2022272033 A2 | 12/2022 |
| WO | WO-2023064945 A2 | 4/2023 |
| WO | WO-2024129537 A2 | 6/2024 |
| WO | WO-2024147891 A1 | 7/2024 |
| WO | WO-2024147897 A2 | 7/2024 |
| WO | WO-2024155457 A2 | 7/2024 |

OTHER PUBLICATIONS

Allard et al., The ectonucleotidases CD39 and CD73: Novel checkpoint inhibitor targets. Immunol Rev., 276(1):121-144 (2018).

Altenhofer et al., The NOX toolbox: validating the role of NADPH oxidases in physiology and disease. Cell Mol Life Sciences 69(14):2327-2343 (2012).

Annual Report Pursuant to Section 13 or 15(d) of the Securities Exchange Act of 1934. 2019 22-24 [online]. [Retrieved on Aug. 5, 2021]. Retrieved from website URL: https://www.annualreports.com/HostedData/AnnualReportArchive/h/NASDAQ_HARP_2018.pdf.

Austin et al. TriTACs, a Novel Class of T-Cell-Engaging Protein Constructs Designed for the Treatment of Solid Tumors. Mol Cancer Ther 20(1):109-120 (2021).

(56) References Cited

OTHER PUBLICATIONS

Ayers et al. IFN-γ-related mRNA profile predicts clinical response to PD-1 blockade. The Journal of Clinical Investigation 127(8):2930-2940 (Aug. 2017).
Balzar et al. Epidermal growth factor-like repeats mediate lateral and reciprocal interactions of Ep-CAM molecules in homophilic adhesions. Mol Cell Biol. 21(7):2570-80 (2001).
Balzar et al. The biology of the 17-1A antigen (Ep-CAM). J. Mol. Med. 77:699-712 (1999).
Bluemel et al. Epitope distance to the target cell membrane and antigen size determine the potency of T cell-mediated lysis by BiTE antibodies specific for a large melanoma surface antigen. Cancer Immunol Immunother 59(8):1197-209 (2010).
Chaubal et al. Ep-CAM—a marker for the detection of disseminated tumor cells in patients suffering from SCCHN. Anticancer Res 19:2237-2242 (1999).
Chen et al. Enhancement and destruction of antibody function U by somatic mutation: unequal occurrence is controlled by V gene combinatorial associations. The EMBO Journal 14(12):2784-2794 (1995).
Chen et al. Preparation and characterization of dexamethasone acetate-loaded solid lipid nanoparticles. Chinese J Pharm 39(4):261-264 (2008) (English abstract).
Cheong et al., A patent review of IDO1 inhibitors for cancer. Expert Opin Ther Pat. 28(4):317-330 (2018).
Colman. Effects of amino acid sequence changes on antibody-antigen interactions. Res Immunol 145(1):33-36 (1994).
Croso et al., Real-time detection of mesothelin in pancreatic cancer cell line supernatant using an acoustic wave immunosensor. Cancer Detect. Prev. 30:180-187 (2006).
Davé et al. Fab-dsFv: A bispecific antibody format with extended serum half-life through albumin binding. MAbs 8(7):1319-1335 (2016).
Dickopf et al. Format and geometries matter: Structure-based design defines the functionality of bispecific antibodies. Comput Struct Biotechnol J 18:1221-1227 (2020).
Dondelinger et al., Understanding the Significance and Implications of Antibody Numbering and Antigen-Binding Surface/Residue Definition. Frontiers in Immunology 9(2278):1-15 (2018).
Eshhar, et al., Specific activation and targeting of cytotoxic lymphocytes through chimeric single chains consisting of antibody-binding domains and the y or s subunits of the immunoglobulin and T-cell receptors. PNAS USA 90:720-724 (1993).
Eyvazi et al. Antibody Based EpCAM Targeted Therapy of Cancer, Review and Update. Curr Cancer Drug Targets. 18(9):857-868 (2018).
Fang et al. Characterization of an anti-human ovarian carcinomaxanti-human CD3 bispecific single-chain antibody with an albumin-original interlinker. Gynecol Oncol 92(1):135-146 (2004).
Galsky et al. Phase I trial of the prostate-specific membrane antigen-directed immunoconjugate MLN2704 in patients with progressive metastatic castration-resistant prostate cancer. J Clin Oncol 26(13):2147-54 (2008).
Gastl et al. Ep-CAM overexpression in breast cancer as a predictor of survival. Lancet. 356:1981-1982 (2000).
Gautam et al., Dual Inhibition of NOX2 and Receptor Tyrosine Kinase by BJ-1301 Enhances Anticancer Therapy Efficacy via Suppression of Autocrine-Stimulatory Factors in Lung Cancer. Mol Cancer Ther 16(10):2144-2156 (2017).
Gianni et al., A novel and specific NADPH oxidase-1 (Nox1) small-molecule inhibitor blocks the formation of functional invadopodia in human colon cancer cells. ACS Chem Biol 5(10):981-93 (2010).
Goettlinger et al. The epithelial cell surface antigen 17-1A, a target for antibody-mediated tumor therapy: its biochemical nature, tissue distribution and recognition by different monoclonal antibodies. Int J Cancer. 38:47-53 (1986).
Gorshkova et al. Single domain antibodies and bioengineering drugs on their basis: new opportunities for diagnostics and therapy. Medical Immunology (Russia) 18(6):505-520 (2016) (English Abstract).

Harris et al. A bispecific antibody agonist of the IL-2 heterodimeric receptor preferentially promotes in vivo expansion of CD8 and NK cells. Sci Rep. 11(1):10592 (2021).
Hassanzadeh-Ghassabeh et al. Nanobodies and their potential applications. Nanomedicine 8(6):1013-1026 (2013).
Henry et al. A prostate-specific membrane antigen-targeted monoclonal antibody- chemotherapeutic conjugate designed for the treatment of prostate cancer. Cancer Res. 64(21):7995-8001 (2004).
Hupe et al. Expression of Prostate-Specific Membrane Antigen (PSMA) on Biopsies Is an Independent Risk Stratifier of Prostate Cancer Patients at Time of Initial Diagnosis. Front Oncol 8:623 (2018).
Jang et al. Human 4-1BB (CD137) signals are mediated by TRAF2 and activate nuclear factor-kappa B. Biochem. Biophys. Res. Commun. 242 (3):613-20 (1998).
Jemaa et al. Co-expression and impact of prostate specific membrane antigen and prostate specific antigen in prostatic pathologies. J Exp Clin Cancer Res 29(1):171 (2010).
Jiang et al. Protritac: A protease cleavable T cell Engager Platform. Scientific Reports 6(Suppl 1):115 Available at https://calidibio.com/wp-content/uploads/2019/10/609-Abstract-_SITC-2018.pdf (2018).
Kakkad et al. Collagen 1 fiber content may predict for recurrence in non-small cell lung cancer. Cancer Research 78(13 Supplement):3691-3691 (2018).
Kauder et al., ALX148 blocks CD47 and enhances innate and adaptive antitumor immunity with a favorable safety profile. PLoS One 13(8):e0201832 (2019).
Kelm et al., Functional groups of sialic acids involved in binding to siglecs (sialoadhesins) deduced from interactions with synthetic analogues. Eur. J. Biochem. 255:663-672 (1998).
Kelm et al., The Sialoadhesins—a family of sialic acid-dependent cellular recognition molecules within the immunoglobulin superfamily. Glycoconj. J. 13:913-926 (1996).
Kim et al., 2077—An oral dual inhibitor of IDO and TDO enhances anti-cancer immunity and synergizes with immune checkpoint blockade. Annals Oncol 29 (suppl_8):viii400-viii441 (2018) (Poster Abstract).
Kim et al. Strategies and 1-17 Advancement in Antibody-Drug Conjugate Optimization for Targeted Cancer Therapeutics. Biomol Ther (Seoul) 23(6):493-509 (2015).
Koprowski et al. Colorectal carcinoma antigens detected by hybridoma antibodies. Somatic Cell Genet. 5:957-971 (1979).
Korenchuk et al. VCaP, a cell-based model system of human prostate cancer. In Vivo. 15(2):163-8 (2001).
Le Gall et al., Immunosuppressive Properties of Anti-CD3 Single-Chain Fv and Diabody. Journal of Immunological Methods 285(1):111-127 (2004).
Lehmann et al. Stability engineering of anti-EGFR scFv antibodies by rational design of a lambda-to-kappa swap of the VL framework using a structure-guided approach. MAbs 7(6):1058-1071 (2015).
Lin et al. Improved affinity of a chicken single-chain antibody to avian infectious bronchitis virus by site-directed mutagenesis of complementarity-determining region H3. African Journal of Biotechnology 10(79):18294-18302 (2011).
Lin et al. ProTriTAC: A Protease-Activatable T Cell Engager Platform that Links Half-Life Extension to Functional Masking Society for Immunotherapy of Cancer (SITC) Annual Meeting. Nov. 2018, Available at https://www.harpoontx.com/file.cfm/43/docs/SITC_2018_ProTriTAC_Poster.pdf .
Litvinov et al. Epithelial cell adhesion molecule (Ep-CAM) modulates cell-cell interactions mediated by classic cadherins. J Cell Biol. 139:1337-1348 (1997).
Litvinov et al. Expression of Ep-CAM in cervical squamous epithelia correlates with an increased proliferation and the disappearance of markers for terminal differentiation. Am. J. Pathol. 148:865-75 (1996).
Loberg et al. Development of the VCaP androgen-independent model of prostate cancer. Urol Oncol 24(2):161-8 (2006).
Lu et al., Characterization of potent and selective iodonium-class inhibitors of NADPH oxidases. Biochem Pharmacol 143:25-38 (2017).

(56) References Cited

OTHER PUBLICATIONS

Lucchi et al. The Masking Game: Design of Activatable Antibodies and Mimetics for Selective Therapeutics Cell Control. ACS Cent Sci 7(5):724-738 (2021).
Lv et al. Mesothelin as a biomarker for targeted therapy. Biomark Res 7:18 (2019).
Ma et al. Combination therapy with T cell engager and PD-L1 blockade enhances the antitumor potency of T cells as predicted by a QSP model. J Immunother Cancer. 8(2):e001141 (2020).
MacCallum, Robert M, et al., Antibody-Antigen Interactions: Contact Analysis and Binding Site Topography. Journal of Molecular Biology 262(5):732-745 (1996).
Magiera-Mularz et al. Bioactive macrocyclic inhibitors of the PD-1/PD-L1 immune checkpoint Angew. Chem. Int. Ed. 56(44):13732-13735 (2017).
McCall et al. Isolation and characterization of an anti-CD16 single-chain Fv fragment and construction of an anti-HER2/neu/anti-CD16 bispecific scFv that triggers CD16-dependent tumor cytolysis Mol Immunol. 36(7):433-46 (1999).
McCarthy et al. Altering the fine specificity of an anti-Legionella single chain antibody by a single amino acid insertion. J Immunol Methods 251(1-2):137-49 (2001).
McDevitt et al. An alpha-particle emitting antibody ([213Bi]J591) for radioimmunotherapy of prostate cancer. Cancer Res. 60:6095-6100 (2000).
Monney et al. Th1-specific cell surface protein Tim-3 regulates macrophage activation and severity of an autoimmune disease. Nature 415:536-41 (2002).
Nakae et al. Phenotypic differences between Th1 and Th17 cells and negative regulation of Th1 cell differentiation by IL-17. J Leukoc Biol 81:1258-68 (2007).
Nicolaou et al., Calicheamicin ↓11: a rationally designed molecule with extremely potent and selective DNA cleaving properties and apoptosis inducing activity. Angew Chem IntlEd. Engl. 33:183-186 (1994).
Osta et al. EpCAM is overexpressed in breast cancer and is a potential target for breast cancer gene therapy. Cancer Res 64:5818-24 (2004).
PCT/US2021/018853 International Search Report and Written Opinion dated Jul. 8, 2021.
PCT/US2021/031790 International Search Report and Written Opinion dated Sep. 16. 2021.
PCT/US2021/058108 International Search Report and Written Opinion dated Apr. 1, 2022.
PCT/US2022/019302 International Search Report and Written Opinion dated Jun. 27, 2022.
PCT/US2022/022871 International Search Report and Written Opinion dated Aug. 3, 2022.
PCT/US2022/031916 International Search Report and Written Opinion dated Sep. 29, 2022.
PCT/US2022/031917 International Search Report and Written Opinion dated Dec. 2, 2022.
PCT/US2022/031919 International Search Report and Written Opinion dated Nov. 21, 2022.
PCT/US2022/034856 International Search Report and Written Opinion dated Dec. 8, 2022.
PCT/US2022/078178 International Search Report and Written Opinion dated Jul. 18, 2023.
Perrot et al., Blocking Antibodies Targeting the CD39/CD73 Immunosuppressive Pathway Unleash Immune Responses in Combination Cancer Therapies. Cell Reports 8:2411-2425.E9 (2019).
Piyathilake et al. The expression of Ep-CAM (17-1A) in squamous cell cancers of the lung. Hum Pathol. 31:482-487 (2000).
Pocztek et al. Ep-Cam levels in prostatic adenocarcinoma and prostatic intraepithelial neoplasia. J Urol. 162:1462-1464 (1999).
Popoli et al., Effects of SCH 58261, an Adenosine A2A receptor antagonist, on quinpirole-induced turning in 6-Hydroxydopamine-lesioned rats: lack of tolerance after chronic caffeine intake. Neuropsychopharm 22:522-529 (2000).

Quak et al. Production of a monoclonal antibody (K 931) to a squamous cell carcinoma associated antigen identified as the 17-1A antigen. Hybridoma 9:377-387 (1990).
Rabia, et al. Understanding and overcoming trade-offs between antibody affinity, specificity, stability and solubility. Biochem Eng J. 137:365-374. (2018).
Roda-Navarro et al. Understanding the Spatial Topology of Artificial Immunological Synapses Assembled in T Cell-Redirecting Strategies: A Major Issue in Cancer Immunotherapy. Front Cell Dev Biol 7:370 (2020).
Ryan et al. Antibody targeting of B-cell maturation antigen on malignant plasma cells. Mol Cancer Ther 6(11):3009-3018 (2007).
Schaer et al. Modulation of GITR for cancer immunotherapy. Curr Opin Immunol. 24(2): 217-224 (2012).
Sheridan. Ido inhibitors move center stage in immuno-oncology. Nat Biotechnol 33:321-322 (2015).
Simon et al. Epithelial glycoprotein is a member of a family of epithelial cell surface antigens homologous to nidogen, a matrix adhesion protein. PNAS USA 87:2755-2759 (1990).
Sramkoski et al. A new human prostate carcinoma cell line, 22Rv1. In Vitro Cell Dev Biol Anim 35(7):403-409 (1999).
Stanciu-Herrera et al., Anti-CD19 and anti-CD22 monoclonal antibodies increase the effectiveness of chemotherapy in Pre-B acute lymphoblastic leukemia cell lines . Leuk Res. 32:625-32 (2008).
Stasi et al., Animal models of Parkinson's disease: Effects of two adenosine A2A receptor antagonists ST4206 and ST3932, metabolites of 2-n-Butyl-9-methyl-8-[1,2,3]triazol-2-yl-9H-purin-6-ylamine (ST1535). Europ J Pharmacol 761:353-361 (2015).
Tamura et al. Structural correlates of an anticarcinoma antibody: identification of specificity-determining residues (SDRs) and development of a minimally immunogenic antibody variant by retention of SDRs only. J Immunol. 164(3):1432-41 (2020).
Tang et al., NOX4, a new genetic target for anti-cancer therapy in digestive system cancer. J Dig Dis 19(10):578-585 (2018).
Trail et al. Antibody drug 1-17 conjugates for treatment of breast cancer: Novel targets and diverse approaches in ADC design. Pharmacol Ther 181:126-142 (2018).
Trebak et al. Oligomeric state of the colon carcinoma-associated glycoprotein GA733-2 (Ep-CAM/EGP40) and its role in GA733-mediated homotypic cell-cell adhesion. J Biol Chem. 276:2299-2309 (2001).
UniProtKB Accession No. A0A3M1V7M7_9EURY, Ig-like_bact domain-containing protein, Feb. 13, 2019 [online] [Retrieved on Jun. 8, 2021]. Retrieved from the internet <url: https://www.uniprotorg/uniprot/A0A3M1V7M7.bct</url :.
U.S. Appl. No. 16/161,986 Office Action dated Dec. 2, 2021.
U.S. Appl. No. 16/339,263 Office Action dated Jan. 11, 2022.
U.S. Appl. No. 16/339,263 Office Action dated Jan. 18, 2023.
U.S. Appl. No. 16/339,263 Office Action dated May 3, 2022.
U.S. Appl. No. 16/489,523 Office Action dated Feb. 14, 2022.
U.S. Appl. No. 16/773,843 Office Action dated Aug. 11, 2022.
U.S. Appl. No. 16/773,843 Office Action dated Feb. 8, 2022.
U.S. Appl. No. 16/802,007 Office Action dated Apr. 14, 2023.
U.S. Appl. No. 16/802,007 Office Action dated Sep. 29, 2022.
U.S. Appl. No. 16/999,773 Office Action dated Apr. 21, 2023.
U.S. Appl. No. 17/030,118 Office Action dated May 5, 2023.
U.S. Appl. No. 17/072,370 Office Action dated Jun. 2, 2023.
U.S. Appl. No. 17/150,272 Office Action dated Sep. 15, 2023.
U.S. Appl. No. 17/165,760 Office Action dated Jan. 19, 2024.
U.S. Appl. No. 17/276,796 Office Action dated Feb. 1, 2024.
Wang et al., A Small Molecule Antagonist of PD-1/PD-L1 Interactions Acts as an Immune Checkpoint Inhibitor for NSCLC and Melanoma Immunotherapy. Front. Immunol. 12:654463.
Wang et al., In vitro characterization of the anti-PD-1 antibody nivolumab, BMS-936558, and in vivo toxicology in non-human primates. Cancer Immunol. Res. 2(9):846-856 (2014).
Watt et al., Homophilic adhesion of human CEACAM1 involves N-terminal domain interactions: structural analysis of the binding site. Blood 98:1469-1479 (2001).
Weir et al., Colony stimulating factor-1 plays a role in osteoclast formation and function in bone resorption induced by parathyroid hormone and parathyroid hormone-related protein. J Bone Mineral Res 11:1474-1481 (1996).

(56) References Cited

OTHER PUBLICATIONS

Ye et al. Androgen and epidermal growth factor down-regulate cyclin-dependent kinase inhibitor p27Kip1 and costimulate proliferation of MDA PCa 2a and MDA PCa 2b prostate cancer cells. Clin Cancer Res 5(8):2171-7 (1999).
Zhao et al. Novel Antibody Therapeutics Targeting Mesothelin in Solid Tumors. Clin Cancer Drugs 3(2):76-86 (2016).
Agata et al. Expression of the PD-1 antigen on the surface of stimulated mouse T and B lymphocytes. Int. Immunol 8:765-75 (1996).
Al-Lazikani et al. Standard conformations for the canonical structures of immunoglobulins. J. Mol Biology 273(4):927-948 (1997).
Almagro et al. Humanization of antibodies. Front Biosci 13:1619-1633 (2008).
Altschul et al. Basic local alignment search tool. J Mol Biol 215(3):403-410 (1990).
Altschul, et al. Gapped BLAST and PSI-BLAST: a new generation of protein database search programs. Nucleic Acids Res 25:3389-3402 (1997).
Argani et al. Mesothelin is overexpressed in the vast majority of ductal adenocarcinomas of the pancreas: identification of a new pancreatic cancer marker by serial analysis of gene expression (SAGE). Clin Cancer Res 7(12):3862-3868 (2001).
Austin et al. Cancer Research (Jul. 2018) vol. 78, No. 13, Supp. Supplement 1. Abstract No. 1781. Meeting Info: 2018 Annual Meeting of the American Association for Cancer Research, AACR 2018. Chicago, IL, United States. Apr. 2, 14018-Apr. 18, 2018).
Baca et al. Antibody humanization using monovalent phage display. J Biol Chem 272(16):10678-10684 (1997).
Baeuerle et al. Bispecific T-cell engaging antibodies for cancer therapy. Cancer Res 69:4941-4944 (2009).
Barrett et al. Treatment of advanced leukemia in mice with mRNA engineered T cells. Hum Gene Ther 22:1575-1586 (2011).
Batzer et al. Enhanced evolutionary PCR using oligonucleotides with inosine at the 3'-terminus. Nucleic Acids Res. 19(18):5081 (1991).
Baum et al. Antitumor activities of PSMAxCD3 diabodies by redirected T-cell lysis of prostate cancer cells. Immunotherapy 5(1):27-38 (2013).
Bedouelle et al. Diversity and junction residues as hotspots of binding energy in an antibody neutralizing the dengue virus. FEBS J 273(1):34-46 (2006).
Bendell et al. Abstract 5552: First-in-human phase I study of HPN424, a tri-specific half-life extended PSMA-targeting T-cell engager in patients with metastatic castration-resistant prostate cancer (mCRPC). J Clin Oncol 38(15):5552 (May 2020).
Bird et al. Single-chain antigen-binding proteins. Science 242(4877):423-426 (1988).
Blank et al. Interaction of PD-L1 on tumor cells with PD-1 on tumor-specific T cells as a mechanism of immune evasion: implications for tumor immunotherapy. Cancer Immunol Immunother 54:307-314 (2005).
Bortoletto et al. Optimizing anti-CD3 affinity for effective T cell targeting against tumor cells. Eur J Immunol 32:3102-3107 (2002).
Bracci et al. Cyclophosphamide enhances the antitumor efficacy of adoptively transferred immune cells through the induction of cytokine expression, B-cell and T-cell homeostatic proliferation, and specific tumor infiltration. Clin Cancer Res 13(2 Pt 1):644-653 (2007).
Brauchle et al. Characterization of a Novel FLT3 BiTE Molecule for the Treatment of Acute Myeloid Leukemia. Mol Cancer Ther 19:1875-88 (2020).
Brown et al. Tolerance of single, but not multiple, amino acid replacements in antibody VH CDR 2: a means of minimizing B cell wastage from somatic hypermutation? J Immunol 156(9):3285-3291 (1996).
Caldas et al. Design and synthesis of germline-based hemi-humanized single-chain Fv against the CD18 surface antigen. Protein Eng 13(5):353-360 (2000).
Caldas et al. Humanization of the anti-CD18 antibody 6.7: an unexpected effect of a framework residue in binding to antigen. Mol Immunol. 39(15):941-952 (2003).
Carter et al. Humanization of an anti-p185HER2 antibody for human cancer therapy. PNAS USA 89(10):4285-4289 (1992).
Carter et al. PD-1: PD-L inhibitory pathway affects both CD4(+) and CD8(+) T cells and is overcome by IL-2. Eur J Immunol 32:634-643 (2002).
Casset et al. A peptide mimetic of an anti-CD4 monoclonal antibody by rational design. Biochemical and Biophysical Research Communication 307:198-205 (2003).
Chang et al. Loop-sequence features and stability determinants in antibody variable domains by high-throughput experiments. Structure 22(1):9-21 (2014).
Chang et al. Molecular cloning of mesothelin, a differentiation antigen present on mesothelium, mesotheliomas, and ovarian cancers. PNAS USA 93:136-140 (1996).
Chatalic et al. A Novel 111 In-labeled Anti-PSMA Nanobody for Targeted SPECT/CT Imaging of Prostate Cancer. J Nucl Med 56(7):1094-1099 and Supplemental Data (2015).
Chen et al. Fusion protein linkers: Property, design and functionality. Advanced Drug Delivery Reviews 65:1357-1369 (2013).
Chen et al. Selection and analysis of an optimized anti-VEGF antibody: Crystal structure of an affinity-matured Fab in complex with antigen. J Mol Bio 293:865-881 (1999).
Chien et al. Significant structural and functional change of an antigen-binding site by a distant amino acid substitution: proposal of a structural mechanism. PNAS USA 86(14):5532-5536 (1989).
Cho et al. Targeting B Cell Maturation Antigen (BCMA) in Multiple Myeloma: Potential Uses of BCMA-Based Immunotherapy. Front Immunol 9:1821 (2018).
Choi et al. Engineering of Immunoglobulin Fc heterodimers using yeast surface-displayed combinatorial Fc library screening. PLOS One 10(12):e0145349 (2015).
Chothia et al. Canonical structures for the hypervariable regions of immunoglobulins. J Mol Biol 196(4):901-917 (1987).
Chothia, et al. Conformations of immunoglobulin hypervariable regions. Nature 342(6252):877-83 (1989).
Corso et al. Real-time detection of mesothelin in pancreatic cancer cell line supernatant using an acoustic wave immunosensor. Cancer Detect Prev 30:180-187 (2006).
Cougot et al. 'Cap-tabolism'. Trends in Biochem Sci 29:436-444 (2001).
Couto et al. Anti-BA46 monoclonal antibody Mc3: humanization using a novel positional consensus and in vivo and in vitro characterization. Cancer Res 55(8):1717-1722 (1995).
Couto et al. Designing human consensus antibodies with minimal positional templates. Cancer Res 55(23 Supp):5973s-5977s (1995).
Creaney et al. Detection of malignant mesothelioma in asbestos-exposed individuals: the potential role of soluble mesothelin-related protein. Hematol. Oncol. Clin. North Am. 19:1025-1040 (2005).
Cristaudo et al. Clinical significance of serum mesothelin in patients with mesothelioma and lung cancer. Clin. Cancer Res. 13:5076-5081 (2007).
Dao et al. Targeting the intracellular WT1 oncogene product with a therapeutic human antibody. Sci Transl Med 5(176):176ra33 (2013).
De Genst et al. Antibody repertoire development in camelids. Dev Comp Immunol 30(1-2):187-198 (2006).
De Pascalis et al. Grafting of "abbreviated" complementarity-determining regions containing specificity-determining residues essential for ligand contact to engineer a less immunogenic humanized monoclonal antibody. J Immunol. 169(6):3076-3084 (2002).
Dennis et al. Imaging Tumors with an Albumin-Binding Fab, a Novel Tumor-Targeting Agent. Cancer Res 67(1):254-61 (2007).
Document D28—Investigation of human CD3ε variants binding to monoclonal antibodies. Submitted by Pfizer to the European Patent Register on Apr. 30, 2014 in connection with their opposition to the EP2155783 patent. (3 pages) (2014).
Document D78—CD3ε N-terminal peptide bound to the CDRs of SP24. Submitted by Janssen Biotech to the European Patent Register on Mar. 18, 2016 in connection with their opposition to the EP2155783 patent (1 page) (2016).

(56) References Cited

OTHER PUBLICATIONS

Document D79 - Interactions between CD3ε and SP34 CDR residues. CD3ε residues are in ellipses, SP34 CDR residues are in boxes. Submitted by Janssen Biotech to the European Patent Register on Mar. 18, 2016 in connection with their opposition to the EP2155783 patent (1 page) (2016).
Document D83—Alignment of variable domains from the prior art and the patent. Submitted by Janssen Biotech to the European Patent Register on Mar. 18, 2016 in connection with their opposition to the EP2155783 patent (1 page) (2016).
Dong et al. B7-H1 pathway and its role in the evasion of tumor immunity. J Mol Med 81:281-287 (2003).
Elango et al. Optimized transfection of mRNA transcribed from a d(A/T) 100 tail-containing vector. Biochim Biophys Res Commun 330:958-966 (2005).
Foote et al. Antibody Framework Residues Affecting the Conformation of the Hypervariable Loops. J. Mol. Biol. 224(2):487-99 (1992).
Frankel et al. Targeting T cells to tumor cells using bispecific antibodies. Curr Opin Chem Biol 17(3):385-392 (2013).
Freeman et al. Engagement of the PD-1 immunoinhibitory receptor by a novel B7 family member leads to negative regulation of lymphocyte activation. J Exp Med 192:1027-1034 (2000).
Garland et al. The use of Teflon cell culture bags to expand functionally active CD8+ cytotoxic T lymphocytes. J Immunol Meth 227(1-2):53-63 (1999).
Giusti et al. Somatic diversification of S107 from an antiphosphocholine to an anti-DNA autoantibody is due to a single base change in its heavy chain variable region. PNAS USA 84(9):2926-30 (1987).
Glaser et al. Novel antibody hinge regions for efficient production of CH2 domain-deleted antibodies. J. Biol. Chem. 280:41494-503 (2005).
Goldman et al. Enhancing Stability of Camelid and Shark Single Domain Antibodies: An Overview. Front. Immunol. 8:865 (2017).
Goodman et al. The Pharmaceutical Basis of Therapeutics. 6th ed. pp. 21-25 (1980).
Goswami et al. Developments and Challenges for mAb-Based Therapeutics. Antibodies 2:452-500 (2013).
Gross et al. Endowing T cells with antibody specificity using chimeric T cell receptors. FASEB J. 6(15):3370-3378 (1992).
Grupp et al. Chimeric antigen receptor-modified T cells for acute lymphoid leukemia. NEJM 368:1509-1518 (2013).
Gubbels et al. Mesothelin-MUC16 binding is a high affinity, N-glycan dependent interaction that facilitates peritoneal metastasis of ovarian tumors. Mol Cancer 5:50 (2006).
Gussow et al. Chapter 5: Humanization of Monoclonal Antibodies. Methods in Enzymology 203:99-121 (1991).
Haanen et al. Selective expansion of cross-reactive CD8(+) memory T cells by viral variants. J Exp Med 190(9):1319-1328 (1999).
Halaby et al. The immunoglobulin fold family: sequence analysis and 3D structure comparisons. Prot Eng 12(7):563-571 (1999).
Han et al. Masked Chimeric Antigen Receptor for Tumor-Specific Activation. Molecular Therapy 25(1):274-284 (2017).
Harding et al. The immunogenicity of humanized and fully human antibodies: residual immunogenicity resides in the CDR regions. MAbs 2(3):256-265 (2010).
Harmsen et al. Properties, production, and applications of camelid single-domain antibody fragments. Appl. Microbiol. Biotechnol. 77:13-22 (2007).
Hassan et al. Detection and quantitation of serum mesothelin, a tumor marker for patients with mesothelioma and ovarian cancer. Clin Cancer Res 12:447-453 (2006).
Hassan et al. Mesothelin: a new target for immunotherapy. Clin Cancer Res 10:3937-3942 (2004).
Hassan et al. Mesothelin targeted cancer immunotherapy. Eur J Cancer 44:46-53 (2008).
Hassan et al. Phase I study of SS1P, a recombinant anti-mesothelin immunotoxin given as a bolus I.V. infusion to patients with mesothelin-expressing mesothelioma, ovarian, and pancreatic cancers. Clin Cancer Res 13(17):5144-5149 (2007).

Hassan et al. Preclinical evaluation of MORAb-009, a chimeric antibody targeting tumor-associated mesothelin. Cancer Immun. 7:20 (2007).
Hellstrom et al. Mesothelin variant 1 is released from tumor cells as a diagnostic marker. Cancer Epidemiol Biomarkers Prey 15:1014-1020 (2006).
Hipp et al. A novel BCMA/CD3 bispecific T-cell engager for the treatment of multiple myeloma induces selective lysis in vitro and in vivo. Leukemia 31(8):1743-1751 (2017).
Ho et al. A novel high-affinity human monoclonal antibody to mesothelin. Int J Cancer 128:2020-2030 (2011).
Ho et al. Mesothelin expression in human lung cancer. Clin Cancer Res 13:1571-1575 (2007).
Ho et al. Mesothelin is shed from tumor cells. Cancer Epidemiol Biomarkers Prey 15:1751 (2006).
Holliger et al. "Diabodies": small bivalent and bispecific antibody fragments. Pnas USA 90(14):6444-6448 (1993).
Holm et al. Functional mapping and single chain construction of the anti-cytokeratin 8 monoclonal antibody TS1. Mol Immunol 44(6):1075-1084 (2007).
Holt et al. Anti-serum albumin domain antibodies for extending the half-lives of short-lived drugs. Protein Eng Des Sel 21(5):283-288 (2008).
Hopp et al. The effects of affinity and valency of an albumin-binding domain (ABD) on the half- life of a single-chain diabody-ABD fusion protein. Protein Eng. Des. Sel. 23(11):827-34 (2010).
Huck et al. Sequence of a human immunoglobulin gamma 3 heavy chain constant region gene: comparison with the other human C gamma genes. Nucl. Acids Res. 14:1779-89 (1986).
Huston et al. Protein engineering of antibody binding sites: recovery of specific activity in an anti-digoxin single-chain Fv analogue produced in *Escherichia coli*. PNAS USA 85(16):5879-5883 (1988).
Hutchinson et al. Mutagenesis at a specific position in a DNA sequence. J Biol Chem 253:6551-6560 (1978).
Izumoto et al. Phase II clinical trial of Wilms tumor 1 peptide vaccination for patients with recurrent glioblastoma multiforme. J Neurosurg 108:963-971 (2008).
Janssen letter—Submission under Rule 116 EPC. Submitted by Janssen Biotech to the European Patent Register on Mar. 18, 2016 in connection with their opposition to the EP2155783 patent (6 pages) (2016).
Jones et al. Replacing the complementarity-determining regions in a human antibody with those from a mouse. Nature 321:522-525 (1986).
Julian et al. Efficient affinity maturation of antibody variable domains requires co-selection of compensatory mutations to maintain thermodynamic stability. Sci Rep 7:45259 (2017).
Kabat et al. Identical V region amino acid sequences and segments of sequences in antibodies of different specificities. Relative contributions of VH and VL genes, minigenes, and complementarity-determining regions to binding of antibody-combining sites. J Immunol 147:1709-1719 (1991).
Kabat et al. Sequences of proteins of immunological interest. NIH Publ. No. 91-3242 1:647-669 (1991).
Kalos et al. T cells with chimeric antigen receptors have potent antitumor effects and can establish memory in patients with advanced leukemia. Sci Transl Med 3(95):95ra73 (2011).
Kojima et al. Molecular cloning and expression of megakaryocyte potentiating factor cDNA. J Biol Chem 270:21984-21990 (1995).
Konishi et al. B7-H1 expression on non-small cell lung cancer cells and its relationship with tumor-infiltrating lymphocytes and their PD-1 expression. Clin Cancer Res 10:5094-5100 (2004).
Škrlec et al. Non-immunoglobulin scaffolds: a focus on their targets. Trends in Biotechnol 33:408-418 (2015).
Krzywinska et al. CD45 Isoform Profile Identifies Natural Killer (NK) Subsets with Differential Activity. PLoS One 11(4):e0150434 (2016).
Laabi et al. The BCMA gene, preferentially expressed during B lymphoid maturation, is bidirectionally transcribed. Nucleic Acids Res 22(7):1147-1154 (1994).
Latchman et al. PD-L2 is a second ligand for PD-1 and inhibits T cell activation. Nat Immunol 2:261-268 (2001).

(56) References Cited

OTHER PUBLICATIONS

Le Gall et al. Immunosuppressive properties of anti-CD3 single-chain Fv and diabody. J Immunol Methods 285(1):111-127 (2004).
Leibl et al. Ovarian granulosa cell tumors frequently express EGFR (Her-1), Her-3, and Her-4: An immunohistochemical study. Gynecol Oncol 101(1):18-23 (2006).
Li et al. Development of novel tetravalent anti-CD20 antibodies with potent antitumor activity. Cancer Res 68:2400-2408 (2008).
Liu et al. A New Format of Single Chain Tri-specific Antibody with Diminished Molecular Size Efficiently Induces Ovarian Tumor Cell Killing. Biotechnology Letters 27(22):1821-1827 (2005).
Liu et al. MGD011, a CD19 x CD3 Dual Affinity Re-Targeting Bi-specific Molecule Incorporating Extended Circulating Half-life for the Treatment of B-cell Malignancies. Clin Cancer Res 23(6):1506-1518 (epub 2016) (2017).
Lowman et al. Monovalent phage display: A method for selecting variant proteins from random libraries. Methods 3:205-216 (1991).
Lu et al. In vitro and in vivo antitumor effect of a trivalent bispecific antibody targeting ErbB2 and CD16. Cancer Biol Ther. 7(11):1744-1750 (2008).
Lutterbuese et al. T cell-engaging BiTE antibodies specific for EGFR potently eliminate KRAS- and BRAF-mutated colorectal cancer cells. PNAS 107:12605-12610 (2007).
MacCallum et al. Antibody-antigen interactions: contact analysis and binding site topography. J Mol Biol. 262(5):732-745 (1996).
Mariuzza et al. The structural basis of antigen-antibody recognition. Annu Rev Biophys Biophys Chem 16:139-159 (1987).
Mason et al. CD79a: a novel marker for B-cell neoplasms in routinely processed tissue samples. Blood 86(4):1453-1459 (1995).
Milone et al. Chimeric receptors containing CD137 signal transduction domains mediate enhanced survival of T cells and increased antileukemic efficacy in vivo. Mol Ther 17(8):1453-1464 (2009).
Mirsky et al. Antibody-Specific Model of Amino Acid Substitution for Immunological Inferences from Alignments of Antibody Sequences. Mol. Biol. Evol. 32(3):806-819 (2014).
Müller et al. Improved Pharmacokinetics of Recombinant Bispecific Antibody Molecules by Fusion to Human Serum Albumin. J. Biol. Chem. 282(17):12650-60 (2007).
Morea et al. Antibody modeling: implications for engineering and design. Methods 20(3):267-279 (2000).
Moschella et al. Unraveling cancer chemoimmunotherapy mechanisms by gene and protein expression profiling of responses to cyclophosphamide. Cancer Res 71(10):3528-3539 (2011).
Muller et al. Improving the pharmacokinetic properties of biologics by fusion to an anti-HSA shark VNAR domain. MAbs 4(6):673-685 (2012).
Mumtaz et al. Design of liposomes for circumventing the reticuloendothelial cells. Glycobiology 5:505-10 (1991).
Muul et al. Persistence and expression of the adenosine deaminase gene for 12 years and immune reaction to gene transfer components: long-term results of the first clinical gene therapy trial. Blood 101(7):2563-2569 (2003).
Muyldermans. Nanobodies: natural single-domain antibodies. Annu Rev Biochem 82:775-797 (2013).
Nacheva et al. Preventing nondesired RNA-primed RNA extension catalyzed by T7 RNA polymerase. Eur J Biochem 270:1458-1465 (2003).
Nazarian et al. Characterization of bispecific T-cell Engager (BiTE) antibodies with a high-capacity T-cell dependent cellular cytotoxicity (TDCC) assay. J Biomol Screen 20:519-527 (2015).
Needleman et al. A general method applicable to the search for similarities in the amino acid sequence of two proteins. J. Mol. Biol. 48:443-453 (1970).
Nelson et al. Antibody fragments Hope and Hype. mAbs 2(1):77-83 (2010).
Nicholson et al. Construction and characterisation of a functional CD19 specific single chain Fv fragment for immunotherapy of B lineage leukaemia and lymphoma. Mol Immun 34(16-17):1157-1165 (1997).

Nishikawa et al. Nonviral vectors in the new millennium: delivery barriers in gene transfer. Human Gene Therapy. 12:861-870 (2001).
Nunez-Prado et al. The coming of age of engineered multivalent antibodies. Drug Discovery Today 20(5):588-594 (2015).
Ohiro et al. A homogeneous and noncompetitive immunoassay based on the enhanced fluorescence resonance energy transfer by leucine zipper interaction. Anal Chem 74(22):5786-5792 (2002).
Ohtsuka et al. An alternative approach to deoxyoligonucleotides as hybridization probes by insertion of Deoxyinosine at Ambiguous Codon Positions. J Biol Chem 260(5):2605-2608 (Mar. 10, 1985).
O'Keefe et al. Chapter 18: Prostate specific membrane antigen. In: Chung L.W.K., Isaacs W.B., Simons J.W. (eds) Prostate Cancer. Contemporary Cancer Research. Humana Press, Totowa, NJ (pp. 307-326) (2001).
Ordonez. Application of mesothelin immunostaining in tumor diagnosis. Am J Surg Pathol 27:1418-1428 (2003).
Padlan. Anatomy of the Antibody Molecule. Mol Immunol 31(3):169-217 (1994).
Padlan, et al., A possible procedure for reducing the immunogenicity of antibody variable domains while preserving their ligand-binding properties. Mol Immunol 28(4-5):489-498 (1991).
Padlan et al. Structure of an antibody-antigen complex: Crystal structure of the HyHEL-10 Fab-lysozyme complex. PNAS USA 86:5938-5942 (1989).
Pawluczkowycz et al. Binding of submaximal C1q promotes complement-dependent cytotoxicity (CDC) of B cells opsonized with anti-CD20 mAbs ofatumumab (OFA) or rituximab (RTX): considerably higher levels of CDC are induced by OFA than by Rtx. J Immunol 183:749-758 (2009).
PCT/US2016/033644 International Search Report and Written Opinion dated Sep. 6, 2016.
PCT/US2017/033665 International Search Report and Written Opinion dated Oct. 18, 2017.
PCT/US2017/033673 International Search Report and Written Opinion dated Oct. 18, 2017.
PCT/US2017/056530 International Search Report and Written Opinion dated Jan. 23, 2018.
PCT/US2017/063121 International Search Report and Written Opinion dated Mar. 26, 2018.
PCT/US2017/063126 International Search Report and Written Opinion dated Apr. 5, 2018.
PCT/US2018/014396 International Search Report and Written Opinion dated Jun. 14, 2018.
PCT/US2018/020185 International Search Report and Written Opinion dated Jun. 15, 2018.
PCT/US2018/020307 International Search Report and Written Opinion dated Aug. 24, 2018.
PCT/US2018/030983 International Search Report and Written Opinion dated Sep. 25, 2018.
PCT/US2018/032418 International Search Report and Written Opinion dated Sep. 24, 2018.
PCT/US2018/032427 International Search Report and Written Opinion dated Sep. 13, 2018.
PCT/US2018/055659 International Search Report and Written Opinion dated Feb. 21, 2019.
PCT/US2018/055682 International Search Report and Written Opinion dated Mar. 1, 2019.
PCT/US2019/032224 International Search Report and Written Opinion dated Aug. 28, 2019.
PCT/US2019/032302 International Search Report and Written Opinion dated Aug. 22, 2019.
PCT/US2019/032306 International Search Report and Written Opinion dated Aug. 22, 2019.
PCT/US2019/032307 International Search Report and Written Opinion dated Aug. 22, 2019.
PCT/US2019/052206 International Search Report and Written Opinion dated Feb. 14, 2020.
PCT/US2019/052270 International Search Report and Written Opinion dated Mar. 5, 2020.
PCT/US2019/053017 International Search Report and Written Opinion dated Jan. 31, 2020.
PCT/US2020/032985 International Search Report and Written Opinion dated Oct. 15, 2020.

(56) References Cited

OTHER PUBLICATIONS

PCT/US2020/060184 International Search Report and Written Opinion dated Mar. 4, 2021.
Pearson et al. Improved Tools for Biological Sequence Comparison. PNAS USA 85:2444-48 (1988).
Pedersen et al. Comparison of surface accessible residues in human and murine immunoglobulin Fv domains. Implication for humanization of murine antibodies. J Mol Biol 235(3):959-973 (1994).
Pfizer letter—Opposition to European Patent EP2155783 (Application 08735001.3). Submitted by Pfizer to the European Patent Register on Apr. 30, 2014 in connection with their opposition to the EP2155783 patent. (pp. 1-23 and Appendix 1 on pp. 24-26) (2014).
Porter et al. Chimeric antigen receptor T cells persist and induce sustained remissions in relapsed refractory chronic lymphocytic leukemia. Sci Trans Med 7(303):303ra319 (2015).
Porter et al. Chimeric antigen receptor-modified T cells in chronic lymphoid leukemia. NEJM 365:725-733 (2011).
Presta: Antibody Engineering. Curr Op Struct Biol 2:593-596 (1992).
Presta et al. Humanization of an antibody directed against IgE. J Immunol 151:2623-2632 (1993).
Ramadoss et al. An Anti-B Cell Maturation Antigen Bispecific Antibody for Multiple Myeloma. J. Ann. Chem. Soc. 137(16):5288-91 (2015).
Riechmann et al. Reshaping human antibodies for therapy. Nature, 332.6162:323-7 (1988).
Riechmann et al. Single domain antibodies: comparison of camel VH and camelised human VH domains. J Immunol Methods 231(1-2):25-38 (1999).
Roguska et al. A comparison of two murine monoclonal antibodies humanized by CDR-grafting and variable domain resurfacing. Protein Eng 9(10):895-904 (1996).
Roguska et al. Humanization of murine monoclonal antibodies through variable domain resurfacing. PNAS 91:969-973 (1994).
Rosenberg et al. Use of tumor-infiltrating lymphocytes and interleukin-2 in the immunotherapy of patients with metastatic melanoma. A preliminary report. NEJM 319:1676 (1988).
Rosok et al. A Combinatorial Library Strategy for the Rapid Humanization of Anticarcinoma BR96 Fab. J Biol Chem 271:22611-22618 (1996).
Rossolini et al. Use of deoxyinosine-containing primers vs degenerate primers for polymerase chain reaction based on ambiguous sequence information. Mol Cell Probes 8(2):91-98 (1994).
Rozan et al. Single-domain antibody-based and linker-free bispecific antibodies targeting FcγRIII induce potent antitumor activity without recruiting regulatory T cells. Mol Cancer Ther 12(8):1481-1491 (2013).
Rudikoff et al. Single amino acid substitution altering antigen-binding Specificity. PNAS USA 79:1979-1983 (1982).
Rump et al. Binding of ovarian cancer antigen CA125/MUC16 to mesothelin mediates cell adhesion. J Biol Chem 279:9190-9198 (2004).
Running Deer et al. High-level expression of proteins in mammalian cells using transcription regulatory sequences from the Chinese hamster EF-1alpha gene. Biotechnol Prog. 20:880-889 (2004).
Sadelain et al. Targeting tumours with genetically enhanced T lymphocytes. Nat Rev Cancer 3(1):35-45 (2003).
Sadelain et al. The basic principles of chimeric antigen receptor design. Cancer Discov. 3(4):388-98 (2013).
Saerens et al. Identification of a universal VHH framework to graft non-canonical antigen- binding loops of camel single-domain antibodies. J. Mol. Biol. 352(3):597-607 (2005).
Sandhu. A rapid procedure for the humanization of monoclonal antibodies. Gene 150(2):409-410 (1994).
Sandler et al. Nondermatologic adverse events associated with anti-EGFR therapy. Oncology (Williston Park) 20(5 Suppl 2):35-40 (2006).
Sastry et al. Targeting hepatitis B virus-infected cells with a T-cell receptor-like antibody. J Virol 85(5):1935-1942 (2011).
Schenborn et al. A novel transcription property of SP6 and T7 RNA polymerases: dependence on template structure. Nuc Acids Res 13:6223-6236 (1985).
SCHERAGA. Predicting three-dimensional structures of oligopeptides. Rev Computational Chem 3:73-142 (1992).
Schmidt et al. Cloning and Characterization of Canine Prostate-Specific Membrane Antigen. The Prostate 73:642-650 (2013).
Schmittgen et al. Expression of prostate specific membrane antigen and three alternatively spliced variants of PSMA in prostate cancer patients. Int J Cancer 107:323-329 (2003).
Sergeeva et al. An anti-PR1/HLA-A2 T-cell receptor-like antibody mediates complement- dependent cytotoxicity against acute myeloid leukemia progenitor cells. Blood 117(16):4262-4272 (2011).
Sheng et al. Novel Transgenic Mouse Model for Studying Human Serum Albumin as a Biomarker of Carcinogenic Exposure. Chem. Res. Toxicol. 29(5):797-809 (2016).
Sims et al. A humanized CD18 antibody can block function without cell destruction. J Immunol. 151:2296-2308 (1993).
Smirnova et al. Identification of new splice variants of the genes BAFF and BCMA. Mol. Immunol. 45 (4):1179-83 (2008).
Smith et al. Comparison of Biosequences. Advances in Applied Mathematics. 2:482-489 (1981).
Song et al. CD27 costimulation augments the survival and antitumor activity of redirected human T cells in vivo. Blood 119(3):696-706 (2012).
Spiess et al. Alternative molecular formats and therapeutic applications for bispecific antibodies. Mol. Immunol. 67(2 Pt A):95-106 (2015).
Stehle et al. Albumin-based drug carriers: comparison between serum albumins of different species on pharmacokinetics and tumor uptake of the conjugate. Anticancer Drugs. 10(8):785-90 (1999).
Stepinski et al. Synthesis and properties of mRNAs containing the novel 'anti-reverse' cap analogs 7-methyl(3'0-methyl)GpppG and 7-methyl(e'-deoxy)GpppG. RNA 7:1486-1495 (2001).
Sternjak et al. Cancer Research, (Jul. 2017) vol. 77, No. 13, Supp. Supplement 1. Abstract No. 3630. Meeting Info: American Association for Cancer Research Annual Meeting 2017. Washington, DC, United States. Apr. 1, 2017-Apr. 5, 2017.
Stirewalt et al. The role of FLT3 in haematopoietic malignancies. Nat Rev Cancer 3:650-665 (2003).
Stork et al. A novel tri-functional antibody fusion protein with improved pharmacokinetic properties generated by fusing a bispecific single-chain diabody with an albumin-binding domain from streptococcal protein G. Protein Eng. Des. Sel. 20(11):569-76 (2007).
Strop. Veracity of microbial transglutaminase. Bioconjugate Chem. 25(5):855-862 (2014).
Studnicka et al. Human-engineered monoclonal antibodies retain full specific binding activity by preserving non-CDR complementarity-modulating residues. Pro Eng 7(6):805-814 (1994).
Su et al. PSMA specific single chain antibody-mediated targeted knockdown of Notch1 inhibits human prostate cancer cell proliferation and tumor growth. Cancer Lett. 338 (2): 282-291 (2013).
Tan et al. Influence of the hinge region on complement activation, C1q binding, and segmental flexibility in chimeric human immunoglobulins. PNAS USA 87:162-166 (1990).
Tan et al. "Superhumanized" antibodies: reduction of immunogenic potential by complementarity-determining region grafting with human germline sequences: application to an anti-CD28. J Immunol 169:1119-1125 (2002).
Tang et al. A human single-domain antibody elicits potent antitumor activity by targeting an epitope in mesothelin close to the cancer cell surface. Mol. Cancer Thera 12(4):416-426 (2013).
Tassev et al. Retargeting NK92 cells using an HLA-A2-restricted, EBNA3C-specific chimeric antigen receptor. Cancer Gene Ther 19(2):84-100 (2012).
Ten Berg et al. Selective expansion of a peripheral blood CD8+ memory T cell subset expressing both granzyme B and L-selectin during primary viral infection in renal allograft recipients. Transplant Proc 30(8):3975-3977 (1998).
Thomas. Cetuximab: adverse event profile and recommendations for toxicity management. Clin J Oncol Nurs. 9(3):332-8 (2005).

(56) References Cited

OTHER PUBLICATIONS

Thomas et al. Mesothelin-specific CD8(+) T cell responses provide evidence of in vivo cross-priming by antigen-presenting cells in vaccinated pancreatic cancer patients. J Exp Med 200:297-306 (2004).
Tijink et al. Improved tumor targeting of anti-epidermal growth factor receptor nanobodies through albumin binding: taking advantage of modular Nanobody technology. Mol. Cancer Ther. 7(8):2288-97 (2008).
Tiller et al. Facile Affinity Maturation of Antibody Variable Domains Using Natural Diversity Mutagenesis. Front. Immunol. 8:986 (2017).
Tutt et al. Trispecific F(ab')3 derivatives that use cooperative signaling via the TCR/CD3 complex and CD2 to activate and redirect resting cytotoxic T cells. J Immunol. 147(1):60-69 (Jul. 1, 1991).
Ui-Tei et al. Sensitive assay of RNA interference in *Drosophila* and Chinese hamster cultured cells using firefly luciferase gene as target. FEBS Letters 479: 79-82 (2000).
U.S. Appl. No. 15/160,984 Office Action dated Feb. 24, 2017.
U.S. Appl. No. 15/160,984 Office Action dated Sep. 22, 2016.
U.S. Appl. No. 15/600,264 Office Action dated Apr. 25, 2019.
U.S. Appl. No. 15/600,264 Office Action dated Apr. 26, 2018.
U.S. Appl. No. 15/600,264 Office Action dated Nov. 27, 2018.
U.S. Appl. No. 15/600,264 Office Action dated Oct. 3, 2017.
U.S. Appl. No. 15/600,582 Office Action dated Nov. 16, 2017.
U.S. Appl. No. 15/630,259 Office Action dated Dec. 30, 2019.
U.S. Appl. No. 15/630,259 Office Action dated Sep. 30, 2020.
U.S. Appl. No. 15/704,620 Office Action dated Oct. 26, 2017.
U.S. Appl. No. 15/821,498 Office Action dated Apr. 21, 2020 .
U.S. Appl. No. 15/821,498 Office Action dated May 3, 2019.
U.S. Appl. No. 15/821,498 Office Action dated Oct. 26, 2018.
U.S. Appl. No. 15/821,530 Office Action dated Apr. 22, 2020 .
U.S. Appl. No. 15/821,530 Office Action dated Apr. 3, 2019.
U.S. Appl. No. 15/821,530 Office Action dated Sep. 25, 2018.
U.S. Appl. No. 15/977,968 Office Action dated Feb. 21, 2019.
U.S. Appl. No. 15/977,988 Office Action dated Aug. 20, 2019.
U.S. Appl. No. 15/977,988 Office Action dated Mar. 26, 2019.
U.S. Appl. No. 15/977,988 Pre-Interview First Office Action dated Jan. 25, 2019.
U.S. Appl. No. 16/159,545 Office Action dated Aug. 6, 2019.
U.S. Appl. No. 16/159,545 Office Action dated Dec. 2, 2019.
U.S. Appl. No. 16/159,554 Office Action dated Jun. 7, 2019.
U.S. Appl. No. 16/159,554 Office Action dated Mar. 16, 2021.
U.S. Appl. No. 16/159,554 Office Action dated Oct. 1, 2019.
U.S. Appl. No. 16/159,554 Office Action dated Oct. 5, 2020.
U.S. Appl. No. 16/583,070 Office Action dated Mar. 3, 2020.
Vajdos et al. Comprehensive functional maps of the antigen-binding site of an anti-ErbB2 antibody obtained with shotgun scanning mutagenesis. J Mol Biol 320:415-428 (2002).
Van Den Beuchken et al. Building novel binding ligands to B7.1 and B7.2 based on human antibody single variable light chain domains. J Mol biol 310:591-601 (2001).
Van Der Linden et al. Induction of immune responses and molecular cloning of the heavy chain antibody repertoire of Lama glama. J Immunol Methods 240:185-195 (2000).
Vaughan et al. Human antibodies by design. Nature Biotech 16:535-539 (1998).
Verhoeyen et al. Reshaping human antibodies: Grafting an antilysozyme activity. Science 239:1534-1536 (1988).
Verma et al. TCR mimic monoclonal antibody targets a specific peptide/HLA class I complex and significantly impedes tumor growth in vivo using breast cancer models. J Immunol 184(4):2156-2165 (2010).
Vincke et al. General strategy to humanize a camelid single-domain antibody and identification of a universal humanized nanobody scaffold. J. Biol. Chem. 284(5):3273-3284 (2009).
Wang et al. A New Recombinant Single Chain Trispecific Antibody Recruits T Lymphocytes to Kill CEA (Carcinoma Embryonic Antigen) Positive Tumor Cells In Vitro Efficiently. Journal of Biochemistry 135(4):555-565 (2004).
Willemsen et al. A phage display selected fab fragment with MHC class I-restricted specificity for MAGE-A1 allows for retargeting of primary human T lymphocytes. Gene Ther 8(21):1601-1608 (2001).
Winkler et al. Changing the antigen binding specificity by single point mutations of an anti-p24 (HIV-1) antibody. J Immunol. 165(8):4505-4514 (2000).
Wu et al. Humanization of a murine monoclonal antibody by simultaneous optimization of framework and CDR residues. J.Mol. Biol. 294:151-162 (1999).
Yan et al. Engineering upper hinge improves stability and effector function of a human IgG1. J. Biol. Chem. 287:5891 (2012).
Yee et al. Adoptive T cell therapy using antigen-specific CD8+ T cell clones for the treatment of patients with metastatic melanoma: in vivo persistence, migration, and antitumor effect of transferred T cells. PNAS USA 99(25):16168-16173 (2002).
Yoshinaga et al. Ig L-chain shuffling for affinity maturation of phage library-derived human anti-human MCP-1 antibody blocking its chemotactic activity. J Biochem 143(5):593-601 (2008).
Yu et al. Rationalization and design of the complementarity determining region sequences in an antibody-antigen recognition interface. PLoS One 7(3):e33340 (2012).
Zabetakis et al. Contributions of the complementarity determining regions to the thermal stability of a single-domain antibody. PLoS One 8(10):e77678 (2013).
Zare et al. Production of nanobodies against prostate-specific membrane antigen (PSMA) recognizing LnCaP cells. Int. J. Biol. Markers 29(2):e169-e179 (2014).
Zhang et al. New High Affinity Monoclonal Antibodies Recognize Non-Overlapping Epitopes on Mesothelin for Monitoring and Treating Mesothelioma. Sci Rep 5:9928 (2015).
Zhu et al. COMBODY: one-domain antibody multimer with improved avidity. Immunology and Cell Biology 88(6):667-675 (2010).
GenBank AHA34196.1, immunoglobulin variable heavy regionJIY-F10 RTA-F10, partial [Vicugna pacos] (Nov. 18, 2013).
Goodall, Laura J et al. Pharmacokinetic and Pharmacodynamic Characterisation of an Anti-Mouse TNF Receptor 1 Domain Antibody Formatted for In Vivo Half-Life Extension. PLoS 10(9):e0137065 (2015).
[$HARP] Harpoon Therapeutics—IPO Preview. Available at https://biocapitalist.tistory.com/71 (Feb. 8, 2019).
Hu et al. Over-expression of human Notch ligand Delta-like 3 promotes proliferation of human gastric cancer cells in vitro. Nan Fang Yi Ke Da Xue Xue Bao 38(1):14-19 (2018) (English Abstract).
Kwant, S. Kathryn et al. TriTAC-XR is an Extended-Release T Cell Engager Platform that Improves Safety by Minimizing Risk of Cytokine Release Syndrome. Poster 2861 AACR. P.1 (2022).
Laporte, Sherry L et al. Abstract A203: Cd3-egfr Bispecific Probody™ Therapeutics Induced Tumor Regressions and Increased Therapeutic Window in Preclinical Studies. Molecular Cancer Therapeutics 14(12_Supplement_2):1-4 (2015).
Li, Jian et al. Modulation of Antigen-Specific T cell by a Non-mitogenic Anti-CD3 Antibody. International Immunopharmacology 6(6):880-891 (2006).
Li, Yiwen et al. Suppression of leukemia expressing wild-type or ITD-mutant FLT3 receptor by a fully human anti-FLT3 neutralizing antibody. Blood 104(4):1137-1144 (2004).
Liang, Benjia et al. Integrinβ6-targeted immunoliposomes mediate tumor-specific drug delivery and enhance therapeutic efficacy in colon carcinoma. Clinical Cancer Research 21(5):1183-1195 (2015).
PCT/US2023/083132 International Search Report and Written Opinion dated Jun. 13, 2024.
PCT/US2023/083564 International Search Report and Written Opinion dated Jun. 13, 2024.
Piloto, Obdulio et al. IMC-EB10, an anti-FLT3 monoclonal antibody, prolongs survival and reduces nonobese diabetic/severe combined immunodeficient engraftment of some acute lymphoblastic leukemia cell lines and primary leukemic samples. Cancer Res 66(9):4843-4851 (2006).
Piloto, Obdulio et al. Inhibitory anti-FLT3 antibodies are capable of mediating antibody-dependent cell-mediated cytotoxicity and reducing engraftment of acute myelogenous leukemia blasts in nonobese diabetic/severe combined immunodeficient mice. Cancer Res 65(4):1514-1522 (2005).

(56) References Cited

OTHER PUBLICATIONS

U.S. Appl. No. 17/055,096 Office Action dated Jun. 17, 2024.
U.S. Appl. No. 17/055,103 Office Action dated May 7, 2024.
U.S. Appl. No. 17/475,216 Office Action dated Jun. 25, 2024.

* cited by examiner

SEQUENCE LISTING

<160> NUMBER OF SEQ ID NOS: 367

<210> SEQ ID NO 1
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Ala Tyr Ile Tyr
            20                  25                  30

Thr Met Asp Trp Tyr Arg Gln Ala Pro Gly Lys Gln Arg Glu Leu Val
        35                  40                  45

Ala Thr Ser Thr Arg Asp Gly Asn Val Asp Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Leu Arg Thr Ala Val Asp Leu Ile Arg Ala Asn Tyr Trp Gly
            100                 105                 110

Gln Gly Thr Gln Val Thr Val Ser Ser
        115                 120

<210> SEQ ID NO 2
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Val Gln Leu Gln Glu Ser Gly Gly Gly Leu Val Gln Ala Gly Asp
1               5                   10                  15

Ser Leu Arg Leu Ser Cys Val Val Ser Gly Arg Thr Asp Ser Trp Tyr
            20                  25                  30

Val Met Gly Trp Phe Arg Gln Ala Pro Gly Lys Asp Arg Glu Phe Val
        35                  40                  45

Ala Gly Val Ser Trp Ser Tyr Gly Asn Thr Tyr Tyr Ala Asp Ser Val
    50                  55                  60

Lys Gly Arg Phe Thr Ala Ser Arg Asp Asn Ala Lys Asn Thr Ala Tyr
65                  70                  75                  80

Leu Gln Met Asn Ser Leu Asn Ala Glu Asp Thr Ala Val Tyr Tyr Cys
                85                  90                  95

Ala Ala Arg Val Ser Arg Glu Val Ile Pro Thr Arg Trp Asp Leu Tyr
            100                 105                 110

Asn Tyr Trp Gly Gln Gly Thr Gln Val Thr Val Ser Ser
        115                 120                 125

<210> SEQ ID NO 3
<211> LENGTH: 114
<212> TYPE: PRT
<213> ORGANISM: Artificial Sequence
<220> FEATURE:
<223> OTHER INFORMATION: Description of Artificial Sequence: Synthetic -continued

```
                polypeptide

<400> SEQUENCE: 3

Gln Val Gln Leu Gln Glu Ser Gly Gly Gly Ser Val Gln Pro Gly Gly
1               5                   10                  15

Ser Leu Arg Val Ser Cys Val Val Ser Arg Thr Ile Ile Ser Ile Asn
            20                  25                  30

Ala Met Thr Trp Tyr His Gln Ala Pro Gly Lys Arg Arg Glu Leu Val
        35                  40                  45

Ala Ile Ile Thr Ser Gly Gly Glu Thr Asn Tyr Ala Asp Ser Val Lys
    50                  55                  60

Gly Arg Phe Thr Ile Ser Arg Asp Asn Ala Lys Asn Thr Ala Tyr Leu
65                  70                  75                  80

Gln Met Asn Asn Leu Lys Pro Glu Asp Thr Gly Val Tyr Tyr Cys Asn
                85                  90                  95

Val Val Pro Pro Leu Gly Ser Trp Gly Gln Gly Thr Gln Val Thr Val
            100                 105                 110

Ser Ser

<210> SEQ ID NO 4
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Val Gln Leu Gln Glu Ser Gly Gly Gly Arg Val Gln Ala Gly Gly
1               5                   10                  15

Ser Leu Arg Leu Ser Cys Ser Ala Ser Ala Arg Thr Leu Arg Leu Tyr
            20                  25                  30

Ala Val Gly Trp Phe Arg Gln Ala Pro Gly Lys Glu Arg Glu Phe Val
        35                  40                  45

Ala Gly Ile Gly Arg Ser Glu Arg Thr Tyr Tyr Thr Asp Ser Val Lys
    50                  55                  60

Gly Arg Phe Thr Leu Ser Arg Asp Asn Ala Lys Asn Thr Val Phe Leu
65                  70                  75                  80

Glu Met Asn Asp Leu Glu Pro Glu Asp Thr Ala Val Tyr Phe Cys Ala
                85                  90                  95

Leu Thr Phe Gln Thr Thr Asp Met Val Asp Val Pro Thr Thr Gln His
            100                 105                 110

Glu Tyr Asp Tyr Trp Gly Arg Gly Thr Gln Val Thr Val Ser Ser
        115                 120                 125

<210> SEQ ID NO 5
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Ala Tyr Ile Tyr
            20                  25                  30
```

Thr Met Asp Trp Tyr Arg Gln Ala Pro Gly Lys Gln Arg Glu Leu Val
        35                  40                  45

Ala Thr Ser Thr His Asp Gly Asn Thr Asp Tyr Ala Asp Ser Val Lys
 50                  55                  60

Gly Arg Phe Thr Ile Ser Arg Asp Asn Val Lys Asn Thr Val Tyr Leu
 65                  70                  75                  80

Gln Met Asn Ser Leu Lys Pro Glu Asp Thr Ala Val Tyr Tyr Cys Asn
                 85                  90                  95

Ala Asp Leu Arg Thr Ala Val Asp Leu Ile Arg Ala Asn Tyr Trp Gly
            100                 105                 110

Gln Gly Thr Gln Val Thr Val Ser Ser
            115                 120

<210> SEQ ID NO 6
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Val Gln Leu Gln Glu Ser Gly Gly Gly Leu Val Gln Pro Gly Gly
 1               5                  10                  15

Ser Leu Arg Leu Ser Cys Ala Ala Ser Gly Ser Ile Ala Tyr Ile Tyr
            20                  25                  30

Thr Met Asp Trp Tyr Arg Gln Ala Pro Gly Lys Gln Arg Glu Leu Val
        35                  40                  45

Ala Thr Ser Thr Arg Asp Gly Asn Thr Asp Tyr Ala Asp Ser Val Lys
 50                  55                  60

Gly Arg Phe Thr Ile Ser Arg Asp Asn Ala Lys Asp Thr Val Tyr Leu
 65                  70                  75                  80

Gln Met Asn Ser Leu Lys Pro Glu Asp Thr Ala Val Tyr Tyr Cys Asn
                 85                  90                  95

Ala Asp Leu Arg Thr Ala Val Asp Leu Ile Arg Ala Asn Tyr Trp Gly
            100                 105                 110

Gln Gly Thr Gln Val Thr Val Ser Ser
            115                 120

<210> SEQ ID NO 7
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Gln Val Gln Leu Gln Glu Ser Gly Gly Gly Leu Val Gln Ala Gly Gly
 1               5                  10                  15

Ser Leu Thr Leu Ser Cys Ala Ala Ser Gly Arg Tyr Gln Met Ala Trp
            20                  25                  30

Phe Arg Gln Ala Pro Glu Lys Glu Arg Glu Phe Val Gly Thr Ile Ser
        35                  40                  45

Ser Gly Asp Ser Thr Trp Tyr Thr Asn Ser Val Lys Gly Arg Phe Ala
 50                  55                  60

Ile Ser Arg Asp Ser Ala Arg Asn Thr Val Tyr Leu Gln Met Asn Asp
 65                  70                  75                  80

```
Leu Lys Pro Glu Asp Thr Ala Ile Tyr Tyr Cys Ala Ala Leu Tyr
             85                  90                  95

Tyr Arg Asp Ser Arg Arg Ala Ala Asp Tyr Pro Tyr Trp Gly Gln Gly
            100                 105                 110

Thr Gln Val Thr Val Ser Ser
        115

<210> SEQ ID NO 8
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Val Gln Leu Gln Glu Ser Gly Gly Gly Arg Val Gln Ala Gly Glu
1               5                   10                  15

Ser Leu Arg Leu Ser Cys Ser Thr Ser Thr Arg Thr Leu Lys Leu Tyr
            20                  25                  30

Ala Val Gly Trp Phe Arg Gln Ala Pro Gly Lys Glu Arg Asp Phe Val
        35                  40                  45

Ala Gly Ile Gly Arg Ser Glu Arg Ile Tyr Tyr Ile Asp Ser Val Lys
    50                  55                  60

Gly Arg Phe Thr Leu Ser Arg Asp Asn Ala Lys Asn Thr Val Phe Leu
65                  70                  75                  80

Glu Met Asn Asp Leu Glu Pro Glu Asp Thr Ala Val Tyr Phe Cys Ala
                85                  90                  95

Ala Thr Phe Gln Thr Ser Asp Asn Val Gly Val Pro Thr Val Gln His
            100                 105                 110

Glu Tyr Asp Tyr Trp Gly Gln Gly Thr Gln Val Thr Val Ser Ser
        115                 120                 125

<210> SEQ ID NO 9
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Ala Tyr Ile Tyr
            20                  25                  30

Thr Met Asp Trp Tyr Arg Gln Ala Pro Gly Lys Gln Arg Glu Leu Val
        35                  40                  45

Ala Thr Ser Thr His Asp Gly Asn Thr Asp Tyr Ala Asp Ser Val Lys
    50                  55                  60

Gly Arg Phe Thr Ile Ser Arg Asp Asn Ala Lys Asn Thr Val Thr Leu
65                  70                  75                  80

Gln Met Asn Ser Leu Lys Pro Glu Asp Thr Ala Val Tyr Tyr Cys Asn
                85                  90                  95

Ala Asp Leu Arg Thr Ala Val Asp Leu Ile Arg Ala Asn Tyr Trp Gly
            100                 105                 110

Gln Gly Thr Gln Val Thr Val Ser Ser
        115                 120
```

<210> SEQ ID NO 10
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Ala Tyr Ile Tyr
            20                  25                  30

Thr Met Asp Trp Tyr Arg Gln Ala Pro Gly Lys Gln Arg Glu Leu Val
        35                  40                  45

Ala Thr Phe Thr Arg Asp Gly Asn Thr Asp Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Thr Asp Leu Arg Thr Ala Val Asp Leu Ile Arg Ala Asn Tyr Trp Gly
            100                 105                 110

Gln Gly Thr Gln Val Thr Val Ser Ser
        115                 120

<210> SEQ ID NO 11
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Ala Tyr Ile Tyr
            20                  25                  30

Thr Met Asp Trp Tyr Arg Gln Ala Pro Gly Lys Gln Arg Glu Leu Val
        35                  40                  45

Ala Thr Ser Thr His Asp Gly Asn Thr Asp Tyr Ala Asp Ser Leu Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Leu Arg Thr Ala Val Asp Leu Ile Arg Ala Asn Tyr Trp Gly
            100                 105                 110

Gln Gly Thr Gln Val Thr Val Ser Ser
        115                 120

<210> SEQ ID NO 12
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 12

Gln Val Gln Leu Gln Glu Ser Gly Gly Gly Ser Val Gln Ala Gly Gly
1               5                   10                  15

Ser Leu Arg Leu Ser Cys Ala Ala Ser Gly Arg Tyr Gln Met Ala Trp
            20                  25                  30

Phe Arg Gln Ala Pro Glu Lys Glu Arg Glu Phe Val Gly Thr Ile Ser
        35                  40                  45

Ser Gly Asp Ser Thr Trp Tyr Thr Asn Ser Leu Lys Gly Arg Phe Ala
    50                  55                  60

Ile Ser Arg Asp Ser Ala Arg Asp Thr Val Tyr Leu Gln Met Asn Asp
65                  70                  75                  80

Leu Lys Pro Glu Asp Thr Ala Val Tyr Tyr Cys Ala Ala Leu Tyr
                85                  90                  95

Tyr Arg Asp Ser Arg Arg Ala Ala Asp Tyr Pro Tyr Trp Gly Gln Gly
                100                 105                 110

Thr Gln Val Thr Val Ser Ser
        115

<210> SEQ ID NO 13
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Gln Glu Ser Gly Gly Gly Leu Val Gln Thr Gly Gly
1               5                   10                  15

Ser Leu Arg Leu Ser Cys Ala Val Ser Gly Ser Ile Val Thr Ile Asn
            20                  25                  30

Ala Met Thr Trp Tyr Arg Gln Ala Pro Gly Lys Arg Arg Glu Leu Val
        35                  40                  45

Ala Ile Ile Thr Ser Gly Gly Glu Thr Asn Tyr Ala Asp Ser Val Lys
    50                  55                  60

Gly Arg Phe Thr Ile Ser Arg Asp Asn Ala Lys Asn Thr Ala His Leu
65                  70                  75                  80

Gln Met Asn Ser Leu Asn Pro Glu Asp Thr Gly Val Tyr Tyr Cys Asn
                85                  90                  95

Val Val Pro Pro Leu Gly Ser Trp Gly Gln Gly Thr Gln Val Thr Val
                100                 105                 110

Ser Ser

<210> SEQ ID NO 14
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Gln Glu Ser Gly Gly Gly Leu Val Gln Thr Gly Gly
1               5                   10                  15

Ser Leu Arg Leu Ser Cys Ala Val Ser Arg Ser Ile Val Ser Ile Lys
            20                  25                  30

Ser Met Thr Trp Tyr Arg Gln Ala Pro Gly Lys Arg Arg Glu Leu Val
        35                  40                  45
```

```
Ala Leu Ile Thr Ser Gly Gly Glu Thr Asn Tyr Ser Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Gly Val Tyr Tyr Cys Asn
                 85                  90                  95

Val Val Pro Pro Leu Gly Ser Trp Gly Gln Gly Thr Gln Val Thr Val
            100                 105                 110

Ser Ser

<210> SEQ ID NO 15
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Gln Glu Ser Gly Gly Gly Leu Val Glu Thr Gly Gly
1               5                   10                  15

Ser Leu Arg Leu Ser Cys Ala Gly Ser Gly Ser Thr Phe Arg His His
                20                  25                  30

Ala Met Ala Trp Phe Arg Gln Thr Pro Gly Lys Glu Arg Glu Phe Val
             35                  40                  45

Ser Ala Ile Asn Asp His Gly Asp Arg Thr Lys Tyr Leu Asp Ser Val
 50                  55                  60

Arg Gly Arg Phe Thr Ile Ser Arg Asp Asn Thr Asp Asn Met Val Tyr
 65                  70                  75                  80

Leu Gln Met Thr Asp Leu Arg Pro Glu Asp Thr Ala Asn Tyr Ser Cys
                 85                  90                  95

Ala Ala Gly Pro Leu Val Asp Tyr Leu Glu Thr Thr Pro Leu Val Tyr
            100                 105                 110

Thr Tyr Trp Gly His Gly Thr Gln Val Thr Val Ser Ser
            115                 120                 125

<210> SEQ ID NO 16
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Ala Tyr Ile Tyr
                20                  25                  30

Thr Met Asp Trp Tyr Arg Gln Ala Pro Gly Lys Gln Arg Glu Leu Val
             35                  40                  45

Ala Thr Ser Thr His Asp Gly Asn Thr Asp Tyr Ala Asp Ser Val Lys
 50                  55                  60

Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Asn
                 85                  90                  95
```

```
Ala Asp Leu Arg Thr Ala Val Asp Leu Ile Arg Ala Asn Tyr Trp Gly
            100                 105                 110

Gln Gly Thr Gln Val Thr Val Ser Ser
        115                 120

<210> SEQ ID NO 17
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Gln Glu Ser Gly Gly Gly Ser Val Gln Ala Gly Gly
1               5                   10                  15

Ser Leu Thr Leu Ser Cys Ala Ala Ser Gly Ser Ile Ala Tyr Ile Tyr
            20                  25                  30

Thr Met Asp Trp Tyr Arg Gln Ala Pro Gly Lys Gln Arg Glu Leu Val
        35                  40                  45

Ala Thr Ser Thr His Asp Gly Asn Thr Asp Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Leu Arg Thr Ala Val Asp Leu Ile Arg Ala Asn Tyr Trp Gly
            100                 105                 110

Gln Gly Thr Gln Val Thr Val Ser Ser
        115                 120

<210> SEQ ID NO 18
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Gln Glu Ser Gly Gly Gly Leu Val Gln Pro Gly Gly
1               5                   10                  15

Ser Leu Arg Leu Ser Cys Thr Ala Ser Val Ser Ile Phe Ser Val Asn
            20                  25                  30

Ala Val Asp Trp Tyr Arg Gln Ser Pro Gly Lys Glu Arg Glu Leu Val
        35                  40                  45

Ala Ile Met Thr Ser Asp Gly Ser Thr Asn Tyr Gly Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Asn Leu Lys Pro Glu Asp Thr Ala Val Tyr Tyr Cys Asn
                85                  90                  95

Thr Val Pro Pro Arg Tyr Trp Gly Gln Gly Thr Gln Val Thr Val Ser
            100                 105                 110

Ser

<210> SEQ ID NO 19
<211> LENGTH: 121
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Ala Tyr Ile Tyr
            20                  25                  30

Thr Met Asp Trp Tyr Arg Gln Ala Pro Gly Lys Gln Arg Glu Leu Val
        35                  40                  45

Ala Thr Ser Thr Arg Asp Gly Asn Ile Asp Tyr Ala Asp Ser Val Lys
    50                  55                  60

Gly Arg Phe Thr Ile Ser Arg Asp Ser Ala Lys Asn Thr Val Tyr Leu
65                  70                  75                  80

Gln Met Ser Ser Leu Lys Pro Glu Asp Thr Ala Val Tyr Tyr Cys Asn
            85                  90                  95

Ala Asp Leu Arg Thr Ala Val Asp Leu Ile Arg Ala Asn Tyr Trp Gly
            100                 105                 110

Gln Gly Thr Gln Val Thr Val Ser Ser
        115                 120

<210> SEQ ID NO 20
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Gln Glu Ser Gly Gly Gly Leu Val Gln Ala Gly Gly
1               5                   10                  15

Ser Leu Thr Leu Ser Cys Ala Ala Ser Gly Arg Tyr Gln Leu Ala Trp
            20                  25                  30

Phe Arg Gln Ala Pro Glu Lys Val Arg Glu Phe Val Gly Thr Ile Ser
        35                  40                  45

Ser Gly Asp Ser Thr Trp Tyr Thr Asn Ser Val Lys Gly Arg Phe Ala
    50                  55                  60

Ile Ser Arg Asp Ser Ala Arg Asn Thr Val Tyr Leu Gln Met Asn Asp
65                  70                  75                  80

Leu Lys Pro Glu Asp Thr Ala Val Tyr Tyr Cys Ala Ala Leu Tyr
            85                  90                  95

Tyr Arg Asp Ser Arg Arg Ala Ala Asp Tyr Pro Tyr Trp Gly Gln Gly
            100                 105                 110

Thr Gln Val Thr Val Ser Ser
        115

<210> SEQ ID NO 21
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Gln Glu Ser Gly Gly Gly Ser Val Gln Ala Gly Gly
1               5                   10                  15
```

```
Ser Leu Arg Leu Ser Cys Ala Ala Ser Gly Arg Tyr His Met Ala Trp
            20                  25                  30

Phe Arg Gln Ala Pro Glu Lys Glu Arg Glu Phe Val Gly Thr Ile Ser
        35                  40                  45

Ser Gly Asp Ser Thr Trp Tyr Thr Asn Ser Val Lys Gly Arg Phe Ala
50                  55                  60

Ile Ser Arg Asp Ser Ala Arg Asn Thr Ala Tyr Leu Gln Met Asn Asp
65                  70                  75                  80

Leu Lys Pro Glu Asp Thr Ala Val Tyr Tyr Cys Ala Ala Ala Leu Tyr
                85                  90                  95

Tyr Gly Asp Ser Arg Arg Ala Ala Asp Tyr Pro Tyr Trp Gly Gln Gly
                100                 105                 110

Thr Gln Val Thr Val Ser Ser
        115

<210> SEQ ID NO 22
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Gln Glu Ser Gly Gly Gly Ser Val Gln Ala Gly Gly
1               5                   10                  15

Ser Leu Arg Leu Ser Cys Ala Ala Ser Gly Ser Ile Ala Tyr Ile Tyr
            20                  25                  30

Thr Met Asp Trp Tyr Arg Gln Ala Pro Gly Lys Gln Arg Glu Leu Val
        35                  40                  45

Ala Thr Ser Thr His Asp Gly Asn Thr Asp Tyr Thr Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Leu Arg Thr Ala Val Asp Leu Ile Arg Ala Asn Tyr Trp Gly
                100                 105                 110

Gln Gly Thr Gln Val Thr Val Ser Ser
        115                 120

<210> SEQ ID NO 23
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Ala Tyr Ile Tyr
            20                  25                  30

Thr Met Asp Trp Tyr Arg Gln Thr Pro Gly Lys Gln Arg Glu Leu Val
        35                  40                  45

Ala Thr Ser Thr Arg Asp Ala Asn Thr Asp Tyr Ala Gly Ser Val Lys
    50                  55                  60
```

Gly Arg Phe Thr Ile Ser Arg Asp Asn Ala Lys Asp Thr Val Tyr Leu
65                  70                  75                  80

Gln Met Asn Ser Leu Lys Pro Glu Asp Thr Ala Val Tyr Tyr Cys His
                85                  90                  95

Ala Asp Leu Arg Thr Ala Val Asp Leu Ile Arg Ala Asn Tyr Trp Gly
            100                 105                 110

Gln Gly Thr Gln Val Thr Val Ser Ser
        115                 120

<210> SEQ ID NO 24
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Tyr Asn Met Ala Trp
            20                  25                  30

Phe Arg Gln Ala Pro Glu Lys Glu Arg Glu Phe Val Gly Thr Ile Thr
        35                  40                  45

Ser Ala Asp Ser Thr Trp Tyr Thr Asn Ser Val Lys Gly Arg Phe Ala
    50                  55                  60

Ile Thr Gln Asp Ser Ala Arg Asn Thr Val Tyr Leu Gln Met Asn Asp
65                  70                  75                  80

Leu Lys Pro Glu Asp Thr Ala Val Tyr Tyr Cys Ala Ala Leu Tyr
                85                  90                  95

Tyr Gly Asp Ser Arg Arg Ala Ala Asp Tyr Pro Tyr Trp Gly Gln Gly
            100                 105                 110

Thr Gln Val Thr Val Ser Ser
        115

<210> SEQ ID NO 25
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Gln Glu Ser Gly Gly Gly Leu Val Gln Pro Gly Gly
1               5                   10                  15

Ser Leu Arg Leu Ser Cys Ala Ala Ser Gly Arg Tyr Gln Met Ala Trp
            20                  25                  30

Phe Arg Gln Ala Pro Glu Lys Glu Arg Glu Phe Val Gly Thr Ile Ser
        35                  40                  45

Ser Gly Asp Ser Thr Trp Tyr Thr Asn Ser Val Lys Gly Arg Phe Ala
    50                  55                  60

Ile Ser Arg Asp Ser Ala Arg Thr Thr Val Tyr Leu Gln Met Asn Asp
65                  70                  75                  80

Leu Lys Pro Glu Asp Thr Ala Val Tyr Tyr Cys Ala Ala Leu Tyr
                85                  90                  95

Tyr Arg Asp Ser Trp Arg Ala Ala Asp Tyr Pro Tyr Trp Gly Gln Gly
            100                 105                 110

Thr Gln Val Thr Val Ser Ser
        115

<210> SEQ ID NO 26
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Val Gln Leu Gln Glu Ser Gly Gly Gly Leu Val Gln Pro Gly Glu
1               5                   10                  15

Ser Leu Arg Leu Ser Cys Ala Ala Thr Gly Arg Tyr His Leu Ala Trp
            20                  25                  30

Phe Arg Gln Ala Pro Glu Lys Glu Arg Glu Phe Val Gly Thr Ile Thr
        35                  40                  45

Ser Ala Asp Ser Thr Trp Tyr Thr Asn Ser Val Lys Gly Arg Phe Ala
    50                  55                  60

Ile Thr Arg Asp Ser Ala Arg Asn Thr Val Tyr Leu Gln Met Asn Asp
65                  70                  75                  80

Leu Lys Pro Glu Asp Thr Ala Val Tyr Tyr Cys Ala Ala Leu Tyr
                85                  90                  95

Tyr Gly Asp Ser Arg Arg Ala Ala Asp Tyr Pro Tyr Trp Gly Gln Gly
            100                 105                 110

Thr Gln Val Thr Val Ser Ser
        115

<210> SEQ ID NO 27
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Gln Glu Ser Gly Gly Gly Leu Val Gln Ala Gly Gly
1               5                   10                  15

Ser Leu Lys Leu Ser Cys Ala Asp Ser Gly Arg Ser Phe Ser Asn Tyr
            20                  25                  30

Ile Met Gly Trp Phe Arg Gln Ala Pro Gly Lys Glu Arg Glu Phe Val
        35                  40                  45

Ala Gly Leu Gly Trp Ser Pro Gly Asn Thr Tyr Tyr Ala Asp Ser Val
    50                  55                  60

Lys Gly Arg Phe Thr Ile Ser Arg Asp Asn Ala Lys Asn Met Val Tyr
65                  70                  75                  80

Leu Gln Met Asn Ser Leu Asn Pro Glu Asp Thr Ala Val Tyr Tyr Cys
                85                  90                  95

Ala Ala Arg Arg Gly Asp Val Ile Tyr Thr Thr Pro Trp Asn Tyr Val
            100                 105                 110

Tyr Trp Gly Gln Gly Thr Gln Val Thr Val Ser Ser
        115                 120

<210> SEQ ID NO 28
<211> LENGTH: 121
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 28

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Ala Tyr Ile Tyr
            20                  25                  30

Thr Met Asp Trp Tyr Arg Gln Ala Pro Gly Lys Gln Arg Glu Leu Val
        35                  40                  45

Ala Thr Ser Thr His Asp Gly Asn Thr Asp Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Leu Arg Thr Pro Val Asp Leu Ile Arg Ala Asn Tyr Trp Gly
            100                 105                 110

Gln Gly Thr Gln Val Thr Val Ser Ser
        115                 120

<210> SEQ ID NO 29
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Gln Glu Ser Gly Gly Gly Ser Val Gln Ala Gly Gly
1               5                   10                  15

Ser Leu Arg Leu Ser Cys Ala Ala Pro Gly Arg Tyr Gln Met Ala Trp
            20                  25                  30

Phe Arg Gln Ala Pro Glu Lys Glu Arg Glu Phe Val Gly Thr Ile Ser
        35                  40                  45

Ser Gly Asp Ser Thr Trp Tyr Thr Asn Ser Val Lys Gly Arg Phe Ala
    50                  55                  60

Ile Ser Arg Asp Ser Ala Arg Asn Thr Val Tyr Leu Gln Met Asn Asp
65                  70                  75                  80

Leu Lys Ser Glu Asp Thr Ala Val Tyr Tyr Cys Ala Ala Leu Tyr
                85                  90                  95

Tyr Arg Asp Ser Arg Arg Ala Ile Asp Tyr Pro Tyr Trp Gly Gln Gly
            100                 105                 110

Thr Gln Val Thr Val Ser Ser
        115

<210> SEQ ID NO 30
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gln Val Gln Leu Gln Glu Ser Gly Gly Gly Ser Val Gln Ala Gly Gly
1               5                   10                  15
```

Ser Leu Arg Leu Ser Cys Ala Ala Ser Gly Leu Thr Phe Ser Ser Tyr
            20                  25                  30

Ala Met Ala Trp Phe Arg Gln Ala Pro Gly Lys Gln Arg Glu Leu Val
        35                  40                  45

Ala Arg Ile Thr Ser Gly Gly Thr Thr Asp Tyr Ala Asp Ser Val Lys
50                  55                  60

Gly Arg Phe Thr Ile Ser Arg Asp Asn Ala Lys Asn Thr Met Tyr Leu
65                  70                  75                  80

Gln Met Asn Ser Leu Lys Pro Glu Asp Thr Ala Val Tyr Tyr Cys Ala
                85                  90                  95

Ala Asp Leu Thr Tyr Arg Asn Leu Leu Leu Lys Leu Pro His Tyr Trp
            100                 105                 110

Gly Gln Gly Thr Gln Val Thr Val Ser Ser
            115                 120

<210> SEQ ID NO 31
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Val Gln Leu Gln Glu Ser Gly Gly Gly Leu Val Gln Ala Gly Gly
1               5                   10                  15

Ser Leu Arg Leu Ser Cys Ala Ala Ser Gly Asn Ile Ala Tyr Ile Tyr
            20                  25                  30

Thr Met Asp Trp Tyr Arg Gln Ala Pro Gly Lys Gln Arg Glu Leu Val
        35                  40                  45

Ala Thr Ser Thr His Asp Gly Ser Thr Asp Tyr Ala Asp Ser Val Lys
50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Leu Arg Thr Pro Val Asp Leu Ile Arg Ala Asn Tyr Trp Gly
            100                 105                 110

Gln Gly Thr Gln Val Thr Val Ser Ser
        115                 120

<210> SEQ ID NO 32
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Ala Tyr Ile Tyr
            20                  25                  30

Thr Met Asp Trp Tyr Arg Gln Ala Pro Gly Lys Gln Arg Glu Leu Val
        35                  40                  45

Ala Thr Ser Thr Trp Asp Gly Asn Thr Asp Tyr Ala Asp Ser Val Lys
50                  55                  60

```
Gly Arg Phe Thr Ile Ser Arg Asp Asn Ala Lys Asn Thr Val Tyr Leu
 65                  70                  75                  80

Gln Met Asn Ser Leu Lys Pro Glu Asp Thr Ala Val Tyr Tyr Cys Asn
                 85                  90                  95

Ala Asp Leu Arg Thr Ala Val Asp Leu Ile Arg Ala Asn Tyr Trp Gly
            100                 105                 110

Gln Gly Thr Gln Val Thr Val Ser Ser
            115                 120

<210> SEQ ID NO 33
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Val Gln Leu Gln Glu Ser Gly Gly Gly Leu Val Gln Ala Gly Gly
  1               5                  10                  15

Ser Leu Arg Leu Ser Cys Ala Ala Ser Gly Ser Ile Ala Tyr Ile Tyr
             20                  25                  30

Thr Met Asp Trp Tyr Arg Gln Ala Pro Gly Lys Gln Arg Glu Leu Val
         35                  40                  45

Ala Thr Ser Thr His Asp Gly Asn Thr Asp Tyr Ala Asp Ser Val Lys
     50                  55                  60

Gly Arg Phe Thr Ile Ser Arg Asp Asn Ala Lys Asn Thr Val Tyr Leu
 65                  70                  75                  80

Gln Met Ser Ser Leu Lys Pro Asp Asp Thr Ala Val Tyr Tyr Cys Asn
                 85                  90                  95

Ala Asp Leu Arg Thr Ala Val Asp Leu Ile Arg Ala Asn Tyr Trp Gly
            100                 105                 110

Gln Gly Thr Gln Val Thr Val Ser Ser
            115                 120

<210> SEQ ID NO 34
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Val Gln Leu Gln Glu Ser Gly Gly Gly Leu Val Gln Ala Gly Glu
  1               5                  10                  15

Ser Leu Ser Leu Ser Cys Ala Ala Ser Gly Asn Asp Phe Val Ile Thr
             20                  25                  30

Asp Met His Trp Tyr Arg Gln Ala Pro Gly Lys Gln Arg Glu Trp Val
         35                  40                  45

Ala Thr Ile Thr Arg Phe Ala Thr Thr Asn Tyr Ala Asp Ser Val Lys
     50                  55                  60

Gly Arg Phe Thr Ile Ser Arg Asp Asn Ala Lys Asn Thr Trp Tyr Leu
 65                  70                  75                  80

Gln Met Asn Ser Leu Lys Pro Asp Asp Thr Ala Val Tyr Tyr Cys Lys
                 85                  90                  95

Ala Ile Gly Leu Arg Gly Val Pro Asp Val Asn Arg Gln Phe Glu Val
            100                 105                 110
```

-continued

Trp Gly Gln Gly Thr Gln Val Thr Val Ser Ser
            115                 120

<210> SEQ ID NO 35
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Val Gln Leu Gln Glu Ser Gly Gly Leu Val Gln Ala Gly Gly
1               5                   10                  15

Ser Leu Arg Leu Ser Cys Ala Ala Ser Gly Ala Ile Ala Tyr Ile Tyr
                20                  25                  30

Gly Met Gly Trp Tyr Arg Gln Ala Pro Gly Asn Gln Arg Glu Leu Val
            35                  40                  45

Ala Ala Ile Ser Ser Gly Gly Ser Thr Asp Tyr Ala Asp Ser Val Lys
        50                  55                  60

Gly Arg Phe Thr Ile Ser Arg Asp Asn Ala Lys Asn Thr Val Tyr Leu
65                  70                  75                  80

Gln Met Ser Ser Leu Lys Pro Glu Asp Thr Ala Val Tyr Tyr Cys Asn
                85                  90                  95

Ala Asp Val Arg Thr Ser Arg Asn Leu Val Arg Ser Tyr Trp Gly
            100                 105                 110

Gln Gly Thr Gln Val Thr Val Ser Ser
            115                 120

<210> SEQ ID NO 36
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Tyr His Thr Ala Trp
                20                  25                  30

Phe Arg Gln Ala Pro Glu Lys Glu Arg Glu Phe Val Gly Thr Ile Ser
            35                  40                  45

Ser Gly Asp Ser Thr Trp Tyr Thr Asn Ser Val Lys Gly Arg Phe Ala
        50                  55                  60

Ile Ser Arg Asp Ser Ala Arg Asn Thr Val Tyr Leu Gln Met Asn Asp
65                  70                  75                  80

Leu Lys Pro Glu Asp Thr Ala Val Tyr Tyr Cys Ala Ala Ala Leu Tyr
                85                  90                  95

Tyr Gly Asp Ser Arg Arg Ala Gly Asp Tyr Pro Tyr Trp Gly Gln Gly
            100                 105                 110

Thr Gln Val Thr Val Ser Ser
        115

<210> SEQ ID NO 37
<211> LENGTH: 121
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 37

Gln Val Gln Leu Gln Glu Ser Gly Gly Gly Leu Val Gln Ala Gly Gly
1               5                   10                  15

Ser Leu Arg Leu Ser Cys Ala Ala Ser Gly Asn Ile Ala Tyr Ile Tyr
            20                  25                  30

Thr Met Asn Trp Tyr Arg Gln Ala Pro Gly Lys Gln Arg Glu Leu Val
        35                  40                  45

Ala Thr Ser Thr His Ala Gly Asn Thr Asp Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Val Asp Leu Arg Thr Ala Val Asp Leu Ile Arg Ala Asn Tyr Trp Gly
            100                 105                 110

Gln Gly Thr Gln Val Thr Val Ser Ser
        115                 120

<210> SEQ ID NO 38
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Gln Val Gln Leu Gln Glu Ser Gly Gly Gly Leu Val Gln Pro Gly Gly
1               5                   10                  15

Ser Leu Arg Leu Ser Cys Ala Ala Ser Gly Asn Ile Ala Tyr Ile Tyr
            20                  25                  30

Thr Met Gly Trp Tyr Arg Gln Ala Pro Gly Lys Gln Arg Glu Leu Val
        35                  40                  45

Ala Thr Ser Thr His Asp Gly Asn Ser Asp Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Thr Leu Lys Pro Asp Asp Thr Ala Val Tyr Tyr Cys Asn
                85                  90                  95

Ala Asp Leu Arg Thr Pro Val Asp Arg Ile Arg Gly Asn Phe Trp Gly
            100                 105                 110

Gln Gly Thr Gln Val Thr Val Ser Ser
        115                 120

<210> SEQ ID NO 39
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Val Gln Leu Leu Glu Ser Gly Gly Gly Leu Val Gln Pro Gly Gly
1               5                   10                  15

Ser Leu Thr Leu Ser Cys Ala Ala Ser Gly Ser Ile Ala Tyr Ile Tyr

```
                    20                  25                  30
Thr Met Asp Trp Tyr Arg Gln Ala Pro Gly Lys Gln Arg Glu Leu Val
            35                  40                  45

Ala Thr Ser Thr Arg Asp Gly Asn Val Asp Tyr Ala Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Asn
                85                  90                  95

Ala Asp Leu Arg Thr Ala Val Asp Leu Ile Arg Ala Asn Tyr Trp Gly
            100                 105                 110

Leu Gly Thr Gln Val Thr Val Ser Ser
        115                 120

<210> SEQ ID NO 40
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Val Gln Leu Leu Glu Ser Gly Gly Gly Leu Val Gln Pro Gly Gly
1               5                   10                  15

Ser Leu Thr Leu Ser Cys Ala Ala Ser Gly Arg Thr Asp Ser Trp Tyr
            20                  25                  30

Val Met Gly Trp Phe Arg Gln Ala Pro Gly Lys Asp Arg Glu Phe Val
        35                  40                  45

Ala Gly Val Ser Trp Ser Tyr Gly Asn Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Arg Val Ser Arg Glu Val Ile Pro Thr Arg Trp Asp Leu Tyr
            100                 105                 110

Asn Tyr Trp Gly Leu Gly Thr Gln Val Thr Val Ser Ser
        115                 120                 125

<210> SEQ ID NO 41
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Val Gln Leu Leu Glu Ser Gly Gly Gly Leu Val Gln Pro Gly Gly
1               5                   10                  15

Ser Leu Thr Leu Ser Cys Ala Ala Ser Ala Arg Thr Leu Arg Leu Tyr
            20                  25                  30

Ala Val Gly Trp Phe Arg Gln Ala Pro Gly Lys Glu Arg Glu Phe Val
        35                  40                  45

Ala Gly Ile Gly Arg Ser Glu Arg Thr Tyr Tyr Thr Asp Ser Val Lys
    50                  55                  60

Gly Arg Phe Thr Ile Ser Arg Asp Asn Ser Lys Asn Thr Leu Tyr Leu
```

```
                65                  70                  75                  80
Gln Met Asn Ser Leu Arg Ala Glu Asp Thr Ala Val Tyr Tyr Cys Ala
                    85                  90                  95

Leu Thr Phe Gln Thr Thr Asp Met Val Asp Val Pro Thr Thr Gln His
                100                 105                 110

Glu Tyr Asp Tyr Trp Gly Leu Gly Thr Gln Val Thr Val Ser Ser
            115                 120                 125

<210> SEQ ID NO 42
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Glu Val Gln Leu Leu Glu Ser Gly Gly Gly Leu Val Gln Pro Gly Gly
1               5                   10                  15

Ser Leu Thr Leu Ser Cys Ala Ala Ser Gly Ser Ile Val Thr Ile Asn
            20                  25                  30

Ala Met Thr Trp Tyr Arg Gln Ala Pro Gly Lys Arg Arg Glu Leu Val
        35                  40                  45

Ala Ile Ile Thr Ser Gly Gly Glu Thr Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Asn
                85                  90                  95

Val Val Pro Pro Leu Gly Ser Trp Gly Leu Gly Thr Gln Val Thr Val
            100                 105                 110

Ser Ser

<210> SEQ ID NO 43
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Val Gln Leu Leu Glu Ser Gly Gly Gly Leu Val Gln Pro Gly Gly
1               5                   10                  15

Ser Leu Thr Leu Ser Cys Ala Ala Ser Gly Arg Tyr His Met Ala Trp
            20                  25                  30

Phe Arg Gln Ala Pro Gly Lys Glu Arg Glu Phe Val Gly Thr Ile Ser
        35                  40                  45

Ser Gly Asp Ser Thr Trp Tyr Thr Asn Ser Val Lys Gly Arg Phe Thr
    50                  55                  60

Ile Ser Arg Asp Asn Ser Lys Asn Thr Leu Tyr Leu Gln Met Asn Ser
65                  70                  75                  80

Leu Arg Ala Glu Asp Thr Ala Val Tyr Tyr Cys Ala Ala Ala Leu Tyr
                85                  90                  95

Tyr Gly Asp Ser Arg Arg Ala Ala Asp Tyr Pro Tyr Trp Gly Leu Gly
            100                 105                 110

Thr Gln Val Thr Val Ser Ser
            115
```

<210> SEQ ID NO 44
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Val Gln Leu Leu Glu Ser Gly Gly Gly Leu Val Gln Pro Gly Gly
1               5                   10                  15

Ser Leu Thr Leu Ser Cys Ala Ala Ser Gly Ser Thr Phe Arg His His
            20                  25                  30

Ala Met Ala Trp Phe Arg Gln Thr Pro Gly Lys Glu Arg Glu Phe Val
        35                  40                  45

Ser Ala Ile Asn Asp His Gly Asp Arg Thr Lys Tyr Leu Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Gly Pro Leu Val Asp Tyr Leu Glu Thr Thr Pro Leu Val Tyr
            100                 105                 110

Thr Tyr Trp Gly Leu Gly Thr Gln Val Thr Val Ser Ser
        115                 120                 125

<210> SEQ ID NO 45
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Glu Val Gln Leu Leu Glu Ser Gly Gly Gly Leu Val Gln Pro Gly Gly
1               5                   10                  15

Ser Leu Thr Leu Ser Cys Ala Ala Ser Gly Arg Ser Phe Ser Asn Tyr
            20                  25                  30

Ile Met Gly Trp Phe Arg Gln Ala Pro Gly Lys Glu Arg Glu Phe Val
        35                  40                  45

Ala Gly Leu Gly Trp Ser Pro Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Arg Arg Gly Asp Val Ile Tyr Thr Thr Pro Trp Asn Tyr Val
            100                 105                 110

Tyr Trp Gly Leu Gly Thr Gln Val Thr Val Ser Ser
        115                 120

<210> SEQ ID NO 46
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Glu Val Gln Leu Leu Glu Ser Gly Gly Gly Leu Val Gln Pro Gly Gly
1               5                   10                  15

Ser Leu Thr Leu Ser Cys Ala Ala Ser Gly Leu Thr Phe Ser Ser Tyr
            20                  25                  30

Ala Met Ala Trp Phe Arg Gln Ala Pro Gly Lys Gln Arg Glu Leu Val
        35                  40                  45

Ala Arg Ile Thr Ser Gly Gly Thr Thr Asp Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Asp Leu Thr Tyr Arg Asn Leu Leu Lys Leu Pro His Tyr Trp
            100                 105                 110

Gly Leu Gly Thr Gln Val Thr Val Ser Ser
        115                 120

<210> SEQ ID NO 47
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Glu Val Gln Leu Leu Glu Ser Gly Gly Gly Leu Val Gln Pro Gly Gly
1               5                   10                  15

Ser Leu Thr Leu Ser Cys Ala Ala Ser Val Ser Ile Phe Ser Val Asn
            20                  25                  30

Ala Val Asp Trp Tyr Arg Gln Ser Pro Gly Lys Glu Arg Glu Leu Val
        35                  40                  45

Ala Ile Met Thr Ser Asp Gly Ser Thr Asn Tyr Asp Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Asn
                85                  90                  95

Thr Val Pro Pro Arg Tyr Trp Gly Leu Gly Thr Gln Val Thr Val Ser
            100                 105                 110

Ser

<210> SEQ ID NO 48
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Glu Val Gln Leu Leu Glu Ser Gly Gly Gly Leu Val Gln Pro Gly Gly
1               5                   10                  15

Ser Leu Thr Leu Ser Cys Ala Ala Ser Gly Asn Asp Phe Val Ile Thr
            20                  25                  30

Asp Met His Trp Tyr Arg Gln Ala Pro Gly Lys Gln Arg Glu Trp Val 35                  40                  45
Ala Thr Ile Thr Arg Phe Ala Thr Thr Asn Tyr Ala Asp Ser Val Lys
            50                  55                  60
Gly Arg Phe Thr Ile Ser Arg Asp Asn Ser Lys Asn Thr Leu Tyr Leu
65                  70                  75                  80
Gln Met Asn Ser Leu Arg Ala Glu Asp Thr Ala Val Tyr Tyr Cys Lys
                85                  90                  95
Ala Ile Gly Leu Arg Gly Val Pro Asp Val Asn Arg Gln Phe Glu Val
            100                 105                 110
Trp Gly Leu Gly Thr Gln Val Thr Val Ser Ser
        115                 120

<210> SEQ ID NO 49
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Val Gln Leu Leu Glu Ser Gly Gly Gly Leu Val Gln Pro Gly Gly
1               5                   10                  15
Ser Leu Thr Leu Ser Cys Ala Ala Ser Gly Ala Ile Ala Tyr Ile Tyr
            20                  25                  30
Gly Met Gly Trp Tyr Arg Gln Ala Pro Gly Lys Gln Arg Glu Leu Val
        35                  40                  45
Ala Ala Ile Ser Ser Gly Gly Ser Thr Asp Tyr Ala Asp Ser Val Lys
            50                  55                  60
Gly Arg Phe Thr Ile Ser Arg Asp Asn Ser Lys Asn Thr Leu Tyr Leu
65                  70                  75                  80
Gln Met Asn Ser Leu Arg Ala Glu Asp Thr Ala Val Tyr Tyr Cys Asn
                85                  90                  95
Ala Asp Val Arg Thr Ser Arg Asn Leu Val Arg Ser Asp Tyr Trp Gly
            100                 105                 110
Leu Gly Thr Gln Val Thr Val Ser Ser
        115                 120

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gly Ser Ile Ala Tyr Ile Tyr Thr Met Asp
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Arg Thr Asp Ser Trp Tyr Val Met Gly
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Thr Ile Ile Ser Ile Asn Ala Met Thr
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ala Arg Thr Leu Arg Leu Tyr Ala Val Gly
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Ser Ile Ala Tyr Ile Tyr Thr Met Asp
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Ser Ile Ala Tyr Ile Tyr Thr Met Asp
1               5                   10

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Gly Arg Tyr Gln Met Ala
1               5

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 57

Thr Arg Thr Leu Lys Leu Tyr Ala Val Gly
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Ser Ile Ala Tyr Ile Tyr Thr Met Asp
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gly Ser Ile Ala Tyr Ile Tyr Thr Met Asp
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Ser Ile Ala Tyr Ile Tyr Thr Met Asp
1               5                   10

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Arg Tyr Gln Met Ala
1               5

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gly Ser Ile Val Thr Ile Asn Ala Met Thr
1               5                   10

<210> SEQ ID NO 63
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Arg Ser Ile Val Ser Ile Lys Ser Met Thr
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Ser Thr Phe Arg His His Ala Met Ala
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gly Ser Ile Ala Tyr Ile Tyr Thr Met Asp
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Ser Ile Ala Tyr Ile Tyr Thr Met Asp
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Val Ser Ile Phe Ser Val Asn Ala Val Asp
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Ser Ile Ala Tyr Ile Tyr Thr Met Asp
```

```
<210> SEQ ID NO 69
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Arg Tyr Gln Leu Ala
1               5

<210> SEQ ID NO 70
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Arg Tyr His Met Ala
1               5

<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gly Ser Ile Ala Tyr Ile Tyr Thr Met Asp
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly Ser Ile Ala Tyr Ile Tyr Thr Met Asp
1               5                   10

<210> SEQ ID NO 73
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gly Arg Tyr Asn Met Ala
1               5

<210> SEQ ID NO 74
<211> LENGTH: 6
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 74

Gly Arg Tyr Gln Met Ala
1               5

<210> SEQ ID NO 75
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Arg Tyr His Leu Ala
1               5

<210> SEQ ID NO 76
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Arg Ser Phe Ser Asn Tyr Ile Met Gly
1               5                   10

<210> SEQ ID NO 77
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Ser Ile Ala Tyr Ile Tyr Thr Met Asp
1               5                   10

<210> SEQ ID NO 78
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Arg Tyr Gln Met Ala
1               5

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Leu Thr Phe Ser Ser Tyr Ala Met Ala
1               5                   10

<210> SEQ ID NO 80

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Asn Ile Ala Tyr Ile Tyr Thr Met Asp
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Ser Ile Ala Tyr Ile Tyr Thr Met Asp
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Gly Ser Ile Ala Tyr Ile Tyr Thr Met Asp
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Asn Asp Phe Val Ile Thr Asp Met His
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Ala Ile Ala Tyr Ile Tyr Gly Met Gly
1               5                   10

<210> SEQ ID NO 85
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85
```

```
Gly Arg Tyr His Thr Ala
1               5

<210> SEQ ID NO 86
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gly Asn Ile Ala Tyr Ile Tyr Thr Met Asn
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gly Asn Ile Ala Tyr Ile Tyr Thr Met Gly
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Ser Ile Ala Tyr Ile Tyr Thr Met Asp
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Arg Thr Asp Ser Trp Tyr Val Met Gly
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ala Arg Thr Leu Arg Leu Tyr Ala Val Gly
1               5                   10

<210> SEQ ID NO 91
<211> LENGTH: 10
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 91

Gly Ser Ile Val Thr Ile Asn Ala Met Thr
1               5                   10

<210> SEQ ID NO 92
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Arg Tyr His Met Ala
1               5

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Ser Thr Phe Arg His His Ala Met Ala
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Arg Ser Phe Ser Asn Tyr Ile Met Gly
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Leu Thr Phe Ser Ser Tyr Ala Met Ala
1               5                   10

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Val Ser Ile Phe Ser Val Asn Ala Val Asp
1               5                   10
```

```
<210> SEQ ID NO 97
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Asn Asp Phe Val Ile Thr Asp Met His
1               5                   10

<210> SEQ ID NO 98
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Ala Ile Ala Tyr Ile Tyr Gly Met Gly
1               5                   10

<210> SEQ ID NO 99
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Thr Ser Thr Arg Asp Gly Asn Val Asp Tyr Ala Glu Ser Val Lys Gly
1               5                   10                  15

<210> SEQ ID NO 100
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Val Ser Trp Ser Tyr Gly Asn Thr Tyr Tyr Ala Asp Ser Val Lys Gly
1               5                   10                  15

<210> SEQ ID NO 101
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ile Ile Thr Ser Gly Gly Glu Thr Asn Tyr Ala Asp Ser Val Lys Gly
1               5                   10                  15

<210> SEQ ID NO 102
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102
```

```
Gly Ile Gly Arg Ser Glu Arg Thr Tyr Tyr Thr Asp Ser Val Lys Gly
1               5                   10                  15

<210> SEQ ID NO 103
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Thr Ser Thr His Asp Gly Asn Thr Asp Tyr Ala Asp Ser Val Lys Gly
1               5                   10                  15

<210> SEQ ID NO 104
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Thr Ser Thr Arg Asp Gly Asn Thr Asp Tyr Ala Asp Ser Val Lys Gly
1               5                   10                  15

<210> SEQ ID NO 105
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Thr Ile Ser Ser Gly Asp Ser Thr Trp Tyr Thr Asn Ser Val Lys Gly
1               5                   10                  15

<210> SEQ ID NO 106
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gly Ile Gly Arg Ser Glu Arg Ile Tyr Tyr Ile Asp Ser Val Lys Gly
1               5                   10                  15

<210> SEQ ID NO 107
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Thr Ser Thr His Asp Gly Asn Thr Asp Tyr Ala Asp Ser Val Lys Gly
1               5                   10                  15

<210> SEQ ID NO 108
<211> LENGTH: 16
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 108

Thr Phe Thr Arg Asp Gly Asn Thr Asp Tyr Ala Asp Ser Val Lys Gly
1               5                   10                  15

<210> SEQ ID NO 109
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Thr Ser Thr His Asp Gly Asn Thr Asp Tyr Ala Asp Ser Leu Lys Gly
1               5                   10                  15

<210> SEQ ID NO 110
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Thr Ile Ser Ser Gly Asp Ser Thr Trp Tyr Thr Asn Ser Leu Lys Gly
1               5                   10                  15

<210> SEQ ID NO 111
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Ile Ile Thr Ser Gly Gly Glu Thr Asn Tyr Ala Asp Ser Val Lys Gly
1               5                   10                  15

<210> SEQ ID NO 112
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Leu Ile Thr Ser Gly Gly Glu Thr Asn Tyr Ser Asp Ser Val Lys Gly
1               5                   10                  15

<210> SEQ ID NO 113
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Ala Ile Asn Asp His Gly Asp Arg Thr Lys Tyr Leu Asp Ser Val Arg
1               5                   10                  15
```

Gly

<210> SEQ ID NO 114
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Thr Ser Thr His Asp Gly Asn Thr Asp Tyr Ala Asp Ser Val Lys Gly
1               5                   10                  15

<210> SEQ ID NO 115
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Thr Ser Thr His Asp Gly Asn Thr Asp Tyr Ala Asp Ser Val Lys Gly
1               5                   10                  15

<210> SEQ ID NO 116
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Ile Met Thr Ser Asp Gly Ser Thr Asn Tyr Gly Asp Ser Val Lys Gly
1               5                   10                  15

<210> SEQ ID NO 117
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Thr Ser Thr Arg Asp Gly Asn Ile Asp Tyr Ala Asp Ser Val Lys Gly
1               5                   10                  15

<210> SEQ ID NO 118
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Thr Ile Ser Ser Gly Asp Ser Thr Trp Tyr Thr Asn Ser Val Lys Gly
1               5                   10                  15

<210> SEQ ID NO 119
<211> LENGTH: 16
<212> TYPE: PRT
<213> ORGANISM: Artificial Sequence
<220> FEATURE:
<223> OTHER INFORMATION: Description of Artificial Sequence: Synthetic -continued peptide

<400> SEQUENCE: 119

Thr Ile Ser Ser Gly Asp Ser Thr Trp Tyr Thr Asn Ser Val Lys Gly
1               5                   10                  15

<210> SEQ ID NO 120
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Thr Ser Thr His Asp Gly Asn Thr Asp Tyr Thr Asp Ser Val Lys Gly
1               5                   10                  15

<210> SEQ ID NO 121
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Thr Ser Thr Arg Asp Ala Asn Thr Asp Tyr Ala Gly Ser Val Lys Gly
1               5                   10                  15

<210> SEQ ID NO 122
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Thr Ile Thr Ser Ala Asp Ser Thr Trp Tyr Thr Asn Ser Val Lys Gly
1               5                   10                  15

<210> SEQ ID NO 123
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Thr Ile Ser Ser Gly Asp Ser Thr Trp Tyr Thr Asn Ser Val Lys Gly
1               5                   10                  15

<210> SEQ ID NO 124
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Thr Ile Thr Ser Ala Asp Ser Thr Trp Tyr Thr Asn Ser Val Lys Gly
1               5                   10                  15

<210> SEQ ID NO 125

```
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gly Leu Gly Trp Ser Pro Gly Asn Thr Tyr Tyr Ala Asp Ser Val Lys
1               5                   10                  15

Gly

<210> SEQ ID NO 126
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Thr Ser Thr His Asp Gly Asn Thr Asp Tyr Ala Asp Ser Val Lys Gly
1               5                   10                  15

<210> SEQ ID NO 127
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Thr Ile Ser Ser Gly Asp Ser Thr Trp Tyr Thr Asn Ser Val Lys Gly
1               5                   10                  15

<210> SEQ ID NO 128
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Arg Ile Thr Ser Gly Gly Thr Thr Asp Tyr Ala Asp Ser Val Lys Gly
1               5                   10                  15

<210> SEQ ID NO 129
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Thr Ser Thr His Asp Gly Ser Thr Asp Tyr Ala Asp Ser Val Lys Gly
1               5                   10                  15

<210> SEQ ID NO 130
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 130

Thr Ser Thr Trp Asp Gly Asn Thr Asp Tyr Ala Asp Ser Val Lys Gly
1               5                   10                  15

<210> SEQ ID NO 131
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Thr Ser Thr His Asp Gly Asn Thr Asp Tyr Ala Asp Ser Val Lys Gly
1               5                   10                  15

<210> SEQ ID NO 132
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Thr Ile Thr Arg Phe Ala Thr Thr Asn Tyr Ala Asp Ser Val Lys Gly
1               5                   10                  15

<210> SEQ ID NO 133
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ala Ile Ser Ser Gly Gly Ser Thr Asp Tyr Ala Asp Ser Val Lys Gly
1               5                   10                  15

<210> SEQ ID NO 134
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Thr Ile Ser Ser Gly Asp Ser Thr Trp Tyr Thr Asn Ser Val Lys Gly
1               5                   10                  15

<210> SEQ ID NO 135
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Thr Ser Thr His Ala Gly Asn Thr Asp Tyr Ala Asp Ser Val Lys Gly
1               5                   10                  15

<210> SEQ ID NO 136
<211> LENGTH: 16
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 136

Thr Ser Thr His Asp Gly Asn Ser Asp Tyr Ala Asp Ser Val Lys Gly
1               5                   10                  15

<210> SEQ ID NO 137
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Thr Ser Thr Arg Asp Gly Asn Val Asp Tyr Ala Asp Ser Val Lys Gly
1               5                   10                  15

<210> SEQ ID NO 138
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Gly Val Ser Trp Ser Tyr Gly Asn Thr Tyr Tyr Ala Asp Ser Val Lys
1               5                   10                  15

Gly

<210> SEQ ID NO 139
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Gly Ile Gly Arg Ser Glu Arg Thr Tyr Tyr Thr Asp Ser Val Lys Gly
1               5                   10                  15

<210> SEQ ID NO 140
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ile Ile Thr Ser Gly Gly Glu Thr Asn Tyr Ala Asp Ser Val Lys Gly
1               5                   10                  15

<210> SEQ ID NO 141
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141
```

Thr Ile Ser Ser Gly Asp Ser Thr Trp Tyr Thr Asn Ser Val Lys Gly
1               5                   10                  15

<210> SEQ ID NO 142
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Ala Ile Asn Asp His Gly Asp Arg Thr Lys Tyr Leu Asp Ser Val Lys
1               5                   10                  15

Gly

<210> SEQ ID NO 143
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gly Leu Gly Trp Ser Pro Gly Asn Thr Tyr Tyr Ala Asp Ser Val Lys
1               5                   10                  15

Gly

<210> SEQ ID NO 144
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Arg Ile Thr Ser Gly Gly Thr Thr Asp Tyr Ala Asp Ser Val Lys Gly
1               5                   10                  15

<210> SEQ ID NO 145
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ile Met Thr Ser Asp Gly Ser Thr Asn Tyr Asp Asp Ser Val Lys Gly
1               5                   10                  15

<210> SEQ ID NO 146
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Thr Ile Thr Arg Phe Ala Thr Thr Asn Tyr Ala Asp Ser Val Lys Gly
1               5                   10                  15

<210> SEQ ID NO 147

```
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Ala Ile Ser Ser Gly Gly Ser Thr Asp Tyr Ala Asp Ser Val Lys Gly
1               5                   10                  15

<210> SEQ ID NO 148
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Asp Leu Arg Thr Ala Val Asp Leu Ile Arg Ala Asn Tyr
1               5                   10

<210> SEQ ID NO 149
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Arg Val Ser Arg Glu Val Ile Pro Thr Arg Trp Asp Leu Tyr Asn Tyr
1               5                   10                  15

<210> SEQ ID NO 150
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Val Pro Pro Leu Gly Ser
1               5

<210> SEQ ID NO 151
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Thr Phe Gln Thr Thr Asp Met Val Asp Val Pro Thr Thr Gln His Glu
1               5                   10                  15

Tyr Asp Tyr

<210> SEQ ID NO 152
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 152

Asp Leu Arg Thr Ala Val Asp Leu Ile Arg Ala Asn Tyr
1               5                   10

<210> SEQ ID NO 153
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Asp Leu Arg Thr Ala Val Asp Leu Ile Arg Ala Asn Tyr
1               5                   10

<210> SEQ ID NO 154
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Ala Leu Tyr Tyr Arg Asp Ser Arg Arg Ala Ala Asp Tyr Pro Tyr
1               5                   10                  15

<210> SEQ ID NO 155
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Thr Phe Gln Thr Ser Asp Asn Val Gly Val Pro Thr Val Gln His Glu
1               5                   10                  15

Tyr Asp Tyr

<210> SEQ ID NO 156
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Asp Leu Arg Thr Ala Val Asp Leu Ile Arg Ala Asn Tyr
1               5                   10

<210> SEQ ID NO 157
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Asp Leu Arg Thr Ala Val Asp Leu Ile Arg Ala Asn Tyr
1               5                   10

<210> SEQ ID NO 158
```

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Asp Leu Arg Thr Ala Val Asp Leu Ile Arg Ala Asn Tyr
1               5                   10

<210> SEQ ID NO 159
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Ala Leu Tyr Tyr Arg Asp Ser Arg Arg Ala Ala Asp Tyr Pro Tyr
1               5                   10                  15

<210> SEQ ID NO 160
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Val Pro Pro Leu Gly Ser
1               5

<210> SEQ ID NO 161
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Val Pro Pro Leu Gly Ser
1               5

<210> SEQ ID NO 162
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Gly Pro Leu Val Asp Tyr Leu Glu Thr Thr Pro Leu Val Tyr Thr Tyr
1               5                   10                  15

<210> SEQ ID NO 163
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163
```

Asp Leu Arg Thr Ala Val Asp Leu Ile Arg Ala Asn Tyr
1               5                   10

<210> SEQ ID NO 164
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Asp Leu Arg Thr Ala Val Asp Leu Ile Arg Ala Asn Tyr
1               5                   10

<210> SEQ ID NO 165
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Val Pro Pro Arg Tyr
1               5

<210> SEQ ID NO 166
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Asp Leu Arg Thr Ala Val Asp Leu Ile Arg Ala Asn Tyr
1               5                   10

<210> SEQ ID NO 167
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Ala Leu Tyr Tyr Arg Asp Ser Arg Arg Ala Ala Asp Tyr Pro Tyr
1               5                   10                  15

<210> SEQ ID NO 168
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Ala Leu Tyr Tyr Gly Asp Ser Arg Arg Ala Ala Asp Tyr Pro Tyr
1               5                   10                  15

<210> SEQ ID NO 169
<211> LENGTH: 13
<212> TYPE: PRT
<213> ORGANISM: Artificial Sequence
<220> FEATURE:

-continued

```
<223> OTHER INFORMATION: Description of Artificial Sequence: Synthetic
      peptide

<400> SEQUENCE: 169

Asp Leu Arg Thr Ala Val Asp Leu Ile Arg Ala Asn Tyr
1               5                   10

<210> SEQ ID NO 170
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Asp Leu Arg Thr Ala Val Asp Leu Ile Arg Ala Asn Tyr
1               5                   10

<210> SEQ ID NO 171
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Ala Leu Tyr Tyr Gly Asp Ser Arg Arg Ala Ala Asp Tyr Pro Tyr
1               5                   10                  15

<210> SEQ ID NO 172
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Ala Leu Tyr Tyr Arg Asp Ser Trp Arg Ala Ala Asp Tyr Pro Tyr
1               5                   10                  15

<210> SEQ ID NO 173
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Ala Leu Tyr Tyr Gly Asp Ser Arg Arg Ala Ala Asp Tyr Pro Tyr
1               5                   10                  15

<210> SEQ ID NO 174
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Arg Arg Gly Asp Val Ile Tyr Thr Thr Pro Trp Asn Tyr Val Tyr
1               5                   10                  15
```

```
<210> SEQ ID NO 175
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Asp Leu Arg Thr Pro Val Asp Leu Ile Arg Ala Asn Tyr
1               5                   10

<210> SEQ ID NO 176
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Ala Leu Tyr Tyr Arg Asp Ser Arg Arg Ala Ile Asp Tyr Pro Tyr
1               5                   10                  15

<210> SEQ ID NO 177
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Asp Leu Thr Tyr Arg Asn Leu Leu Leu Lys Leu Pro His Tyr
1               5                   10

<210> SEQ ID NO 178
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Asp Leu Arg Thr Pro Val Asp Leu Ile Arg Ala Asn Tyr
1               5                   10

<210> SEQ ID NO 179
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Asp Leu Arg Thr Ala Val Asp Leu Ile Arg Ala Asn Tyr
1               5                   10

<210> SEQ ID NO 180
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180
```

```
Asp Leu Arg Thr Ala Val Asp Leu Ile Arg Ala Asn Tyr
1               5                   10

<210> SEQ ID NO 181
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Ile Gly Leu Arg Gly Val Pro Asp Val Asn Arg Gln Phe Glu Val
1               5                   10                  15

<210> SEQ ID NO 182
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Asp Val Arg Thr Ser Arg Asn Leu Val Arg Ser Asp Tyr
1               5                   10

<210> SEQ ID NO 183
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Ala Leu Tyr Tyr Gly Asp Ser Arg Arg Ala Gly Asp Tyr Pro Tyr
1               5                   10                  15

<210> SEQ ID NO 184
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Asp Leu Arg Thr Ala Val Asp Leu Ile Arg Ala Asn Tyr
1               5                   10

<210> SEQ ID NO 185
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Asp Leu Arg Thr Pro Val Asp Arg Ile Arg Gly Asn Phe
1               5                   10

<210> SEQ ID NO 186
<211> LENGTH: 13
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 186

Asp Leu Arg Thr Ala Val Asp Leu Ile Arg Ala Asn Tyr
1               5                   10

<210> SEQ ID NO 187
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Arg Val Ser Arg Glu Val Ile Pro Thr Arg Trp Asp Leu Tyr Asn Tyr
1               5                   10                  15

<210> SEQ ID NO 188
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Thr Phe Gln Thr Thr Asp Met Val Asp Val Pro Thr Thr Gln His Glu
1               5                   10                  15

Tyr Asp Tyr

<210> SEQ ID NO 189
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Val Pro Pro Leu Gly Ser
1               5

<210> SEQ ID NO 190
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Ala Leu Tyr Tyr Gly Asp Ser Arg Arg Ala Ala Asp Tyr Pro Tyr
1               5                   10                  15

<210> SEQ ID NO 191
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Gly Pro Leu Val Asp Tyr Leu Glu Thr Thr Pro Leu Val Tyr Thr Tyr
```

```
<210> SEQ ID NO 192
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Arg Arg Gly Asp Val Ile Tyr Thr Thr Pro Trp Asn Tyr Val Tyr
1               5                   10                  15

<210> SEQ ID NO 193
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Asp Leu Thr Tyr Arg Asn Leu Leu Leu Lys Leu Pro His Tyr
1               5                   10

<210> SEQ ID NO 194
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Val Pro Pro Arg Tyr
1               5

<210> SEQ ID NO 195
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Ile Gly Leu Arg Gly Val Pro Asp Val Asn Arg Gln Phe Glu Val
1               5                   10                  15

<210> SEQ ID NO 196
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Asp Val Arg Thr Ser Arg Asn Leu Val Arg Ser Asp Tyr
1               5                   10

<210> SEQ ID NO 197
<211> LENGTH: 20
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<221> NAME/KEY: MISC_FEATURE
<222> LOCATION: (1)..(20)
<223> OTHER INFORMATION: This sequence may encompass 1-10 "Gly Ser"
      repeating units

<400> SEQUENCE: 197

Gly Ser Gly Ser Gly Ser Gly Ser Gly Ser Gly Ser Gly Ser Gly Ser
1               5                   10                  15

Gly Ser Gly Ser
            20

<210> SEQ ID NO 198
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(30)
<223> OTHER INFORMATION: This sequence may encompass 1-10 "Gly Gly Ser"
      repeating units

<400> SEQUENCE: 198

Gly Gly Ser Gly Gly Ser Gly Gly Ser Gly Gly Ser Gly Gly Ser Gly
1               5                   10                  15

Ser Gly Gly Ser Gly Gly Ser Gly Gly Ser Gly Gly Ser
            20                  25                  30

<210> SEQ ID NO 199
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(40)
<223> OTHER INFORMATION: This sequence may encompass 1-10 "Gly Gly Gly
      Ser" repeating units

<400> SEQUENCE: 199

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
            35                  40

<210> SEQ ID NO 200
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(40)
<223> OTHER INFORMATION: This sequence may encompass 1-10 "Gly Gly Ser
      Gly" repeating units

<400> SEQUENCE: 200

Gly Gly Ser Gly Gly Gly Ser Gly Gly Gly Ser Gly Gly Gly Ser Gly
```

```
                1               5                   10                  15
Gly Gly Ser Gly Gly Gly Ser Gly Gly Gly Ser Gly Gly Gly Ser Gly
                        20                  25                  30
Gly Gly Ser Gly Gly Gly Ser Gly
                35                  40
```

<210> SEQ ID NO 201
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(50)
<223> OTHER INFORMATION: This sequence may encompass 1-10 "Gly Gly Ser
      Gly Gly" repeating units

<400> SEQUENCE: 201

```
Gly Gly Ser Gly Gly Gly Ser Gly Gly Gly Ser Gly Gly Gly Ser Gly
1               5                   10                  15
Gly Ser Gly Gly Gly Ser Gly Gly Gly Ser Gly Gly Gly Ser Gly Gly
                20                  25                  30
Ser Gly Gly Gly Gly Ser Gly Gly Gly Gly Ser Gly Gly Gly Gly Ser
        35                  40                  45
Gly Gly
    50
```

<210> SEQ ID NO 202
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(50)
<223> OTHER INFORMATION: This sequence may encompass 1-10 "Gly Gly Gly
      Gly Ser" repeating units

<400> SEQUENCE: 202

```
Gly Gly Gly Gly Ser Gly Gly Gly Gly Ser Gly Gly Gly Gly Ser Gly
1               5                   10                  15
Gly Gly Gly Ser Gly Gly Gly Gly Ser Gly Gly Gly Gly Ser Gly Gly
                20                  25                  30
Gly Gly Ser Gly Gly Gly Gly Ser Gly Gly Gly Gly Ser Gly Gly Gly
        35                  40                  45
Gly Ser
    50
```

<210> SEQ ID NO 203
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(50)
<223> OTHER INFORMATION: This sequence may encompass 1-10 "Gly Gly Gly
      Gly Gly" repeating units

<400> SEQUENCE: 203

Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly
        35                  40                  45

Gly Gly
    50

<210> SEQ ID NO 204
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(30)
<223> OTHER INFORMATION: This sequence may encompass 1-10 "Gly Gly Gly"
      repeating units

<400> SEQUENCE: 204

Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly
            20                  25                  30

<210> SEQ ID NO 205
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Arg Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 206
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide -continued

```
<400> SEQUENCE: 206

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ala Asp Thr Leu Tyr Ala Asp Ser Leu
50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Lys Ser Ser Gln Gly Thr Leu Val Thr
            100                 105                 110

Val Ser Ser
        115

<210> SEQ ID NO 207
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Tyr Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Lys Ser Ser Gln Gly Thr Leu Val Thr
            100                 105                 110

Val Ser Ser
        115

<210> SEQ ID NO 208
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Ala Pro Gly Lys Gly Leu Glu Trp Val
```

```
                35                  40                  45

Ser Ser Ile Ser Gly Ser Gly Thr Asp Thr Leu Tyr Ala Asp Ser Val
        50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Gln Gly Thr Leu Val Thr
            100                 105                 110

Val Ser Ser
        115

<210> SEQ ID NO 209
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Glu Val Gln Leu Val Glu Ser Gly Gly Gly Leu Val Gln Pro Gly Asn
  1               5                  10                  15

Ser Leu Arg Leu Ser Cys Ala Ala Ser Gly Phe Thr Phe Ser Arg Phe
                 20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Lys Ser Ser Gln Gly Thr Leu Val Thr
            100                 105                 110

Val Ser Ser
        115

<210> SEQ ID NO 210
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Glu Val Gln Leu Val Glu Ser Gly Gly Gly Leu Val Gln Pro Gly Asn
  1               5                  10                  15

Ser Leu Arg Leu Ser Cys Ala Ala Ser Gly Phe Thr Phe Ser Lys Phe
                 20                  25                  30

Gly Met Ser Trp Val Arg Gln Ala Pro Gly Lys Gly Leu Glu Trp Val
            35                  40                  45

Ser Ser Ile Ser Gly Ser Gly Arg Asp Thr Leu Tyr Ala Asp Ser Val
        50                  55                  60

Lys Gly Arg Phe Thr Ile Ser Arg Asp Asn Ala Lys Thr Thr Leu Tyr
 65                  70                  75                  80

Leu Gln Met Asn Ser Leu Arg Pro Glu Asp Thr Ala Val Tyr Tyr Cys
```

```
                    85                  90                  95

Thr Ile Gly Gly Ser Leu Ser Val Ser Ser Gln Gly Thr Leu Val Thr
                100                 105                 110

Val Ser Ser
        115

<210> SEQ ID NO 211
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
                20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
                100                 105                 110

Val Ser Ser
        115

<210> SEQ ID NO 212
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Arg Phe
                20                  25                  30

Gly Met Ser Trp Val Arg Gln Ala Pro Gly Lys Gly Leu Glu Trp Val
            35                  40                  45

Ser Ser Ile Ser Gly Ser Gly Ser Asp Thr Leu Tyr Ala Glu Ser Val
        50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
                100                 105                 110

Val Ser Ser
        115
```

<210> SEQ ID NO 213
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Thr Asp Thr Leu Tyr Ala Glu Ser Val
50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 214
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Lys Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Arg Asp Thr Leu Tyr Ala Glu Ser Val
50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Val Ser Ser Gln Gly Thr Leu Val Thr
            100                 105                 110

Val Ser Ser
        115

<210> SEQ ID NO 215
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

```
Gly Phe Thr Phe Ser Ser Phe Gly Met Ser
1               5                   10

<210> SEQ ID NO 216
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Ser Ile Ser Gly Ser Gly Ser Asp Thr Leu Tyr Ala Asp Ser Val Lys
1               5                   10                  15

<210> SEQ ID NO 217
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Gly Gly Ser Leu Ser Arg
1               5

<210> SEQ ID NO 218
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Gly Phe Thr Phe Ser Arg Phe Gly Met Ser
1               5                   10

<210> SEQ ID NO 219
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Gly Phe Thr Phe Ser Lys Phe Gly Met Ser
1               5                   10

<210> SEQ ID NO 220
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Gly Phe Thr Tyr Ser Ser Phe Gly Met Ser
1               5                   10

<210> SEQ ID NO 221
<211> LENGTH: 16
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 221

Ser Ile Ser Gly Ser Gly Ala Asp Thr Leu Tyr Ala Asp Ser Leu Lys
1               5                   10                  15

<210> SEQ ID NO 222
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Ser Ile Ser Gly Ser Gly Thr Asp Thr Leu Tyr Ala Asp Ser Val Lys
1               5                   10                  15

<210> SEQ ID NO 223
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Ser Ile Ser Gly Ser Gly Arg Asp Thr Leu Tyr Ala Asp Ser Val Lys
1               5                   10                  15

<210> SEQ ID NO 224
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Ser Ile Ser Gly Ser Gly Ser Asp Thr Leu Tyr Ala Glu Ser Val Lys
1               5                   10                  15

<210> SEQ ID NO 225
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Ser Ile Ser Gly Ser Gly Thr Asp Thr Leu Tyr Ala Glu Ser Val Lys
1               5                   10                  15

<210> SEQ ID NO 226
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Ser Ile Ser Gly Ser Gly Arg Asp Thr Leu Tyr Ala Glu Ser Val Lys
1               5                   10                  15

<210> SEQ ID NO 227
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Gly Gly Ser Leu Ser Lys
1               5

<210> SEQ ID NO 228
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Gly Gly Ser Leu Ser Val
1               5

<210> SEQ ID NO 229
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Glu Val Gln Leu Val Glu Ser Gly Gly Leu Val Gln Pro Gly Gly
1               5                   10                  15

Ser Leu Lys Leu Ser Cys Ala Ala Ser Gly Phe Thr Phe Asn Lys Tyr
                20                  25                  30

Ala Ile Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Gln Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Ala Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Ala Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Val Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp

Glu Ala Glu Tyr Tyr Cys Thr Leu Trp Tyr Ser Asn Arg Trp Val Phe
225                 230                 235                 240

Gly Gly Gly Thr Lys Leu Thr Val Leu
                245

<210> SEQ ID NO 230
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Glu Phe Asn Lys Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Lys Tyr Ala Thr Tyr Tyr Ala Asp
        50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Phe Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Asp Asn Arg Trp Val Phe
225                 230                 235                 240

Gly Gly Gly Thr Lys Leu Thr Val Leu
                245

<210> SEQ ID NO 231
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 231

Glu Val Gln Leu Val Glu Ser Gly Gly Gly Leu Val Gln Pro Gly Gly

```
1               5                   10                  15
Ser Leu Lys Leu Ser Cys Ala Ala Ser Gly Phe Thr Phe Asn Lys Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
50                      55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser His Ile Ser Tyr Trp
                100                 105                 110

Ala Tyr Trp Gly Gln Gly Thr Leu Val Thr Val Ser Ser Gly Gly Gly
            115                 120                 125

Gly Ser Gly Gly Gly Ser Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Tyr Val Thr Ser Gly Asn Tyr Pro Asn
                165                 170                 175

Trp Val Gln Gln Lys Pro Gly Gln Ala Pro Arg Gly Leu Ile Gly Gly
                180                 185                 190

Thr Ser Phe Leu Ala Pro Gly Thr Pro Ala Arg Phe Ser Gly Ser Leu
                195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Ile Phe
225                 230                 235                 240

Gly Gly Gly Thr Lys Leu Thr Val Leu
                245
```

<210> SEQ ID NO 232
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 232

```
Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Met Phe Asn Lys Tyr
            20                  25                  30

Ala Met Asn Trp Val Arg Gln Ala Pro Gly Lys Gly Leu Glu Trp Val
            35                  40                  45

Ala Arg Ile Arg Ser Lys Ser Asn Asn Tyr Ala Thr Tyr Tyr Ala Asp
50                      55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
                100                 105                 110
```

Ala Thr Trp Gly Gln Gly Thr Leu Val Thr Val Ser Ser Gly Gly
            115                 120                 125

Gly Ser Gly Gly Gly Ser Gly Gly Gly Ser Gln Thr Val Val
        130                 135                 140

Thr Gln Glu Pro Ser Leu Thr Val Ser Pro Gly Gly Thr Val Thr Leu
145                 150                 155                 160

Thr Cys Gly Ser Ser Phe Gly Ala Val Thr Ser Gly Asn Tyr Pro Asn
                165                 170                 175

Trp Val Gln Gln Lys Pro Gly Gln Ala Pro Arg Gly Leu Ile Gly Gly
                180                 185                 190

Thr Lys Leu Leu Ala Pro Gly Thr Pro Ala Arg Phe Ser Gly Ser Leu
            195                 200                 205

Leu Gly Gly Lys Ala Ala Leu Thr Leu Ser Gly Val Gln Pro Glu Asp
210                 215                 220

Glu Ala Glu Tyr Tyr Cys Val Leu Trp Tyr Ser Asn Ser Trp Val Phe
225                 230                 235                 240

Gly Gly Gly Thr Lys Leu Thr Val Leu
                245

<210> SEQ ID NO 233
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 233

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Lys Asp
50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Pro Ile Ser Tyr Trp
            100                 105                 110

Ala Tyr Trp Gly Gln Gly Thr Leu Val Thr Val Ser Ser Gly Gly Gly
            115                 120                 125

Gly Ser Gly Gly Gly Gly Ser Gly Gly Gly Ser Gln Thr Val Val
        130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Val Ser Gly Asn Tyr Pro Asn
                165                 170                 175

Trp Val Gln Gln Lys Pro Gly Gln Ala Pro Arg Gly Leu Ile Gly Gly
                180                 185                 190

Thr Glu Phe Leu Ala Pro Gly Thr Pro Ala Arg Phe Ser Gly Ser Leu
            195                 200                 205

Leu Gly Gly Lys Ala Ala Leu Thr Leu Ser Gly Val Gln Pro Glu Asp
210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245

<210> SEQ ID NO 234
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 234

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Tyr Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
50                  55                  60

Glu Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Pro Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
130                 135                 140

Thr Gln Glu Pro Ser Leu Thr Val Ser Pro Gly Gly Thr Val Thr Leu
145                 150                 155                 160

Thr Cys Gly Ser Ser Lys Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Glu Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
210                 215                 220

Glu Ala Glu Tyr Tyr Cys Thr Leu Trp Tyr Ser Asn Arg Trp Val Phe
225                 230                 235                 240

Gly Gly Gly Thr Lys Leu Thr Val Leu
                245

<210> SEQ ID NO 235
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 235

Glu Val Gln Leu Val Glu Ser Gly Gly Gly Leu Val Gln Pro Gly Gly
1               5                   10                  15

Ser Leu Lys Leu Ser Cys Ala Ala Ser Gly Asn Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Glu Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Thr Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
        130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Tyr Tyr Pro Asn
                165                 170                 175

Trp Val Gln Gln Lys Pro Gly Gln Ala Pro Arg Gly Leu Ile Gly
                180                 185                 190

Thr Tyr Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245

<210> SEQ ID NO 236
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 236

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Asn Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ala Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Gln Ile Ser Tyr Trp
            100                 105                 110

Ala Tyr Trp Gly Gln Gly Thr Leu Val Thr Val Ser Ser Gly Gly Gly

```
            115                 120                 125
Gly Ser Gly Gly Gly Ser Gly Gly Gly Ser Gln Thr Val Val
        130                 135                 140
Thr Gln Glu Pro Ser Leu Thr Val Ser Pro Gly Gly Thr Val Thr Leu
145                 150                 155                 160
Thr Cys Gly Ser Ser Thr Gly Ala Val Thr Asp Gly Asn Tyr Pro Asn
                165                 170                 175
Trp Val Gln Gln Lys Pro Gly Gln Ala Pro Arg Gly Leu Ile Gly Gly
                180                 185                 190
Ile Lys Phe Leu Ala Pro Gly Thr Pro Ala Arg Phe Ser Gly Ser Leu
                195                 200                 205
Leu Gly Gly Lys Ala Ala Leu Thr Leu Ser Gly Val Gln Pro Glu Asp
        210                 215                 220
Glu Ala Glu Tyr Tyr Cys Val Leu Trp Tyr Ser Asn Arg Trp Val Phe
225                 230                 235                 240
Gly Gly Gly Thr Lys Leu Thr Val Leu
                245

<210> SEQ ID NO 237
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 237

Glu Val Gln Leu Val Glu Ser Gly Gly Gly Leu Val Gln Pro Gly Gly
1               5                   10                  15
Ser Leu Lys Leu Ser Cys Ala Ala Ser Gly Phe Thr Phe Asn Lys Tyr
                20                  25                  30
Ala Val Asn Trp Val Arg Gln Ala Pro Gly Lys Gly Leu Glu Trp Val
            35                  40                  45
Ala Arg Ile Arg Ser Lys Tyr Asn Asn Tyr Ala Thr Tyr Tyr Ala Asp
        50                  55                  60
Ser Val Lys Asp Arg Phe Thr Ile Ser Arg Asp Asp Ser Lys Asn Thr
65                  70                  75                  80
Ala Tyr Leu Gln Met Asn Asn Leu Lys Thr Glu Asp Thr Ala Val Tyr
                85                  90                  95
Tyr Cys Val Arg His Gly Asn Phe Gly Asn Ser Tyr Ile Ser Tyr Trp
                100                 105                 110
Ala Tyr Trp Gly Gln Gly Thr Leu Val Thr Val Ser Ser Gly Gly Gly
            115                 120                 125
Gly Ser Gly Gly Gly Gly Ser Gly Gly Gly Ser Gln Thr Val Val
        130                 135                 140
Thr Gln Glu Pro Ser Leu Thr Val Ser Pro Gly Gly Thr Val Thr Leu
145                 150                 155                 160
Thr Cys Gly Glu Ser Thr Gly Ala Val Thr Ser Gly Asn Tyr Pro Asn
                165                 170                 175
Trp Val Gln Gln Lys Pro Gly Gln Ala Pro Arg Gly Leu Ile Gly Gly
                180                 185                 190
Thr Lys Ile Leu Ala Pro Gly Thr Pro Ala Arg Phe Ser Gly Ser Leu
                195                 200                 205
Leu Gly Gly Lys Ala Ala Leu Thr Leu Ser Gly Val Gln Pro Glu Asp
        210                 215                 220
```

Glu Ala Glu Tyr Tyr Cys Val Leu Trp Tyr Ser Asn Arg Trp Val Phe
225                 230                 235                 240

Gly Gly Gly Thr Lys Leu Thr Val Leu
            245

<210> SEQ ID NO 238
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 238

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Pro Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Asn Glu Asp Thr Ala Val Tyr
                85                  90                  95

Tyr Cys Val Arg His Gly Asn Phe Asn Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Lys Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Met Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Ala Leu Trp Tyr Ser Asn Arg Trp Val Phe
225                 230                 235                 240

Gly Gly Gly Thr Lys Leu Thr Val Leu
            245

<210> SEQ ID NO 239
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 239

Glu Val Gln Leu Val Glu Ser Gly Gly Gly Leu Val Gln Pro Gly Gly
1               5                   10                  15

```
Ser Leu Lys Leu Ser Cys Ala Ala Ser Gly Phe Thr Phe Asn Gly Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Glu Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Pro Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Ser Gly Gly Gly Ser Gln Thr Val Val
        130                 135             140

Thr Gln Glu Pro Ser Leu Thr Val Ser Pro Gly Gly Thr Val Thr Leu
145                 150                 155                 160

Thr Cys Gly Ser Ser Thr Gly Ala Val Val Ser Gly Asn Tyr Pro Asn
                165                 170                 175

Trp Val Gln Gln Lys Pro Gly Gln Ala Pro Arg Gly Leu Ile Gly Gly
        180                 185                 190

Thr Glu Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
            245

<210> SEQ ID NO 240
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Glu Val Gln Leu Val Glu Ser Gly Gly Gly Leu Val Gln Pro Gly Gly
1               5                   10                  15

Ser Leu Lys Leu Ser Cys Ala Ala Ser Gly Asn Thr Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asp Ser Tyr Ile Ser Tyr Trp
            100                 105                 110

Ala Tyr Trp Gly Gln Gly Thr Leu Val Thr Val Ser Ser Gly Gly Gly
        115                 120                 125
```

Gly Ser Gly Gly Gly Ser Gly Gly Gly Ser Gln Thr Val Val
            130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr His Gly Asn Tyr Pro Asn
                165                 170                 175

Trp Val Gln Gln Lys Pro Gly Gln Ala Pro Arg Gly Leu Ile Gly Gly
                180                 185                 190

Thr Lys Val Leu Ala Pro Gly Thr Pro Ala Arg Phe Ser Gly Ser Leu
            195                 200                 205

Leu Gly Gly Lys Ala Ala Leu Thr Leu Ser Gly Val Gln Pro Glu Asp
210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
            245

<210> SEQ ID NO 241
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 241

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Asn Tyr
                20                  25                  30

Ala Met Asn Trp Val Arg Gln Ala Pro Gly Lys Gly Leu Glu Trp Val
            35                  40                  45

Ala Arg Ile Arg Ser Gly Tyr Asn Asn Tyr Ala Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
            130                 135                 140

Thr Gln Glu Pro Ser Leu Thr Val Ser Pro Gly Gly Thr Val Thr Leu
145                 150                 155                 160

Thr Cys Gly Ser Tyr Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
                180                 185                 190

Thr Lys Phe Asn Ala Pro Gly Thr Pro Ala Arg Phe Ser Gly Ser Leu
            195                 200                 205

Leu Gly Gly Lys Ala Ala Leu Thr Leu Ser Gly Val Gln Pro Glu Asp
210                 215                 220

Glu Ala Glu Tyr Tyr Cys Val Leu Trp Tyr Ala Asn Arg Trp Val Phe

Gly Gly Gly Thr Lys Leu Thr Val Leu
                245

<210> SEQ ID NO 242
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 242

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Glu Phe Asn Lys Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Glu Thr Tyr Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Leu Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Ser Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Gly Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245

<210> SEQ ID NO 243
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr

```
            20                  25                  30
Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Tyr Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Ser Gly Gly Gly Ser Gln Thr Val Val
        130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
            180                 185                 190

Thr Lys Phe Leu Ala Pro Gly Thr Pro Ala Arg Phe Ser Gly Ser Leu
        195                 200                 205

Leu Gly Gly Lys Ala Ala Leu Thr Leu Ser Gly Val Gln Pro Glu Asp
    210                 215                 220

Glu Ala Glu Tyr Tyr Cys Val Leu Trp Tyr Ser Asn Arg Trp Val Phe
225                 230                 235                 240

Gly Gly Gly Thr Lys Leu Thr Val Leu
                245

<210> SEQ ID NO 244
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 244

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Lys Tyr
            20                  25                  30

Ala Leu Asn Trp Val Arg Gln Ala Pro Gly Lys Gly Leu Glu Trp Val
        35                  40                  45

Ala Arg Ile Arg Ser Lys Tyr Asn Asn Tyr Ala Thr Glu Tyr Ala Asp
    50                  55                  60

Ser Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Pro Ile Ser Tyr Trp
            100                 105                 110

Ala Tyr Trp Gly Gln Gly Thr Leu Val Thr Val Ser Ser Gly Gly Gly
        115                 120                 125
```

Gly Ser Gly Gly Gly Ser Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Ser Gly Asn Tyr Pro Asn
                165                 170                 175

Trp Val Gln Gln Lys Pro Gly Gln Ala Pro Arg Gly Leu Ile Gly Gly
                180                 185                 190

Thr Asn Phe Leu Ala Pro Gly Thr Pro Glu Arg Phe Ser Gly Ser Leu
                195                 200                 205

Leu Gly Gly Lys Ala Ala Leu Thr Leu Ser Gly Val Gln Pro Glu Asp
            210                 215                 220

Glu Ala Glu Tyr Tyr Cys Val Leu Trp Tyr Ser Asn Arg Trp Ala Phe
225                 230                 235                 240

Gly Gly Gly Thr Lys Leu Thr Val Leu
                245

<210> SEQ ID NO 245
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 245

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Glu Tyr
                20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
        50                  55                  60

Asp Val Lys Asp Arg Phe Thr Ile Ser Arg Asp Asp Ser Lys Asn Thr
65                  70                  75                  80

Ala Tyr Leu Gln Met Asn Asn Leu Lys Thr Glu Asp Thr Ala Val Tyr
                85                  90                  95

Tyr Cys Val Arg His Gly Asn Phe Gly Asn Ser Gly Ile Ser Tyr Trp
            100                 105                 110

Ala Tyr Trp Gly Gln Gly Thr Leu Val Thr Val Ser Ser Gly Gly Gly
        115                 120                 125

Gly Ser Gly Gly Gly Gly Ser Gly Gly Gly Gly Ser Gln Thr Val Val
    130                 135                 140

Thr Gln Glu Pro Ser Leu Thr Val Ser Pro Gly Gly Thr Val Thr Leu
145                 150                 155                 160

Thr Cys Gly Ser Ser Thr Gly Ala Val Thr Val Gly Asn Tyr Pro Asn
                165                 170                 175

Trp Val Gln Gln Lys Pro Gly Gln Ala Pro Arg Gly Leu Ile Gly Gly
                180                 185                 190

Thr Glu Phe Leu Ala Pro Gly Thr Pro Ala Arg Phe Ser Gly Ser Leu
                195                 200                 205

Leu Gly Gly Lys Ala Ala Leu Thr Leu Ser Gly Val Gln Pro Glu Asp
            210                 215                 220

Glu Ala Glu Tyr Tyr Cys Val Leu Trp Tyr Ser Asn Arg Trp Val Phe
225                 230                 235                 240

```
Gly Gly Gly Thr Lys Leu Thr Val Leu
                245

<210> SEQ ID NO 246
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Gly Gly Gly Gly Ser Gly Gly Gly Ser
1               5

<210> SEQ ID NO 247
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 247

His His His His His His
1               5

<210> SEQ ID NO 248
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Gly Asn Thr Phe Asn Lys Tyr Ala Met Asn
1               5                   10

<210> SEQ ID NO 249
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Gly Phe Glu Phe Asn Lys Tyr Ala Met Asn
1               5                   10

<210> SEQ ID NO 250
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Gly Phe Met Phe Asn Lys Tyr Ala Met Asn
1               5                   10

<210> SEQ ID NO 251
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 251

Gly Phe Thr Tyr Asn Lys Tyr Ala Met Asn
1               5                   10

<210> SEQ ID NO 252
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Gly Phe Thr Phe Asn Asn Tyr Ala Met Asn
1               5                   10

<210> SEQ ID NO 253
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Gly Phe Thr Phe Asn Gly Tyr Ala Met Asn
1               5                   10

<210> SEQ ID NO 254
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Gly Phe Thr Phe Asn Thr Tyr Ala Met Asn
1               5                   10

<210> SEQ ID NO 255
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Gly Phe Thr Phe Asn Glu Tyr Ala Met Asn
1               5                   10

<210> SEQ ID NO 256
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Gly Phe Thr Phe Asn Lys Tyr Pro Met Asn
1               5                   10
```

```
<210> SEQ ID NO 257
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Gly Phe Thr Phe Asn Lys Tyr Ala Val Asn
1               5                   10

<210> SEQ ID NO 258
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Gly Phe Thr Phe Asn Lys Tyr Ala Ile Asn
1               5                   10

<210> SEQ ID NO 259
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Gly Phe Thr Phe Asn Lys Tyr Ala Leu Asn
1               5                   10

<210> SEQ ID NO 260
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Arg Ile Arg Ser Gly Tyr Asn Asn Tyr Ala Thr Tyr Tyr Ala Asp Ser
1               5                   10                  15

Val Lys

<210> SEQ ID NO 261
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Arg Ile Arg Ser Lys Ser Asn Asn Tyr Ala Thr Tyr Tyr Ala Asp Ser
1               5                   10                  15

Val Lys

<210> SEQ ID NO 262
<211> LENGTH: 18
<212> TYPE: PRT
<213> ORGANISM: Artificial Sequence
```

<220> FEATURE:
<223> OTHER INFORMATION: Description of Artificial Sequence: Synthetic
      peptide

<400> SEQUENCE: 262

Arg Ile Arg Ser Lys Tyr Asn Lys Tyr Ala Thr Tyr Tyr Ala Asp Ser
1               5                   10                  15

Val Lys

<210> SEQ ID NO 263
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Arg Ile Arg Ser Lys Tyr Asn Asn Tyr Glu Thr Tyr Tyr Ala Asp Ser
1               5                   10                  15

Val Lys

<210> SEQ ID NO 264
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Arg Ile Arg Ser Lys Tyr Asn Asn Tyr Ala Thr Glu Tyr Ala Asp Ser
1               5                   10                  15

Val Lys

<210> SEQ ID NO 265
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Arg Ile Arg Ser Lys Tyr Asn Asn Tyr Ala Thr Tyr Tyr Lys Asp Ser
1               5                   10                  15

Val Lys

<210> SEQ ID NO 266
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Arg Ile Arg Ser Lys Tyr Asn Asn Tyr Ala Thr Tyr Tyr Ala Asp Glu
1               5                   10                  15

Val Lys

<210> SEQ ID NO 267
<211> LENGTH: 18
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 267

Arg Ile Arg Ser Lys Tyr Asn Asn Tyr Ala Thr Tyr Tyr Ala Asp Ala
1               5                   10                  15

Val Lys

<210> SEQ ID NO 268
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Arg Ile Arg Ser Lys Tyr Asn Asn Tyr Ala Thr Tyr Tyr Ala Asp Gln
1               5                   10                  15

Val Lys

<210> SEQ ID NO 269
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Arg Ile Arg Ser Lys Tyr Asn Asn Tyr Ala Thr Tyr Tyr Ala Asp Asp
1               5                   10                  15

Val Lys

<210> SEQ ID NO 270
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

His Ala Asn Phe Gly Asn Ser Tyr Ile Ser Tyr Trp Ala Tyr
1               5                   10

<210> SEQ ID NO 271
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

His Thr Asn Phe Gly Asn Ser Tyr Ile Ser Tyr Trp Ala Tyr
1               5                   10

<210> SEQ ID NO 272
<211> LENGTH: 14
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 272

His Gly Asn Phe Asn Asn Ser Tyr Ile Ser Tyr Trp Ala Tyr
1               5                   10

<210> SEQ ID NO 273
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

His Gly Asn Phe Gly Asp Ser Tyr Ile Ser Tyr Trp Ala Tyr
1               5                   10

<210> SEQ ID NO 274
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

His Gly Asn Phe Gly Asn Ser His Ile Ser Tyr Trp Ala Tyr
1               5                   10

<210> SEQ ID NO 275
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

His Gly Asn Phe Gly Asn Ser Pro Ile Ser Tyr Trp Ala Tyr
1               5                   10

<210> SEQ ID NO 276
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

His Gly Asn Phe Gly Asn Ser Gln Ile Ser Tyr Trp Ala Tyr
1               5                   10

<210> SEQ ID NO 277
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

His Gly Asn Phe Gly Asn Ser Leu Ile Ser Tyr Trp Ala Tyr
1               5                   10

<210> SEQ ID NO 278

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

His Gly Asn Phe Gly Asn Ser Gly Ile Ser Tyr Trp Ala Tyr
1               5                   10

<210> SEQ ID NO 279
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

His Gly Asn Phe Gly Asn Ser Tyr Ile Ser Tyr Trp Ala Thr
1               5                   10

<210> SEQ ID NO 280
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Ala Ser Ser Thr Gly Ala Val Thr Ser Gly Asn Tyr Pro Asn
1               5                   10

<210> SEQ ID NO 281
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Gly Glu Ser Thr Gly Ala Val Thr Ser Gly Asn Tyr Pro Asn
1               5                   10

<210> SEQ ID NO 282
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Gly Ser Tyr Thr Gly Ala Val Thr Ser Gly Asn Tyr Pro Asn
1               5                   10

<210> SEQ ID NO 283
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283
```

Gly Ser Ser Phe Gly Ala Val Thr Ser Gly Asn Tyr Pro Asn
1               5                   10

<210> SEQ ID NO 284
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Gly Ser Ser Lys Gly Ala Val Thr Ser Gly Asn Tyr Pro Asn
1               5                   10

<210> SEQ ID NO 285
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Gly Ser Ser Ser Gly Ala Val Thr Ser Gly Asn Tyr Pro Asn
1               5                   10

<210> SEQ ID NO 286
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Gly Ser Ser Thr Gly Tyr Val Thr Ser Gly Asn Tyr Pro Asn
1               5                   10

<210> SEQ ID NO 287
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Gly Ser Ser Thr Gly Ala Val Val Ser Gly Asn Tyr Pro Asn
1               5                   10

<210> SEQ ID NO 288
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Gly Ser Ser Thr Gly Ala Val Thr Asp Gly Asn Tyr Pro Asn
1               5                   10

<210> SEQ ID NO 289
<211> LENGTH: 14
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 289

Gly Ser Ser Thr Gly Ala Val Thr Lys Gly Asn Tyr Pro Asn
1               5                   10

<210> SEQ ID NO 290
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

Gly Ser Ser Thr Gly Ala Val Thr His Gly Asn Tyr Pro Asn
1               5                   10

<210> SEQ ID NO 291
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Gly Ser Ser Thr Gly Ala Val Thr Val Gly Asn Tyr Pro Asn
1               5                   10

<210> SEQ ID NO 292
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Gly Ser Ser Thr Gly Ala Val Thr Ser Gly Tyr Tyr Pro Asn
1               5                   10

<210> SEQ ID NO 293
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Gly Ile Lys Phe Leu Ala Pro
1               5

<210> SEQ ID NO 294
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Gly Thr Glu Phe Leu Ala Pro
1               5
```

```
<210> SEQ ID NO 295
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Gly Thr Tyr Phe Leu Ala Pro
1               5

<210> SEQ ID NO 296
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Gly Thr Ser Phe Leu Ala Pro
1               5

<210> SEQ ID NO 297
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Gly Thr Asn Phe Leu Ala Pro
1               5

<210> SEQ ID NO 298
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Gly Thr Lys Leu Leu Ala Pro
1               5

<210> SEQ ID NO 299
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Gly Thr Lys Glu Leu Ala Pro
1               5

<210> SEQ ID NO 300
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300
```

Gly Thr Lys Ile Leu Ala Pro
1               5

<210> SEQ ID NO 301
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Gly Thr Lys Met Leu Ala Pro
1               5

<210> SEQ ID NO 302
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Gly Thr Lys Val Leu Ala Pro
1               5

<210> SEQ ID NO 303
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Gly Thr Lys Phe Asn Ala Pro
1               5

<210> SEQ ID NO 304
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Gly Thr Lys Phe Gly Ala Pro
1               5

<210> SEQ ID NO 305
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Gly Thr Lys Phe Leu Val Pro
1               5

<210> SEQ ID NO 306
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 306

Thr Leu Trp Tyr Ser Asn Arg Trp Val
1               5

<210> SEQ ID NO 307
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Ala Leu Trp Tyr Ser Asn Arg Trp Val
1               5

<210> SEQ ID NO 308
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Val Leu Trp Tyr Asp Asn Arg Trp Val
1               5

<210> SEQ ID NO 309
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Val Leu Trp Tyr Ala Asn Arg Trp Val
1               5

<210> SEQ ID NO 310
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Val Leu Trp Tyr Ser Asn Ser Trp Val
1               5

<210> SEQ ID NO 311
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Val Leu Trp Tyr Ser Asn Arg Trp Ile
1               5
```

<210> SEQ ID NO 312
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 312

Val Leu Trp Tyr Ser Asn Arg Trp Ala
1               5

<210> SEQ ID NO 313
<211> LENGTH: 5
<212> TYPE: PRT
<213> ORGANISM: Unknown
<220> FEATURE:
<223> OTHER INFORMATION: Description of Unknown:
      sortase recognition sequence

<400> SEQUENCE: 313

Leu Pro Glu Thr Gly
1               5

<210> SEQ ID NO 314
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Gly Gly Gly Gly Ser Gly Gly Gly Gly Ser Gly Gly Gly Gly Ser
1               5                   10                  15

<210> SEQ ID NO 315
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Gly Gly Gly Gly Ser Gly Gly Gly Gly Ser Gly Gly Gly Gly Ser Gly
1               5                   10                  15

Gly Gly Gly Ser
            20

<210> SEQ ID NO 316
<211> LENGTH: 1091
<212> TYPE: PRT
<213> ORGANISM: Homo sapiens

<400> SEQUENCE: 316

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

```
Leu Glu Ile Thr Tyr Val Gln Arg Asn Tyr Asp Leu Ser Phe Leu Lys
 65                  70                  75                  80

Thr Ile Gln Glu Val Ala Gly Tyr Val Leu Ile Ala Leu Asn Thr Val
                 85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Gly Gln Lys
        130                 135                 140

Cys Asp Pro Ser Cys Pro Asn Gly Ser Cys Trp Gly Ala Gly Glu Glu
145                 150                 155                 160

Asn Cys Gln Lys Leu Thr Lys Ile Ile Cys Ala Gln Gln Cys Ser Gly
                165                 170                 175

Arg Cys Arg Gly Lys Ser Pro Ser Asp Cys Cys His Asn Gln Cys Ala
            180                 185                 190

Ala Gly Cys Thr Gly Pro Arg Glu Ser Asp Cys Leu Val Cys Arg Lys
            195                 200                 205

Phe Arg Asp Glu Ala Thr Cys Lys Asp Thr Cys Pro Pro Leu Met Leu
210                 215                 220

Tyr Asn Pro Thr Thr Tyr Gln Met Asp Val Asn Pro Glu Gly Lys Tyr
225                 230                 235                 240

Ser Phe Gly Ala Thr Cys Val Lys Lys Cys Pro Arg Asn Tyr Val Val
                245                 250                 255

Thr Asp His Gly Ser Cys Val Arg Ala Cys Gly Ala Asp Ser Tyr Glu
            260                 265                 270

Met Glu Glu Asp Gly Val Arg Lys Cys Lys Lys Cys Glu Gly Pro Cys
        275                 280                 285

Arg Lys Val Cys Asn Gly Ile Gly Ile Gly Glu Phe Lys Asp Ser Leu
        290                 295                 300

Ser Ile Asn Ala Thr Asn Ile Lys His Phe Lys Asn Cys Thr Ser Ile
305                 310                 315                 320

Ser Gly Asp Leu His Ile Leu Pro Val Ala Phe Arg Gly Asp Ser Phe
                325                 330                 335

Thr His Thr Pro Pro Leu Asp Pro Gln Glu Leu Asp Ile Leu Lys Thr
            340                 345                 350

Val Lys Glu Ile Thr Gly Phe Leu Leu Ile Gln Ala Trp Pro Glu Asn
        355                 360                 365

Arg Thr Asp Leu His Ala Phe Glu Asn Leu Glu Ile Ile Arg Gly Arg
        370                 375                 380

Thr Lys Gln His Gly Gln Phe Ser Leu Ala Val Val Ser Leu Asn Ile
385                 390                 395                 400

Thr Ser Leu Gly Leu Arg Ser Leu Lys Glu Ile Ser Asp Gly Asp Val
                405                 410                 415

Ile Ile Ser Gly Asn Lys Asn Leu Cys Tyr Ala Asn Thr Ile Asn Trp
            420                 425                 430

Lys Lys Leu Phe Gly Thr Ser Gly Gln Lys Thr Lys Ile Ile Ser Asn
        435                 440                 445

Arg Gly Glu Asn Ser Cys Lys Ala Thr Gly Gln Val Cys His Ala Leu
        450                 455                 460

Cys Ser Pro Glu Gly Cys Trp Gly Pro Glu Pro Arg Asp Cys Val Ser
465                 470                 475                 480

Cys Arg Asn Val Ser Arg Gly Arg Glu Cys Val Asp Lys Cys Asn Leu
```

```
                485                 490                 495
Leu Glu Gly Glu Pro Arg Glu Phe Val Glu Asn Ser Glu Cys Ile Gln
                500                 505                 510
Cys His Pro Glu Cys Leu Pro Gln Ala Met Asn Ile Thr Cys Thr Gly
                515                 520                 525
Arg Gly Pro Asp Asn Cys Ile Gln Cys Ala His Tyr Ile Asp Gly Pro
            530                 535                 540
His Cys Val Lys Thr Cys Pro Ala Gly Val Met Gly Glu Asn Asn Thr
545                 550                 555                 560
Leu Val Trp Lys Tyr Ala Asp Ala Gly His Val Cys His Leu Cys His
                565                 570                 575
Pro Asn Cys Thr Tyr Gly Cys Thr Gly Pro Gly Leu Glu Gly Cys Pro
            580                 585                 590
Thr Asn Gly Pro Lys Ile Pro Ser Ile Ala Thr Gly Met Val Gly Ala
            595                 600                 605
Leu Leu Leu Leu Leu Val Val Ala Leu Gly Ile Gly Leu Phe Met Arg
            610                 615                 620
Arg Arg His Ile Val Arg Lys Arg Thr Leu Arg Arg Leu Leu Gln Glu
625                 630                 635                 640
Arg Glu Leu Val Glu Pro Leu Thr Pro Ser Gly Glu Ala Pro Asn Gln
                645                 650                 655
Ala Leu Leu Arg Ile Leu Lys Glu Thr Glu Phe Lys Lys Ile Lys Val
            660                 665                 670
Leu Gly Ser Gly Ala Phe Gly Thr Val Tyr Lys Gly Leu Trp Ile Pro
            675                 680                 685
Glu Gly Glu Lys Val Lys Ile Pro Val Ala Ile Lys Glu Leu Arg Glu
            690                 695                 700
Ala Thr Ser Pro Lys Ala Asn Lys Glu Ile Leu Asp Glu Ala Tyr Val
705                 710                 715                 720
Met Ala Ser Val Asp Asn Pro His Val Cys Arg Leu Leu Gly Ile Cys
                725                 730                 735
Leu Thr Ser Thr Val Gln Leu Ile Thr Gln Leu Met Pro Phe Gly Cys
            740                 745                 750
Leu Leu Asp Tyr Val Arg Glu His Lys Asp Asn Ile Gly Ser Gln Tyr
            755                 760                 765
Leu Leu Asn Trp Cys Val Gln Ile Ala Lys Gly Met Asn Tyr Leu Glu
            770                 775                 780
Asp Arg Arg Leu Val His Arg Asp Leu Ala Ala Arg Asn Val Leu Val
785                 790                 795                 800
Lys Thr Pro Gln His Val Lys Ile Thr Asp Phe Gly Leu Ala Lys Leu
                805                 810                 815
Leu Gly Ala Glu Glu Lys Glu Tyr His Ala Glu Gly Gly Lys Val Pro
            820                 825                 830
Ile Lys Trp Met Ala Leu Glu Ser Ile Leu His Arg Ile Tyr Thr His
            835                 840                 845
Gln Ser Asp Val Trp Ser Tyr Gly Val Thr Val Trp Glu Leu Met Thr
850                 855                 860
Phe Gly Ser Lys Pro Tyr Asp Gly Ile Pro Ala Ser Glu Ile Ser Ser
865                 870                 875                 880
Ile Leu Glu Lys Gly Glu Arg Leu Pro Gln Pro Pro Ile Cys Thr Ile
                885                 890                 895
Asp Val Tyr Met Ile Met Val Lys Cys Trp Met Ile Asp Ala Asp Ser
            900                 905                 910
```

```
Arg Pro Lys Phe Arg Glu Leu Ile Ile Glu Phe Ser Lys Met Ala Arg
        915                 920                 925

Asp Pro Gln Arg Tyr Leu Val Ile Gln Gly Asp Glu Arg Met His Leu
    930                 935                 940

Pro Ser Pro Thr Asp Ser Asn Phe Tyr Arg Ala Leu Met Asp Glu Glu
945                 950                 955                 960

Asp Met Asp Asp Val Val Asp Ala Asp Glu Tyr Leu Ile Pro Gln Gln
                965                 970                 975

Gly Phe Phe Ser Ser Pro Ser Thr Ser Arg Thr Pro Leu Leu Ser Ser
            980                 985                 990

Leu Ser Ala Thr Ser Asn Asn Ser Thr Val Ala Cys Ile Asp Arg Asn
        995                 1000                1005

Gly Leu Gln Ser Cys Pro Ile Lys Glu Asp Ser Phe Leu Gln Arg
    1010                1015                1020

Tyr Ser Ser Asp Pro Thr Gly Ala Leu Thr Glu Asp Ser Ile Asp
    1025                1030                1035

Asp Thr Phe Leu Pro Val Pro Gly Glu Trp Leu Val Trp Lys Gln
    1040                1045                1050

Ser Cys Ser Ser Thr Ser Ser Thr His Ser Ala Ala Ala Ser Leu
    1055                1060                1065

Gln Cys Pro Ser Gln Val Leu Pro Pro Ala Ser Pro Glu Gly Glu
    1070                1075                1080

Thr Val Ala Asp Leu Gln Thr Gln
    1085                1090

<210> SEQ ID NO 317
<211> LENGTH: 1210
<212> TYPE: PRT
<213> ORGANISM: Mus musculus

<400> SEQUENCE: 317

Met Arg Pro Ser Gly Thr Ala Arg Thr Thr Leu Leu Val Leu Leu Thr
1               5                   10                  15

Ala Leu Cys Ala Ala Gly Gly Ala Leu Glu Glu Lys Lys Val Cys Gln
            20                  25                  30

Gly Thr Ser Asn Arg Leu Thr Gln Leu Gly Thr Phe Glu Asp His Phe
        35                  40                  45

Leu Ser Leu Gln Arg Met Tyr Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Ala Leu
            100                 105                 110

Tyr Glu Asn Thr Tyr Ala Leu Ala Ile Leu Ser Asn Tyr Gly Thr Asn
        115                 120                 125

Arg Thr Gly Leu Arg Glu Leu Pro Met Arg Asn Leu Gln Glu Ile Leu
    130                 135                 140

Ile Gly Ala Val Arg Phe Ser Asn Asn Pro Ile Leu Cys Asn Met Asp
145                 150                 155                 160

Thr Ile Gln Trp Arg Asp Ile Val Gln Asn Val Phe Met Ser Asn Met
                165                 170                 175

Ser Met Asp Leu Gln Ser His Pro Ser Ser Cys Pro Lys Cys Asp Pro
```

-continued

```
                180             185             190
Ser Cys Pro Asn Gly Ser Cys Trp Gly Gly Glu Glu Asn Cys Gln
            195                 200                 205

Lys Leu Thr Lys Ile Ile Cys Ala Gln Gln Cys Ser His Arg Cys Arg
        210                 215                 220

Gly Arg Ser Pro Ser Asp Cys Cys His Asn Gln Cys Ala Ala Gly Cys
225                 230                 235                 240

Thr Gly Pro Arg Glu Ser Asp Cys Leu Val Cys Gln Lys Phe Gln Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
            290                 295                 300

Gly Ser Cys Val Arg Ala Cys Gly Pro Asp Tyr Tyr Glu Val Glu Glu
305                 310                 315                 320

Asp Gly Ile Arg Lys Cys Lys Lys Cys Asp Gly Pro Cys Arg Lys Val
                325                 330                 335

Cys Asn Gly Ile Gly Ile Gly Glu Phe Lys Asp Thr Leu Ser Ile Asn
                340                 345                 350

Ala Thr Asn Ile Lys His Phe Lys Tyr Cys Thr Ala Ile Ser Gly Asp
            355                 360                 365

Leu His Ile Leu Pro Val Ala Phe Lys Gly Asp Ser Phe Thr Arg Thr
        370                 375                 380

Pro Pro Leu Asp Pro Arg Glu Leu Glu Ile Leu Lys Thr Val Lys Glu
385                 390                 395                 400

Ile Thr Gly Phe Leu Leu Ile Gln Ala Trp Pro Asp Asn Trp Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Gly Leu Asn Ile Thr Ser Leu
        435                 440                 445

Gly Leu Arg Ser Leu Lys Glu Ile Ser Asp Gly Asp Val Ile Ile Ser
        450                 455                 460

Gly Asn Arg Asn Leu Cys Tyr Ala Asn Thr Ile Asn Trp Lys Lys Leu
465                 470                 475                 480

Phe Gly Thr Pro Asn Gln Lys Thr Lys Ile Met Asn Asn Arg Ala Glu
                485                 490                 495

Lys Asp Cys Lys Ala Val Asn His Val Cys Asn Pro Leu Cys Ser Ser
            500                 505                 510

Glu Gly Cys Trp Gly Pro Glu Pro Arg Asp Cys Val Ser Cys Gln Asn
        515                 520                 525

Val Ser Arg Gly Arg Glu Cys Val Glu Lys Cys Asn Ile Leu Glu Gly
        530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
            565                 570                 575

Asp Asn Cys Ile Gln Cys Ala His Tyr Ile Asp Gly Pro His Cys Val
            580                 585                 590

Lys Thr Cys Pro Ala Gly Ile Met Gly Glu Asn Asn Thr Leu Val Trp
            595                 600                 605
```

```
Lys Tyr Ala Asp Ala Asn Asn Val Cys His Leu Cys His Ala Asn Cys
        610                 615                 620
Thr Tyr Gly Cys Ala Gly Pro Gly Leu Gln Gly Cys Glu Val Trp Pro
625                 630                 635                 640
Ser Gly Pro Lys Ile Pro Ser Ile Ala Thr Gly Ile Val Gly Gly Leu
                645                 650                 655
Leu Phe Ile Val Val Ala Leu Gly Ile Gly Leu Phe Met Arg Arg
        660                 665                 670
Arg His Ile Val Arg Lys Arg Thr Leu Arg Arg Leu Leu Gln Glu Arg
        675                 680                 685
Glu Leu Val Glu Pro Leu Thr Pro Ser Gly Glu Ala Pro Asn Gln Ala
690                 695                 700
His Leu Arg Ile Leu Lys Glu Thr Glu Phe Lys Lys Ile Lys Val Leu
705                 710                 715                 720
Gly Ser Gly Ala Phe Gly Thr Val Tyr Lys Gly Leu Trp Ile Pro Glu
                725                 730                 735
Gly Glu Lys Val Lys Ile Pro Val Ala Ile Lys Glu Leu Arg Glu Ala
                740                 745                 750
Thr Ser Pro Lys Ala Asn Lys Glu Ile Leu Asp Glu Ala Tyr Val Met
        755                 760                 765
Ala Ser Val Asp Asn Pro His Val Cys Arg Leu Leu Gly Ile Cys Leu
770                 775                 780
Thr Ser Thr Val Gln Leu Ile Thr Gln Leu Met Pro Tyr Gly Cys Leu
785                 790                 795                 800
Leu Asp Tyr Val Arg Glu His Lys Asp Asn Ile Gly Ser Gln Tyr Leu
                805                 810                 815
Leu Asn Trp Cys Val Gln Ile Ala Lys Gly Met Asn Tyr Leu Glu Asp
                820                 825                 830
Arg Arg Leu Val His Arg Asp Leu Ala Ala Arg Asn Val Leu Val Lys
        835                 840                 845
Thr Pro Gln His Val Lys Ile Thr Asp Phe Gly Leu Ala Lys Leu Leu
850                 855                 860
Gly Ala Glu Glu Lys Glu Tyr His Ala Glu Gly Gly Lys Val Pro Ile
865                 870                 875                 880
Lys Trp Met Ala Leu Glu Ser Ile Leu His Arg Ile Tyr Thr His Gln
                885                 890                 895
Ser Asp Val Trp Ser Tyr Gly Val Thr Val Trp Glu Leu Met Thr Phe
        900                 905                 910
Gly Ser Lys Pro Tyr Asp Gly Ile Pro Ala Ser Asp Ile Ser Ser Ile
        915                 920                 925
Leu Glu Lys Gly Glu Arg Leu Pro Gln Pro Ile Cys Thr Ile Asp
930                 935                 940
Val Tyr Met Ile Met Val Lys Cys Trp Met Ile Asp Ala Asp Ser Arg
945                 950                 955                 960
Pro Lys Phe Arg Glu Leu Ile Leu Glu Phe Ser Lys Met Ala Arg Asp
                965                 970                 975
Pro Gln Arg Tyr Leu Val Ile Gln Gly Asp Glu Arg Met His Leu Pro
                980                 985                 990
Ser Pro Thr Asp Ser Asn Phe Tyr Arg Ala Leu Met Asp Glu Glu Asp
        995                 1000                1005
Met Glu Asp Val Val Asp Ala Asp Glu Tyr Leu Ile Pro Gln Gln
    1010                1015                1020
```

```
Gly Phe Phe Asn Ser Pro Ser Thr Ser Arg Thr Pro Leu Leu Ser
    1025                1030                1035

Ser Leu Ser Ala Thr Ser Asn Asn Ser Thr Val Ala Cys Ile Asn
    1040                1045                1050

Arg Asn Gly Ser Cys Arg Val Lys Glu Asp Ala Phe Leu Gln Arg
    1055                1060                1065

Tyr Ser Ser Asp Pro Thr Gly Ala Val Thr Glu Asp Asn Ile Asp
    1070                1075                1080

Asp Ala Phe Leu Pro Val Pro Glu Tyr Val Asn Gln Ser Val Pro
    1085                1090                1095

Lys Arg Pro Ala Gly Ser Val Gln Asn Pro Val Tyr His Asn Gln
    1100                1105                1110

Pro Leu His Pro Ala Pro Gly Arg Asp Leu His Tyr Gln Asn Pro
    1115                1120                1125

His Ser Asn Ala Val Gly Asn Pro Glu Tyr Leu Asn Thr Ala Gln
    1130                1135                1140

Pro Thr Cys Leu Ser Ser Gly Phe Asn Ser Pro Ala Leu Trp Ile
    1145                1150                1155

Gln Lys Gly Ser His Gln Met Ser Leu Asp Asn Pro Asp Tyr Gln
    1160                1165                1170

Gln Asp Phe Phe Pro Lys Glu Thr Lys Pro Asn Gly Ile Phe Lys
    1175                1180                1185

Gly Pro Thr Ala Glu Asn Ala Glu Tyr Leu Arg Val Ala Pro Pro
    1190                1195                1200

Ser Ser Glu Phe Ile Gly Ala
    1205                1210

<210> SEQ ID NO 318
<211> LENGTH: 1210
<212> TYPE: PRT
<213> ORGANISM: Macaca fascicularis

<400> SEQUENCE: 318

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Glu Phe Leu Ser Asn Met
                165                 170                 175
```

```
Ser Met Asp Phe Gln Asn His Leu Gly Ser Cys Gln Lys Cys Asp Pro
        180                 185                 190
Ser Cys Pro Asn Gly Ser Cys Trp Gly Ala Gly Glu Glu Asn Cys Gln
        195                 200                 205
Lys Leu Thr Lys Ile Ile Cys Ala Gln Gln Cys Ser Gly Arg Cys Arg
        210                 215                 220
Gly Lys Ser Pro Ser Asp Cys Cys His Asn Gln Cys Ala Ala Gly Cys
225                 230                 235                 240
Thr Gly Pro Arg Glu Ser Asp Cys Leu Val Cys Arg Lys Phe Arg Asp
                245                 250                 255
Glu Ala Thr Cys Lys Asp Thr Cys Pro Pro Leu Met Leu Tyr Asn Pro
            260                 265                 270
Thr Thr Tyr Gln Met Asp Val Asn Pro Glu Gly Lys Tyr Ser Phe Gly
        275                 280                 285
Ala Thr Cys Val Lys Lys Cys Pro Arg Asn Tyr Val Val Thr Asp His
        290                 295                 300
Gly Ser Cys Val Arg Ala Cys Gly Ala Asp Ser Tyr Glu Met Glu Glu
305                 310                 315                 320
Asp Gly Val Arg Lys Cys Lys Lys Cys Glu Gly Pro Cys Arg Lys Val
                325                 330                 335
Cys Asn Gly Ile Gly Ile Gly Glu Phe Lys Asp Thr Leu Ser Ile Asn
            340                 345                 350
Ala Thr Asn Ile Lys His Phe Lys Asn Cys Thr Ser Ile Ser Gly Asp
        355                 360                 365
Leu His Ile Leu Pro Val Ala Phe Arg Gly Asp Ser Phe Thr His Thr
        370                 375                 380
Pro Pro Leu Asp Pro Gln Glu Leu Asp Ile Leu Lys Thr Val Lys Glu
385                 390                 395                 400
Ile Thr Gly Phe Leu Leu Ile Gln Ala Trp Pro Glu Asn Arg Thr Asp
                405                 410                 415
Leu His Ala Phe Glu Asn Leu Glu Ile Ile Arg Gly Arg Thr Lys Gln
            420                 425                 430
His Gly Gln Phe Ser Leu Ala Val Val Ser Leu Asn Ile Thr Ser Leu
        435                 440                 445
Gly Leu Arg Ser Leu Lys Glu Ile Ser Asp Gly Asp Val Ile Ile Ser
450                 455                 460
Gly Asn Lys Asn Leu Cys Tyr Ala Asn Thr Ile Asn Trp Lys Lys Leu
465                 470                 475                 480
Phe Gly Thr Ser Ser Gln Lys Thr Lys Ile Ile Ser Asn Arg Gly Glu
                485                 490                 495
Asn Ser Cys Lys Ala Thr Gly Gln Val Cys His Ala Leu Cys Ser Pro
            500                 505                 510
Glu Gly Cys Trp Gly Pro Glu Pro Arg Asp Cys Val Ser Cys Gln Asn
        515                 520                 525
Val Ser Arg Gly Arg Glu Cys Val Asp Lys Cys Asn Ile Leu Glu Gly
        530                 535                 540
Glu Pro Arg Glu Phe Val Glu Asn Ser Glu Cys Ile Gln Cys His Pro
545                 550                 555                 560
Glu Cys Leu Pro Gln Val Met Asn Ile Thr Cys Thr Gly Arg Gly Pro
                565                 570                 575
Asp Asn Cys Ile Gln Cys Ala His Tyr Ile Asp Gly Pro His Cys Val
            580                 585                 590
```

```
Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
        610                 615                 620

Thr Tyr Gly Cys Thr Gly Pro Gly Leu Glu Gly Cys Ala Arg Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala  Leu Met Asp Glu Glu  Asp Met Asp
        995                 1000                1005

Asp Val  Val Asp Ala Asp Glu  Tyr Leu Ile Pro Gln  Gln Gly Phe
```

```
                    1010                1015                1020

Phe Ser  Ser Pro Ser Thr Ser  Arg Thr Pro Leu Leu  Ser Ser Leu
    1025                1030                1035

Ser Ala  Thr Ser Asn Asn Ser  Thr Val Ala Cys Ile  Asp Arg Asn
    1040                1045                1050

Gly Leu  Gln Ser Cys Pro Ile  Lys Glu Asp Ser Phe  Leu Gln Arg
    1055                1060                1065

Tyr Ser  Ser Asp Pro Thr Gly  Ala Leu Thr Glu Asp  Ser Ile Asp
    1070                1075                1080

Asp Thr  Phe Leu Pro Val Pro  Glu Tyr Ile Asn Gln  Ser Val Pro
    1085                1090                1095

Lys Arg  Pro Ala Gly Ser Val  Gln Asn Pro Val Tyr  His Asn Gln
    1100                1105                1110

Pro Leu  Asn Pro Ala Pro Ser  Arg Asp Pro His Tyr  Gln Asp Pro
    1115                1120                1125

His Ser  Thr Ala Val Gly Asn  Pro Glu Tyr Leu Asn  Thr Val Gln
    1130                1135                1140

Pro Thr  Cys Val Asn Ser Thr  Phe Asp Ser Pro Ala  His Trp Ala
    1145                1150                1155

Gln Lys  Gly Ser His Gln Ile  Ser Leu Asp Asn Pro  Asp Tyr Gln
    1160                1165                1170

Gln Asp  Phe Phe Pro Lys Glu  Ala Lys Pro Asn Gly  Ile Phe Lys
    1175                1180                1185

Gly Ser  Thr Ala Glu Asn Ala  Glu Tyr Leu Arg Val  Ala Pro Gln
    1190                1195                1200

Ser Ser  Glu Phe Ile Gly Ala
    1205                1210

<210> SEQ ID NO 319
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 319

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Ala Tyr Ile Tyr
            20                  25                  30

Thr Met Asp Trp Tyr Arg Gln Ala Pro Gly Lys Gln Arg Glu Leu Val
        35                  40                  45

Ala Thr Ser Thr Arg Asp Gly Asn Val Asp Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Leu Arg Thr Ala Val Asp Leu Ile Arg Ala Asn Tyr Trp Gly
            100                 105                 110

Gln Gly Thr Gln Val Thr Val Ser Ser Gly Gly Gly Ser Gly Gly
        115                 120                 125

Gly Ser Glu Val Gln Leu Val Glu Ser Gly Gly Gly Leu Val Gln Pro
    130                 135                 140
```

Gly Asn Ser Leu Arg Leu Ser Cys Ala Ala Ser Gly Phe Thr Phe Ser
145                 150                 155                 160

Lys Phe Gly Met Ser Trp Val Arg Gln Ala Pro Gly Lys Gly Leu Glu
                165                 170                 175

Trp Val Ser Ser Ile Ser Gly Ser Gly Arg Asp Thr Leu Tyr Ala Asp
            180                 185                 190

Ser Val Lys Gly Arg Phe Thr Ile Ser Arg Asp Asn Ala Lys Thr Thr
        195                 200                 205

Leu Tyr Leu Gln Met Asn Ser Leu Arg Pro Glu Asp Thr Ala Val Tyr
    210                 215                 220

Tyr Cys Thr Ile Gly Gly Ser Leu Ser Val Ser Ser Gln Gly Thr Leu
225                 230                 235                 240

Val Thr Val Ser Ser Gly Gly Gly Gly Ser Gly Gly Gly Ser Glu Val
                245                 250                 255

Gln Leu Val Glu Ser Gly Gly Gly Leu Val Gln Pro Gly Gly Ser Leu
                260                 265                 270

Lys Leu Ser Cys Ala Ala Ser Gly Phe Thr Phe Asn Lys Tyr Ala Ile
            275                 280                 285

Asn Trp Val Arg Gln Ala Pro Gly Lys Gly Leu Glu Trp Val Ala Arg
        290                 295                 300

Ile Arg Ser Lys Tyr Asn Asn Tyr Ala Thr Tyr Tyr Ala Asp Gln Val
305                 310                 315                 320

Lys Asp Arg Phe Thr Ile Ser Arg Asp Asp Ser Lys Asn Thr Ala Tyr
                325                 330                 335

Leu Gln Met Asn Asn Leu Lys Thr Glu Asp Thr Ala Val Tyr Tyr Cys
                340                 345                 350

Val Arg His Ala Asn Phe Gly Asn Ser Tyr Ile Ser Tyr Trp Ala Tyr
            355                 360                 365

Trp Gly Gln Gly Thr Leu Val Thr Val Ser Ser Gly Gly Gly Gly Ser
        370                 375                 380

Gly Gly Gly Gly Ser Gly Gly Gly Ser Gln Thr Val Val Thr Gln
385                 390                 395                 400

Glu Pro Ser Leu Thr Val Ser Pro Gly Gly Thr Val Thr Leu Thr Cys
                405                 410                 415

Ala Ser Ser Thr Gly Ala Val Thr Ser Gly Asn Tyr Pro Asn Trp Val
            420                 425                 430

Gln Gln Lys Pro Gly Gln Ala Pro Arg Gly Leu Ile Gly Gly Thr Lys
        435                 440                 445

Phe Leu Val Pro Gly Thr Pro Ala Arg Phe Ser Gly Ser Leu Leu Gly
450                 455                 460

Gly Lys Ala Ala Leu Thr Leu Ser Gly Val Gln Pro Glu Asp Glu Ala
465                 470                 475                 480

Glu Tyr Tyr Cys Thr Leu Trp Tyr Ser Asn Arg Trp Val Phe Gly Gly
                485                 490                 495

Gly Thr Lys Leu Thr Val Leu His His His His His
            500                 505

<210> SEQ ID NO 320
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 320

-continued

```
Gln Val Gln Leu Gln Glu Ser Gly Gly Gly Leu Val Gln Ala Gly Asp
1               5                   10                  15
Ser Leu Arg Leu Ser Cys Val Val Ser Gly Arg Thr Asp Ser Trp Tyr
            20                  25                  30
Val Met Gly Trp Phe Arg Gln Ala Pro Gly Lys Asp Arg Glu Phe Val
        35                  40                  45
Ala Gly Val Ser Trp Ser Tyr Gly Asn Thr Tyr Tyr Ala Asp Ser Val
    50                  55                  60
Lys Gly Arg Phe Thr Ala Ser Arg Asp Asn Ala Lys Asn Thr Ala Tyr
65                  70                  75                  80
Leu Gln Met Asn Ser Leu Asn Ala Glu Asp Thr Ala Val Tyr Tyr Cys
                85                  90                  95
Ala Ala Arg Val Ser Arg Glu Val Ile Pro Thr Arg Trp Asp Leu Tyr
            100                 105                 110
Asn Tyr Trp Gly Gln Gly Thr Gln Val Thr Val Ser Ser Gly Gly Gly
        115                 120                 125
Gly Ser Gly Gly Gly Ser Glu Val Gln Leu Val Glu Ser Gly Gly Gly
    130                 135                 140
Leu Val Gln Pro Gly Asn Ser Leu Arg Leu Ser Cys Ala Ala Ser Gly
145                 150                 155                 160
Phe Thr Phe Ser Lys Phe Gly Met Ser Trp Val Arg Gln Ala Pro Gly
                165                 170                 175
Lys Gly Leu Glu Trp Val Ser Ser Ile Ser Gly Ser Gly Arg Asp Thr
            180                 185                 190
Leu Tyr Ala Asp Ser Val Lys Gly Arg Phe Thr Ile Ser Arg Asp Asn
        195                 200                 205
Ala Lys Thr Thr Leu Tyr Leu Gln Met Asn Ser Leu Arg Pro Glu Asp
    210                 215                 220
Thr Ala Val Tyr Tyr Cys Thr Ile Gly Gly Ser Leu Ser Val Ser Ser
225                 230                 235                 240
Gln Gly Thr Leu Val Thr Val Ser Ser Gly Gly Gly Ser Gly Gly Gly
                245                 250                 255
Gly Ser Glu Val Gln Leu Val Glu Ser Gly Gly Gly Leu Val Gln Pro
            260                 265                 270
Gly Gly Ser Leu Lys Leu Ser Cys Ala Ala Ser Gly Phe Thr Phe Asn
        275                 280                 285
Lys Tyr Ala Ile Asn Trp Val Arg Gln Ala Pro Gly Lys Gly Leu Glu
    290                 295                 300
Trp Val Ala Arg Ile Arg Ser Lys Tyr Asn Asn Tyr Ala Thr Tyr Tyr
305                 310                 315                 320
Ala Asp Gln Val Lys Asp Arg Phe Thr Ile Ser Arg Asp Asp Ser Lys
                325                 330                 335
Asn Thr Ala Tyr Leu Gln Met Asn Asn Leu Lys Thr Glu Asp Thr Ala
            340                 345                 350
Val Tyr Tyr Cys Val Arg His Ala Asn Phe Gly Asn Ser Tyr Ile Ser
        355                 360                 365
Tyr Trp Ala Tyr Trp Gly Gln Gly Thr Leu Val Thr Val Ser Ser Gly
    370                 375                 380
Gly Gly Ser Gly Gly Gly Gly Ser Gly Gly Gly Ser Gln Thr
385                 390                 395                 400
Val Val Thr Gln Glu Pro Ser Leu Thr Val Ser Pro Gly Gly Thr Val
                405                 410                 415
```

```
Thr Leu Thr Cys Ala Ser Ser Thr Gly Ala Val Ser Gly Asn Tyr
            420                 425                 430
Pro Asn Trp Val Gln Gln Lys Pro Gly Gln Ala Pro Arg Gly Leu Ile
        435                 440                 445
Gly Gly Thr Lys Phe Leu Val Pro Gly Thr Pro Ala Arg Phe Ser Gly
450                 455                 460
Ser Leu Leu Gly Gly Lys Ala Ala Leu Thr Leu Ser Gly Val Gln Pro
465                 470                 475                 480
Glu Asp Glu Ala Glu Tyr Tyr Cys Thr Leu Trp Tyr Ser Asn Arg Trp
                485                 490                 495
Val Phe Gly Gly Gly Thr Lys Leu Thr Val Leu His His His His
                500                 505                 510
His
```

<210> SEQ ID NO 321
<211> LENGTH: 502
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 321

```
Gln Val Gln Leu Gln Glu Ser Gly Gly Gly Ser Val Gln Pro Gly Gly
1               5                   10                  15
Ser Leu Arg Val Ser Cys Val Val Ser Arg Thr Ile Ile Ser Ile Asn
            20                  25                  30
Ala Met Thr Trp Tyr His Gln Ala Pro Gly Lys Arg Arg Glu Leu Val
        35                  40                  45
Ala Ile Ile Thr Ser Gly Gly Glu Thr Asn Tyr Ala Asp Ser Val Lys
    50                  55                  60
Gly Arg Phe Thr Ile Ser Arg Asp Asn Ala Lys Asn Thr Ala Tyr Leu
65                  70                  75                  80
Gln Met Asn Asn Leu Lys Pro Glu Asp Thr Gly Val Tyr Tyr Cys Asn
                85                  90                  95
Val Val Pro Pro Leu Gly Ser Trp Gly Gln Gly Thr Gln Val Thr Val
            100                 105                 110
Ser Ser Gly Gly Gly Gly Ser Gly Gly Gly Ser Glu Val Gln Leu Val
        115                 120                 125
Glu Ser Gly Gly Gly Leu Val Gln Pro Gly Asn Ser Leu Arg Leu Ser
    130                 135                 140
Cys Ala Ala Ser Gly Phe Thr Phe Ser Lys Phe Gly Met Ser Trp Val
145                 150                 155                 160
Arg Gln Ala Pro Gly Lys Gly Leu Glu Trp Val Ser Ser Ile Ser Gly
                165                 170                 175
Ser Gly Arg Asp Thr Leu Tyr Ala Asp Ser Val Lys Gly Arg Phe Thr
            180                 185                 190
Ile Ser Arg Asp Asn Ala Lys Thr Thr Leu Tyr Leu Gln Met Asn Ser
        195                 200                 205
Leu Arg Pro Glu Asp Thr Ala Val Tyr Tyr Cys Thr Ile Gly Gly Ser
    210                 215                 220
Leu Ser Val Ser Ser Gln Gly Thr Leu Val Thr Val Ser Ser Gly Gly
225                 230                 235                 240
Gly Gly Ser Gly Gly Gly Ser Glu Val Gln Leu Val Glu Ser Gly Gly
                245                 250                 255
```

```
Gly Leu Val Gln Pro Gly Gly Ser Leu Lys Leu Ser Cys Ala Ala Ser
            260                 265                 270

Gly Phe Thr Phe Asn Lys Tyr Ala Ile Asn Trp Val Arg Gln Ala Pro
        275                 280                 285

Gly Lys Gly Leu Glu Trp Val Ala Arg Ile Arg Ser Lys Tyr Asn Asn
    290                 295                 300

Tyr Ala Thr Tyr Tyr Ala Asp Gln Val Lys Asp Arg Phe Thr Ile Ser
305                 310                 315                 320

Arg Asp Asp Ser Lys Asn Thr Ala Tyr Leu Gln Met Asn Asn Leu Lys
                325                 330                 335

Thr Glu Asp Thr Ala Val Tyr Tyr Cys Val Arg His Ala Asn Phe Gly
            340                 345                 350

Asn Ser Tyr Ile Ser Tyr Trp Ala Tyr Trp Gly Gln Gly Thr Leu Val
        355                 360                 365

Thr Val Ser Ser Gly Gly Gly Gly Ser Gly Gly Gly Gly Ser Gly Gly
    370                 375                 380

Gly Gly Ser Gln Thr Val Val Thr Gln Glu Pro Ser Leu Thr Val Ser
385                 390                 395                 400

Pro Gly Gly Thr Val Thr Leu Thr Cys Ala Ser Ser Thr Gly Ala Val
                405                 410                 415

Thr Ser Gly Asn Tyr Pro Asn Trp Val Gln Gln Lys Pro Gly Gln Ala
            420                 425                 430

Pro Arg Gly Leu Ile Gly Gly Thr Lys Phe Leu Val Pro Gly Thr Pro
        435                 440                 445

Ala Arg Phe Ser Gly Ser Leu Leu Gly Gly Lys Ala Ala Leu Thr Leu
    450                 455                 460

Ser Gly Val Gln Pro Glu Asp Glu Ala Glu Tyr Tyr Cys Thr Leu Trp
465                 470                 475                 480

Tyr Ser Asn Arg Trp Val Phe Gly Gly Gly Thr Lys Leu Thr Val Leu
                485                 490                 495

His His His His His His
            500

<210> SEQ ID NO 322
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 322

Gln Val Gln Leu Gln Glu Ser Gly Gly Gly Arg Val Gln Ala Gly Gly
1               5                   10                  15

Ser Leu Arg Leu Ser Cys Ser Ala Ser Ala Arg Thr Leu Arg Leu Tyr
            20                  25                  30

Ala Val Gly Trp Phe Arg Gln Ala Pro Gly Lys Glu Arg Glu Phe Val
        35                  40                  45

Ala Gly Ile Gly Arg Ser Glu Arg Thr Tyr Tyr Thr Asp Ser Val Lys
    50                  55                  60

Gly Arg Phe Thr Leu Ser Arg Asp Asn Ala Lys Asn Thr Val Phe Leu
65                  70                  75                  80

Glu Met Asn Asp Leu Glu Pro Glu Asp Thr Ala Val Tyr Phe Cys Ala
                85                  90                  95

Leu Thr Phe Gln Thr Thr Asp Met Val Asp Val Pro Thr Thr Gln His
            100                 105                 110
```

Glu Tyr Asp Tyr Trp Gly Arg Gly Thr Gln Val Thr Val Ser Ser Gly
            115                 120                 125

Gly Gly Gly Ser Gly Gly Gly Ser Glu Val Gln Leu Val Glu Ser Gly
        130                 135                 140

Gly Gly Leu Val Gln Pro Gly Asn Ser Leu Arg Leu Ser Cys Ala Ala
145                 150                 155                 160

Ser Gly Phe Thr Phe Ser Lys Phe Gly Met Ser Trp Val Arg Gln Ala
                165                 170                 175

Pro Gly Lys Gly Leu Glu Trp Val Ser Ser Ile Ser Gly Ser Gly Arg
            180                 185                 190

Asp Thr Leu Tyr Ala Asp Ser Val Lys Gly Arg Phe Thr Ile Ser Arg
        195                 200                 205

Asp Asn Ala Lys Thr Thr Leu Tyr Leu Gln Met Asn Ser Leu Arg Pro
    210                 215                 220

Glu Asp Thr Ala Val Tyr Tyr Cys Thr Ile Gly Gly Ser Leu Ser Val
225                 230                 235                 240

Ser Ser Gln Gly Thr Leu Val Thr Val Ser Ser Gly Gly Gly Gly Ser
                245                 250                 255

Gly Gly Gly Ser Glu Val Gln Leu Val Glu Ser Gly Gly Gly Leu Val
            260                 265                 270

Gln Pro Gly Gly Ser Leu Lys Leu Ser Cys Ala Ala Ser Gly Phe Thr
        275                 280                 285

Phe Asn Lys Tyr Ala Ile Asn Trp Val Arg Gln Ala Pro Gly Lys Gly
    290                 295                 300

Leu Glu Trp Val Ala Arg Ile Arg Ser Lys Tyr Asn Asn Tyr Ala Thr
305                 310                 315                 320

Tyr Tyr Ala Asp Gln Val Lys Asp Arg Phe Thr Ile Ser Arg Asp Asp
                325                 330                 335

Ser Lys Asn Thr Ala Tyr Leu Gln Met Asn Asn Leu Lys Thr Glu Asp
            340                 345                 350

Thr Ala Val Tyr Tyr Cys Val Arg His Ala Asn Phe Gly Asn Ser Tyr
        355                 360                 365

Ile Ser Tyr Trp Ala Tyr Trp Gly Gln Gly Thr Leu Val Thr Val Ser
    370                 375                 380

Ser Gly Gly Gly Gly Ser Gly Gly Gly Gly Ser Gly Gly Gly Gly Ser
385                 390                 395                 400

Gln Thr Val Val Thr Gln Glu Pro Ser Leu Thr Val Ser Pro Gly Gly
                405                 410                 415

Thr Val Thr Leu Thr Cys Ala Ser Ser Thr Gly Ala Val Thr Ser Gly
            420                 425                 430

Asn Tyr Pro Asn Trp Val Gln Gln Lys Pro Gly Gln Ala Pro Arg Gly
        435                 440                 445

Leu Ile Gly Gly Thr Lys Phe Leu Val Pro Gly Thr Pro Ala Arg Phe
450                 455                 460

Ser Gly Ser Leu Leu Gly Gly Lys Ala Ala Leu Thr Leu Ser Gly Val
465                 470                 475                 480

Gln Pro Glu Asp Glu Ala Glu Tyr Tyr Cys Thr Leu Trp Tyr Ser Asn
                485                 490                 495

Arg Trp Val Phe Gly Gly Gly Thr Lys Leu Thr Val Leu His His
            500                 505                 510

His His His
        515

<210> SEQ ID NO 323
<211> LENGTH: 509
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 323

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Ala Tyr Ile Tyr
            20                  25                  30

Thr Met Asp Trp Tyr Arg Gln Ala Pro Gly Lys Gln Arg Glu Leu Val
        35                  40                  45

Ala Thr Ser Thr His Asp Gly Asn Thr Asp Tyr Ala Asp Ser Val Lys
    50                  55                  60

Gly Arg Phe Thr Ile Ser Arg Asp Asn Val Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Leu Arg Thr Ala Val Asp Leu Ile Arg Ala Asn Tyr Trp Gly
            100                 105                 110

Gln Gly Thr Gln Val Thr Val Ser Ser Gly Gly Gly Ser Gly Gly
        115                 120                 125

Gly Ser Glu Val Gln Leu Val Glu Ser Gly Gly Gly Leu Val Gln Pro
    130                 135                 140

Gly Asn Ser Leu Arg Leu Ser Cys Ala Ala Ser Gly Phe Thr Phe Ser
145                 150                 155                 160

Lys Phe Gly Met Ser Trp Val Arg Gln Ala Pro Gly Lys Gly Leu Glu
                165                 170                 175

Trp Val Ser Ser Ile Ser Gly Ser Gly Arg Asp Thr Leu Tyr Ala Asp
            180                 185                 190

Ser Val Lys Gly Arg Phe Thr Ile Ser Arg Asp Asn Ala Lys Thr Thr
        195                 200                 205

Leu Tyr Leu Gln Met Asn Ser Leu Arg Pro Glu Asp Thr Ala Val Tyr
    210                 215                 220

Tyr Cys Thr Ile Gly Gly Ser Leu Ser Val Ser Ser Gln Gly Thr Leu
225                 230                 235                 240

Val Thr Val Ser Ser Gly Gly Gly Gly Ser Gly Gly Gly Ser Glu Val
                245                 250                 255

Gln Leu Val Glu Ser Gly Gly Gly Leu Val Gln Pro Gly Gly Ser Leu
            260                 265                 270

Lys Leu Ser Cys Ala Ala Ser Gly Phe Thr Phe Asn Lys Tyr Ala Ile
        275                 280                 285

Asn Trp Val Arg Gln Ala Pro Gly Lys Gly Leu Glu Trp Val Ala Arg
    290                 295                 300

Ile Arg Ser Lys Tyr Asn Asn Tyr Ala Thr Tyr Tyr Ala Asp Gln Val
305                 310                 315                 320

Lys Asp Arg Phe Thr Ile Ser Arg Asp Asp Ser Lys Asn Thr Ala Tyr
                325                 330                 335

Leu Gln Met Asn Asn Leu Lys Thr Glu Asp Thr Ala Val Tyr Tyr Cys
            340                 345                 350

Val Arg His Ala Asn Phe Gly Asn Ser Tyr Ile Ser Tyr Trp Ala Tyr
        355                 360                 365

```
Trp Gly Gln Gly Thr Leu Val Thr Val Ser Ser Gly Gly Gly Ser
            370                 375                 380

Gly Gly Gly Gly Ser Gly Gly Gly Ser Gln Thr Val Val Thr Gln
385                 390                 395                 400

Glu Pro Ser Leu Thr Val Ser Pro Gly Gly Thr Val Thr Leu Thr Cys
                405                 410                 415

Ala Ser Ser Thr Gly Ala Val Thr Ser Gly Asn Tyr Pro Asn Trp Val
                420                 425                 430

Gln Gln Lys Pro Gly Gln Ala Pro Arg Gly Leu Ile Gly Gly Thr Lys
            435                 440                 445

Phe Leu Val Pro Gly Thr Pro Ala Arg Phe Ser Gly Ser Leu Leu Gly
            450                 455                 460

Gly Lys Ala Ala Leu Thr Leu Ser Gly Val Gln Pro Glu Asp Glu Ala
465                 470                 475                 480

Glu Tyr Tyr Cys Thr Leu Trp Tyr Ser Asn Arg Trp Val Phe Gly Gly
                485                 490                 495

Gly Thr Lys Leu Thr Val Leu His His His His His
            500                 505

<210> SEQ ID NO 324
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 324

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Ala Tyr Ile Tyr
                20                  25                  30

Thr Met Asp Trp Tyr Arg Gln Ala Pro Gly Lys Gln Arg Glu Leu Val
            35                  40                  45

Ala Thr Ser Thr Arg Asp Gly Asn Thr Asp Tyr Ala Asp Ser Val Lys
        50                  55                  60

Gly Arg Phe Thr Ile Ser Arg Asp Asn Ala Lys Asp Thr Val Tyr Leu
65                  70                  75                  80

Gln Met Asn Ser Leu Lys Pro Glu Asp Thr Ala Val Tyr Tyr Cys Asn
                85                  90                  95

Ala Asp Leu Arg Thr Ala Val Asp Leu Ile Arg Ala Asn Tyr Trp Gly
                100                 105                 110

Gln Gly Thr Gln Val Thr Val Ser Ser Gly Gly Gly Ser Gly Gly
            115                 120                 125

Gly Ser Glu Val Gln Leu Val Glu Ser Gly Gly Gly Leu Val Gln Pro
            130                 135                 140

Gly Asn Ser Leu Arg Leu Ser Cys Ala Ala Ser Gly Phe Thr Phe Ser
145                 150                 155                 160

Lys Phe Gly Met Ser Trp Val Arg Gln Ala Pro Gly Lys Gly Leu Glu
                165                 170                 175

Trp Val Ser Ser Ile Ser Gly Ser Gly Arg Asp Thr Leu Tyr Ala Asp
                180                 185                 190

Ser Val Lys Gly Arg Phe Thr Ile Ser Arg Asp Asn Ala Lys Thr Thr
            195                 200                 205

Leu Tyr Leu Gln Met Asn Ser Leu Arg Pro Glu Asp Thr Ala Val Tyr
```

```
            210                 215                 220
Tyr Cys Thr Ile Gly Gly Ser Leu Ser Val Ser Ser Gln Gly Thr Leu
225                 230                 235                 240

Val Thr Val Ser Ser Gly Gly Gly Ser Gly Gly Gly Ser Glu Val
                245                 250                 255

Gln Leu Val Glu Ser Gly Gly Gly Leu Val Gln Pro Gly Gly Ser Leu
                260                 265                 270

Lys Leu Ser Cys Ala Ala Ser Gly Phe Thr Phe Asn Lys Tyr Ala Ile
                275                 280                 285

Asn Trp Val Arg Gln Ala Pro Gly Lys Gly Leu Glu Trp Val Ala Arg
            290                 295                 300

Ile Arg Ser Lys Tyr Asn Asn Tyr Ala Thr Tyr Tyr Ala Asp Gln Val
305                 310                 315                 320

Lys Asp Arg Phe Thr Ile Ser Arg Asp Asp Ser Lys Asn Thr Ala Tyr
                325                 330                 335

Leu Gln Met Asn Asn Leu Lys Thr Glu Asp Thr Ala Val Tyr Tyr Cys
                340                 345                 350

Val Arg His Ala Asn Phe Gly Asn Ser Tyr Ile Ser Tyr Trp Ala Tyr
            355                 360                 365

Trp Gly Gln Gly Thr Leu Val Thr Val Ser Ser Gly Gly Gly Gly Ser
            370                 375                 380

Gly Gly Gly Gly Ser Gly Gly Gly Ser Gln Thr Val Val Thr Gln
385                 390                 395                 400

Glu Pro Ser Leu Thr Val Ser Pro Gly Gly Thr Val Thr Leu Thr Cys
                405                 410                 415

Ala Ser Ser Thr Gly Ala Val Thr Ser Gly Asn Tyr Pro Asn Trp Val
                420                 425                 430

Gln Gln Lys Pro Gly Gln Ala Pro Arg Gly Leu Ile Gly Gly Thr Lys
                435                 440                 445

Phe Leu Val Pro Gly Thr Pro Ala Arg Phe Ser Gly Ser Leu Leu Gly
            450                 455                 460

Gly Lys Ala Ala Leu Thr Leu Ser Gly Val Gln Pro Glu Asp Glu Ala
465                 470                 475                 480

Glu Tyr Tyr Cys Thr Leu Trp Tyr Ser Asn Arg Trp Val Phe Gly Gly
                485                 490                 495

Gly Thr Lys Leu Thr Val Leu His His His His His
            500                 505

<210> SEQ ID NO 325
<211> LENGTH: 507
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 325

Gln Val Gln Leu Gln Glu Ser Gly Gly Gly Leu Val Gln Ala Gly Gly
1               5                   10                  15

Ser Leu Thr Leu Ser Cys Ala Ala Ser Gly Arg Tyr Gln Met Ala Trp
                20                  25                  30

Phe Arg Gln Ala Pro Glu Lys Glu Arg Glu Phe Val Gly Thr Ile Ser
                35                  40                  45

Ser Gly Asp Ser Thr Trp Tyr Thr Asn Ser Val Lys Gly Arg Phe Ala
            50                  55                  60
```

```
Ile Ser Arg Asp Ser Ala Arg Asn Thr Val Tyr Leu Gln Met Asn Asp
 65                  70                  75                  80

Leu Lys Pro Glu Asp Thr Ala Ile Tyr Tyr Cys Ala Ala Ala Leu Tyr
                 85                  90                  95

Tyr Arg Asp Ser Arg Arg Ala Ala Asp Tyr Pro Tyr Trp Gly Gln Gly
            100                 105                 110

Thr Gln Val Thr Val Ser Ser Gly Gly Gly Ser Gly Gly Gly Gly Ser
        115                 120                 125

Glu Val Gln Leu Val Glu Ser Gly Gly Gly Leu Val Gln Pro Gly Asn
    130                 135                 140

Ser Leu Arg Leu Ser Cys Ala Ala Ser Gly Phe Thr Phe Ser Lys Phe
145                 150                 155                 160

Gly Met Ser Trp Val Arg Gln Ala Pro Gly Lys Gly Leu Glu Trp Val
                165                 170                 175

Ser Ser Ile Ser Gly Ser Gly Arg Asp Thr Leu Tyr Ala Asp Ser Val
                180                 185                 190

Lys Gly Arg Phe Thr Ile Ser Arg Asp Asn Ala Lys Thr Thr Leu Tyr
            195                 200                 205

Leu Gln Met Asn Ser Leu Arg Pro Glu Asp Thr Ala Val Tyr Tyr Cys
        210                 215                 220

Thr Ile Gly Gly Ser Leu Ser Val Ser Ser Gln Gly Thr Leu Val Thr
225                 230                 235                 240

Val Ser Ser Gly Gly Gly Gly Ser Gly Gly Gly Ser Glu Val Gln Leu
                245                 250                 255

Val Glu Ser Gly Gly Gly Leu Val Gln Pro Gly Gly Ser Leu Lys Leu
            260                 265                 270

Ser Cys Ala Ala Ser Gly Phe Thr Phe Asn Lys Tyr Ala Ile Asn Trp
        275                 280                 285

Val Arg Gln Ala Pro Gly Lys Gly Leu Glu Trp Val Ala Arg Ile Arg
    290                 295                 300

Ser Lys Tyr Asn Asn Tyr Ala Thr Tyr Tyr Ala Asp Gln Val Lys Asp
305                 310                 315                 320

Arg Phe Thr Ile Ser Arg Asp Asp Ser Lys Asn Thr Ala Tyr Leu Gln
                325                 330                 335

Met Asn Asn Leu Lys Thr Glu Asp Thr Ala Val Tyr Tyr Cys Val Arg
            340                 345                 350

His Ala Asn Phe Gly Asn Ser Tyr Ile Ser Tyr Trp Ala Tyr Trp Gly
        355                 360                 365

Gln Gly Thr Leu Val Thr Val Ser Ser Gly Gly Gly Gly Ser Gly Gly
    370                 375                 380

Gly Gly Ser Gly Gly Gly Gly Ser Gln Thr Val Val Thr Gln Glu Pro
385                 390                 395                 400

Ser Leu Thr Val Ser Pro Gly Gly Thr Val Thr Leu Thr Cys Ala Ser
                405                 410                 415

Ser Thr Gly Ala Val Thr Ser Gly Asn Tyr Pro Asn Trp Val Gln Gln
            420                 425                 430

Lys Pro Gly Gln Ala Pro Arg Gly Leu Ile Gly Gly Thr Lys Phe Leu
        435                 440                 445

Val Pro Gly Thr Pro Ala Arg Phe Ser Gly Ser Leu Leu Gly Gly Lys
    450                 455                 460

Ala Ala Leu Thr Leu Ser Gly Val Gln Pro Glu Asp Glu Ala Glu Tyr
465                 470                 475                 480

Tyr Cys Thr Leu Trp Tyr Ser Asn Arg Trp Val Phe Gly Gly Gly Thr
```

```
                    485                 490                 495
Lys Leu Thr Val Leu His His His His His
                500                 505

<210> SEQ ID NO 326
<211> LENGTH: 515
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 326

Gln Val Gln Leu Gln Glu Ser Gly Gly Gly Arg Val Gln Ala Gly Glu
1               5                   10                  15

Ser Leu Arg Leu Ser Cys Ser Thr Ser Thr Arg Thr Leu Lys Leu Tyr
                20                  25                  30

Ala Val Gly Trp Phe Arg Gln Ala Pro Gly Lys Glu Arg Asp Phe Val
                35                  40                  45

Ala Gly Ile Gly Arg Ser Glu Arg Ile Tyr Tyr Ile Asp Ser Val Lys
            50                  55                  60

Gly Arg Phe Thr Leu Ser Arg Asp Asn Ala Lys Asn Thr Val Phe Leu
65                  70                  75                  80

Glu Met Asn Asp Leu Glu Pro Glu Asp Thr Ala Val Tyr Phe Cys Ala
                85                  90                  95

Ala Thr Phe Gln Thr Ser Asp Asn Val Gly Val Pro Thr Val Gln His
                100                 105                 110

Glu Tyr Asp Tyr Trp Gly Gln Gly Thr Gln Val Thr Val Ser Ser Gly
                115                 120                 125

Gly Gly Gly Ser Gly Gly Gly Ser Glu Val Gln Leu Val Glu Ser Gly
            130                 135                 140

Gly Gly Leu Val Gln Pro Gly Asn Ser Leu Arg Leu Ser Cys Ala Ala
145                 150                 155                 160

Ser Gly Phe Thr Phe Ser Lys Phe Gly Met Ser Trp Val Arg Gln Ala
                165                 170                 175

Pro Gly Lys Gly Leu Glu Trp Val Ser Ser Ile Ser Gly Ser Gly Arg
                180                 185                 190

Asp Thr Leu Tyr Ala Asp Ser Val Lys Gly Arg Phe Thr Ile Ser Arg
            195                 200                 205

Asp Asn Ala Lys Thr Thr Leu Tyr Leu Gln Met Asn Ser Leu Arg Pro
210                 215                 220

Glu Asp Thr Ala Val Tyr Tyr Cys Thr Ile Gly Gly Ser Leu Ser Val
225                 230                 235                 240

Ser Ser Gln Gly Thr Leu Val Thr Val Ser Ser Gly Gly Gly Gly Ser
                245                 250                 255

Gly Gly Gly Ser Glu Val Gln Leu Val Glu Ser Gly Gly Gly Leu Val
                260                 265                 270

Gln Pro Gly Gly Ser Leu Lys Leu Ser Cys Ala Ala Ser Gly Phe Thr
            275                 280                 285

Phe Asn Lys Tyr Ala Ile Asn Trp Val Arg Gln Ala Pro Gly Lys Gly
290                 295                 300

Leu Glu Trp Val Ala Arg Ile Arg Ser Lys Tyr Asn Asn Tyr Ala Thr
305                 310                 315                 320

Tyr Tyr Ala Asp Gln Val Lys Asp Arg Phe Thr Ile Ser Arg Asp Asp
                325                 330                 335
```

Ser Lys Asn Thr Ala Tyr Leu Gln Met Asn Asn Leu Lys Thr Glu Asp
                340                 345                 350

Thr Ala Val Tyr Tyr Cys Val Arg His Ala Asn Phe Gly Asn Ser Tyr
            355                 360                 365

Ile Ser Tyr Trp Ala Tyr Trp Gly Gln Gly Thr Leu Val Thr Val Ser
        370                 375                 380

Ser Gly Gly Gly Gly Ser Gly Gly Gly Gly Ser Gly Gly Gly Gly Ser
385                 390                 395                 400

Gln Thr Val Val Thr Gln Glu Pro Ser Leu Thr Val Ser Pro Gly Gly
                405                 410                 415

Thr Val Thr Leu Thr Cys Ala Ser Ser Thr Gly Ala Val Thr Ser Gly
            420                 425                 430

Asn Tyr Pro Asn Trp Val Gln Gln Lys Pro Gly Gln Ala Pro Arg Gly
        435                 440                 445

Leu Ile Gly Gly Thr Lys Phe Leu Val Pro Gly Thr Pro Ala Arg Phe
    450                 455                 460

Ser Gly Ser Leu Leu Gly Gly Lys Ala Ala Leu Thr Leu Ser Gly Val
465                 470                 475                 480

Gln Pro Glu Asp Glu Ala Glu Tyr Tyr Cys Thr Leu Trp Tyr Ser Asn
                485                 490                 495

Arg Trp Val Phe Gly Gly Gly Thr Lys Leu Thr Val Leu His His His
            500                 505                 510

His His His
        515

<210> SEQ ID NO 327
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 327

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Ala Tyr Ile Tyr
                20                  25                  30

Thr Met Asp Trp Tyr Arg Gln Ala Pro Gly Lys Gln Arg Glu Leu Val
            35                  40                  45

Ala Thr Ser Thr His Asp Gly Asn Thr Asp Tyr Ala Asp Ser Val Lys
        50                  55                  60

Gly Arg Phe Thr Ile Ser Arg Asp Asn Ala Lys Asn Thr Val Thr Leu
65                  70                  75                  80

Gln Met Asn Ser Leu Lys Pro Glu Asp Thr Ala Val Tyr Tyr Cys Asn
                85                  90                  95

Ala Asp Leu Arg Thr Ala Val Asp Leu Ile Arg Ala Asn Tyr Trp Gly
            100                 105                 110

Gln Gly Thr Gln Val Thr Val Ser Ser Gly Gly Gly Ser Gly Gly
        115                 120                 125

Gly Ser Glu Val Gln Leu Val Glu Ser Gly Gly Gly Leu Val Gln Pro
    130                 135                 140

Gly Asn Ser Leu Arg Leu Ser Cys Ala Ala Ser Gly Phe Thr Phe Ser
145                 150                 155                 160

Lys Phe Gly Met Ser Trp Val Arg Gln Ala Pro Gly Lys Gly Leu Glu
                165                 170                 175

```
Trp Val Ser Ser Ile Ser Gly Ser Gly Arg Asp Thr Leu Tyr Ala Asp
            180                 185                 190

Ser Val Lys Gly Arg Phe Thr Ile Ser Arg Asp Asn Ala Lys Thr Thr
        195                 200                 205

Leu Tyr Leu Gln Met Asn Ser Leu Arg Pro Glu Asp Thr Ala Val Tyr
    210                 215                 220

Tyr Cys Thr Ile Gly Gly Ser Leu Ser Val Ser Ser Gln Gly Thr Leu
225                 230                 235                 240

Val Thr Val Ser Ser Gly Gly Gly Ser Gly Gly Gly Ser Glu Val
                245                 250                 255

Gln Leu Val Glu Ser Gly Gly Gly Leu Val Gln Pro Gly Gly Ser Leu
            260                 265                 270

Lys Leu Ser Cys Ala Ala Ser Gly Phe Thr Phe Asn Lys Tyr Ala Ile
        275                 280                 285

Asn Trp Val Arg Gln Ala Pro Gly Lys Gly Leu Glu Trp Val Ala Arg
    290                 295                 300

Ile Arg Ser Lys Tyr Asn Asn Tyr Ala Thr Tyr Tyr Ala Asp Gln Val
305                 310                 315                 320

Lys Asp Arg Phe Thr Ile Ser Arg Asp Asp Ser Lys Asn Thr Ala Tyr
                325                 330                 335

Leu Gln Met Asn Asn Leu Lys Thr Glu Asp Thr Ala Val Tyr Tyr Cys
            340                 345                 350

Val Arg His Ala Asn Phe Gly Asn Ser Tyr Ile Ser Tyr Trp Ala Tyr
        355                 360                 365

Trp Gly Gln Gly Thr Leu Val Thr Val Ser Ser Gly Gly Gly Gly Ser
    370                 375                 380

Gly Gly Gly Gly Ser Gly Gly Gly Ser Gln Thr Val Val Thr Gln
385                 390                 395                 400

Glu Pro Ser Leu Thr Val Ser Pro Gly Gly Thr Val Thr Leu Thr Cys
                405                 410                 415

Ala Ser Ser Thr Gly Ala Val Thr Ser Gly Asn Tyr Pro Asn Trp Val
            420                 425                 430

Gln Gln Lys Pro Gly Gln Ala Pro Arg Gly Leu Ile Gly Gly Thr Lys
        435                 440                 445

Phe Leu Val Pro Gly Thr Pro Ala Arg Phe Ser Gly Ser Leu Leu Gly
    450                 455                 460

Gly Lys Ala Ala Leu Thr Leu Ser Gly Val Gln Pro Glu Asp Glu Ala
465                 470                 475                 480

Glu Tyr Tyr Cys Thr Leu Trp Tyr Ser Asn Arg Trp Val Phe Gly Gly
                485                 490                 495

Gly Thr Lys Leu Thr Val Leu His His His His His
            500                 505

<210> SEQ ID NO 328
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 328

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Ala Tyr Ile Tyr
```

```
            20                  25                  30
Thr Met Asp Trp Tyr Arg Gln Ala Pro Gly Lys Gln Arg Glu Leu Val
        35                  40                  45
Ala Thr Phe Thr Arg Asp Gly Asn Thr Asp Tyr Ala Asp Ser Val Lys
        50                  55                  60
Gly Arg Phe Thr Ile Ser Arg Asp Asn Ala Lys Asn Thr Val Tyr Leu
65                  70                  75                  80
Gln Met Asn Ser Leu Lys Pro Glu Asp Thr Ala Val Tyr Tyr Cys Asn
                85                  90                  95
Thr Asp Leu Arg Thr Ala Val Asp Leu Ile Arg Ala Asn Tyr Trp Gly
                100                 105                 110
Gln Gly Thr Gln Val Thr Val Ser Gly Gly Gly Ser Gly Gly
                115                 120                 125
Gly Ser Glu Val Gln Leu Val Glu Ser Gly Gly Gly Leu Val Gln Pro
                130                 135                 140
Gly Asn Ser Leu Arg Leu Ser Cys Ala Ala Ser Gly Phe Thr Phe Ser
145                 150                 155                 160
Lys Phe Gly Met Ser Trp Val Arg Gln Ala Pro Gly Lys Gly Leu Glu
                165                 170                 175
Trp Val Ser Ser Ile Ser Gly Ser Gly Arg Asp Thr Leu Tyr Ala Asp
                180                 185                 190
Ser Val Lys Gly Arg Phe Thr Ile Ser Arg Asp Asn Ala Lys Thr Thr
                195                 200                 205
Leu Tyr Leu Gln Met Asn Ser Leu Arg Pro Glu Asp Thr Ala Val Tyr
        210                 215                 220
Tyr Cys Thr Ile Gly Gly Ser Leu Ser Val Ser Ser Gln Gly Thr Leu
225                 230                 235                 240
Val Thr Val Ser Ser Gly Gly Gly Gly Ser Gly Gly Gly Ser Glu Val
                245                 250                 255
Gln Leu Val Glu Ser Gly Gly Gly Leu Val Gln Pro Gly Gly Ser Leu
                260                 265                 270
Lys Leu Ser Cys Ala Ala Ser Gly Phe Thr Phe Asn Lys Tyr Ala Ile
                275                 280                 285
Asn Trp Val Arg Gln Ala Pro Gly Lys Gly Leu Glu Trp Val Ala Arg
        290                 295                 300
Ile Arg Ser Lys Tyr Asn Asn Tyr Ala Thr Tyr Tyr Ala Asp Gln Val
305                 310                 315                 320
Lys Asp Arg Phe Thr Ile Ser Arg Asp Asp Ser Lys Asn Thr Ala Tyr
                325                 330                 335
Leu Gln Met Asn Asn Leu Lys Thr Glu Asp Thr Ala Val Tyr Tyr Cys
                340                 345                 350
Val Arg His Ala Asn Phe Gly Asn Ser Tyr Ile Ser Tyr Trp Ala Tyr
                355                 360                 365
Trp Gly Gln Gly Thr Leu Val Thr Val Ser Ser Gly Gly Gly Gly Ser
        370                 375                 380
Gly Gly Gly Gly Ser Gly Gly Gly Ser Gln Thr Val Val Thr Gln
385                 390                 395                 400
Glu Pro Ser Leu Thr Val Ser Pro Gly Gly Thr Val Thr Leu Thr Cys
                405                 410                 415
Ala Ser Ser Thr Gly Ala Val Thr Ser Gly Asn Tyr Pro Asn Trp Val
                420                 425                 430
Gln Gln Lys Pro Gly Gln Ala Pro Arg Gly Leu Ile Gly Gly Thr Lys
                435                 440                 445
```

```
Phe Leu Val Pro Gly Thr Pro Ala Arg Phe Ser Gly Ser Leu Leu Gly
    450                 455                 460

Gly Lys Ala Ala Leu Thr Leu Ser Gly Val Gln Pro Glu Asp Glu Ala
465                 470                 475                 480

Glu Tyr Tyr Cys Thr Leu Trp Tyr Ser Asn Arg Trp Val Phe Gly Gly
                485                 490                 495

Gly Thr Lys Leu Thr Val Leu His His His His His His
            500                 505
```

<210> SEQ ID NO 329
<211> LENGTH: 509
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 329

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Ala Tyr Ile Tyr
                20                  25                  30

Thr Met Asp Trp Tyr Arg Gln Ala Pro Gly Lys Gln Arg Glu Leu Val
            35                  40                  45

Ala Thr Ser Thr His Asp Gly Asn Thr Asp Tyr Ala Asp Ser Leu Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Leu Arg Thr Ala Val Asp Leu Ile Arg Ala Asn Tyr Trp Gly
            100                 105                 110

Gln Gly Thr Gln Val Thr Val Ser Ser Gly Gly Gly Ser Gly Gly Gly
        115                 120                 125

Gly Ser Glu Val Gln Leu Val Glu Ser Gly Gly Gly Leu Val Gln Pro
130                 135                 140

Gly Asn Ser Leu Arg Leu Ser Cys Ala Ala Ser Gly Phe Thr Phe Ser
145                 150                 155                 160

Lys Phe Gly Met Ser Trp Val Arg Gln Ala Pro Gly Lys Gly Leu Glu
                165                 170                 175

Trp Val Ser Ser Ile Ser Gly Ser Gly Arg Asp Thr Leu Tyr Ala Asp
            180                 185                 190

Ser Val Lys Gly Arg Phe Thr Ile Ser Arg Asp Asn Ala Lys Thr Thr
        195                 200                 205

Leu Tyr Leu Gln Met Asn Ser Leu Arg Pro Glu Asp Thr Ala Val Tyr
    210                 215                 220

Tyr Cys Thr Ile Gly Gly Ser Leu Ser Val Ser Ser Gln Gly Thr Leu
225                 230                 235                 240

Val Thr Val Ser Ser Gly Gly Gly Gly Ser Gly Gly Gly Ser Glu Val
                245                 250                 255

Gln Leu Val Glu Ser Gly Gly Gly Leu Val Gln Pro Gly Gly Ser Leu
            260                 265                 270

Lys Leu Ser Cys Ala Ala Ser Gly Phe Thr Phe Asn Lys Tyr Ala Ile
        275                 280                 285

Asn Trp Val Arg Gln Ala Pro Gly Lys Gly Leu Glu Trp Val Ala Arg
```

```
            290                 295                 300
Ile Arg Ser Lys Tyr Asn Asn Tyr Ala Thr Tyr Tyr Ala Asp Gln Val
305                 310                 315                 320

Lys Asp Arg Phe Thr Ile Ser Arg Asp Asp Ser Lys Asn Thr Ala Tyr
                325                 330                 335

Leu Gln Met Asn Asn Leu Lys Thr Glu Asp Thr Ala Val Tyr Tyr Cys
            340                 345                 350

Val Arg His Ala Asn Phe Gly Asn Ser Tyr Ile Ser Tyr Trp Ala Tyr
        355                 360                 365

Trp Gly Gln Gly Thr Leu Val Thr Val Ser Ser Gly Gly Gly Gly Ser
    370                 375                 380

Gly Gly Gly Gly Ser Gly Gly Gly Ser Gln Thr Val Val Thr Gln
385                 390                 395                 400

Glu Pro Ser Leu Thr Val Ser Pro Gly Gly Thr Val Thr Leu Thr Cys
                405                 410                 415

Ala Ser Ser Thr Gly Ala Val Thr Ser Gly Asn Tyr Pro Asn Trp Val
            420                 425                 430

Gln Gln Lys Pro Gly Gln Ala Pro Arg Gly Leu Ile Gly Gly Thr Lys
        435                 440                 445

Phe Leu Val Pro Gly Thr Pro Ala Arg Phe Ser Gly Ser Leu Leu Gly
    450                 455                 460

Gly Lys Ala Ala Leu Thr Leu Ser Gly Val Gln Pro Glu Asp Glu Ala
465                 470                 475                 480

Glu Tyr Tyr Cys Thr Leu Trp Tyr Ser Asn Arg Trp Val Phe Gly Gly
                485                 490                 495

Gly Thr Lys Leu Thr Val Leu His His His His His
            500                 505

<210> SEQ ID NO 330
<211> LENGTH: 507
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 330

Gln Val Gln Leu Gln Glu Ser Gly Gly Gly Ser Val Gln Ala Gly Gly
1               5                   10                  15

Ser Leu Arg Leu Ser Cys Ala Ala Ser Gly Arg Tyr Gln Met Ala Trp
            20                  25                  30

Phe Arg Gln Ala Pro Glu Lys Glu Arg Glu Phe Val Gly Thr Ile Ser
        35                  40                  45

Ser Gly Asp Ser Thr Trp Tyr Thr Asn Ser Leu Lys Gly Arg Phe Ala
    50                  55                  60

Ile Ser Arg Asp Ser Ala Arg Asp Thr Val Tyr Leu Gln Met Asn Asp
65                  70                  75                  80

Leu Lys Pro Glu Asp Thr Ala Val Tyr Tyr Cys Ala Ala Ala Leu Tyr
                85                  90                  95

Tyr Arg Asp Ser Arg Arg Ala Ala Asp Tyr Pro Tyr Trp Gly Gln Gly
            100                 105                 110

Thr Gln Val Thr Val Ser Ser Gly Gly Gly Ser Gly Gly Gly Ser
        115                 120                 125

Glu Val Gln Leu Val Glu Ser Gly Gly Gly Leu Val Gln Pro Gly Asn
    130                 135                 140
```

```
Ser Leu Arg Leu Ser Cys Ala Ala Ser Gly Phe Thr Phe Ser Lys Phe
145                 150                 155                 160

Gly Met Ser Trp Val Arg Gln Ala Pro Gly Lys Gly Leu Glu Trp Val
            165                 170                 175

Ser Ser Ile Ser Gly Ser Gly Arg Asp Thr Leu Tyr Ala Asp Ser Val
            180                 185                 190

Lys Gly Arg Phe Thr Ile Ser Arg Asp Asn Ala Lys Thr Thr Leu Tyr
            195                 200                 205

Leu Gln Met Asn Ser Leu Arg Pro Glu Asp Thr Ala Val Tyr Tyr Cys
    210                 215                 220

Thr Ile Gly Gly Ser Leu Ser Val Ser Ser Gln Gly Thr Leu Val Thr
225                 230                 235                 240

Val Ser Ser Gly Gly Gly Gly Ser Gly Gly Gly Ser Glu Val Gln Leu
            245                 250                 255

Val Glu Ser Gly Gly Gly Leu Val Gln Pro Gly Gly Ser Leu Lys Leu
            260                 265                 270

Ser Cys Ala Ala Ser Gly Phe Thr Phe Asn Lys Tyr Ala Ile Asn Trp
    275                 280                 285

Val Arg Gln Ala Pro Gly Lys Gly Leu Glu Trp Val Ala Arg Ile Arg
290                 295                 300

Ser Lys Tyr Asn Asn Tyr Ala Thr Tyr Tyr Ala Asp Gln Val Lys Asp
305                 310                 315                 320

Arg Phe Thr Ile Ser Arg Asp Asp Ser Lys Asn Thr Ala Tyr Leu Gln
            325                 330                 335

Met Asn Asn Leu Lys Thr Glu Asp Thr Ala Val Tyr Tyr Cys Val Arg
    340                 345                 350

His Ala Asn Phe Gly Asn Ser Tyr Ile Ser Tyr Trp Ala Tyr Trp Gly
    355                 360                 365

Gln Gly Thr Leu Val Thr Val Ser Ser Gly Gly Gly Gly Ser Gly Gly
    370                 375                 380

Gly Gly Ser Gly Gly Gly Gly Ser Gln Thr Val Val Thr Gln Glu Pro
385                 390                 395                 400

Ser Leu Thr Val Ser Pro Gly Gly Thr Val Thr Leu Thr Cys Ala Ser
            405                 410                 415

Ser Thr Gly Ala Val Thr Ser Gly Asn Tyr Pro Asn Trp Val Gln Gln
            420                 425                 430

Lys Pro Gly Gln Ala Pro Arg Gly Leu Ile Gly Gly Thr Lys Phe Leu
            435                 440                 445

Val Pro Gly Thr Pro Ala Arg Phe Ser Gly Ser Leu Leu Gly Gly Lys
            450                 455                 460

Ala Ala Leu Thr Leu Ser Gly Val Gln Pro Glu Asp Glu Ala Glu Tyr
465                 470                 475                 480

Tyr Cys Thr Leu Trp Tyr Ser Asn Arg Trp Val Phe Gly Gly Gly Thr
            485                 490                 495

Lys Leu Thr Val Leu His His His His His
            500                 505

<210> SEQ ID NO 331
<211> LENGTH: 502
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 331
```

-continued

```
Gln Val Gln Leu Gln Glu Ser Gly Gly Gly Leu Val Gln Thr Gly Gly
 1               5                  10                  15
Ser Leu Arg Leu Ser Cys Ala Val Ser Gly Ser Ile Val Thr Ile Asn
            20                  25                  30
Ala Met Thr Trp Tyr Arg Gln Ala Pro Gly Lys Arg Arg Glu Leu Val
        35                  40                  45
Ala Ile Ile Thr Ser Gly Gly Glu Thr Asn Tyr Ala Asp Ser Val Lys
    50                  55                  60
Gly Arg Phe Thr Ile Ser Arg Asp Asn Ala Lys Asn Thr Ala His Leu
65                  70                  75                  80
Gln Met Asn Ser Leu Asn Pro Glu Asp Thr Gly Val Tyr Tyr Cys Asn
                85                  90                  95
Val Val Pro Pro Leu Gly Ser Trp Gly Gln Gly Thr Gln Val Thr Val
            100                 105                 110
Ser Ser Gly Gly Gly Gly Ser Gly Gly Gly Ser Glu Val Gln Leu Val
        115                 120                 125
Glu Ser Gly Gly Gly Leu Val Gln Pro Gly Asn Ser Leu Arg Leu Ser
    130                 135                 140
Cys Ala Ala Ser Gly Phe Thr Phe Ser Lys Phe Gly Met Ser Trp Val
145                 150                 155                 160
Arg Gln Ala Pro Gly Lys Gly Leu Glu Trp Val Ser Ser Ile Ser Gly
                165                 170                 175
Ser Gly Arg Asp Thr Leu Tyr Ala Asp Ser Val Lys Gly Arg Phe Thr
            180                 185                 190
Ile Ser Arg Asp Asn Ala Lys Thr Thr Leu Tyr Leu Gln Met Asn Ser
        195                 200                 205
Leu Arg Pro Glu Asp Thr Ala Val Tyr Tyr Cys Thr Ile Gly Gly Ser
    210                 215                 220
Leu Ser Val Ser Ser Gln Gly Thr Leu Val Thr Val Ser Ser Gly Gly
225                 230                 235                 240
Gly Gly Ser Gly Gly Gly Ser Glu Val Gln Leu Val Glu Ser Gly Gly
                245                 250                 255
Gly Leu Val Gln Pro Gly Gly Ser Leu Lys Leu Ser Cys Ala Ala Ser
            260                 265                 270
Gly Phe Thr Phe Asn Lys Tyr Ala Ile Asn Trp Val Arg Gln Ala Pro
        275                 280                 285
Gly Lys Gly Leu Glu Trp Val Ala Arg Ile Arg Ser Lys Tyr Asn Asn
    290                 295                 300
Tyr Ala Thr Tyr Tyr Ala Asp Gln Val Lys Asp Arg Phe Thr Ile Ser
305                 310                 315                 320
Arg Asp Asp Ser Lys Asn Thr Ala Tyr Leu Gln Met Asn Asn Leu Lys
                325                 330                 335
Thr Glu Asp Thr Ala Val Tyr Tyr Cys Val Arg His Ala Asn Phe Gly
            340                 345                 350
Asn Ser Tyr Ile Ser Tyr Trp Ala Tyr Trp Gly Gln Gly Thr Leu Val
        355                 360                 365
Thr Val Ser Ser Gly Gly Gly Gly Ser Gly Gly Gly Gly Ser Gly Gly
    370                 375                 380
Gly Gly Ser Gln Thr Val Val Thr Gln Glu Pro Ser Leu Thr Val Ser
385                 390                 395                 400
Pro Gly Gly Thr Val Thr Leu Thr Cys Ala Ser Ser Thr Gly Ala Val
                405                 410                 415
```

```
Thr Ser Gly Asn Tyr Pro Asn Trp Val Gln Lys Pro Gly Gln Ala
            420                 425                 430

Pro Arg Gly Leu Ile Gly Gly Thr Lys Phe Leu Val Pro Gly Thr Pro
        435                 440                 445

Ala Arg Phe Ser Gly Ser Leu Leu Gly Gly Lys Ala Ala Leu Thr Leu
    450                 455                 460

Ser Gly Val Gln Pro Glu Asp Glu Ala Glu Tyr Tyr Cys Thr Leu Trp
465                 470                 475                 480

Tyr Ser Asn Arg Trp Val Phe Gly Gly Thr Lys Leu Thr Val Leu
            485                 490                 495

His His His His His His
            500

<210> SEQ ID NO 332
<211> LENGTH: 502
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 332

Gln Val Gln Leu Gln Glu Ser Gly Gly Gly Leu Val Gln Thr Gly Gly
1               5                   10                  15

Ser Leu Arg Leu Ser Cys Ala Val Ser Arg Ser Ile Val Ser Ile Lys
            20                  25                  30

Ser Met Thr Trp Tyr Arg Gln Ala Pro Gly Lys Arg Arg Glu Leu Val
        35                  40                  45

Ala Leu Ile Thr Ser Gly Gly Glu Thr Asn Tyr Ser Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Gly Val Tyr Tyr Cys Asn
            85                  90                  95

Val Val Pro Pro Leu Gly Ser Trp Gly Gln Gly Thr Gln Val Thr Val
        100                 105                 110

Ser Ser Gly Gly Gly Gly Ser Gly Gly Gly Ser Glu Val Gln Leu Val
    115                 120                 125

Glu Ser Gly Gly Gly Leu Val Gln Pro Gly Asn Ser Leu Arg Leu Ser
130                 135                 140

Cys Ala Ala Ser Gly Phe Thr Phe Ser Lys Phe Gly Met Ser Trp Val
145                 150                 155                 160

Arg Gln Ala Pro Gly Lys Gly Leu Glu Trp Val Ser Ser Ile Ser Gly
            165                 170                 175

Ser Gly Arg Asp Thr Leu Tyr Ala Asp Ser Val Lys Gly Arg Phe Thr
        180                 185                 190

Ile Ser Arg Asp Asn Ala Lys Thr Thr Leu Tyr Leu Gln Met Asn Ser
    195                 200                 205

Leu Arg Pro Glu Asp Thr Ala Val Tyr Tyr Cys Thr Ile Gly Gly Ser
210                 215                 220

Leu Ser Val Ser Ser Gln Gly Thr Leu Val Thr Val Ser Ser Gly Gly
225                 230                 235                 240

Gly Gly Ser Gly Gly Gly Ser Glu Val Gln Leu Val Glu Ser Gly Gly
            245                 250                 255

Gly Leu Val Gln Pro Gly Gly Ser Leu Lys Leu Ser Cys Ala Ala Ser
        260                 265                 270
```

```
Gly Phe Thr Phe Asn Lys Tyr Ala Ile Asn Trp Val Arg Gln Ala Pro
            275                 280                 285

Gly Lys Gly Leu Glu Trp Val Ala Arg Ile Arg Ser Lys Tyr Asn Asn
        290                 295                 300

Tyr Ala Thr Tyr Tyr Ala Asp Gln Val Lys Asp Arg Phe Thr Ile Ser
305                 310                 315                 320

Arg Asp Asp Ser Lys Asn Thr Ala Tyr Leu Gln Met Asn Asn Leu Lys
                325                 330                 335

Thr Glu Asp Thr Ala Val Tyr Tyr Cys Val Arg His Ala Asn Phe Gly
            340                 345                 350

Asn Ser Tyr Ile Ser Tyr Trp Ala Tyr Trp Gly Gln Gly Thr Leu Val
            355                 360                 365

Thr Val Ser Ser Gly Gly Gly Ser Gly Gly Gly Ser Gly Gly
        370                 375                 380

Gly Gly Ser Gln Thr Val Val Thr Gln Glu Pro Ser Leu Thr Val Ser
385                 390                 395                 400

Pro Gly Gly Thr Val Thr Leu Thr Cys Ala Ser Ser Thr Gly Ala Val
                405                 410                 415

Thr Ser Gly Asn Tyr Pro Asn Trp Val Gln Gln Lys Pro Gly Gln Ala
            420                 425                 430

Pro Arg Gly Leu Ile Gly Gly Thr Lys Phe Leu Val Pro Gly Thr Pro
                435                 440                 445

Ala Arg Phe Ser Gly Ser Leu Leu Gly Gly Lys Ala Ala Leu Thr Leu
            450                 455                 460

Ser Gly Val Gln Pro Glu Asp Glu Ala Glu Tyr Tyr Cys Thr Leu Trp
465                 470                 475                 480

Tyr Ser Asn Arg Trp Val Phe Gly Gly Gly Thr Lys Leu Thr Val Leu
                485                 490                 495

His His His His His His
            500

<210> SEQ ID NO 333
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 333

Gln Val Gln Leu Gln Glu Ser Gly Gly Gly Leu Val Glu Thr Gly Gly
1               5                   10                  15

Ser Leu Arg Leu Ser Cys Ala Gly Ser Gly Ser Thr Phe Arg His His
            20                  25                  30

Ala Met Ala Trp Phe Arg Gln Thr Pro Gly Lys Glu Arg Glu Phe Val
        35                  40                  45

Ser Ala Ile Asn Asp His Gly Asp Arg Thr Lys Tyr Leu Asp Ser Val
    50                  55                  60

Arg Gly Arg Phe Thr Ile Ser Arg Asp Asn Thr Asp Asn Met Val Tyr
65                  70                  75                  80

Leu Gln Met Thr Asp Leu Arg Pro Glu Asp Thr Ala Asn Tyr Ser Cys
                85                  90                  95

Ala Ala Gly Pro Leu Val Asp Tyr Leu Glu Thr Thr Pro Leu Val Tyr
            100                 105                 110

Thr Tyr Trp Gly His Gly Thr Gln Val Thr Val Ser Ser Gly Gly Gly
```

```
            115                 120                 125
Gly Ser Gly Gly Gly Ser Glu Val Gln Leu Val Glu Ser Gly Gly
            130                 135                 140
Leu Val Gln Pro Gly Asn Ser Leu Arg Leu Ser Cys Ala Ala Ser Gly
145                 150                 155                 160
Phe Thr Phe Ser Lys Phe Gly Met Ser Trp Val Arg Gln Ala Pro Gly
                165                 170                 175
Lys Gly Leu Glu Trp Val Ser Ile Ser Gly Ser Gly Arg Asp Thr
                180                 185                 190
Leu Tyr Ala Asp Ser Val Lys Gly Arg Phe Thr Ile Ser Arg Asp Asn
            195                 200                 205
Ala Lys Thr Thr Leu Tyr Leu Gln Met Asn Ser Leu Arg Pro Glu Asp
            210                 215                 220
Thr Ala Val Tyr Tyr Cys Thr Ile Gly Gly Ser Leu Ser Val Ser Ser
225                 230                 235                 240
Gln Gly Thr Leu Val Thr Val Ser Ser Gly Gly Gly Ser Gly Gly
                245                 250                 255
Gly Ser Glu Val Gln Leu Val Glu Ser Gly Gly Leu Val Gln Pro
            260                 265                 270
Gly Gly Ser Leu Lys Leu Ser Cys Ala Ala Ser Gly Phe Thr Phe Asn
            275                 280                 285
Lys Tyr Ala Ile Asn Trp Val Arg Gln Ala Pro Gly Lys Gly Leu Glu
            290                 295                 300
Trp Val Ala Arg Ile Arg Ser Lys Tyr Asn Asn Tyr Ala Thr Tyr Tyr
305                 310                 315                 320
Ala Asp Gln Val Lys Asp Arg Phe Thr Ile Ser Arg Asp Asp Ser Lys
                325                 330                 335
Asn Thr Ala Tyr Leu Gln Met Asn Asn Leu Lys Thr Glu Asp Thr Ala
                340                 345                 350
Val Tyr Tyr Cys Val Arg His Ala Asn Phe Gly Asn Ser Tyr Ile Ser
                355                 360                 365
Tyr Trp Ala Tyr Trp Gly Gln Gly Thr Leu Val Thr Val Ser Ser Gly
            370                 375                 380
Gly Gly Gly Ser Gly Gly Gly Gly Ser Gly Gly Gly Gly Ser Gln Thr
385                 390                 395                 400
Val Val Thr Gln Glu Pro Ser Leu Thr Val Ser Pro Gly Gly Thr Val
                405                 410                 415
Thr Leu Thr Cys Ala Ser Ser Thr Gly Ala Val Thr Ser Gly Asn Tyr
                420                 425                 430
Pro Asn Trp Val Gln Gln Lys Pro Gly Gln Ala Pro Arg Gly Leu Ile
            435                 440                 445
Gly Gly Thr Lys Phe Leu Val Pro Gly Thr Pro Ala Arg Phe Ser Gly
            450                 455                 460
Ser Leu Leu Gly Gly Lys Ala Ala Leu Thr Leu Ser Gly Val Gln Pro
465                 470                 475                 480
Glu Asp Glu Ala Glu Tyr Tyr Cys Thr Leu Trp Tyr Ser Asn Arg Trp
                485                 490                 495
Val Phe Gly Gly Gly Thr Lys Leu Thr Val Leu His His His His His
                500                 505                 510
His

<210> SEQ ID NO 334
<211> LENGTH: 509
```

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 334

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Ala Tyr Ile Tyr
            20                  25                  30

Thr Met Asp Trp Tyr Arg Gln Ala Pro Gly Lys Gln Arg Glu Leu Val
        35                  40                  45

Ala Thr Ser Thr His Asp Gly Asn Thr Asp Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Leu Arg Thr Ala Val Asp Leu Ile Arg Ala Asn Tyr Trp Gly
            100                 105                 110

Gln Gly Thr Gln Val Thr Val Ser Gly Gly Gly Gly Ser Gly Gly Gly
        115                 120                 125

Gly Ser Glu Val Gln Leu Val Glu Ser Gly Gly Gly Leu Val Gln Pro
    130                 135                 140

Gly Asn Ser Leu Arg Leu Ser Cys Ala Ala Ser Gly Phe Thr Phe Ser
145                 150                 155                 160

Lys Phe Gly Met Ser Trp Val Arg Gln Ala Pro Gly Lys Gly Leu Glu
                165                 170                 175

Trp Val Ser Ser Ile Ser Gly Ser Gly Arg Asp Thr Leu Tyr Ala Asp
            180                 185                 190

Ser Val Lys Gly Arg Phe Thr Ile Ser Arg Asp Asn Ala Lys Thr Thr
        195                 200                 205

Leu Tyr Leu Gln Met Asn Ser Leu Arg Pro Glu Asp Thr Ala Val Tyr
    210                 215                 220

Tyr Cys Thr Ile Gly Gly Ser Leu Ser Val Ser Ser Gln Gly Thr Leu
225                 230                 235                 240

Val Thr Val Ser Ser Gly Gly Gly Gly Ser Gly Gly Gly Ser Glu Val
                245                 250                 255

Gln Leu Val Glu Ser Gly Gly Gly Leu Val Gln Pro Gly Gly Ser Leu
            260                 265                 270

Lys Leu Ser Cys Ala Ala Ser Gly Phe Thr Phe Asn Lys Tyr Ala Ile
        275                 280                 285

Asn Trp Val Arg Gln Ala Pro Gly Lys Gly Leu Glu Trp Val Ala Arg
    290                 295                 300

Ile Arg Ser Lys Tyr Asn Asn Tyr Ala Thr Tyr Tyr Ala Asp Gln Val
305                 310                 315                 320

Lys Asp Arg Phe Thr Ile Ser Arg Asp Asp Ser Lys Asn Thr Ala Tyr
                325                 330                 335

Leu Gln Met Asn Asn Leu Lys Thr Glu Asp Thr Ala Val Tyr Tyr Cys
            340                 345                 350

Val Arg His Ala Asn Phe Gly Asn Ser Tyr Ile Ser Tyr Trp Ala Tyr
        355                 360                 365

Trp Gly Gln Gly Thr Leu Val Thr Val Ser Ser Gly Gly Gly Gly Ser
    370                 375                 380
```

```
Gly Gly Gly Gly Ser Gly Gly Gly Ser Gln Thr Val Val Thr Gln
385                 390                 395                 400

Glu Pro Ser Leu Thr Val Ser Pro Gly Gly Thr Val Thr Leu Thr Cys
            405                 410                 415

Ala Ser Ser Thr Gly Ala Val Thr Ser Gly Asn Tyr Pro Asn Trp Val
            420                 425                 430

Gln Gln Lys Pro Gly Gln Ala Pro Arg Gly Leu Ile Gly Gly Thr Lys
        435                 440                 445

Phe Leu Val Pro Gly Thr Pro Ala Arg Phe Ser Gly Ser Leu Leu Gly
    450                 455                 460

Gly Lys Ala Ala Leu Thr Leu Ser Gly Val Gln Pro Glu Asp Glu Ala
465                 470                 475                 480

Glu Tyr Tyr Cys Thr Leu Trp Tyr Ser Asn Arg Trp Val Phe Gly Gly
            485                 490                 495

Gly Thr Lys Leu Thr Val Leu His His His His His His
            500                 505

<210> SEQ ID NO 335
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 335

Gln Val Gln Leu Gln Glu Ser Gly Gly Gly Ser Val Gln Ala Gly Gly
1               5                   10                  15

Ser Leu Thr Leu Ser Cys Ala Ala Ser Gly Ser Ile Ala Tyr Ile Tyr
            20                  25                  30

Thr Met Asp Trp Tyr Arg Gln Ala Pro Gly Lys Gln Arg Glu Leu Val
        35                  40                  45

Ala Thr Ser Thr His Asp Gly Asn Thr Asp Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
            85                  90                  95

Ala Asp Leu Arg Thr Ala Val Asp Leu Ile Arg Ala Asn Tyr Trp Gly
            100                 105                 110

Gln Gly Thr Gln Val Thr Val Ser Ser Gly Gly Gly Ser Gly Gly
        115                 120                 125

Gly Ser Glu Val Gln Leu Val Glu Ser Gly Gly Gly Leu Val Gln Pro
    130                 135                 140

Gly Asn Ser Leu Arg Leu Ser Cys Ala Ala Ser Gly Phe Thr Phe Ser
145                 150                 155                 160

Lys Phe Gly Met Ser Trp Val Arg Gln Ala Pro Gly Lys Gly Leu Glu
            165                 170                 175

Trp Val Ser Ser Ile Ser Gly Ser Gly Arg Asp Thr Leu Tyr Ala Asp
            180                 185                 190

Ser Val Lys Gly Arg Phe Thr Ile Ser Arg Asp Asn Ala Lys Thr Thr
        195                 200                 205

Leu Tyr Leu Gln Met Asn Ser Leu Arg Pro Glu Asp Thr Ala Val Tyr
    210                 215                 220

Tyr Cys Thr Ile Gly Gly Ser Leu Ser Val Ser Ser Gln Gly Thr Leu
```

```
                225                 230                 235                 240
Val Thr Val Ser Ser Gly Gly Gly Ser Gly Gly Ser Glu Val
                    245                 250                 255

Gln Leu Val Glu Ser Gly Gly Leu Val Gln Pro Gly Gly Ser Leu
                260                 265                 270

Lys Leu Ser Cys Ala Ala Ser Gly Phe Thr Phe Asn Lys Tyr Ala Ile
            275                 280                 285

Asn Trp Val Arg Gln Ala Pro Gly Lys Gly Leu Glu Trp Val Ala Arg
        290                 295                 300

Ile Arg Ser Lys Tyr Asn Asn Tyr Ala Thr Tyr Tyr Ala Asp Gln Val
305                 310                 315                 320

Lys Asp Arg Phe Thr Ile Ser Arg Asp Asp Ser Lys Asn Thr Ala Tyr
                325                 330                 335

Leu Gln Met Asn Asn Leu Lys Thr Glu Asp Thr Ala Val Tyr Tyr Cys
            340                 345                 350

Val Arg His Ala Asn Phe Gly Asn Ser Tyr Ile Ser Tyr Trp Ala Tyr
        355                 360                 365

Trp Gly Gln Gly Thr Leu Val Thr Val Ser Ser Gly Gly Gly Gly Ser
    370                 375                 380

Gly Gly Gly Gly Ser Gly Gly Gly Ser Gln Thr Val Val Thr Gln
385                 390                 395                 400

Glu Pro Ser Leu Thr Val Ser Pro Gly Gly Thr Val Thr Leu Thr Cys
                405                 410                 415

Ala Ser Ser Thr Gly Ala Val Thr Ser Gly Asn Tyr Pro Asn Trp Val
            420                 425                 430

Gln Gln Lys Pro Gly Gln Ala Pro Arg Gly Leu Ile Gly Gly Thr Lys
        435                 440                 445

Phe Leu Val Pro Gly Thr Pro Ala Arg Phe Ser Gly Ser Leu Leu Gly
    450                 455                 460

Gly Lys Ala Ala Leu Thr Leu Ser Gly Val Gln Pro Glu Asp Glu Ala
465                 470                 475                 480

Glu Tyr Tyr Cys Thr Leu Trp Tyr Ser Asn Arg Trp Val Phe Gly Gly
                485                 490                 495

Gly Thr Lys Leu Thr Val Leu His His His His His
            500                 505

<210> SEQ ID NO 336
<211> LENGTH: 501
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 336

Gln Val Gln Leu Gln Glu Ser Gly Gly Gly Leu Val Gln Pro Gly Gly
1               5                   10                  15

Ser Leu Arg Leu Ser Cys Thr Ala Ser Val Ser Ile Phe Ser Val Asn
            20                  25                  30

Ala Val Asp Trp Tyr Arg Gln Ser Pro Gly Lys Glu Arg Glu Leu Val
        35                  40                  45

Ala Ile Met Thr Ser Asp Gly Ser Thr Asn Tyr Gly Asp Ser Val Lys
    50                  55                  60

Gly Arg Phe Thr Ile Ser Arg Asp Asn Ala Lys Asn Thr Val Tyr Leu
65                  70                  75                  80
```

```
Gln Met Asn Asn Leu Lys Pro Glu Asp Thr Ala Val Tyr Tyr Cys Asn
                 85                  90                  95

Thr Val Pro Pro Arg Tyr Trp Gly Gln Gly Thr Gln Val Thr Val Ser
            100                 105                 110

Ser Gly Gly Gly Gly Ser Gly Gly Gly Ser Glu Val Gln Leu Val Glu
        115                 120                 125

Ser Gly Gly Gly Leu Val Gln Pro Gly Asn Ser Leu Arg Leu Ser Cys
        130                 135                 140

Ala Ala Ser Gly Phe Thr Phe Ser Lys Phe Gly Met Ser Trp Val Arg
145                 150                 155                 160

Gln Ala Pro Gly Lys Gly Leu Glu Trp Val Ser Ser Ile Ser Gly Ser
                165                 170                 175

Gly Arg Asp Thr Leu Tyr Ala Asp Ser Val Lys Gly Arg Phe Thr Ile
            180                 185                 190

Ser Arg Asp Asn Ala Lys Thr Thr Leu Tyr Leu Gln Met Asn Ser Leu
        195                 200                 205

Arg Pro Glu Asp Thr Ala Val Tyr Tyr Cys Thr Ile Gly Gly Ser Leu
    210                 215                 220

Ser Val Ser Ser Gln Gly Thr Leu Val Thr Val Ser Ser Gly Gly Gly
225                 230                 235                 240

Gly Ser Gly Gly Gly Ser Glu Val Gln Leu Val Glu Ser Gly Gly Gly
                245                 250                 255

Leu Val Gln Pro Gly Gly Ser Leu Lys Leu Ser Cys Ala Ala Ser Gly
            260                 265                 270

Phe Thr Phe Asn Lys Tyr Ala Ile Asn Trp Val Arg Gln Ala Pro Gly
        275                 280                 285

Lys Gly Leu Glu Trp Val Ala Arg Ile Arg Ser Lys Tyr Asn Asn Tyr
    290                 295                 300

Ala Thr Tyr Tyr Ala Asp Gln Val Lys Asp Arg Phe Thr Ile Ser Arg
305                 310                 315                 320

Asp Asp Ser Lys Asn Thr Ala Tyr Leu Gln Met Asn Asn Leu Lys Thr
                325                 330                 335

Glu Asp Thr Ala Val Tyr Tyr Cys Val Arg His Ala Asn Phe Gly Asn
            340                 345                 350

Ser Tyr Ile Ser Tyr Trp Ala Tyr Trp Gly Gln Gly Thr Leu Val Thr
        355                 360                 365

Val Ser Ser Gly Gly Gly Gly Ser Gly Gly Gly Gly Ser Gly Gly Gly
        370                 375                 380

Gly Ser Gln Thr Val Val Thr Gln Glu Pro Ser Leu Thr Val Ser Pro
385                 390                 395                 400

Gly Gly Thr Val Thr Leu Thr Cys Ala Ser Ser Thr Gly Ala Val Thr
                405                 410                 415

Ser Gly Asn Tyr Pro Asn Trp Val Gln Gln Lys Pro Gly Gln Ala Pro
            420                 425                 430

Arg Gly Leu Ile Gly Gly Thr Lys Phe Leu Val Pro Gly Thr Pro Ala
        435                 440                 445

Arg Phe Ser Gly Ser Leu Leu Gly Gly Lys Ala Ala Leu Thr Leu Ser
    450                 455                 460

Gly Val Gln Pro Glu Asp Glu Ala Glu Tyr Tyr Cys Thr Leu Trp Tyr
465                 470                 475                 480

Ser Asn Arg Trp Val Phe Gly Gly Gly Thr Lys Leu Thr Val Leu His
                485                 490                 495

His His His His His
```

<210> SEQ ID NO 337
<211> LENGTH: 509
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 337

```
Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Ala Tyr Ile Tyr
            20                  25                  30

Thr Met Asp Trp Tyr Arg Gln Ala Pro Gly Lys Gln Arg Glu Leu Val
        35                  40                  45

Ala Thr Ser Thr Arg Asp Gly Asn Ile Asp Tyr Ala Asp Ser Val Lys
    50                  55                  60

Gly Arg Phe Thr Ile Ser Arg Asp Ser Ala Lys Asn Thr Val Tyr Leu
65                  70                  75                  80

Gln Met Ser Ser Leu Lys Pro Glu Asp Thr Ala Val Tyr Tyr Cys Asn
                85                  90                  95

Ala Asp Leu Arg Thr Ala Val Asp Leu Ile Arg Ala Asn Tyr Trp Gly
            100                 105                 110

Gln Gly Thr Gln Val Thr Val Ser Ser Gly Gly Gly Ser Gly Gly
        115                 120                 125

Gly Ser Glu Val Gln Leu Val Glu Ser Gly Gly Gly Leu Val Gln Pro
    130                 135                 140

Gly Asn Ser Leu Arg Leu Ser Cys Ala Ala Ser Gly Phe Thr Phe Ser
145                 150                 155                 160

Lys Phe Gly Met Ser Trp Val Arg Gln Ala Pro Gly Lys Gly Leu Glu
                165                 170                 175

Trp Val Ser Ser Ile Ser Gly Ser Gly Arg Asp Thr Leu Tyr Ala Asp
            180                 185                 190

Ser Val Lys Gly Arg Phe Thr Ile Ser Arg Asp Asn Ala Lys Thr Thr
        195                 200                 205

Leu Tyr Leu Gln Met Asn Ser Leu Arg Pro Glu Asp Thr Ala Val Tyr
    210                 215                 220

Tyr Cys Thr Ile Gly Gly Ser Leu Ser Val Ser Ser Gln Gly Thr Leu
225                 230                 235                 240

Val Thr Val Ser Ser Gly Gly Gly Gly Ser Gly Gly Gly Ser Glu Val
                245                 250                 255

Gln Leu Val Glu Ser Gly Gly Gly Leu Val Gln Pro Gly Gly Ser Leu
            260                 265                 270

Lys Leu Ser Cys Ala Ala Ser Gly Phe Thr Phe Asn Lys Tyr Ala Ile
        275                 280                 285

Asn Trp Val Arg Gln Ala Pro Gly Lys Gly Leu Glu Trp Val Ala Arg
    290                 295                 300

Ile Arg Ser Lys Tyr Asn Asn Tyr Ala Thr Tyr Tyr Ala Asp Gln Val
305                 310                 315                 320

Lys Asp Arg Phe Thr Ile Ser Arg Asp Asp Ser Lys Asn Thr Ala Tyr
                325                 330                 335

Leu Gln Met Asn Asn Leu Lys Thr Glu Asp Thr Ala Val Tyr Tyr Cys
            340                 345                 350
```

```
Val Arg His Ala Asn Phe Gly Asn Ser Tyr Ile Ser Tyr Trp Ala Tyr
        355                 360                 365

Trp Gly Gln Gly Thr Leu Val Thr Val Ser Ser Gly Gly Gly Gly Ser
    370                 375                 380

Gly Gly Gly Gly Ser Gly Gly Gly Ser Gln Thr Val Val Thr Gln
385                 390                 395                 400

Glu Pro Ser Leu Thr Val Ser Pro Gly Gly Thr Val Thr Leu Thr Cys
                405                 410                 415

Ala Ser Ser Thr Gly Ala Val Thr Ser Gly Asn Tyr Pro Asn Trp Val
            420                 425                 430

Gln Gln Lys Pro Gly Gln Ala Pro Arg Gly Leu Ile Gly Gly Thr Lys
        435                 440                 445

Phe Leu Val Pro Gly Thr Pro Ala Arg Phe Ser Gly Ser Leu Leu Gly
    450                 455                 460

Gly Lys Ala Ala Leu Thr Leu Ser Gly Val Gln Pro Glu Asp Glu Ala
465                 470                 475                 480

Glu Tyr Tyr Cys Thr Leu Trp Tyr Ser Asn Arg Trp Val Phe Gly Gly
                485                 490                 495

Gly Thr Lys Leu Thr Val Leu His His His His His His
                500                 505
```

<210> SEQ ID NO 338
<211> LENGTH: 507
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 338

```
Gln Val Gln Leu Gln Glu Ser Gly Gly Gly Leu Val Gln Ala Gly Gly
1               5                   10                  15

Ser Leu Thr Leu Ser Cys Ala Ala Ser Gly Arg Tyr Gln Leu Ala Trp
            20                  25                  30

Phe Arg Gln Ala Pro Glu Lys Val Arg Glu Phe Val Gly Thr Ile Ser
        35                  40                  45

Ser Gly Asp Ser Thr Trp Tyr Thr Asn Ser Val Lys Gly Arg Phe Ala
    50                  55                  60

Ile Ser Arg Asp Ser Ala Arg Asn Thr Val Tyr Leu Gln Met Asn Asp
65                  70                  75                  80

Leu Lys Pro Glu Asp Thr Ala Val Tyr Tyr Cys Ala Ala Ala Leu Tyr
                85                  90                  95

Tyr Arg Asp Ser Arg Arg Ala Ala Asp Tyr Pro Tyr Trp Gly Gln Gly
            100                 105                 110

Thr Gln Val Thr Val Ser Ser Gly Gly Gly Gly Ser Gly Gly Gly Ser
        115                 120                 125

Glu Val Gln Leu Val Glu Ser Gly Gly Gly Leu Val Gln Pro Gly Asn
    130                 135                 140

Ser Leu Arg Leu Ser Cys Ala Ala Ser Gly Phe Thr Phe Ser Lys Phe
145                 150                 155                 160

Gly Met Ser Trp Val Arg Gln Ala Pro Gly Lys Gly Leu Glu Trp Val
                165                 170                 175

Ser Ser Ile Ser Gly Ser Gly Arg Asp Thr Leu Tyr Ala Asp Ser Val
            180                 185                 190

Lys Gly Arg Phe Thr Ile Ser Arg Asp Asn Ala Lys Thr Thr Leu Tyr
        195                 200                 205
```

Leu Gln Met Asn Ser Leu Arg Pro Glu Asp Thr Ala Val Tyr Tyr Cys
            210                 215                 220

Thr Ile Gly Gly Ser Leu Ser Val Ser Ser Gln Gly Thr Leu Val Thr
225                 230                 235                 240

Val Ser Ser Gly Gly Gly Gly Ser Gly Gly Gly Ser Glu Val Gln Leu
                245                 250                 255

Val Glu Ser Gly Gly Gly Leu Val Gln Pro Gly Gly Ser Leu Lys Leu
                260                 265                 270

Ser Cys Ala Ala Ser Gly Phe Thr Phe Asn Lys Tyr Ala Ile Asn Trp
            275                 280                 285

Val Arg Gln Ala Pro Gly Lys Gly Leu Glu Trp Val Ala Arg Ile Arg
            290                 295                 300

Ser Lys Tyr Asn Asn Tyr Ala Thr Tyr Tyr Ala Asp Gln Val Lys Asp
305                 310                 315                 320

Arg Phe Thr Ile Ser Arg Asp Asp Ser Lys Asn Thr Ala Tyr Leu Gln
                325                 330                 335

Met Asn Asn Leu Lys Thr Glu Asp Thr Ala Val Tyr Tyr Cys Val Arg
            340                 345                 350

His Ala Asn Phe Gly Asn Ser Tyr Ile Ser Tyr Trp Ala Tyr Trp Gly
            355                 360                 365

Gln Gly Thr Leu Val Thr Val Ser Ser Gly Gly Gly Gly Ser Gly Gly
370                 375                 380

Gly Gly Ser Gly Gly Gly Gly Ser Gln Thr Val Val Thr Gln Glu Pro
385                 390                 395                 400

Ser Leu Thr Val Ser Pro Gly Gly Thr Val Thr Leu Thr Cys Ala Ser
                405                 410                 415

Ser Thr Gly Ala Val Thr Ser Gly Asn Tyr Pro Asn Trp Val Gln Gln
            420                 425                 430

Lys Pro Gly Gln Ala Pro Arg Gly Leu Ile Gly Gly Thr Lys Phe Leu
            435                 440                 445

Val Pro Gly Thr Pro Ala Arg Phe Ser Gly Ser Leu Leu Gly Gly Lys
            450                 455                 460

Ala Ala Leu Thr Leu Ser Gly Val Gln Pro Glu Asp Glu Ala Glu Tyr
465                 470                 475                 480

Tyr Cys Thr Leu Trp Tyr Ser Asn Arg Trp Val Phe Gly Gly Gly Thr
                485                 490                 495

Lys Leu Thr Val Leu His His His His His His
            500                 505

<210> SEQ ID NO 339
<211> LENGTH: 507
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 339

Gln Val Gln Leu Gln Glu Ser Gly Gly Gly Ser Val Gln Ala Gly Gly
1               5                   10                  15

Ser Leu Arg Leu Ser Cys Ala Ala Ser Gly Arg Tyr His Met Ala Trp
            20                  25                  30

Phe Arg Gln Ala Pro Glu Lys Glu Arg Glu Phe Val Gly Thr Ile Ser
            35                  40                  45

Ser Gly Asp Ser Thr Trp Tyr Thr Asn Ser Val Lys Gly Arg Phe Ala

```
              50                  55                  60
Ile Ser Arg Asp Ser Ala Arg Asn Thr Ala Tyr Leu Gln Met Asn Asp
 65                  70                  75                  80

Leu Lys Pro Glu Asp Thr Ala Val Tyr Tyr Cys Ala Ala Leu Tyr
                     85                  90                  95

Tyr Gly Asp Ser Arg Arg Ala Ala Asp Tyr Pro Tyr Trp Gly Gln Gly
                    100                 105                 110

Thr Gln Val Thr Val Ser Ser Gly Gly Gly Ser Gly Gly Gly Ser
                    115                 120                 125

Glu Val Gln Leu Val Glu Ser Gly Gly Leu Val Gln Pro Gly Asn
                    130                 135                 140

Ser Leu Arg Leu Ser Cys Ala Ala Ser Gly Phe Thr Phe Ser Lys Phe
145                 150                 155                 160

Gly Met Ser Trp Val Arg Gln Ala Pro Gly Lys Gly Leu Glu Trp Val
                    165                 170                 175

Ser Ser Ile Ser Gly Ser Gly Arg Asp Thr Leu Tyr Ala Asp Ser Val
                    180                 185                 190

Lys Gly Arg Phe Thr Ile Ser Arg Asp Asn Ala Lys Thr Thr Leu Tyr
                    195                 200                 205

Leu Gln Met Asn Ser Leu Arg Pro Glu Asp Thr Ala Val Tyr Tyr Cys
                    210                 215                 220

Thr Ile Gly Gly Ser Leu Ser Val Ser Ser Gln Gly Thr Leu Val Thr
225                 230                 235                 240

Val Ser Ser Gly Gly Gly Gly Ser Gly Gly Ser Glu Val Gln Leu
                    245                 250                 255

Val Glu Ser Gly Gly Gly Leu Val Gln Pro Gly Gly Ser Leu Lys Leu
                    260                 265                 270

Ser Cys Ala Ala Ser Gly Phe Thr Phe Asn Lys Tyr Ala Ile Asn Trp
                    275                 280                 285

Val Arg Gln Ala Pro Gly Lys Gly Leu Glu Trp Val Ala Arg Ile Arg
                    290                 295                 300

Ser Lys Tyr Asn Asn Tyr Ala Thr Tyr Tyr Ala Asp Gln Val Lys Asp
305                 310                 315                 320

Arg Phe Thr Ile Ser Arg Asp Asp Ser Lys Asn Thr Ala Tyr Leu Gln
                    325                 330                 335

Met Asn Asn Leu Lys Thr Glu Asp Thr Ala Val Tyr Tyr Cys Val Arg
                    340                 345                 350

His Ala Asn Phe Gly Asn Ser Tyr Ile Ser Tyr Trp Ala Tyr Trp Gly
                    355                 360                 365

Gln Gly Thr Leu Val Thr Val Ser Ser Gly Gly Gly Ser Gly Gly
                    370                 375                 380

Gly Gly Ser Gly Gly Gly Ser Gln Thr Val Thr Gln Glu Pro
385                 390                 395                 400

Ser Leu Thr Val Ser Pro Gly Gly Thr Val Thr Leu Thr Cys Ala Ser
                    405                 410                 415

Ser Thr Gly Ala Val Thr Ser Gly Asn Tyr Pro Asn Trp Val Gln Gln
                    420                 425                 430

Lys Pro Gly Gln Ala Pro Arg Gly Leu Ile Gly Gly Thr Lys Phe Leu
                    435                 440                 445

Val Pro Gly Thr Pro Ala Arg Phe Ser Gly Ser Leu Leu Gly Gly Lys
                    450                 455                 460

Ala Ala Leu Thr Leu Ser Gly Val Gln Pro Glu Asp Glu Ala Glu Tyr
465                 470                 475                 480
```

Tyr Cys Thr Leu Trp Tyr Ser Asn Arg Trp Val Phe Gly Gly Gly Thr
          485                 490                 495

Lys Leu Thr Val Leu His His His His His
          500                 505

<210> SEQ ID NO 340
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 340

Gln Val Gln Leu Gln Glu Ser Gly Gly Gly Ser Val Gln Ala Gly Gly
1               5                   10                  15

Ser Leu Arg Leu Ser Cys Ala Ala Ser Gly Ser Ile Ala Tyr Ile Tyr
            20                  25                  30

Thr Met Asp Trp Tyr Arg Gln Ala Pro Gly Lys Gln Arg Glu Leu Val
        35                  40                  45

Ala Thr Ser Thr His Asp Gly Asn Thr Asp Tyr Thr Asp Ser Val Lys
50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Leu Arg Thr Ala Val Asp Leu Ile Arg Ala Asn Tyr Trp Gly
            100                 105                 110

Gln Gly Thr Gln Val Thr Val Ser Ser Gly Gly Gly Ser Gly Gly
        115                 120                 125

Gly Ser Glu Val Gln Leu Val Glu Ser Gly Gly Leu Val Gln Pro
    130                 135                 140

Gly Asn Ser Leu Arg Leu Ser Cys Ala Ala Ser Gly Phe Thr Phe Ser
145                 150                 155                 160

Lys Phe Gly Met Ser Trp Val Arg Gln Ala Pro Gly Lys Gly Leu Glu
                165                 170                 175

Trp Val Ser Ser Ile Ser Gly Ser Gly Arg Asp Thr Leu Tyr Ala Asp
            180                 185                 190

Ser Val Lys Gly Arg Phe Thr Ile Ser Arg Asp Asn Ala Lys Thr Thr
        195                 200                 205

Leu Tyr Leu Gln Met Asn Ser Leu Arg Pro Glu Asp Thr Ala Val Tyr
    210                 215                 220

Tyr Cys Thr Ile Gly Gly Ser Leu Ser Val Ser Ser Gln Gly Thr Leu
225                 230                 235                 240

Val Thr Val Ser Ser Gly Gly Gly Gly Ser Gly Gly Gly Ser Glu Val
                245                 250                 255

Gln Leu Val Glu Ser Gly Gly Gly Leu Val Gln Pro Gly Gly Ser Leu
            260                 265                 270

Lys Leu Ser Cys Ala Ala Ser Gly Phe Thr Phe Asn Lys Tyr Ala Ile
        275                 280                 285

Asn Trp Val Arg Gln Ala Pro Gly Lys Gly Leu Glu Trp Val Ala Arg
    290                 295                 300

Ile Arg Ser Lys Tyr Asn Asn Tyr Ala Thr Tyr Tyr Ala Asp Gln Val
305                 310                 315                 320

Lys Asp Arg Phe Thr Ile Ser Arg Asp Asp Ser Lys Asn Thr Ala Tyr

```
                325                 330                 335
Leu Gln Met Asn Asn Leu Lys Thr Glu Asp Thr Ala Val Tyr Tyr Cys
            340                 345                 350
Val Arg His Ala Asn Phe Gly Asn Ser Tyr Ile Ser Tyr Trp Ala Tyr
            355                 360                 365
Trp Gly Gln Gly Thr Leu Val Thr Val Ser Ser Gly Gly Gly Gly Ser
    370                 375                 380
Gly Gly Gly Gly Ser Gly Gly Gly Ser Gln Thr Val Val Thr Gln
385                 390                 395                 400
Glu Pro Ser Leu Thr Val Ser Pro Gly Gly Thr Val Thr Leu Thr Cys
            405                 410                 415
Ala Ser Ser Thr Gly Ala Val Thr Ser Gly Asn Tyr Pro Asn Trp Val
            420                 425                 430
Gln Gln Lys Pro Gly Gln Ala Pro Arg Gly Leu Ile Gly Gly Thr Lys
            435                 440                 445
Phe Leu Val Pro Gly Thr Pro Ala Arg Phe Ser Gly Ser Leu Leu Gly
        450                 455                 460
Gly Lys Ala Ala Leu Thr Leu Ser Gly Val Gln Pro Glu Asp Glu Ala
465                 470                 475                 480
Glu Tyr Tyr Cys Thr Leu Trp Tyr Ser Asn Arg Trp Val Phe Gly Gly
                485                 490                 495
Gly Thr Lys Leu Thr Val Leu His His His His His His
            500                 505
```

```
<210> SEQ ID NO 341
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 341

Gln Val Gln Leu Gln Glu Ser Gly Gly Gly Leu Val Gln Ala Gly Gly
1               5                   10                  15
Ser Leu Arg Leu Ser Cys Ala Ala Ser Gly Ser Ile Ala Tyr Ile Tyr
            20                  25                  30
Thr Met Asp Trp Tyr Arg Gln Thr Pro Gly Lys Gln Arg Glu Leu Val
        35                  40                  45
Ala Thr Ser Thr Arg Asp Ala Asn Thr Asp Tyr Ala Gly Ser Val Lys
    50                  55                  60
Gly Arg Phe Thr Ile Ser Arg Asp Asn Ala Lys Asp Thr Val Tyr Leu
65                  70                  75                  80
Gln Met Asn Ser Leu Lys Pro Glu Asp Thr Ala Val Tyr Tyr Cys His
                85                  90                  95
Ala Asp Leu Arg Thr Ala Val Asp Leu Ile Arg Ala Asn Tyr Trp Gly
            100                 105                 110
Gln Gly Thr Gln Val Thr Val Ser Gly Gly Gly Ser Gly Gly
        115                 120                 125
Gly Ser Glu Val Gln Leu Val Glu Ser Gly Gly Gly Leu Val Gln Pro
    130                 135                 140
Gly Asn Ser Leu Arg Leu Ser Cys Ala Ala Ser Gly Phe Thr Phe Ser
145                 150                 155                 160
Lys Phe Gly Met Ser Trp Val Arg Gln Ala Pro Gly Lys Gly Leu Glu
                165                 170                 175
```

Trp Val Ser Ser Ile Ser Gly Ser Gly Arg Asp Thr Leu Tyr Ala Asp
            180                 185                 190

Ser Val Lys Gly Arg Phe Thr Ile Ser Arg Asp Asn Ala Lys Thr Thr
        195                 200                 205

Leu Tyr Leu Gln Met Asn Ser Leu Arg Pro Glu Asp Thr Ala Val Tyr
    210                 215                 220

Tyr Cys Thr Ile Gly Gly Ser Leu Ser Val Ser Ser Gln Gly Thr Leu
225                 230                 235                 240

Val Thr Val Ser Ser Gly Gly Gly Gly Ser Gly Gly Gly Ser Glu Val
                245                 250                 255

Gln Leu Val Glu Ser Gly Gly Gly Leu Val Gln Pro Gly Gly Ser Leu
            260                 265                 270

Lys Leu Ser Cys Ala Ala Ser Gly Phe Thr Phe Asn Lys Tyr Ala Ile
        275                 280                 285

Asn Trp Val Arg Gln Ala Pro Gly Lys Gly Leu Glu Trp Val Ala Arg
    290                 295                 300

Ile Arg Ser Lys Tyr Asn Asn Tyr Ala Thr Tyr Tyr Ala Asp Gln Val
305                 310                 315                 320

Lys Asp Arg Phe Thr Ile Ser Arg Asp Asp Ser Lys Asn Thr Ala Tyr
                325                 330                 335

Leu Gln Met Asn Asn Leu Lys Thr Glu Asp Thr Ala Val Tyr Tyr Cys
            340                 345                 350

Val Arg His Ala Asn Phe Gly Asn Ser Tyr Ile Ser Tyr Trp Ala Tyr
        355                 360                 365

Trp Gly Gln Gly Thr Leu Val Thr Val Ser Ser Gly Gly Gly Gly Ser
    370                 375                 380

Gly Gly Gly Gly Ser Gly Gly Gly Ser Gln Thr Val Val Thr Gln
385                 390                 395                 400

Glu Pro Ser Leu Thr Val Ser Pro Gly Gly Thr Val Thr Leu Thr Cys
                405                 410                 415

Ala Ser Ser Thr Gly Ala Val Thr Ser Gly Asn Tyr Pro Asn Trp Val
            420                 425                 430

Gln Gln Lys Pro Gly Gln Ala Pro Arg Gly Leu Ile Gly Gly Thr Lys
        435                 440                 445

Phe Leu Val Pro Gly Thr Pro Ala Arg Phe Ser Gly Ser Leu Leu Gly
    450                 455                 460

Gly Lys Ala Ala Leu Thr Leu Ser Gly Val Gln Pro Glu Asp Glu Ala
465                 470                 475                 480

Glu Tyr Tyr Cys Thr Leu Trp Tyr Ser Asn Arg Trp Val Phe Gly Gly
                485                 490                 495

Gly Thr Lys Leu Thr Val Leu His His His His His His
            500                 505

<210> SEQ ID NO 342
<211> LENGTH: 507
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 342

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Tyr Asn Met Ala Trp
            20                  25                  30

-continued

Phe Arg Gln Ala Pro Glu Lys Glu Arg Glu Phe Val Gly Thr Ile Thr
            35                  40                  45

Ser Ala Asp Ser Thr Trp Tyr Thr Asn Ser Val Lys Gly Arg Phe Ala
 50                  55                  60

Ile Thr Gln Asp Ser Ala Arg Asn Thr Val Tyr Leu Gln Met Asn Asp
65                  70                  75                  80

Leu Lys Pro Glu Asp Thr Ala Val Tyr Tyr Cys Ala Ala Leu Tyr
                85                  90                  95

Tyr Gly Asp Ser Arg Arg Ala Ala Asp Tyr Pro Tyr Trp Gly Gln Gly
                100                 105                 110

Thr Gln Val Thr Val Ser Ser Gly Gly Gly Ser Gly Gly Gly Ser
                115                 120                 125

Glu Val Gln Leu Val Glu Ser Gly Gly Gly Leu Val Gln Pro Gly Asn
                130                 135                 140

Ser Leu Arg Leu Ser Cys Ala Ala Ser Gly Phe Thr Phe Ser Lys Phe
145                 150                 155                 160

Gly Met Ser Trp Val Arg Gln Ala Pro Gly Lys Gly Leu Glu Trp Val
                165                 170                 175

Ser Ser Ile Ser Gly Ser Gly Arg Asp Thr Leu Tyr Ala Asp Ser Val
                180                 185                 190

Lys Gly Arg Phe Thr Ile Ser Arg Asp Asn Ala Lys Thr Thr Leu Tyr
                195                 200                 205

Leu Gln Met Asn Ser Leu Arg Pro Glu Asp Thr Ala Val Tyr Tyr Cys
                210                 215                 220

Thr Ile Gly Gly Ser Leu Ser Val Ser Ser Gln Gly Thr Leu Val Thr
225                 230                 235                 240

Val Ser Ser Gly Gly Gly Gly Ser Gly Gly Gly Ser Glu Val Gln Leu
                245                 250                 255

Val Glu Ser Gly Gly Gly Leu Val Gln Pro Gly Gly Ser Leu Lys Leu
                260                 265                 270

Ser Cys Ala Ala Ser Gly Phe Thr Phe Asn Lys Tyr Ala Ile Asn Trp
                275                 280                 285

Val Arg Gln Ala Pro Gly Lys Gly Leu Glu Trp Val Ala Arg Ile Arg
                290                 295                 300

Ser Lys Tyr Asn Asn Tyr Ala Thr Tyr Tyr Ala Asp Gln Val Lys Asp
305                 310                 315                 320

Arg Phe Thr Ile Ser Arg Asp Asp Ser Lys Asn Thr Ala Tyr Leu Gln
                325                 330                 335

Met Asn Asn Leu Lys Thr Glu Asp Thr Ala Val Tyr Tyr Cys Val Arg
                340                 345                 350

His Ala Asn Phe Gly Asn Ser Tyr Ile Ser Tyr Trp Ala Tyr Trp Gly
                355                 360                 365

Gln Gly Thr Leu Val Thr Val Ser Ser Gly Gly Gly Gly Ser Gly Gly
                370                 375                 380

Gly Gly Ser Gly Gly Gly Ser Gln Thr Val Val Thr Gln Glu Pro
385                 390                 395                 400

Ser Leu Thr Val Ser Pro Gly Gly Thr Val Thr Leu Thr Cys Ala Ser
                405                 410                 415

Ser Thr Gly Ala Val Thr Ser Gly Asn Tyr Pro Asn Trp Val Gln Gln
                420                 425                 430

Lys Pro Gly Gln Ala Pro Arg Gly Leu Ile Gly Gly Thr Lys Phe Leu
                435                 440                 445

```
Val Pro Gly Thr Pro Ala Arg Phe Ser Gly Ser Leu Leu Gly Gly Lys
            450                 455                 460

Ala Ala Leu Thr Leu Ser Gly Val Gln Pro Glu Asp Glu Ala Glu Tyr
465                 470                 475                 480

Tyr Cys Thr Leu Trp Tyr Ser Asn Arg Trp Val Phe Gly Gly Gly Thr
                485                 490                 495

Lys Leu Thr Val Leu His His His His His His
            500                 505

<210> SEQ ID NO 343
<211> LENGTH: 507
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 343

Gln Val Gln Leu Gln Glu Ser Gly Gly Leu Val Gln Pro Gly Gly
1               5                   10                  15

Ser Leu Arg Leu Ser Cys Ala Ala Ser Gly Arg Tyr Gln Met Ala Trp
            20                  25                  30

Phe Arg Gln Ala Pro Glu Lys Glu Arg Glu Phe Val Gly Thr Ile Ser
        35                  40                  45

Ser Gly Asp Ser Thr Trp Tyr Thr Asn Ser Val Lys Gly Arg Phe Ala
50                  55                  60

Ile Ser Arg Asp Ser Ala Arg Thr Thr Val Tyr Leu Gln Met Asn Asp
65                  70                  75                  80

Leu Lys Pro Glu Asp Thr Ala Val Tyr Tyr Cys Ala Ala Leu Tyr
                85                  90                  95

Tyr Arg Asp Ser Trp Arg Ala Ala Asp Tyr Pro Tyr Trp Gly Gln Gly
                100                 105                 110

Thr Gln Val Thr Val Ser Ser Gly Gly Gly Gly Ser Gly Gly Gly Ser
            115                 120                 125

Glu Val Gln Leu Val Glu Ser Gly Gly Gly Leu Val Gln Pro Gly Asn
            130                 135                 140

Ser Leu Arg Leu Ser Cys Ala Ala Ser Gly Phe Thr Phe Ser Lys Phe
145                 150                 155                 160

Gly Met Ser Trp Val Arg Gln Ala Pro Gly Lys Gly Leu Glu Trp Val
                165                 170                 175

Ser Ser Ile Ser Gly Ser Gly Arg Asp Thr Leu Tyr Ala Asp Ser Val
                180                 185                 190

Lys Gly Arg Phe Thr Ile Ser Arg Asp Asn Ala Lys Thr Thr Leu Tyr
            195                 200                 205

Leu Gln Met Asn Ser Leu Arg Pro Glu Asp Thr Ala Val Tyr Tyr Cys
            210                 215                 220

Thr Ile Gly Gly Ser Leu Ser Val Ser Ser Gln Gly Thr Leu Val Thr
225                 230                 235                 240

Val Ser Ser Gly Gly Gly Gly Ser Gly Gly Ser Glu Val Gln Leu
                245                 250                 255

Val Glu Ser Gly Gly Gly Leu Val Gln Pro Gly Gly Ser Leu Lys Leu
            260                 265                 270

Ser Cys Ala Ala Ser Gly Phe Thr Phe Asn Lys Tyr Ala Ile Asn Trp
            275                 280                 285

Val Arg Gln Ala Pro Gly Lys Gly Leu Glu Trp Val Ala Arg Ile Arg
            290                 295                 300
```

```
Ser Lys Tyr Asn Asn Tyr Ala Thr Tyr Tyr Ala Asp Gln Val Lys Asp
305                 310                 315                 320

Arg Phe Thr Ile Ser Arg Asp Asp Ser Lys Asn Thr Ala Tyr Leu Gln
            325                 330                 335

Met Asn Asn Leu Lys Thr Glu Asp Thr Ala Val Tyr Tyr Cys Val Arg
            340                 345                 350

His Ala Asn Phe Gly Asn Ser Tyr Ile Ser Tyr Trp Ala Tyr Trp Gly
        355                 360                 365

Gln Gly Thr Leu Val Thr Val Ser Ser Gly Gly Gly Ser Gly Gly
        370                 375                 380

Gly Gly Ser Gly Gly Gly Ser Gln Thr Val Val Thr Gln Glu Pro
385                 390                 395                 400

Ser Leu Thr Val Ser Pro Gly Gly Thr Val Thr Leu Thr Cys Ala Ser
                405                 410                 415

Ser Thr Gly Ala Val Thr Ser Gly Asn Tyr Pro Asn Trp Val Gln Gln
            420                 425                 430

Lys Pro Gly Gln Ala Pro Arg Gly Leu Ile Gly Gly Thr Lys Phe Leu
            435                 440                 445

Val Pro Gly Thr Pro Ala Arg Phe Ser Gly Ser Leu Leu Gly Gly Lys
    450                 455                 460

Ala Ala Leu Thr Leu Ser Gly Val Gln Pro Glu Asp Glu Ala Glu Tyr
465                 470                 475                 480

Tyr Cys Thr Leu Trp Tyr Ser Asn Arg Trp Val Phe Gly Gly Gly Thr
                485                 490                 495

Lys Leu Thr Val Leu His His His His His
                500                 505

<210> SEQ ID NO 344
<211> LENGTH: 507
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 344

Gln Val Gln Leu Gln Glu Ser Gly Gly Gly Leu Val Gln Pro Gly Glu
1               5                   10                  15

Ser Leu Arg Leu Ser Cys Ala Ala Thr Gly Arg Tyr His Leu Ala Trp
            20                  25                  30

Phe Arg Gln Ala Pro Glu Lys Glu Arg Glu Phe Val Gly Thr Ile Thr
        35                  40                  45

Ser Ala Asp Ser Thr Trp Tyr Thr Asn Ser Val Lys Gly Arg Phe Ala
    50                  55                  60

Ile Thr Arg Asp Ser Ala Arg Asn Thr Val Tyr Leu Gln Met Asn Asp
65                  70                  75                  80

Leu Lys Pro Glu Asp Thr Ala Val Tyr Tyr Cys Ala Ala Ala Leu Tyr
                85                  90                  95

Tyr Gly Asp Ser Arg Arg Ala Ala Asp Tyr Pro Tyr Trp Gly Gln Gly
            100                 105                 110

Thr Gln Val Thr Val Ser Ser Gly Gly Gly Gly Ser Gly Gly Gly Ser
            115                 120                 125

Glu Val Gln Leu Val Glu Ser Gly Gly Gly Leu Val Gln Pro Gly Asn
            130                 135                 140

Ser Leu Arg Leu Ser Cys Ala Ala Ser Gly Phe Thr Phe Ser Lys Phe
```

```
            145                 150                 155                 160

Gly Met Ser Trp Val Arg Gln Ala Pro Gly Lys Gly Leu Glu Trp Val
                165                 170                 175

Ser Ser Ile Ser Gly Ser Gly Arg Asp Thr Leu Tyr Ala Asp Ser Val
                180                 185                 190

Lys Gly Arg Phe Thr Ile Ser Arg Asp Asn Ala Lys Thr Thr Leu Tyr
                195                 200                 205

Leu Gln Met Asn Ser Leu Arg Pro Glu Asp Thr Ala Val Tyr Tyr Cys
                210                 215                 220

Thr Ile Gly Gly Ser Leu Ser Val Ser Ser Gln Gly Thr Leu Val Thr
225                 230                 235                 240

Val Ser Ser Gly Gly Gly Gly Ser Gly Gly Gly Ser Glu Val Gln Leu
                245                 250                 255

Val Glu Ser Gly Gly Gly Leu Val Gln Pro Gly Gly Ser Leu Lys Leu
                260                 265                 270

Ser Cys Ala Ala Ser Gly Phe Thr Phe Asn Lys Tyr Ala Ile Asn Trp
                275                 280                 285

Val Arg Gln Ala Pro Gly Lys Gly Leu Glu Trp Val Ala Arg Ile Arg
                290                 295                 300

Ser Lys Tyr Asn Asn Tyr Ala Thr Tyr Tyr Ala Asp Gln Val Lys Asp
305                 310                 315                 320

Arg Phe Thr Ile Ser Arg Asp Asp Ser Lys Asn Thr Ala Tyr Leu Gln
                325                 330                 335

Met Asn Asn Leu Lys Thr Glu Asp Thr Ala Val Tyr Tyr Cys Val Arg
                340                 345                 350

His Ala Asn Phe Gly Asn Ser Tyr Ile Ser Tyr Trp Ala Tyr Trp Gly
                355                 360                 365

Gln Gly Thr Leu Val Thr Val Ser Ser Gly Gly Gly Ser Gly Gly
                370                 375                 380

Gly Gly Ser Gly Gly Gly Ser Gln Thr Val Val Thr Gln Glu Pro
385                 390                 395                 400

Ser Leu Thr Val Ser Pro Gly Gly Thr Val Thr Leu Thr Cys Ala Ser
                405                 410                 415

Ser Thr Gly Ala Val Thr Ser Gly Asn Tyr Pro Asn Trp Val Gln Gln
                420                 425                 430

Lys Pro Gly Gln Ala Pro Arg Gly Leu Ile Gly Gly Thr Lys Phe Leu
                435                 440                 445

Val Pro Gly Thr Pro Ala Arg Phe Ser Gly Ser Leu Leu Gly Gly Lys
                450                 455                 460

Ala Ala Leu Thr Leu Ser Gly Val Gln Pro Glu Asp Glu Ala Glu Tyr
465                 470                 475                 480

Tyr Cys Thr Leu Trp Tyr Ser Asn Arg Trp Val Phe Gly Gly Gly Thr
                485                 490                 495

Lys Leu Thr Val Leu His His His His His His
                500                 505

<210> SEQ ID NO 345
<211> LENGTH: 512
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 345
```

```
Gln Val Gln Leu Gln Glu Ser Gly Gly Gly Leu Val Gln Ala Gly Gly
  1               5                  10                  15

Ser Leu Lys Leu Ser Cys Ala Asp Ser Gly Arg Ser Phe Ser Asn Tyr
             20                  25                  30

Ile Met Gly Trp Phe Arg Gln Ala Pro Gly Lys Glu Arg Glu Phe Val
             35                  40                  45

Ala Gly Leu Gly Trp Ser Pro Gly Asn Thr Tyr Tyr Ala Asp Ser Val
 50                  55                  60

Lys Gly Arg Phe Thr Ile Ser Arg Asp Asn Ala Lys Asn Met Val Tyr
 65                  70                  75                  80

Leu Gln Met Asn Ser Leu Asn Pro Glu Asp Thr Ala Val Tyr Tyr Cys
                 85                  90                  95

Ala Ala Arg Arg Gly Asp Val Ile Tyr Thr Thr Pro Trp Asn Tyr Val
             100                 105                 110

Tyr Trp Gly Gln Gly Thr Gln Val Thr Val Ser Ser Gly Gly Gly Gly
             115                 120                 125

Ser Gly Gly Gly Ser Glu Val Gln Leu Val Glu Ser Gly Gly Gly Leu
             130                 135                 140

Val Gln Pro Gly Asn Ser Leu Arg Leu Ser Cys Ala Ala Ser Gly Phe
145                 150                 155                 160

Thr Phe Ser Lys Phe Gly Met Ser Trp Val Arg Gln Ala Pro Gly Lys
             165                 170                 175

Gly Leu Glu Trp Val Ser Ser Ile Ser Gly Ser Gly Arg Asp Thr Leu
             180                 185                 190

Tyr Ala Asp Ser Val Lys Gly Arg Phe Thr Ile Ser Arg Asp Asn Ala
             195                 200                 205

Lys Thr Thr Leu Tyr Leu Gln Met Asn Ser Leu Arg Pro Glu Asp Thr
210                 215                 220

Ala Val Tyr Tyr Cys Thr Ile Gly Gly Ser Leu Ser Val Ser Ser Gln
225                 230                 235                 240

Gly Thr Leu Val Thr Val Ser Ser Gly Gly Gly Gly Ser Gly Gly Gly
             245                 250                 255

Ser Glu Val Gln Leu Val Glu Ser Gly Gly Gly Leu Val Gln Pro Gly
             260                 265                 270

Gly Ser Leu Lys Leu Ser Cys Ala Ala Ser Gly Phe Thr Phe Asn Lys
             275                 280                 285

Tyr Ala Ile Asn Trp Val Arg Gln Ala Pro Gly Lys Gly Leu Glu Trp
             290                 295                 300

Val Ala Arg Ile Arg Ser Lys Tyr Asn Asn Tyr Ala Thr Tyr Tyr Ala
305                 310                 315                 320

Asp Gln Val Lys Asp Arg Phe Thr Ile Ser Arg Asp Asp Ser Lys Asn
             325                 330                 335

Thr Ala Tyr Leu Gln Met Asn Asn Leu Lys Thr Glu Asp Thr Ala Val
             340                 345                 350

Tyr Tyr Cys Val Arg His Ala Asn Phe Gly Asn Ser Tyr Ile Ser Tyr
             355                 360                 365

Trp Ala Tyr Trp Gly Gln Gly Thr Leu Val Thr Val Ser Ser Gly Gly
             370                 375                 380

Gly Gly Ser Gly Gly Gly Gly Ser Gly Gly Gly Gly Ser Gln Thr Val
385                 390                 395                 400

Val Thr Gln Glu Pro Ser Leu Thr Val Ser Pro Gly Gly Thr Val Thr
             405                 410                 415

Leu Thr Cys Ala Ser Ser Thr Gly Ala Val Thr Ser Gly Asn Tyr Pro
```

```
                420             425             430
Asn Trp Val Gln Gln Lys Pro Gly Gln Ala Pro Arg Gly Leu Ile Gly
            435                 440                 445

Gly Thr Lys Phe Leu Val Pro Gly Thr Pro Ala Arg Phe Ser Gly Ser
            450                 455                 460

Leu Leu Gly Gly Lys Ala Ala Leu Thr Leu Ser Gly Val Gln Pro Glu
465                 470                 475                 480

Asp Glu Ala Glu Tyr Tyr Cys Thr Leu Trp Tyr Ser Asn Arg Trp Val
                485                 490                 495

Phe Gly Gly Gly Thr Lys Leu Thr Val Leu His His His His His His
            500                 505                 510
```

<210> SEQ ID NO 346
<211> LENGTH: 509
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 346

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Ala Tyr Ile Tyr
            20                  25                  30

Thr Met Asp Trp Tyr Arg Gln Ala Pro Gly Lys Gln Arg Glu Leu Val
        35                  40                  45

Ala Thr Ser Thr His Asp Gly Asn Thr Asp Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Leu Arg Thr Pro Val Asp Leu Ile Arg Ala Asn Tyr Trp Gly
            100                 105                 110

Gln Gly Thr Gln Val Thr Val Ser Ser Gly Gly Gly Ser Gly Gly Gly
        115                 120                 125

Gly Ser Glu Val Gln Leu Val Glu Ser Gly Gly Gly Leu Val Gln Pro
    130                 135                 140

Gly Asn Ser Leu Arg Leu Ser Cys Ala Ala Ser Gly Phe Thr Phe Ser
145                 150                 155                 160

Lys Phe Gly Met Ser Trp Val Arg Gln Ala Pro Gly Lys Gly Leu Glu
                165                 170                 175

Trp Val Ser Ser Ile Ser Gly Ser Gly Arg Asp Thr Leu Tyr Ala Asp
            180                 185                 190

Ser Val Lys Gly Arg Phe Thr Ile Ser Arg Asp Asn Ala Lys Thr Thr
        195                 200                 205

Leu Tyr Leu Gln Met Asn Ser Leu Arg Pro Glu Asp Thr Ala Val Tyr
    210                 215                 220

Tyr Cys Thr Ile Gly Gly Ser Leu Ser Val Ser Ser Gln Gly Thr Leu
225                 230                 235                 240

Val Thr Val Ser Ser Gly Gly Gly Gly Ser Gly Gly Gly Ser Glu Val
                245                 250                 255

Gln Leu Val Glu Ser Gly Gly Gly Leu Val Gln Pro Gly Gly Ser Leu
            260                 265                 270
```

```
Lys Leu Ser Cys Ala Ala Ser Gly Phe Thr Phe Asn Lys Tyr Ala Ile
            275                 280                 285

Asn Trp Val Arg Gln Ala Pro Gly Lys Gly Leu Glu Trp Val Ala Arg
        290                 295                 300

Ile Arg Ser Lys Tyr Asn Asn Tyr Ala Thr Tyr Tyr Ala Asp Gln Val
305                 310                 315                 320

Lys Asp Arg Phe Thr Ile Ser Arg Asp Asp Ser Lys Asn Thr Ala Tyr
            325                 330                 335

Leu Gln Met Asn Asn Leu Lys Thr Glu Asp Thr Ala Val Tyr Tyr Cys
        340                 345                 350

Val Arg His Ala Asn Phe Gly Asn Ser Tyr Ile Ser Tyr Trp Ala Tyr
            355                 360                 365

Trp Gly Gln Gly Thr Leu Val Thr Val Ser Ser Gly Gly Gly Gly Ser
        370                 375                 380

Gly Gly Gly Gly Ser Gly Gly Gly Ser Gln Thr Val Val Thr Gln
385                 390                 395                 400

Glu Pro Ser Leu Thr Val Ser Pro Gly Gly Thr Val Thr Leu Thr Cys
            405                 410                 415

Ala Ser Ser Thr Gly Ala Val Thr Ser Gly Asn Tyr Pro Asn Trp Val
        420                 425                 430

Gln Gln Lys Pro Gly Gln Ala Pro Arg Gly Leu Ile Gly Gly Thr Lys
            435                 440                 445

Phe Leu Val Pro Gly Thr Pro Ala Arg Phe Ser Gly Ser Leu Leu Gly
        450                 455                 460

Gly Lys Ala Ala Leu Thr Leu Ser Gly Val Gln Pro Glu Asp Glu Ala
465                 470                 475                 480

Glu Tyr Tyr Cys Thr Leu Trp Tyr Ser Asn Arg Trp Val Phe Gly Gly
            485                 490                 495

Gly Thr Lys Leu Thr Val Leu His His His His His
            500                 505

<210> SEQ ID NO 347
<211> LENGTH: 507
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 347

Gln Val Gln Leu Gln Glu Ser Gly Gly Gly Ser Val Gln Ala Gly Gly
1               5                   10                  15

Ser Leu Arg Leu Ser Cys Ala Ala Pro Gly Arg Tyr Gln Met Ala Trp
            20                  25                  30

Phe Arg Gln Ala Pro Glu Lys Glu Arg Glu Phe Val Gly Thr Ile Ser
        35                  40                  45

Ser Gly Asp Ser Thr Trp Tyr Thr Asn Ser Val Lys Gly Arg Phe Ala
    50                  55                  60

Ile Ser Arg Asp Ser Ala Arg Asn Thr Val Tyr Leu Gln Met Asn Asp
65                  70                  75                  80

Leu Lys Ser Glu Asp Thr Ala Val Tyr Tyr Cys Ala Ala Ala Leu Tyr
            85                  90                  95

Tyr Arg Asp Ser Arg Arg Ala Ile Asp Tyr Pro Tyr Trp Gly Gln Gly
        100                 105                 110

Thr Gln Val Thr Val Ser Ser Gly Gly Gly Gly Ser Gly Gly Gly Ser
    115                 120                 125
```

Glu Val Gln Leu Val Glu Ser Gly Gly Gly Leu Val Gln Pro Gly Asn
130                 135                 140

Ser Leu Arg Leu Ser Cys Ala Ala Ser Gly Phe Thr Phe Ser Lys Phe
145                 150                 155                 160

Gly Met Ser Trp Val Arg Gln Ala Pro Gly Lys Gly Leu Glu Trp Val
                165                 170                 175

Ser Ser Ile Ser Gly Ser Gly Arg Asp Thr Leu Tyr Ala Asp Ser Val
            180                 185                 190

Lys Gly Arg Phe Thr Ile Ser Arg Asp Asn Ala Lys Thr Thr Leu Tyr
        195                 200                 205

Leu Gln Met Asn Ser Leu Arg Pro Glu Asp Thr Ala Val Tyr Tyr Cys
210                 215                 220

Thr Ile Gly Gly Ser Leu Ser Val Ser Ser Gln Gly Thr Leu Val Thr
225                 230                 235                 240

Val Ser Ser Gly Gly Gly Gly Ser Gly Gly Gly Ser Glu Val Gln Leu
                245                 250                 255

Val Glu Ser Gly Gly Gly Leu Val Gln Pro Gly Gly Ser Leu Lys Leu
            260                 265                 270

Ser Cys Ala Ala Ser Gly Phe Thr Phe Asn Lys Tyr Ala Ile Asn Trp
    275                 280                 285

Val Arg Gln Ala Pro Gly Lys Gly Leu Glu Trp Val Ala Arg Ile Arg
290                 295                 300

Ser Lys Tyr Asn Asn Tyr Ala Thr Tyr Tyr Ala Asp Gln Val Lys Asp
305                 310                 315                 320

Arg Phe Thr Ile Ser Arg Asp Asp Ser Lys Asn Thr Ala Tyr Leu Gln
                325                 330                 335

Met Asn Asn Leu Lys Thr Glu Asp Thr Ala Val Tyr Tyr Cys Val Arg
            340                 345                 350

His Ala Asn Phe Gly Asn Ser Tyr Ile Ser Tyr Trp Ala Tyr Trp Gly
        355                 360                 365

Gln Gly Thr Leu Val Thr Val Ser Ser Gly Gly Gly Gly Ser Gly Gly
370                 375                 380

Gly Gly Ser Gly Gly Gly Ser Gln Thr Val Val Thr Gln Glu Pro
385                 390                 395                 400

Ser Leu Thr Val Ser Pro Gly Gly Thr Val Thr Leu Thr Cys Ala Ser
                405                 410                 415

Ser Thr Gly Ala Val Thr Ser Gly Asn Tyr Pro Asn Trp Val Gln Gln
            420                 425                 430

Lys Pro Gly Gln Ala Pro Arg Gly Leu Ile Gly Gly Thr Lys Phe Leu
        435                 440                 445

Val Pro Gly Thr Pro Ala Arg Phe Ser Gly Ser Leu Leu Gly Gly Lys
450                 455                 460

Ala Ala Leu Thr Leu Ser Gly Val Gln Pro Glu Asp Glu Ala Glu Tyr
465                 470                 475                 480

Tyr Cys Thr Leu Trp Tyr Ser Asn Arg Trp Val Phe Gly Gly Gly Thr
                485                 490                 495

Lys Leu Thr Val Leu His His His His His His
            500                 505

<210> SEQ ID NO 348
<211> LENGTH: 510
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 348

```
Gln Val Gln Leu Gln Glu Ser Gly Gly Gly Val Gln Ala Gly Gly
1               5                   10                  15

Ser Leu Arg Leu Ser Cys Ala Ala Ser Gly Leu Thr Phe Ser Ser Tyr
            20                  25                  30

Ala Met Ala Trp Phe Arg Gln Ala Pro Gly Lys Gln Arg Glu Leu Val
        35                  40                  45

Ala Arg Ile Thr Ser Gly Gly Thr Thr Asp Tyr Ala Asp Ser Val Lys
    50                  55                  60

Gly Arg Phe Thr Ile Ser Arg Asp Asn Ala Lys Asn Thr Met Tyr Leu
65              70                  75                  80

Gln Met Asn Ser Leu Lys Pro Glu Asp Thr Ala Val Tyr Tyr Cys Ala
            85                  90                  95

Ala Asp Leu Thr Tyr Arg Asn Leu Leu Leu Lys Leu Pro His Tyr Trp
        100                 105                 110

Gly Gln Gly Thr Gln Val Thr Val Ser Ser Gly Gly Gly Ser Gly
    115                 120                 125

Gly Gly Ser Glu Val Gln Leu Val Glu Ser Gly Gly Gly Leu Val Gln
130                 135                 140

Pro Gly Asn Ser Leu Arg Leu Ser Cys Ala Ala Ser Gly Phe Thr Phe
145                 150                 155                 160

Ser Lys Phe Gly Met Ser Trp Val Arg Gln Ala Pro Gly Lys Gly Leu
            165                 170                 175

Glu Trp Val Ser Ser Ile Ser Gly Ser Gly Arg Asp Thr Leu Tyr Ala
        180                 185                 190

Asp Ser Val Lys Gly Arg Phe Thr Ile Ser Arg Asp Asn Ala Lys Thr
    195                 200                 205

Thr Leu Tyr Leu Gln Met Asn Ser Leu Arg Pro Glu Asp Thr Ala Val
210                 215                 220

Tyr Tyr Cys Thr Ile Gly Gly Ser Leu Ser Val Ser Ser Gln Gly Thr
225                 230                 235                 240

Leu Val Thr Val Ser Ser Gly Gly Gly Gly Ser Gly Gly Gly Ser Glu
            245                 250                 255

Val Gln Leu Val Glu Ser Gly Gly Gly Leu Val Gln Pro Gly Gly Ser
        260                 265                 270

Leu Lys Leu Ser Cys Ala Ala Ser Gly Phe Thr Phe Asn Lys Tyr Ala
    275                 280                 285

Ile Asn Trp Val Arg Gln Ala Pro Gly Lys Gly Leu Glu Trp Val Ala
290                 295                 300

Arg Ile Arg Ser Lys Tyr Asn Asn Tyr Ala Thr Tyr Tyr Ala Asp Gln
305                 310                 315                 320

Val Lys Asp Arg Phe Thr Ile Ser Arg Asp Asp Ser Lys Asn Thr Ala
            325                 330                 335

Tyr Leu Gln Met Asn Asn Leu Lys Thr Glu Asp Thr Ala Val Tyr Tyr
        340                 345                 350

Cys Val Arg His Ala Asn Phe Gly Asn Ser Tyr Ile Ser Tyr Trp Ala
    355                 360                 365

Tyr Trp Gly Gln Gly Thr Leu Val Thr Val Ser Ser Gly Gly Gly Gly
370                 375                 380

Ser Gly Gly Gly Gly Ser Gly Gly Gly Gly Ser Gln Thr Val Val Thr
385                 390                 395                 400
```

```
Gln Glu Pro Ser Leu Thr Val Ser Pro Gly Gly Thr Val Thr Leu Thr
                405                 410                 415

Cys Ala Ser Ser Thr Gly Ala Val Thr Ser Gly Asn Tyr Pro Asn Trp
            420                 425                 430

Val Gln Gln Lys Pro Gly Gln Ala Pro Arg Gly Leu Ile Gly Gly Thr
                435                 440                 445

Lys Phe Leu Val Pro Gly Thr Pro Ala Arg Phe Ser Gly Ser Leu Leu
450                 455                 460

Gly Gly Lys Ala Ala Leu Thr Leu Ser Gly Val Gln Pro Glu Asp Glu
465                 470                 475                 480

Ala Glu Tyr Tyr Cys Thr Leu Trp Tyr Ser Asn Arg Trp Val Phe Gly
                485                 490                 495

Gly Gly Thr Lys Leu Thr Val Leu His His His His His His
                500                 505                 510

<210> SEQ ID NO 349
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 349

Gln Val Gln Leu Gln Glu Ser Gly Gly Gly Leu Val Gln Ala Gly Gly
1               5                   10                  15

Ser Leu Arg Leu Ser Cys Ala Ala Ser Gly Asn Ile Ala Tyr Ile Tyr
                20                  25                  30

Thr Met Asp Trp Tyr Arg Gln Ala Pro Gly Lys Gln Arg Glu Leu Val
            35                  40                  45

Ala Thr Ser Thr His Asp Gly Ser Thr Asp Tyr Ala Asp Ser Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Asp Leu Arg Thr Pro Val Asp Leu Ile Arg Ala Asn Tyr Trp Gly
            100                 105                 110

Gln Gly Thr Gln Val Thr Val Ser Gly Gly Gly Gly Ser Gly Gly
        115                 120                 125

Gly Ser Glu Val Gln Leu Val Glu Ser Gly Gly Gly Leu Val Gln Pro
    130                 135                 140

Gly Asn Ser Leu Arg Leu Ser Cys Ala Ala Ser Gly Phe Thr Phe Ser
145                 150                 155                 160

Lys Phe Gly Met Ser Trp Val Arg Gln Ala Pro Gly Lys Gly Leu Glu
                165                 170                 175

Trp Val Ser Ser Ile Ser Gly Ser Gly Arg Asp Thr Leu Tyr Ala Asp
            180                 185                 190

Ser Val Lys Gly Arg Phe Thr Ile Ser Arg Asp Asn Ala Lys Thr Thr
        195                 200                 205

Leu Tyr Leu Gln Met Asn Ser Leu Arg Pro Glu Asp Thr Ala Val Tyr
    210                 215                 220

Tyr Cys Thr Ile Gly Gly Ser Leu Ser Val Ser Ser Gln Gly Thr Leu
225                 230                 235                 240

Val Thr Val Ser Ser Gly Gly Gly Gly Ser Gly Gly Gly Ser Glu Val
```

245                 250                 255
Gln Leu Val Glu Ser Gly Gly Leu Val Gln Pro Gly Gly Ser Leu
                260                 265                 270

Lys Leu Ser Cys Ala Ala Ser Gly Phe Thr Phe Asn Lys Tyr Ala Ile
            275                 280                 285

Asn Trp Val Arg Gln Ala Pro Gly Lys Gly Leu Glu Trp Val Ala Arg
        290                 295                 300

Ile Arg Ser Lys Tyr Asn Asn Tyr Ala Thr Tyr Tyr Ala Asp Gln Val
305                 310                 315                 320

Lys Asp Arg Phe Thr Ile Ser Arg Asp Asp Ser Lys Asn Thr Ala Tyr
                325                 330                 335

Leu Gln Met Asn Asn Leu Lys Thr Glu Asp Thr Ala Val Tyr Tyr Cys
            340                 345                 350

Val Arg His Ala Asn Phe Gly Asn Ser Tyr Ile Ser Tyr Trp Ala Tyr
        355                 360                 365

Trp Gly Gln Gly Thr Leu Val Thr Val Ser Ser Gly Gly Gly Gly Ser
    370                 375                 380

Gly Gly Gly Gly Ser Gly Gly Gly Ser Gln Thr Val Val Thr Gln
385                 390                 395                 400

Glu Pro Ser Leu Thr Val Ser Pro Gly Gly Thr Val Thr Leu Thr Cys
                405                 410                 415

Ala Ser Ser Thr Gly Ala Val Thr Ser Gly Asn Tyr Pro Asn Trp Val
            420                 425                 430

Gln Gln Lys Pro Gly Gln Ala Pro Arg Gly Leu Ile Gly Gly Thr Lys
        435                 440                 445

Phe Leu Val Pro Gly Thr Pro Ala Arg Phe Ser Gly Ser Leu Leu Gly
    450                 455                 460

Gly Lys Ala Ala Leu Thr Leu Ser Gly Val Gln Pro Glu Asp Glu Ala
465                 470                 475                 480

Glu Tyr Tyr Cys Thr Leu Trp Tyr Ser Asn Arg Trp Val Phe Gly Gly
                485                 490                 495

Gly Thr Lys Leu Thr Val Leu His His His His His His
            500                 505

<210> SEQ ID NO 350
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 350

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Ala Tyr Ile Tyr
            20                  25                  30

Thr Met Asp Trp Tyr Arg Gln Ala Pro Gly Lys Gln Arg Glu Leu Val
        35                  40                  45

Ala Thr Ser Thr Trp Asp Gly Asn Thr Asp Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

```
Ala Asp Leu Arg Thr Ala Val Asp Leu Ile Arg Ala Asn Tyr Trp Gly
            100                 105                 110

Gln Gly Thr Gln Val Thr Val Ser Ser Gly Gly Gly Ser Gly Gly
        115                 120                 125

Gly Ser Glu Val Gln Leu Val Glu Ser Gly Gly Leu Val Gln Pro
    130                 135                 140

Gly Asn Ser Leu Arg Leu Ser Cys Ala Ala Ser Gly Phe Thr Phe Ser
145                 150                 155                 160

Lys Phe Gly Met Ser Trp Val Arg Gln Ala Pro Gly Lys Gly Leu Glu
                165                 170                 175

Trp Val Ser Ser Ile Ser Gly Ser Gly Arg Asp Thr Leu Tyr Ala Asp
                180                 185                 190

Ser Val Lys Gly Arg Phe Thr Ile Ser Arg Asp Asn Ala Lys Thr Thr
                195                 200                 205

Leu Tyr Leu Gln Met Asn Ser Leu Arg Pro Glu Asp Thr Ala Val Tyr
            210                 215                 220

Tyr Cys Thr Ile Gly Gly Ser Leu Ser Val Ser Ser Gln Gly Thr Leu
225                 230                 235                 240

Val Thr Val Ser Ser Gly Gly Gly Gly Ser Gly Gly Gly Ser Glu Val
                245                 250                 255

Gln Leu Val Glu Ser Gly Gly Gly Leu Val Gln Pro Gly Gly Ser Leu
            260                 265                 270

Lys Leu Ser Cys Ala Ala Ser Gly Phe Thr Phe Asn Lys Tyr Ala Ile
            275                 280                 285

Asn Trp Val Arg Gln Ala Pro Gly Lys Gly Leu Glu Trp Val Ala Arg
            290                 295                 300

Ile Arg Ser Lys Tyr Asn Asn Tyr Ala Thr Tyr Tyr Ala Asp Gln Val
305                 310                 315                 320

Lys Asp Arg Phe Thr Ile Ser Arg Asp Asp Ser Lys Asn Thr Ala Tyr
                325                 330                 335

Leu Gln Met Asn Asn Leu Lys Thr Glu Asp Thr Ala Val Tyr Tyr Cys
            340                 345                 350

Val Arg His Ala Asn Phe Gly Asn Ser Tyr Ile Ser Tyr Trp Ala Tyr
            355                 360                 365

Trp Gly Gln Gly Thr Leu Val Thr Val Ser Ser Gly Gly Gly Gly Ser
    370                 375                 380

Gly Gly Gly Gly Ser Gly Gly Gly Ser Gln Thr Val Val Thr Gln
385                 390                 395                 400

Glu Pro Ser Leu Thr Val Ser Pro Gly Gly Thr Val Thr Leu Thr Cys
            405                 410                 415

Ala Ser Ser Thr Gly Ala Val Thr Ser Gly Asn Tyr Pro Asn Trp Val
            420                 425                 430

Gln Gln Lys Pro Gly Gln Ala Pro Arg Gly Leu Ile Gly Gly Thr Lys
            435                 440                 445

Phe Leu Val Pro Gly Thr Pro Ala Arg Phe Ser Gly Ser Leu Leu Gly
            450                 455                 460

Gly Lys Ala Ala Leu Thr Leu Ser Gly Val Gln Pro Glu Asp Glu Ala
465                 470                 475                 480

Glu Tyr Tyr Cys Thr Leu Trp Tyr Ser Asn Arg Trp Val Phe Gly Gly
                485                 490                 495

Gly Thr Lys Leu Thr Val Leu His His His His His
            500                 505
```

-continued

```
<210> SEQ ID NO 351
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 351

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ser Ile Ala Tyr Ile Tyr
            20                  25                  30

Thr Met Asp Trp Tyr Arg Gln Ala Pro Gly Lys Gln Arg Glu Leu Val
        35                  40                  45

Ala Thr Ser Thr His Asp Gly Asn Thr Asp Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Lys Pro Asp Asp Thr Ala Val Tyr Tyr Cys Asn
                85                  90                  95

Ala Asp Leu Arg Thr Ala Val Asp Leu Ile Arg Ala Asn Tyr Trp Gly
            100                 105                 110

Gln Gly Thr Gln Val Thr Val Ser Ser Gly Gly Gly Ser Gly Gly
        115                 120                 125

Gly Ser Glu Val Gln Leu Val Glu Ser Gly Gly Gly Leu Val Gln Pro
130                 135                 140

Gly Asn Ser Leu Arg Leu Ser Cys Ala Ala Ser Gly Phe Thr Phe Ser
145                 150                 155                 160

Lys Phe Gly Met Ser Trp Val Arg Gln Ala Pro Gly Lys Gly Leu Glu
                165                 170                 175

Trp Val Ser Ser Ile Ser Gly Ser Gly Arg Asp Thr Leu Tyr Ala Asp
            180                 185                 190

Ser Val Lys Gly Arg Phe Thr Ile Ser Arg Asp Asn Ala Lys Thr Thr
        195                 200                 205

Leu Tyr Leu Gln Met Asn Ser Leu Arg Pro Glu Asp Thr Ala Val Tyr
    210                 215                 220

Tyr Cys Thr Ile Gly Gly Ser Leu Ser Val Ser Ser Gln Gly Thr Leu
225                 230                 235                 240

Val Thr Val Ser Ser Gly Gly Gly Gly Ser Gly Gly Gly Ser Glu Val
                245                 250                 255

Gln Leu Val Glu Ser Gly Gly Gly Leu Val Gln Pro Gly Gly Ser Leu
            260                 265                 270

Lys Leu Ser Cys Ala Ala Ser Gly Phe Thr Phe Asn Lys Tyr Ala Ile
        275                 280                 285

Asn Trp Val Arg Gln Ala Pro Gly Lys Gly Leu Glu Trp Val Ala Arg
    290                 295                 300

Ile Arg Ser Lys Tyr Asn Asn Tyr Ala Thr Tyr Ala Asp Gln Val
305                 310                 315                 320

Lys Asp Arg Phe Thr Ile Ser Arg Asp Asp Ser Lys Asn Thr Ala Tyr
                325                 330                 335

Leu Gln Met Asn Asn Leu Lys Thr Glu Asp Thr Ala Val Tyr Tyr Cys
            340                 345                 350

Val Arg His Ala Asn Phe Gly Asn Ser Tyr Ile Ser Tyr Trp Ala Tyr
        355                 360                 365
```

```
Trp Gly Gln Gly Thr Leu Val Thr Val Ser Ser Gly Gly Gly Ser
        370                 375                 380

Gly Gly Gly Gly Ser Gly Gly Gly Ser Gln Thr Val Val Thr Gln
385                 390                 395                 400

Glu Pro Ser Leu Thr Val Ser Pro Gly Gly Thr Val Thr Leu Thr Cys
                405                 410                 415

Ala Ser Ser Thr Gly Ala Val Thr Ser Gly Asn Tyr Pro Asn Trp Val
            420                 425                 430

Gln Gln Lys Pro Gly Gln Ala Pro Arg Gly Leu Ile Gly Gly Thr Lys
        435                 440                 445

Phe Leu Val Pro Gly Thr Pro Ala Arg Phe Ser Gly Ser Leu Leu Gly
    450                 455                 460

Gly Lys Ala Ala Leu Thr Leu Ser Gly Val Gln Pro Glu Asp Glu Ala
465                 470                 475                 480

Glu Tyr Tyr Cys Thr Leu Trp Tyr Ser Asn Arg Trp Val Phe Gly Gly
                485                 490                 495

Gly Thr Lys Leu Thr Val Leu His His His His His His
            500                 505
```

<210> SEQ ID NO 352
<211> LENGTH: 511
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 352

```
Gln Val Gln Leu Gln Glu Ser Gly Gly Gly Leu Val Gln Ala Gly Glu
1               5                   10                  15

Ser Leu Ser Leu Ser Cys Ala Ala Ser Gly Asn Asp Phe Val Ile Thr
            20                  25                  30

Asp Met His Trp Tyr Arg Gln Ala Pro Gly Lys Gln Arg Glu Trp Val
        35                  40                  45

Ala Thr Ile Thr Arg Phe Ala Thr Thr Asn Tyr Ala Asp Ser Val Lys
    50                  55                  60

Gly Arg Phe Thr Ile Ser Arg Asp Asn Ala Lys Asn Thr Trp Tyr Leu
65                  70                  75                  80

Gln Met Asn Ser Leu Lys Pro Asp Asp Thr Ala Val Tyr Tyr Cys Lys
                85                  90                  95

Ala Ile Gly Leu Arg Gly Val Pro Asp Val Asn Arg Gln Phe Glu Val
            100                 105                 110

Trp Gly Gln Gly Thr Gln Val Thr Val Ser Ser Gly Gly Gly Gly Ser
        115                 120                 125

Gly Gly Gly Ser Glu Val Gln Leu Val Glu Ser Gly Gly Gly Leu Val
    130                 135                 140

Gln Pro Gly Asn Ser Leu Arg Leu Ser Cys Ala Ala Ser Gly Phe Thr
145                 150                 155                 160

Phe Ser Lys Phe Gly Met Ser Trp Val Arg Gln Ala Pro Gly Lys Gly
                165                 170                 175

Leu Glu Trp Val Ser Ser Ile Ser Gly Ser Gly Arg Asp Thr Leu Tyr
            180                 185                 190

Ala Asp Ser Val Lys Gly Arg Phe Thr Ile Ser Arg Asp Asn Ala Lys
        195                 200                 205

Thr Thr Leu Tyr Leu Gln Met Asn Ser Leu Arg Pro Glu Asp Thr Ala
    210                 215                 220
```

-continued

```
Val Tyr Tyr Cys Thr Ile Gly Gly Ser Leu Ser Val Ser Ser Gln Gly
225                 230                 235                 240

Thr Leu Val Thr Val Ser Ser Gly Gly Gly Ser Gly Gly Gly Ser
                245                 250                 255

Glu Val Gln Leu Val Glu Ser Gly Gly Gly Leu Val Gln Pro Gly Gly
            260                 265                 270

Ser Leu Lys Leu Ser Cys Ala Ala Ser Gly Phe Thr Phe Asn Lys Tyr
        275                 280                 285

Ala Ile Asn Trp Val Arg Gln Ala Pro Gly Lys Gly Leu Glu Trp Val
    290                 295                 300

Ala Arg Ile Arg Ser Lys Tyr Asn Asn Tyr Ala Thr Tyr Tyr Ala Asp
305                 310                 315                 320

Gln Val Lys Asp Arg Phe Thr Ile Ser Arg Asp Asp Ser Lys Asn Thr
                325                 330                 335

Ala Tyr Leu Gln Met Asn Asn Leu Lys Thr Glu Asp Thr Ala Val Tyr
            340                 345                 350

Tyr Cys Val Arg His Ala Asn Phe Gly Asn Ser Tyr Ile Ser Tyr Trp
        355                 360                 365

Ala Tyr Trp Gly Gln Gly Thr Leu Val Thr Val Ser Ser Gly Gly Gly
    370                 375                 380

Gly Ser Gly Gly Gly Gly Ser Gly Gly Gly Gly Ser Gln Thr Val Val
385                 390                 395                 400

Thr Gln Glu Pro Ser Leu Thr Val Ser Pro Gly Gly Thr Val Thr Leu
                405                 410                 415

Thr Cys Ala Ser Ser Thr Gly Ala Val Thr Ser Gly Asn Tyr Pro Asn
            420                 425                 430

Trp Val Gln Gln Lys Pro Gly Gln Ala Pro Arg Gly Leu Ile Gly Gly
        435                 440                 445

Thr Lys Phe Leu Val Pro Gly Thr Pro Ala Arg Phe Ser Gly Ser Leu
    450                 455                 460

Leu Gly Gly Lys Ala Ala Leu Thr Leu Ser Gly Val Gln Pro Glu Asp
465                 470                 475                 480

Glu Ala Glu Tyr Tyr Cys Thr Leu Trp Tyr Ser Asn Arg Trp Val Phe
                485                 490                 495

Gly Gly Gly Thr Lys Leu Thr Val Leu His His His His His His
            500                 505                 510

<210> SEQ ID NO 353
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 353

Gln Val Gln Leu Gln Glu Ser Gly Gly Gly Leu Val Gln Ala Gly Gly
1               5                   10                  15

Ser Leu Arg Leu Ser Cys Ala Ala Ser Gly Ala Ile Ala Tyr Ile Tyr
            20                  25                  30

Gly Met Gly Trp Tyr Arg Gln Ala Pro Gly Asn Gln Arg Glu Leu Val
        35                  40                  45

Ala Ala Ile Ser Ser Gly Gly Ser Thr Asp Tyr Ala Asp Ser Val Lys
    50                  55                  60

Gly Arg Phe Thr Ile Ser Arg Asp Asn Ala Lys Asn Thr Val Tyr Leu
```

```
                65                  70                  75                  80
Gln Met Ser Ser Leu Lys Pro Glu Asp Thr Ala Val Tyr Tyr Cys Asn
                    85                  90                  95

Ala Asp Val Arg Thr Ser Arg Asn Leu Val Arg Ser Asp Tyr Trp Gly
                    100                 105                 110

Gln Gly Thr Gln Val Thr Val Ser Gly Gly Gly Ser Gly Gly
                    115                 120                 125

Gly Ser Glu Val Gln Leu Val Glu Ser Gly Gly Leu Val Gln Pro
            130                 135                 140

Gly Asn Ser Leu Arg Leu Ser Cys Ala Ala Ser Gly Phe Thr Phe Ser
145                 150                 155                 160

Lys Phe Gly Met Ser Trp Val Arg Gln Ala Pro Gly Lys Gly Leu Glu
                    165                 170                 175

Trp Val Ser Ser Ile Ser Gly Ser Gly Arg Asp Thr Leu Tyr Ala Asp
                    180                 185                 190

Ser Val Lys Gly Arg Phe Thr Ile Ser Arg Asp Asn Ala Lys Thr Thr
                    195                 200                 205

Leu Tyr Leu Gln Met Asn Ser Leu Arg Pro Glu Asp Thr Ala Val Tyr
            210                 215                 220

Tyr Cys Thr Ile Gly Gly Ser Leu Ser Val Ser Ser Gln Gly Thr Leu
225                 230                 235                 240

Val Thr Val Ser Ser Gly Gly Gly Gly Ser Gly Gly Gly Ser Glu Val
                    245                 250                 255

Gln Leu Val Glu Ser Gly Gly Gly Leu Val Gln Pro Gly Gly Ser Leu
            260                 265                 270

Lys Leu Ser Cys Ala Ala Ser Gly Phe Thr Phe Asn Lys Tyr Ala Ile
            275                 280                 285

Asn Trp Val Arg Gln Ala Pro Gly Lys Gly Leu Glu Trp Val Ala Arg
            290                 295                 300

Ile Arg Ser Lys Tyr Asn Asn Tyr Ala Thr Tyr Tyr Ala Asp Gln Val
305                 310                 315                 320

Lys Asp Arg Phe Thr Ile Ser Arg Asp Asp Ser Lys Asn Thr Ala Tyr
                    325                 330                 335

Leu Gln Met Asn Asn Leu Lys Thr Glu Asp Thr Ala Val Tyr Tyr Cys
            340                 345                 350

Val Arg His Ala Asn Phe Gly Asn Ser Tyr Ile Ser Tyr Trp Ala Tyr
            355                 360                 365

Trp Gly Gln Gly Thr Leu Val Thr Val Ser Ser Gly Gly Gly Gly Ser
    370                 375                 380

Gly Gly Gly Gly Ser Gly Gly Gly Ser Gln Thr Val Val Thr Gln
385                 390                 395                 400

Glu Pro Ser Leu Thr Val Ser Pro Gly Gly Thr Val Thr Leu Thr Cys
                    405                 410                 415

Ala Ser Ser Thr Gly Ala Val Thr Ser Gly Asn Tyr Pro Asn Trp Val
                    420                 425                 430

Gln Gln Lys Pro Gly Gln Ala Pro Arg Gly Leu Ile Gly Gly Thr Lys
            435                 440                 445

Phe Leu Val Pro Gly Thr Pro Ala Arg Phe Ser Gly Ser Leu Leu Gly
            450                 455                 460

Gly Lys Ala Ala Leu Thr Leu Ser Gly Val Gln Pro Glu Asp Glu Ala
465                 470                 475                 480

Glu Tyr Tyr Cys Thr Leu Trp Tyr Ser Asn Arg Trp Val Phe Gly Gly
                    485                 490                 495
```

Gly Thr Lys Leu Thr Val Leu His His His His His
            500                 505

<210> SEQ ID NO 354
<211> LENGTH: 507
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 354

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Tyr His Thr Ala Trp
            20                  25                  30

Phe Arg Gln Ala Pro Glu Lys Glu Arg Glu Phe Val Gly Thr Ile Ser
        35                  40                  45

Ser Gly Asp Ser Thr Trp Tyr Thr Asn Ser Val Lys Gly Arg Phe Ala
    50                  55                  60

Ile Ser Arg Asp Ser Ala Arg Asn Thr Val Tyr Leu Gln Met Asn Asp
65                  70                  75                  80

Leu Lys Pro Glu Asp Thr Ala Val Tyr Tyr Cys Ala Ala Leu Tyr
            85                  90                  95

Tyr Gly Asp Ser Arg Arg Ala Gly Asp Tyr Pro Tyr Trp Gly Gln Gly
            100                 105                 110

Thr Gln Val Thr Val Ser Ser Gly Gly Gly Ser Gly Gly Gly Ser
        115                 120                 125

Glu Val Gln Leu Val Glu Ser Gly Gly Gly Leu Val Gln Pro Gly Asn
    130                 135                 140

Ser Leu Arg Leu Ser Cys Ala Ala Ser Gly Phe Thr Phe Ser Lys Phe
145                 150                 155                 160

Gly Met Ser Trp Val Arg Gln Ala Pro Gly Lys Gly Leu Glu Trp Val
            165                 170                 175

Ser Ser Ile Ser Gly Ser Gly Arg Asp Thr Leu Tyr Ala Asp Ser Val
            180                 185                 190

Lys Gly Arg Phe Thr Ile Ser Arg Asp Asn Ala Lys Thr Thr Leu Tyr
        195                 200                 205

Leu Gln Met Asn Ser Leu Arg Pro Glu Asp Thr Ala Val Tyr Tyr Cys
    210                 215                 220

Thr Ile Gly Gly Ser Leu Ser Val Ser Ser Gln Gly Thr Leu Val Thr
225                 230                 235                 240

Val Ser Ser Gly Gly Gly Gly Ser Gly Gly Ser Glu Val Gln Leu
            245                 250                 255

Val Glu Ser Gly Gly Gly Leu Val Gln Pro Gly Gly Ser Leu Lys Leu
            260                 265                 270

Ser Cys Ala Ala Ser Gly Phe Thr Phe Asn Lys Tyr Ala Ile Asn Trp
            275                 280                 285

Val Arg Gln Ala Pro Gly Lys Gly Leu Glu Trp Val Ala Arg Ile Arg
        290                 295                 300

Ser Lys Tyr Asn Asn Tyr Ala Thr Tyr Ala Asp Gln Val Lys Asp
305                 310                 315                 320

Arg Phe Thr Ile Ser Arg Asp Asp Ser Lys Asn Thr Ala Tyr Leu Gln
            325                 330                 335

Met Asn Asn Leu Lys Thr Glu Asp Thr Ala Val Tyr Tyr Cys Val Arg

```
                    340                 345                 350
His Ala Asn Phe Gly Asn Ser Tyr Ile Ser Tyr Trp Ala Tyr Trp Gly
            355                 360                 365

Gln Gly Thr Leu Val Thr Val Ser Ser Gly Gly Gly Ser Gly Gly
    370                 375                 380

Gly Gly Ser Gly Gly Gly Ser Gln Thr Val Val Thr Gln Glu Pro
385                 390                 395                 400

Ser Leu Thr Val Ser Pro Gly Gly Thr Val Thr Leu Thr Cys Ala Ser
                405                 410                 415

Ser Thr Gly Ala Val Thr Ser Gly Asn Tyr Pro Asn Trp Val Gln Gln
            420                 425                 430

Lys Pro Gly Gln Ala Pro Arg Gly Leu Ile Gly Gly Thr Lys Phe Leu
        435                 440                 445

Val Pro Gly Thr Pro Ala Arg Phe Ser Gly Ser Leu Leu Gly Gly Lys
        450                 455                 460

Ala Ala Leu Thr Leu Ser Gly Val Gln Pro Glu Asp Glu Ala Glu Tyr
465                 470                 475                 480

Tyr Cys Thr Leu Trp Tyr Ser Asn Arg Trp Val Phe Gly Gly Gly Thr
                485                 490                 495

Lys Leu Thr Val Leu His His His His His His
            500                 505

<210> SEQ ID NO 355
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 355

Gln Val Gln Leu Gln Glu Ser Gly Gly Gly Leu Val Gln Ala Gly Gly
1               5                   10                  15

Ser Leu Arg Leu Ser Cys Ala Ala Ser Gly Asn Ile Ala Tyr Ile Tyr
            20                  25                  30

Thr Met Asn Trp Tyr Arg Gln Ala Pro Gly Lys Gln Arg Glu Leu Val
        35                  40                  45

Ala Thr Ser Thr His Ala Gly Asn Thr Asp Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
            85                  90                  95

Val Asp Leu Arg Thr Ala Val Asp Leu Ile Arg Ala Asn Tyr Trp Gly
            100                 105                 110

Gln Gly Thr Gln Val Thr Val Ser Ser Gly Gly Gly Ser Gly Gly
        115                 120                 125

Gly Ser Glu Val Gln Leu Val Glu Ser Gly Gly Leu Val Gln Pro
    130                 135                 140

Gly Asn Ser Leu Arg Leu Ser Cys Ala Ala Ser Gly Phe Thr Phe Ser
145                 150                 155                 160

Lys Phe Gly Met Ser Trp Val Arg Gln Ala Pro Gly Lys Gly Leu Glu
                165                 170                 175

Trp Val Ser Ser Ile Ser Gly Ser Gly Arg Asp Thr Leu Tyr Ala Asp
            180                 185                 190
```

Ser Val Lys Gly Arg Phe Thr Ile Ser Arg Asp Asn Ala Lys Thr Thr
            195                 200                 205

Leu Tyr Leu Gln Met Asn Ser Leu Arg Pro Glu Asp Thr Ala Val Tyr
    210                 215                 220

Tyr Cys Thr Ile Gly Gly Ser Leu Ser Val Ser Ser Gln Gly Thr Leu
225                 230                 235                 240

Val Thr Val Ser Ser Gly Gly Gly Gly Ser Gly Gly Gly Ser Glu Val
                245                 250                 255

Gln Leu Val Glu Ser Gly Gly Gly Leu Val Gln Pro Gly Gly Ser Leu
            260                 265                 270

Lys Leu Ser Cys Ala Ala Ser Gly Phe Thr Phe Asn Lys Tyr Ala Ile
        275                 280                 285

Asn Trp Val Arg Gln Ala Pro Gly Lys Gly Leu Glu Trp Val Ala Arg
    290                 295                 300

Ile Arg Ser Lys Tyr Asn Asn Tyr Ala Thr Tyr Tyr Ala Asp Gln Val
305                 310                 315                 320

Lys Asp Arg Phe Thr Ile Ser Arg Asp Asp Ser Lys Asn Thr Ala Tyr
                325                 330                 335

Leu Gln Met Asn Asn Leu Lys Thr Glu Asp Thr Ala Val Tyr Tyr Cys
            340                 345                 350

Val Arg His Ala Asn Phe Gly Asn Ser Tyr Ile Ser Tyr Trp Ala Tyr
        355                 360                 365

Trp Gly Gln Gly Thr Leu Val Thr Val Ser Ser Gly Gly Gly Gly Ser
    370                 375                 380

Gly Gly Gly Gly Ser Gly Gly Gly Ser Gln Thr Val Val Thr Gln
385                 390                 395                 400

Glu Pro Ser Leu Thr Val Ser Pro Gly Gly Thr Val Thr Leu Thr Cys
                405                 410                 415

Ala Ser Ser Thr Gly Ala Val Thr Ser Gly Asn Tyr Pro Asn Trp Val
            420                 425                 430

Gln Gln Lys Pro Gly Gln Ala Pro Arg Gly Leu Ile Gly Gly Thr Lys
        435                 440                 445

Phe Leu Val Pro Gly Thr Pro Ala Arg Phe Ser Gly Ser Leu Leu Gly
    450                 455                 460

Gly Lys Ala Ala Leu Thr Leu Ser Gly Val Gln Pro Glu Asp Glu Ala
465                 470                 475                 480

Glu Tyr Tyr Cys Thr Leu Trp Tyr Ser Asn Arg Trp Val Phe Gly Gly
                485                 490                 495

Gly Thr Lys Leu Thr Val Leu His His His His His His
            500                 505

<210> SEQ ID NO 356
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 356

Gln Val Gln Leu Gln Glu Ser Gly Gly Gly Leu Val Gln Pro Gly Gly
1               5                   10                  15

Ser Leu Arg Leu Ser Cys Ala Ala Ser Gly Asn Ile Ala Tyr Ile Tyr
            20                  25                  30

Thr Met Gly Trp Tyr Arg Gln Ala Pro Gly Lys Gln Arg Glu Leu Val
        35                  40                  45

```
Ala Thr Ser Thr His Asp Gly Asn Ser Asp Tyr Ala Asp Ser Val Lys
     50                  55                  60
Gly Arg Phe Thr Ile Ser Arg Asp Asn Ala Lys Asn Thr Val Tyr Leu
 65                  70                  75                  80
Gln Met Asn Thr Leu Lys Pro Asp Asp Thr Ala Val Tyr Tyr Cys Asn
                 85                  90                  95
Ala Asp Leu Arg Thr Pro Val Asp Arg Ile Arg Gly Asn Phe Trp Gly
            100                 105                 110
Gln Gly Thr Gln Val Thr Val Ser Ser Gly Gly Gly Gly Ser Gly Gly
        115                 120                 125
Gly Ser Glu Val Gln Leu Val Glu Ser Gly Gly Gly Leu Val Gln Pro
    130                 135                 140
Gly Asn Ser Leu Arg Leu Ser Cys Ala Ala Ser Gly Phe Thr Phe Ser
145                 150                 155                 160
Lys Phe Gly Met Ser Trp Val Arg Gln Ala Pro Gly Lys Gly Leu Glu
                165                 170                 175
Trp Val Ser Ser Ile Ser Gly Ser Gly Arg Asp Thr Leu Tyr Ala Asp
            180                 185                 190
Ser Val Lys Gly Arg Phe Thr Ile Ser Arg Asp Asn Ala Lys Thr Thr
        195                 200                 205
Leu Tyr Leu Gln Met Asn Ser Leu Arg Pro Glu Asp Thr Ala Val Tyr
    210                 215                 220
Tyr Cys Thr Ile Gly Gly Ser Leu Ser Val Ser Ser Gln Gly Thr Leu
225                 230                 235                 240
Val Thr Val Ser Ser Gly Gly Gly Gly Ser Gly Gly Gly Gly Ser Glu Val
                245                 250                 255
Gln Leu Val Glu Ser Gly Gly Gly Leu Val Gln Pro Gly Gly Ser Leu
        260                 265                 270
Lys Leu Ser Cys Ala Ala Ser Gly Phe Thr Phe Asn Lys Tyr Ala Ile
    275                 280                 285
Asn Trp Val Arg Gln Ala Pro Gly Lys Gly Leu Glu Trp Val Ala Arg
290                 295                 300
Ile Arg Ser Lys Tyr Asn Asn Tyr Ala Thr Tyr Tyr Ala Asp Gln Val
305                 310                 315                 320
Lys Asp Arg Phe Thr Ile Ser Arg Asp Asp Ser Lys Asn Thr Ala Tyr
                325                 330                 335
Leu Gln Met Asn Asn Leu Lys Thr Glu Asp Thr Ala Val Tyr Tyr Cys
            340                 345                 350
Val Arg His Ala Asn Phe Gly Asn Ser Tyr Ile Ser Tyr Trp Ala Tyr
        355                 360                 365
Trp Gly Gln Gly Thr Leu Val Thr Val Ser Ser Gly Gly Gly Gly Ser
    370                 375                 380
Gly Gly Gly Gly Ser Gly Gly Gly Ser Gln Thr Val Val Thr Gln
385                 390                 395                 400
Glu Pro Ser Leu Thr Val Ser Pro Gly Gly Thr Val Thr Leu Thr Cys
                405                 410                 415
Ala Ser Ser Thr Gly Ala Val Thr Ser Gly Asn Tyr Pro Asn Trp Val
            420                 425                 430
Gln Gln Lys Pro Gly Gln Ala Pro Arg Gly Leu Ile Gly Gly Thr Lys
        435                 440                 445
Phe Leu Val Pro Gly Thr Pro Ala Arg Phe Ser Gly Ser Leu Leu Gly
    450                 455                 460
```

```
Gly Lys Ala Ala Leu Thr Leu Ser Gly Val Gln Pro Glu Asp Glu Ala
465                 470                 475                 480

Glu Tyr Tyr Cys Thr Leu Trp Tyr Ser Asn Arg Trp Val Phe Gly Gly
                485                 490                 495

Gly Thr Lys Leu Thr Val Leu His His His His His His
            500                 505
```

<210> SEQ ID NO 357
<211> LENGTH: 509
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 357

```
Glu Val Gln Leu Leu Glu Ser Gly Gly Gly Leu Val Gln Pro Gly Gly
1               5                   10                  15

Ser Leu Thr Leu Ser Cys Ala Ala Ser Gly Ser Ile Ala Tyr Ile Tyr
            20                  25                  30

Thr Met Asp Trp Tyr Arg Gln Ala Pro Gly Lys Gln Arg Glu Leu Val
        35                  40                  45

Ala Thr Ser Thr Arg Asp Gly Asn Val Asp Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Asn
                85                  90                  95

Ala Asp Leu Arg Thr Ala Val Asp Leu Ile Arg Ala Asn Tyr Trp Gly
            100                 105                 110

Leu Gly Thr Gln Val Thr Val Ser Ser Gly Gly Gly Ser Gly Gly
        115                 120                 125

Gly Ser Glu Val Gln Leu Val Glu Ser Gly Gly Gly Leu Val Gln Pro
130                 135                 140

Gly Asn Ser Leu Arg Leu Ser Cys Ala Ala Ser Gly Phe Thr Phe Ser
145                 150                 155                 160

Lys Phe Gly Met Ser Trp Val Arg Gln Ala Pro Gly Lys Gly Leu Glu
            165                 170                 175

Trp Val Ser Ser Ile Ser Gly Ser Gly Arg Asp Thr Leu Tyr Ala Asp
            180                 185                 190

Ser Val Lys Gly Arg Phe Thr Ile Ser Arg Asp Asn Ala Lys Thr Thr
        195                 200                 205

Leu Tyr Leu Gln Met Asn Ser Leu Arg Pro Glu Asp Thr Ala Val Tyr
    210                 215                 220

Tyr Cys Thr Ile Gly Gly Ser Leu Ser Val Ser Ser Gln Gly Thr Leu
225                 230                 235                 240

Val Thr Val Ser Ser Gly Gly Gly Gly Ser Gly Gly Gly Ser Glu Val
            245                 250                 255

Gln Leu Val Glu Ser Gly Gly Gly Leu Val Gln Pro Gly Gly Ser Leu
        260                 265                 270

Lys Leu Ser Cys Ala Ala Ser Gly Phe Thr Phe Asn Lys Tyr Ala Ile
    275                 280                 285

Asn Trp Val Arg Gln Ala Pro Gly Lys Gly Leu Glu Trp Val Ala Arg
290                 295                 300

Ile Arg Ser Lys Tyr Asn Asn Tyr Ala Thr Tyr Tyr Ala Asp Gln Val
305                 310                 315                 320
```

```
Lys Asp Arg Phe Thr Ile Ser Arg Asp Asp Ser Lys Asn Thr Ala Tyr
                325                 330                 335
Leu Gln Met Asn Asn Leu Lys Thr Glu Asp Thr Ala Val Tyr Tyr Cys
            340                 345                 350
Val Arg His Ala Asn Phe Gly Asn Ser Tyr Ile Ser Tyr Trp Ala Tyr
        355                 360                 365
Trp Gly Gln Gly Thr Leu Val Thr Val Ser Ser Gly Gly Gly Gly Ser
    370                 375                 380
Gly Gly Gly Gly Ser Gly Gly Gly Ser Gln Thr Val Val Thr Gln
385                 390                 395                 400
Glu Pro Ser Leu Thr Val Ser Pro Gly Gly Thr Val Thr Leu Thr Cys
                405                 410                 415
Ala Ser Ser Thr Gly Ala Val Thr Ser Gly Asn Tyr Pro Asn Trp Val
            420                 425                 430
Gln Gln Lys Pro Gly Gln Ala Pro Arg Gly Leu Ile Gly Gly Thr Lys
        435                 440                 445
Phe Leu Val Pro Gly Thr Pro Ala Arg Phe Ser Gly Ser Leu Leu Gly
    450                 455                 460
Gly Lys Ala Ala Leu Thr Leu Ser Gly Val Gln Pro Glu Asp Glu Ala
465                 470                 475                 480
Glu Tyr Tyr Cys Thr Leu Trp Tyr Ser Asn Arg Trp Val Phe Gly Gly
                485                 490                 495
Gly Thr Lys Leu Thr Val Leu His His His His His His
            500                 505

<210> SEQ ID NO 358
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 358

Glu Val Gln Leu Leu Glu Ser Gly Gly Gly Leu Val Gln Pro Gly Gly
1               5                   10                  15
Ser Leu Thr Leu Ser Cys Ala Ala Ser Gly Arg Thr Asp Ser Trp Tyr
            20                  25                  30
Val Met Gly Trp Phe Arg Gln Ala Pro Gly Lys Asp Arg Glu Phe Val
        35                  40                  45
Ala Gly Val Ser Trp Ser Tyr Gly Asn Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Ala Arg Val Ser Arg Glu Val Ile Pro Thr Arg Trp Asp Leu Tyr
            100                 105                 110
Asn Tyr Trp Gly Leu Gly Thr Gln Val Thr Val Ser Ser Gly Gly Gly
        115                 120                 125
Gly Ser Gly Gly Gly Ser Glu Val Gln Leu Val Glu Ser Gly Gly Gly
    130                 135                 140
Leu Val Gln Pro Gly Asn Ser Leu Arg Leu Ser Cys Ala Ala Ser Gly
145                 150                 155                 160
Phe Thr Phe Ser Lys Phe Gly Met Ser Trp Val Arg Gln Ala Pro Gly
```

```
                165                 170                 175
Lys Gly Leu Glu Trp Val Ser Ser Ile Ser Gly Ser Gly Arg Asp Thr
            180                 185                 190
Leu Tyr Ala Asp Ser Val Lys Gly Arg Phe Thr Ile Ser Arg Asp Asn
        195                 200                 205
Ala Lys Thr Thr Leu Tyr Leu Gln Met Asn Ser Leu Arg Pro Glu Asp
    210                 215                 220
Thr Ala Val Tyr Tyr Cys Thr Ile Gly Gly Ser Leu Ser Val Ser Ser
225                 230                 235                 240
Gln Gly Thr Leu Val Thr Val Ser Ser Gly Gly Gly Ser Gly Gly
                245                 250                 255
Gly Ser Glu Val Gln Leu Val Glu Ser Gly Gly Leu Val Gln Pro
            260                 265                 270
Gly Gly Ser Leu Lys Leu Ser Cys Ala Ala Ser Gly Phe Thr Phe Asn
            275                 280                 285
Lys Tyr Ala Ile Asn Trp Val Arg Gln Ala Pro Gly Lys Gly Leu Glu
        290                 295                 300
Trp Val Ala Arg Ile Arg Ser Lys Tyr Asn Asn Tyr Ala Thr Tyr Tyr
305                 310                 315                 320
Ala Asp Gln Val Lys Asp Arg Phe Thr Ile Ser Arg Asp Asp Ser Lys
                325                 330                 335
Asn Thr Ala Tyr Leu Gln Met Asn Asn Leu Lys Thr Glu Asp Thr Ala
            340                 345                 350
Val Tyr Tyr Cys Val Arg His Ala Asn Phe Gly Asn Ser Tyr Ile Ser
        355                 360                 365
Tyr Trp Ala Tyr Trp Gly Gln Gly Thr Leu Val Thr Val Ser Ser Gly
    370                 375                 380
Gly Gly Gly Ser Gly Gly Gly Ser Gly Gly Gly Ser Gln Thr
385                 390                 395                 400
Val Val Thr Gln Glu Pro Ser Leu Thr Val Ser Pro Gly Gly Thr Val
                405                 410                 415
Thr Leu Thr Cys Ala Ser Ser Thr Gly Ala Val Thr Ser Gly Asn Tyr
            420                 425                 430
Pro Asn Trp Val Gln Gln Lys Pro Gly Gln Ala Pro Arg Gly Leu Ile
        435                 440                 445
Gly Gly Thr Lys Phe Leu Val Pro Gly Thr Pro Ala Arg Phe Ser Gly
    450                 455                 460
Ser Leu Leu Gly Lys Ala Ala Leu Thr Leu Ser Gly Val Gln Pro
465                 470                 475                 480
Glu Asp Glu Ala Glu Tyr Tyr Cys Thr Leu Trp Tyr Ser Asn Arg Trp
                485                 490                 495
Val Phe Gly Gly Gly Thr Lys Leu Thr Val Leu His His His His
            500                 505                 510
His
```

<210> SEQ ID NO 359
<211> LENGTH: 515
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 359

Glu Val Gln Leu Leu Glu Ser Gly Gly Gly Leu Val Gln Pro Gly Gly

-continued

```
1               5                   10                  15
Ser Leu Thr Leu Ser Cys Ala Ala Ser Ala Arg Thr Leu Arg Leu Tyr
            20                  25                  30
Ala Val Gly Trp Phe Arg Gln Ala Pro Gly Lys Glu Arg Glu Phe Val
            35                  40                  45
Ala Gly Ile Gly Arg Ser Glu Arg Thr Tyr Tyr Thr Asp Ser Val Lys
            50                  55                  60
Gly Arg Phe Thr Ile Ser Arg Asp Asn Ser Lys Asn Thr Leu Tyr Leu
65                  70                  75                  80
Gln Met Asn Ser Leu Arg Ala Glu Asp Thr Ala Val Tyr Tyr Cys Ala
            85                  90                  95
Leu Thr Phe Gln Thr Thr Asp Met Val Asp Val Pro Thr Thr Gln His
            100                 105                 110
Glu Tyr Asp Tyr Trp Gly Leu Gly Thr Gln Val Thr Val Ser Ser Gly
            115                 120                 125
Gly Gly Gly Ser Gly Gly Ser Glu Val Gln Leu Val Glu Ser Gly
            130                 135                 140
Gly Gly Leu Val Gln Pro Gly Asn Ser Leu Arg Leu Ser Cys Ala Ala
145                 150                 155                 160
Ser Gly Phe Thr Phe Ser Lys Phe Gly Met Ser Trp Val Arg Gln Ala
            165                 170                 175
Pro Gly Lys Gly Leu Glu Trp Val Ser Ser Ile Ser Gly Ser Gly Arg
            180                 185                 190
Asp Thr Leu Tyr Ala Asp Ser Val Lys Gly Arg Phe Thr Ile Ser Arg
            195                 200                 205
Asp Asn Ala Lys Thr Thr Leu Tyr Leu Gln Met Asn Ser Leu Arg Pro
            210                 215                 220
Glu Asp Thr Ala Val Tyr Tyr Cys Thr Ile Gly Gly Ser Leu Ser Val
225                 230                 235                 240
Ser Ser Gln Gly Thr Leu Val Thr Val Ser Ser Gly Gly Gly Gly Ser
            245                 250                 255
Gly Gly Gly Ser Glu Val Gln Leu Val Glu Ser Gly Gly Leu Val
            260                 265                 270
Gln Pro Gly Gly Ser Leu Lys Leu Ser Cys Ala Ala Ser Gly Phe Thr
            275                 280                 285
Phe Asn Lys Tyr Ala Ile Asn Trp Val Arg Gln Ala Pro Gly Lys Gly
            290                 295                 300
Leu Glu Trp Val Ala Arg Ile Arg Ser Lys Tyr Asn Asn Tyr Ala Thr
305                 310                 315                 320
Tyr Tyr Ala Asp Gln Val Lys Asp Arg Phe Thr Ile Ser Arg Asp Asp
            325                 330                 335
Ser Lys Asn Thr Ala Tyr Leu Gln Met Asn Asn Leu Lys Thr Glu Asp
            340                 345                 350
Thr Ala Val Tyr Tyr Cys Val Arg His Ala Asn Phe Gly Asn Ser Tyr
            355                 360                 365
Ile Ser Tyr Trp Ala Tyr Trp Gly Gln Gly Thr Leu Val Thr Val Ser
            370                 375                 380
Ser Gly Gly Gly Gly Ser Gly Gly Gly Ser Gly Gly Gly Ser
385                 390                 395                 400
Gln Thr Val Val Thr Gln Glu Pro Ser Leu Thr Val Ser Pro Gly Gly
            405                 410                 415
Thr Val Thr Leu Thr Cys Ala Ser Ser Thr Gly Ala Val Thr Ser Gly
            420                 425                 430
```

```
Asn Tyr Pro Asn Trp Val Gln Gln Lys Pro Gly Gln Ala Pro Arg Gly
            435                 440                 445

Leu Ile Gly Gly Thr Lys Phe Leu Val Pro Gly Thr Pro Ala Arg Phe
        450                 455                 460

Ser Gly Ser Leu Leu Gly Gly Lys Ala Ala Leu Thr Leu Ser Gly Val
465                 470                 475                 480

Gln Pro Glu Asp Glu Ala Glu Tyr Tyr Cys Thr Leu Trp Tyr Ser Asn
                485                 490                 495

Arg Trp Val Phe Gly Gly Gly Thr Lys Leu Thr Val Leu His His His
                500                 505                 510

His His His
        515

<210> SEQ ID NO 360
<211> LENGTH: 502
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 360

Glu Val Gln Leu Leu Glu Ser Gly Gly Gly Leu Val Gln Pro Gly Gly
1               5                   10                  15

Ser Leu Thr Leu Ser Cys Ala Ala Ser Gly Ser Ile Val Thr Ile Asn
            20                  25                  30

Ala Met Thr Trp Tyr Arg Gln Ala Pro Gly Lys Arg Arg Glu Leu Val
        35                  40                  45

Ala Ile Ile Thr Ser Gly Gly Glu Thr Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Asn
                85                  90                  95

Val Val Pro Pro Leu Gly Ser Trp Gly Leu Gly Thr Gln Val Thr Val
                100                 105                 110

Ser Ser Gly Gly Gly Gly Ser Gly Gly Gly Ser Glu Val Gln Leu Val
            115                 120                 125

Glu Ser Gly Gly Gly Leu Val Gln Pro Gly Asn Ser Leu Arg Leu Ser
        130                 135                 140

Cys Ala Ala Ser Gly Phe Thr Phe Ser Lys Phe Gly Met Ser Trp Val
145                 150                 155                 160

Arg Gln Ala Pro Gly Lys Gly Leu Glu Trp Val Ser Ser Ile Ser Gly
                165                 170                 175

Ser Gly Arg Asp Thr Leu Tyr Ala Asp Ser Val Lys Gly Arg Phe Thr
                180                 185                 190

Ile Ser Arg Asp Asn Ala Lys Thr Thr Leu Tyr Leu Gln Met Asn Ser
            195                 200                 205

Leu Arg Pro Glu Asp Thr Ala Val Tyr Tyr Cys Thr Ile Gly Gly Ser
        210                 215                 220

Leu Ser Val Ser Ser Gln Gly Thr Leu Val Thr Val Ser Ser Gly Gly
225                 230                 235                 240

Gly Gly Ser Gly Gly Gly Ser Glu Val Gln Leu Val Glu Ser Gly Gly
                245                 250                 255

Gly Leu Val Gln Pro Gly Gly Ser Leu Lys Leu Ser Cys Ala Ala Ser
```

```
            260                 265                 270
Gly Phe Thr Phe Asn Lys Tyr Ala Ile Asn Trp Val Arg Gln Ala Pro
            275                 280                 285
Gly Lys Gly Leu Glu Trp Val Ala Arg Ile Arg Ser Lys Tyr Asn Asn
            290                 295                 300
Tyr Ala Thr Tyr Tyr Ala Asp Gln Val Lys Asp Arg Phe Thr Ile Ser
305                 310                 315                 320
Arg Asp Asp Ser Lys Asn Thr Ala Tyr Leu Gln Met Asn Asn Leu Lys
                325                 330                 335
Thr Glu Asp Thr Ala Val Tyr Tyr Cys Val Arg His Ala Asn Phe Gly
            340                 345                 350
Asn Ser Tyr Ile Ser Tyr Trp Ala Tyr Trp Gly Gln Gly Thr Leu Val
            355                 360                 365
Thr Val Ser Ser Gly Gly Gly Ser Gly Gly Gly Ser Gly Gly Gly Ser
        370                 375                 380
Gly Gly Ser Gln Thr Val Val Thr Gln Glu Pro Ser Leu Thr Val Ser
385                 390                 395                 400
Pro Gly Gly Thr Val Thr Leu Thr Cys Ala Ser Ser Thr Gly Ala Val
                405                 410                 415
Thr Ser Gly Asn Tyr Pro Asn Trp Val Gln Gln Lys Pro Gly Gln Ala
            420                 425                 430
Pro Arg Gly Leu Ile Gly Gly Thr Lys Phe Leu Val Pro Gly Thr Pro
            435                 440                 445
Ala Arg Phe Ser Gly Ser Leu Leu Gly Gly Lys Ala Ala Leu Thr Leu
            450                 455                 460
Ser Gly Val Gln Pro Glu Asp Glu Ala Glu Tyr Tyr Cys Thr Leu Trp
465                 470                 475                 480
Tyr Ser Asn Arg Trp Val Phe Gly Gly Gly Thr Lys Leu Thr Val Leu
                485                 490                 495
His His His His His His
            500

<210> SEQ ID NO 361
<211> LENGTH: 507
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 361

Glu Val Gln Leu Leu Glu Ser Gly Gly Gly Leu Val Gln Pro Gly Gly
1               5                   10                  15
Ser Leu Thr Leu Ser Cys Ala Ala Ser Gly Arg Tyr His Met Ala Trp
            20                  25                  30
Phe Arg Gln Ala Pro Gly Lys Glu Arg Glu Phe Val Gly Thr Ile Ser
        35                  40                  45
Ser Gly Asp Ser Thr Trp Tyr Thr Asn Ser Val Lys Gly Arg Phe Thr
    50                  55                  60
Ile Ser Arg Asp Asn Ser Lys Asn Thr Leu Tyr Leu Gln Met Asn Ser
65                  70                  75                  80
Leu Arg Ala Glu Asp Thr Ala Val Tyr Tyr Cys Ala Ala Ala Leu Tyr
                85                  90                  95
Tyr Gly Asp Ser Arg Arg Ala Ala Asp Tyr Pro Tyr Trp Gly Leu Gly
            100                 105                 110
```

```
Thr Gln Val Thr Val Ser Ser Gly Gly Gly Ser Gly Gly Ser
            115                 120                 125

Glu Val Gln Leu Val Glu Ser Gly Gly Gly Leu Val Gln Pro Gly Asn
130                 135                 140

Ser Leu Arg Leu Ser Cys Ala Ala Ser Gly Phe Thr Phe Ser Lys Phe
145                 150                 155                 160

Gly Met Ser Trp Val Arg Gln Ala Pro Gly Lys Gly Leu Glu Trp Val
                165                 170                 175

Ser Ser Ile Ser Gly Ser Gly Arg Asp Thr Leu Tyr Ala Asp Ser Val
            180                 185                 190

Lys Gly Arg Phe Thr Ile Ser Arg Asp Asn Ala Lys Thr Thr Leu Tyr
        195                 200                 205

Leu Gln Met Asn Ser Leu Arg Pro Glu Asp Thr Ala Val Tyr Tyr Cys
    210                 215                 220

Thr Ile Gly Gly Ser Leu Ser Val Ser Ser Gln Gly Thr Leu Val Thr
225                 230                 235                 240

Val Ser Ser Gly Gly Gly Gly Ser Gly Gly Gly Ser Glu Val Gln Leu
                245                 250                 255

Val Glu Ser Gly Gly Gly Leu Val Gln Pro Gly Gly Ser Leu Lys Leu
            260                 265                 270

Ser Cys Ala Ala Ser Gly Phe Thr Phe Asn Lys Tyr Ala Ile Asn Trp
    275                 280                 285

Val Arg Gln Ala Pro Gly Lys Gly Leu Glu Trp Val Ala Arg Ile Arg
290                 295                 300

Ser Lys Tyr Asn Asn Tyr Ala Thr Tyr Tyr Ala Asp Gln Val Lys Asp
305                 310                 315                 320

Arg Phe Thr Ile Ser Arg Asp Asp Ser Lys Asn Thr Ala Tyr Leu Gln
                325                 330                 335

Met Asn Asn Leu Lys Thr Glu Asp Thr Ala Val Tyr Tyr Cys Val Arg
            340                 345                 350

His Ala Asn Phe Gly Asn Ser Tyr Ile Ser Tyr Trp Ala Tyr Trp Gly
        355                 360                 365

Gln Gly Thr Leu Val Thr Val Ser Ser Gly Gly Gly Gly Ser Gly Gly
    370                 375                 380

Gly Gly Ser Gly Gly Gly Ser Gln Thr Val Val Thr Gln Glu Pro
385                 390                 395                 400

Ser Leu Thr Val Ser Pro Gly Gly Thr Val Thr Leu Thr Cys Ala Ser
                405                 410                 415

Ser Thr Gly Ala Val Thr Ser Gly Asn Tyr Pro Asn Trp Val Gln Gln
            420                 425                 430

Lys Pro Gly Gln Ala Pro Arg Gly Leu Ile Gly Gly Thr Lys Phe Leu
        435                 440                 445

Val Pro Gly Thr Pro Ala Arg Phe Ser Gly Ser Leu Leu Gly Gly Lys
    450                 455                 460

Ala Ala Leu Thr Leu Ser Gly Val Gln Pro Glu Asp Glu Ala Glu Tyr
465                 470                 475                 480

Tyr Cys Thr Leu Trp Tyr Ser Asn Arg Trp Val Phe Gly Gly Gly Thr
                485                 490                 495

Lys Leu Thr Val Leu His His His His His
            500                 505

<210> SEQ ID NO 362
<211> LENGTH: 513
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 362

Glu Val Gln Leu Leu Glu Ser Gly Gly Gly Leu Val Gln Pro Gly Gly
1               5                   10                  15

Ser Leu Thr Leu Ser Cys Ala Ala Ser Gly Ser Thr Phe Arg His His
            20                  25                  30

Ala Met Ala Trp Phe Arg Gln Thr Pro Gly Lys Glu Arg Glu Phe Val
        35                  40                  45

Ser Ala Ile Asn Asp His Gly Asp Arg Thr Lys Tyr Leu Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Gly Pro Leu Val Asp Tyr Leu Glu Thr Thr Pro Leu Val Tyr
            100                 105                 110

Thr Tyr Trp Gly Leu Gly Thr Gln Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Ser Lys Phe Gly Met Ser Trp Val Arg Gln Ala Pro Gly
                165                 170                 175

Lys Gly Leu Glu Trp Val Ser Ser Ile Ser Gly Ser Gly Arg Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Val Ser Ser
225                 230                 235                 240

Gln Gly Thr Leu Val Thr Val Ser Ser Gly Gly Gly Ser Gly Gly
                245                 250                 255

Gly Ser Glu Val Gln Leu Val Glu Ser Gly Gly Gly Leu Val Gln Pro
            260                 265                 270

Gly Gly Ser Leu Lys Leu Ser Cys Ala Ala Ser Gly Phe Thr Phe Asn
        275                 280                 285

Lys Tyr Ala Ile Asn Trp Val Arg Gln Ala Pro Gly Lys Gly Leu Glu
    290                 295                 300

Trp Val Ala Arg Ile Arg Ser Lys Tyr Asn Asn Tyr Ala Thr Tyr Tyr
305                 310                 315                 320

Ala Asp Gln Val Lys Asp Arg Phe Thr Ile Ser Arg Asp Asp Ser Lys
                325                 330                 335

Asn Thr Ala Tyr Leu Gln Met Asn Asn Leu Lys Thr Glu Asp Thr Ala
            340                 345                 350

Val Tyr Tyr Cys Val Arg His Ala Asn Phe Gly Asn Ser Tyr Ile Ser
        355                 360                 365

Tyr Trp Ala Tyr Trp Gly Gln Gly Thr Leu Val Thr Val Ser Ser Gly
    370                 375                 380

Gly Gly Gly Ser Gly Gly Gly Ser Gly Gly Gly Ser Gln Thr
385                 390                 395                 400

Val Val Thr Gln Glu Pro Ser Leu Thr Val Ser Pro Gly Gly Thr Val
            405                 410                 415

Thr Leu Thr Cys Ala Ser Ser Thr Gly Ala Val Thr Ser Gly Asn Tyr
            420                 425                 430

Pro Asn Trp Val Gln Gln Lys Pro Gly Gln Ala Pro Arg Gly Leu Ile
            435                 440                 445

Gly Gly Thr Lys Phe Leu Val Pro Gly Thr Pro Ala Arg Phe Ser Gly
450                 455                 460

Ser Leu Leu Gly Gly Lys Ala Ala Leu Thr Leu Ser Gly Val Gln Pro
465                 470                 475                 480

Glu Asp Glu Ala Glu Tyr Tyr Cys Thr Leu Trp Tyr Ser Asn Arg Trp
            485                 490                 495

Val Phe Gly Gly Gly Thr Lys Leu Thr Val Leu His His His His
            500                 505                 510

His

<210> SEQ ID NO 363
<211> LENGTH: 512
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 363

Glu Val Gln Leu Leu Glu Ser Gly Gly Gly Leu Val Gln Pro Gly Gly
1               5                   10                  15

Ser Leu Thr Leu Ser Cys Ala Ala Ser Gly Arg Ser Phe Ser Asn Tyr
            20                  25                  30

Ile Met Gly Trp Phe Arg Gln Ala Pro Gly Lys Glu Arg Glu Phe Val
        35                  40                  45

Ala Gly Leu Gly Trp Ser Pro Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Arg Arg Gly Asp Val Ile Tyr Thr Thr Pro Trp Asn Tyr Val
            100                 105                 110

Tyr Trp Gly Leu Gly Thr Gln Val Thr Val Ser Ser Gly Gly Gly Gly
        115                 120                 125

Ser Gly Gly Gly Ser Glu Val Gln Leu Val Glu Ser Gly Gly Gly Leu
130                 135                 140

Val Gln Pro Gly Asn Ser Leu Arg Leu Ser Cys Ala Ala Ser Gly Phe
145                 150                 155                 160

Thr Phe Ser Lys Phe Gly Met Ser Trp Val Arg Gln Ala Pro Gly Lys
            165                 170                 175

Gly Leu Glu Trp Val Ser Ser Ile Ser Gly Ser Gly Arg Asp Thr Leu
        180                 185                 190

Tyr Ala Asp Ser Val Lys Gly Arg Phe Thr Ile Ser Arg Asp Asn Ala
    195                 200                 205

Lys Thr Thr Leu Tyr Leu Gln Met Asn Ser Leu Arg Pro Glu Asp Thr
210                 215                 220

Ala Val Tyr Tyr Cys Thr Ile Gly Gly Ser Leu Ser Val Ser Ser Gln
225                 230                 235                 240

Gly Thr Leu Val Thr Val Ser Ser Gly Gly Gly Ser Gly Gly Gly
            245                 250                 255

Ser Glu Val Gln Leu Val Glu Ser Gly Gly Gly Leu Val Gln Pro Gly
                260                 265                 270

Gly Ser Leu Lys Leu Ser Cys Ala Ala Ser Gly Phe Thr Phe Asn Lys
            275                 280                 285

Tyr Ala Ile Asn Trp Val Arg Gln Ala Pro Gly Lys Gly Leu Glu Trp
        290                 295                 300

Val Ala Arg Ile Arg Ser Lys Tyr Asn Asn Tyr Ala Thr Tyr Tyr Ala
305                 310                 315                 320

Asp Gln Val Lys Asp Arg Phe Thr Ile Ser Arg Asp Asp Ser Lys Asn
                325                 330                 335

Thr Ala Tyr Leu Gln Met Asn Asn Leu Lys Thr Glu Asp Thr Ala Val
            340                 345                 350

Tyr Tyr Cys Val Arg His Ala Asn Phe Gly Asn Ser Tyr Ile Ser Tyr
        355                 360                 365

Trp Ala Tyr Trp Gly Gln Gly Thr Leu Val Thr Val Ser Ser Gly Gly
        370                 375                 380

Gly Gly Ser Gly Gly Gly Ser Gly Gly Gly Ser Gln Thr Val
385                 390                 395                 400

Val Thr Gln Glu Pro Ser Leu Thr Val Ser Pro Gly Gly Thr Val Thr
                405                 410                 415

Leu Thr Cys Ala Ser Ser Thr Gly Ala Val Thr Ser Gly Asn Tyr Pro
            420                 425                 430

Asn Trp Val Gln Gln Lys Pro Gly Gln Ala Pro Arg Gly Leu Ile Gly
        435                 440                 445

Gly Thr Lys Phe Leu Val Pro Gly Thr Pro Ala Arg Phe Ser Gly Ser
        450                 455                 460

Leu Leu Gly Gly Lys Ala Ala Leu Thr Leu Ser Gly Val Gln Pro Glu
465                 470                 475                 480

Asp Glu Ala Glu Tyr Tyr Cys Thr Leu Trp Tyr Ser Asn Arg Trp Val
                485                 490                 495

Phe Gly Gly Gly Thr Lys Leu Thr Val Leu His His His His His His
            500                 505                 510

<210> SEQ ID NO 364
<211> LENGTH: 510
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 364

Glu Val Gln Leu Leu Glu Ser Gly Gly Gly Leu Val Gln Pro Gly Gly
1               5                   10                  15

Ser Leu Thr Leu Ser Cys Ala Ala Ser Gly Leu Thr Phe Ser Ser Tyr
            20                  25                  30

Ala Met Ala Trp Phe Arg Gln Ala Pro Gly Lys Gln Arg Glu Leu Val
        35                  40                  45

Ala Arg Ile Thr Ser Gly Gly Thr Thr Asp Tyr Ala Asp Ser Val Lys
    50                  55                  60

Gly Arg Phe Thr Ile Ser Arg Asp Asn Ser Lys Asn Thr Leu Tyr Leu
65                  70                  75                  80

-continued

```
Gln Met Asn Ser Leu Arg Ala Glu Asp Thr Ala Val Tyr Tyr Cys Ala
                85                  90                  95

Ala Asp Leu Thr Tyr Arg Asn Leu Leu Leu Lys Leu Pro His Tyr Trp
            100                 105                 110

Gly Leu Gly Thr Gln Val Thr Val Ser Ser Gly Gly Gly Gly Ser Gly
            115                 120                 125

Gly Gly Ser Glu Val Gln Leu Val Glu Ser Gly Gly Gly Leu Val Gln
130                 135                 140

Pro Gly Asn Ser Leu Arg Leu Ser Cys Ala Ala Ser Gly Phe Thr Phe
145                 150                 155                 160

Ser Lys Phe Gly Met Ser Trp Val Arg Gln Ala Pro Lys Gly Leu
                165                 170                 175

Glu Trp Val Ser Ser Ile Ser Gly Ser Gly Arg Asp Thr Leu Tyr Ala
                180                 185                 190

Asp Ser Val Lys Gly Arg Phe Thr Ile Ser Arg Asp Asn Ala Lys Thr
            195                 200                 205

Thr Leu Tyr Leu Gln Met Asn Ser Leu Arg Pro Glu Asp Thr Ala Val
            210                 215                 220

Tyr Tyr Cys Thr Ile Gly Gly Ser Leu Ser Val Ser Ser Gln Gly Thr
225                 230                 235                 240

Leu Val Thr Val Ser Ser Gly Gly Gly Ser Gly Gly Gly Ser Glu
                245                 250                 255

Val Gln Leu Val Glu Ser Gly Gly Leu Val Gln Pro Gly Gly Ser
                260                 265                 270

Leu Lys Leu Ser Cys Ala Ala Ser Gly Phe Thr Phe Asn Lys Tyr Ala
                275                 280                 285

Ile Asn Trp Val Arg Gln Ala Pro Gly Lys Gly Leu Glu Trp Val Ala
        290                 295                 300

Arg Ile Arg Ser Lys Tyr Asn Asn Tyr Ala Thr Tyr Tyr Ala Asp Gln
305                 310                 315                 320

Val Lys Asp Arg Phe Thr Ile Ser Arg Asp Asp Ser Lys Asn Thr Ala
                325                 330                 335

Tyr Leu Gln Met Asn Asn Leu Lys Thr Glu Asp Thr Ala Val Tyr Tyr
            340                 345                 350

Cys Val Arg His Ala Asn Phe Gly Asn Ser Tyr Ile Ser Tyr Trp Ala
            355                 360                 365

Tyr Trp Gly Gln Gly Thr Leu Val Thr Val Ser Ser Gly Gly Gly Gly
        370                 375                 380

Ser Gly Gly Gly Gly Ser Gly Gly Gly Gly Ser Gln Thr Val Val Thr
385                 390                 395                 400

Gln Glu Pro Ser Leu Thr Val Ser Pro Gly Gly Thr Val Thr Leu Thr
                405                 410                 415

Cys Ala Ser Ser Thr Gly Ala Val Thr Ser Gly Asn Tyr Pro Asn Trp
            420                 425                 430

Val Gln Gln Lys Pro Gly Gln Ala Pro Arg Gly Leu Ile Gly Gly Thr
            435                 440                 445

Lys Phe Leu Val Pro Gly Thr Pro Ala Arg Phe Ser Gly Ser Leu Leu
        450                 455                 460

Gly Gly Lys Ala Ala Leu Thr Leu Ser Gly Val Gln Pro Glu Asp Glu
465                 470                 475                 480

Ala Glu Tyr Tyr Cys Thr Leu Trp Tyr Ser Asn Arg Trp Val Phe Gly
                485                 490                 495
```

Gly Gly Thr Lys Leu Thr Val Leu His His His His His His
                    500                 505                 510

<210> SEQ ID NO 365
<211> LENGTH: 501
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 365

Glu Val Gln Leu Leu Glu Ser Gly Gly Gly Leu Val Gln Pro Gly Gly
1               5                   10                  15

Ser Leu Thr Leu Ser Cys Ala Ala Ser Val Ser Ile Phe Ser Val Asn
            20                  25                  30

Ala Val Asp Trp Tyr Arg Gln Ser Pro Gly Lys Glu Arg Glu Leu Val
        35                  40                  45

Ala Ile Met Thr Ser Asp Gly Ser Thr Asn Tyr Asp Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Asn
                85                  90                  95

Thr Val Pro Pro Arg Tyr Trp Gly Leu Gly Thr Gln Val Thr Val Ser
            100                 105                 110

Ser Gly Gly Gly Gly Ser Gly Gly Gly Ser Glu Val Gln Leu Val Glu
        115                 120                 125

Ser Gly Gly Gly Leu Val Gln Pro Gly Asn Ser Leu Arg Leu Ser Cys
    130                 135                 140

Ala Ala Ser Gly Phe Thr Phe Ser Lys Phe Gly Met Ser Trp Val Arg
145                 150                 155                 160

Gln Ala Pro Gly Lys Gly Leu Glu Trp Val Ser Ser Ile Ser Gly Ser
                165                 170                 175

Gly Arg Asp Thr Leu Tyr Ala Asp Ser Val Lys Gly Arg Phe Thr Ile
            180                 185                 190

Ser Arg Asp Asn Ala Lys Thr Thr Leu Tyr Leu Gln Met Asn Ser Leu
        195                 200                 205

Arg Pro Glu Asp Thr Ala Val Tyr Tyr Cys Thr Ile Gly Gly Ser Leu
    210                 215                 220

Ser Val Ser Ser Gln Gly Thr Leu Val Thr Val Ser Ser Gly Gly Gly
225                 230                 235                 240

Gly Ser Gly Gly Gly Ser Glu Val Gln Leu Val Glu Ser Gly Gly Gly
                245                 250                 255

Leu Val Gln Pro Gly Gly Ser Leu Lys Leu Ser Cys Ala Ala Ser Gly
            260                 265                 270

Phe Thr Phe Asn Lys Tyr Ala Ile Asn Trp Val Arg Gln Ala Pro Gly
        275                 280                 285

Lys Gly Leu Glu Trp Val Ala Arg Ile Arg Ser Lys Tyr Asn Asn Tyr
    290                 295                 300

Ala Thr Tyr Tyr Ala Asp Gln Val Lys Asp Arg Phe Thr Ile Ser Arg
305                 310                 315                 320

Asp Asp Ser Lys Asn Thr Ala Tyr Leu Gln Met Asn Asn Leu Lys Thr
                325                 330                 335

Glu Asp Thr Ala Val Tyr Tyr Cys Val Arg His Ala Asn Phe Gly Asn
            340                 345                 350

```
Ser Tyr Ile Ser Tyr Trp Ala Tyr Trp Gly Gln Gly Thr Leu Val Thr
            355                 360                 365

Val Ser Ser Gly Gly Gly Gly Ser Gly Gly Gly Gly Ser Gly Gly Gly
    370                 375                 380

Gly Ser Gln Thr Val Val Thr Gln Glu Pro Ser Leu Thr Val Ser Pro
385                 390                 395                 400

Gly Gly Thr Val Thr Leu Thr Cys Ala Ser Ser Thr Gly Ala Val Thr
                405                 410                 415

Ser Gly Asn Tyr Pro Asn Trp Val Gln Gln Lys Pro Gly Gln Ala Pro
            420                 425                 430

Arg Gly Leu Ile Gly Gly Thr Lys Phe Leu Val Pro Gly Thr Pro Ala
            435                 440                 445

Arg Phe Ser Gly Ser Leu Leu Gly Gly Lys Ala Ala Leu Thr Leu Ser
    450                 455                 460

Gly Val Gln Pro Glu Asp Glu Ala Glu Tyr Tyr Cys Thr Leu Trp Tyr
465                 470                 475                 480

Ser Asn Arg Trp Val Phe Gly Gly Gly Thr Lys Leu Thr Val Leu His
            485                 490                 495

His His His His His
            500

<210> SEQ ID NO 366
<211> LENGTH: 511
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 366

Glu Val Gln Leu Leu Glu Ser Gly Gly Gly Leu Val Gln Pro Gly Gly
1               5                   10                  15

Ser Leu Thr Leu Ser Cys Ala Ala Ser Gly Asn Asp Phe Val Ile Thr
            20                  25                  30

Asp Met His Trp Tyr Arg Gln Ala Pro Gly Lys Gln Arg Glu Trp Val
        35                  40                  45

Ala Thr Ile Thr Arg Phe Ala Thr Thr Asn Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Lys
            85                  90                  95

Ala Ile Gly Leu Arg Gly Val Pro Asp Val Asn Arg Gln Phe Glu Val
        100                 105                 110

Trp Gly Leu Gly Thr Gln Val Thr Val Ser Ser Gly Gly Gly Gly Ser
    115                 120                 125

Gly Gly Gly Ser Glu Val Gln Leu Val Glu Ser Gly Gly Leu Val
        130                 135                 140

Gln Pro Gly Asn Ser Leu Arg Leu Ser Cys Ala Ala Ser Gly Phe Thr
145                 150                 155                 160

Phe Ser Lys Phe Gly Met Ser Trp Val Arg Gln Ala Pro Gly Lys Gly
            165                 170                 175

Leu Glu Trp Val Ser Ser Ile Ser Gly Ser Gly Arg Asp Thr Leu Tyr
        180                 185                 190

Ala Asp Ser Val Lys Gly Arg Phe Thr Ile Ser Arg Asp Asn Ala Lys
```

```
            195                 200                 205
Thr Thr Leu Tyr Leu Gln Met Asn Ser Leu Arg Pro Glu Asp Thr Ala
210                 215                 220
Val Tyr Tyr Cys Thr Ile Gly Gly Ser Leu Ser Val Ser Ser Gln Gly
225                 230                 235                 240
Thr Leu Val Thr Val Ser Ser Gly Gly Gly Ser Gly Gly Gly Ser
                    245                 250                 255
Glu Val Gln Leu Val Glu Ser Gly Gly Gly Leu Val Gln Pro Gly Gly
                260                 265                 270
Ser Leu Lys Leu Ser Cys Ala Ala Ser Gly Phe Thr Phe Asn Lys Tyr
                275                 280                 285
Ala Ile Asn Trp Val Arg Gln Ala Pro Gly Lys Gly Leu Glu Trp Val
                290                 295                 300
Ala Arg Ile Arg Ser Lys Tyr Asn Asn Tyr Ala Thr Tyr Tyr Ala Asp
305                 310                 315                 320
Gln Val Lys Asp Arg Phe Thr Ile Ser Arg Asp Asp Ser Lys Asn Thr
                    325                 330                 335
Ala Tyr Leu Gln Met Asn Asn Leu Lys Thr Glu Asp Thr Ala Val Tyr
                340                 345                 350
Tyr Cys Val Arg His Ala Asn Phe Gly Asn Ser Tyr Ile Ser Tyr Trp
                355                 360                 365
Ala Tyr Trp Gly Gln Gly Thr Leu Val Thr Val Ser Ser Gly Gly Gly
                370                 375                 380
Gly Ser Gly Gly Gly Gly Ser Gly Gly Gly Gly Ser Gln Thr Val Val
385                 390                 395                 400
Thr Gln Glu Pro Ser Leu Thr Val Ser Pro Gly Gly Thr Val Thr Leu
                    405                 410                 415
Thr Cys Ala Ser Ser Thr Gly Ala Val Thr Ser Gly Asn Tyr Pro Asn
                    420                 425                 430
Trp Val Gln Gln Lys Pro Gly Gln Ala Pro Arg Gly Leu Ile Gly Gly
                    435                 440                 445
Thr Lys Phe Leu Val Pro Gly Thr Pro Ala Arg Phe Ser Gly Ser Leu
450                 455                 460
Leu Gly Gly Lys Ala Ala Leu Thr Leu Ser Gly Val Gln Pro Glu Asp
465                 470                 475                 480
Glu Ala Glu Tyr Tyr Cys Thr Leu Trp Tyr Ser Asn Arg Trp Val Phe
                    485                 490                 495
Gly Gly Gly Thr Lys Leu Thr Val Leu His His His His His His
                    500                 505                 510

<210> SEQ ID NO 367
<211> LENGTH: 509
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 367

Glu Val Gln Leu Leu Glu Ser Gly Gly Gly Leu Val Gln Pro Gly Gly
1               5                   10                  15

Ser Leu Thr Leu Ser Cys Ala Ala Ser Gly Ala Ile Ala Tyr Ile Tyr
                20                  25                  30

Gly Met Gly Trp Tyr Arg Gln Ala Pro Gly Lys Gln Arg Glu Leu Val
                35                  40                  45
```

-continued

```
Ala Ala Ile Ser Ser Gly Gly Ser Thr Asp Tyr Ala Asp Ser Val Lys
 50              55                  60
Gly Arg Phe Thr Ile Ser Arg Asp Asn Ser Lys Asn Thr Leu Tyr Leu
 65              70              75                  80
Gln Met Asn Ser Leu Arg Ala Glu Asp Thr Ala Val Tyr Tyr Cys Asn
             85                  90                  95
Ala Asp Val Arg Thr Ser Arg Asn Leu Val Arg Ser Asp Tyr Trp Gly
            100             105             110
Leu Gly Thr Gln Val Thr Val Ser Gly Gly Gly Ser Gly Gly
            115                 120             125
Gly Ser Glu Val Gln Leu Val Glu Ser Gly Gly Leu Val Gln Pro
130             135                 140
Gly Asn Ser Leu Arg Leu Ser Cys Ala Ala Ser Gly Phe Thr Phe Ser
145             150             155                 160
Lys Phe Gly Met Ser Trp Val Arg Gln Ala Pro Gly Lys Gly Leu Glu
                165             170             175
Trp Val Ser Ser Ile Ser Gly Ser Gly Arg Asp Thr Leu Tyr Ala Asp
            180             185             190
Ser Val Lys Gly Arg Phe Thr Ile Ser Arg Asp Asn Ala Lys Thr Thr
            195             200             205
Leu Tyr Leu Gln Met Asn Ser Leu Arg Pro Glu Asp Thr Ala Val Tyr
210             215             220
Tyr Cys Thr Ile Gly Gly Ser Leu Ser Val Ser Ser Gln Gly Thr Leu
225             230             235                 240
Val Thr Val Ser Ser Gly Gly Gly Gly Ser Gly Gly Gly Ser Glu Val
            245             250             255
Gln Leu Val Glu Ser Gly Gly Gly Leu Val Gln Pro Gly Gly Ser Leu
            260             265             270
Lys Leu Ser Cys Ala Ala Ser Gly Phe Thr Phe Asn Lys Tyr Ala Ile
            275             280             285
Asn Trp Val Arg Gln Ala Pro Gly Lys Gly Leu Glu Trp Val Ala Arg
            290             295             300
Ile Arg Ser Lys Tyr Asn Asn Tyr Ala Thr Tyr Tyr Ala Asp Gln Val
305             310             315             320
Lys Asp Arg Phe Thr Ile Ser Arg Asp Asp Ser Lys Asn Thr Ala Tyr
                325             330             335
Leu Gln Met Asn Asn Leu Lys Thr Glu Asp Thr Ala Val Tyr Tyr Cys
            340             345             350
Val Arg His Ala Asn Phe Gly Asn Ser Tyr Ile Ser Tyr Trp Ala Tyr
            355             360             365
Trp Gly Gln Gly Thr Leu Val Thr Val Ser Ser Gly Gly Gly Gly Ser
370             375                 380
Gly Gly Gly Gly Ser Gly Gly Gly Ser Gln Thr Val Val Thr Gln
385             390             395                 400
Glu Pro Ser Leu Thr Val Ser Pro Gly Gly Thr Val Thr Leu Thr Cys
                405             410             415
Ala Ser Ser Thr Gly Ala Val Thr Ser Gly Asn Tyr Pro Asn Trp Val
                420             425             430
Gln Gln Lys Pro Gly Gln Ala Pro Arg Gly Leu Ile Gly Thr Lys
            435             440             445
Phe Leu Val Pro Gly Thr Pro Ala Arg Phe Ser Gly Ser Leu Leu Gly
450                 455             460
Gly Lys Ala Ala Leu Thr Leu Ser Gly Val Gln Pro Glu Asp Glu Ala
```

```
465            470            475            480
Glu Tyr Tyr Cys Thr Leu Trp Tyr Ser Asn Arg Trp Val Phe Gly Gly
                485            490            495

Gly Thr Lys Leu Thr Val Leu His His His His His
            500            505
```

EGFR BINDING PROTEINS AND METHODS OF USE

CROSS-REFERENCE

This application is the U.S. National Stage Application of PCT/US2019/052206 filed on Sep. 20, 2019, and claims the benefit of U.S. Provisional Application Nos. 62/734,892 filed on Sep. 21, 2018, and 62/734,908 filed on Sep. 21, 2018, all of which are incorporated by reference herein in their entirety.

BACKGROUND OF THE INVENTION

The selective destruction of an individual cell or a specific cell type is often desirable in a variety of clinical settings. For example, it is a primary goal of cancer therapy to specifically destroy tumor cells, while leaving healthy cells and tissues intact and undamaged. One such method is by inducing an immune response against the tumor, to make immune effector cells such as natural killer (NK) cells or cytotoxic T lymphocytes (CTLs) attack and destroy tumor cells.

Epidermal growth factor receptor (EGFR) has been causally implicated in human malignancy. Abnormal activity of the Her family of receptors is involved with breast cancer. EGFR, Her-3, and Her-4 are frequently expressed in ovarian granulosa cell tumors (Leibl, S. et al., Gynecol Oncol 101:18-23 (2005). In particular, increased expression of EGFR has been observed in breast, bladder, lung, head, neck and stomach cancer as well as glioblastomas.

Increased EGFR receptor expression may be associated with increased production of a EGFR ligand, transforming growth factor alpha (TGF-α), by the same tumor cells resulting in receptor activation by an autocrine stimulatory pathway.

Cetuximab (Erbitux™), an anti-EGFR antibody, has been associated with potentially life threatening infusion reactions (Thomas, M., Clin J Oncol Nurs. 9(3):332-8 (2005)). Gefitinib (Iressa™) and erlotinib (Tarceva™), both EGFR specific small molecule inhibitors, are associated with a risk of interstitial lung disease (Sandler A, Oncology 20(5 Suppl 2):35-40 (2006)). Individual patients may be predisposed to particular types of complications that affect the choice of drug treatment. There is a need for a greater choice of treatment options which allows physicians to select the therapeutic with the best side effect profile for an individual patient. The present disclosure provides novel polypeptides and protein therapeutics useful in methods of treatment, particularly for treatment of conditions associated with abnormal expression of EGFR.

SUMMARY OF THE INVENTION

One embodiment provides an EGFR binding trispecific protein, wherein said protein comprises (a) a first domain (A) which specifically binds to human CD3; (b) a second domain (B) which is a half-life extension domain; and (c) a third domain (C) which specifically binds to EGFR, wherein the domains are linked in the order H2N-(A)-(B)—(C)—COOH, H2N-(A)-(C)—(B)—COOH, H2N—(B)-(A)-(C)—COOH, H2N—(B)—(C)-(A)-COOH, H2N—(C)—(B)-(A)-COOH, or H2N—(C)-(A)-(B)—COOH, or by linkers L1 and L2 in the following order H2N-(A)-L1-(B)-L2-(C)—COOH, H2N-(A)-L1-(C)-L2-(B)—COOH, H2N—(B)-L1-(A)-L2-(C)—COOH, H2N—(B)-L1-(C)-L2-(A)-COOH, H2N—(C)-L1-(B)-L2-(A)-COOH, or H2N—(C)-L1-(A)-L2-(B)—COOH. In some embodiments, said first domain comprises a variable light domain and variable heavy domain each of which is capable of specifically binding to human CD3. In some embodiments, said first, second, and third domain independently comprise humanized or human sequences. In some embodiments, said second domain binds albumin. In some embodiments, said second domain comprises a scFv, a variable heavy domain (VH), a variable light domain (VL), a peptide, a ligand, or a small molecule. In some embodiments, said third domain comprises a VHH domain, a scFv, a VH domain, a VL domain, a non-Ig domain, a ligand, a knottin, or a small molecule entity that specifically binds to EGFR. In some embodiments, said third domain comprises the VHH domain. In some embodiments, said third domain comprises a complementarity determining region (CDR1) comprising a sequence that is at least about 75% identical to a sequence selected from the group consisting of: SEQ ID Nos. 50-98. In some embodiments, said third domain comprises a complementarity determining region (CDR2) comprising a sequence that is at least about 75% identical to a sequence selected from the group consisting of: SEQ ID Nos. 99-147. In some embodiments, said third domain comprises a complementarity determining region (CDR3) comprising a sequence that is at least about 75% identical to a sequence selected from the group consisting of: SEQ ID Nos. 148-196. In some embodiments, said third domain comprises a complementarity determining region (CDR1) comprising a sequence identical to or having one or more amino acid substitutions relative to a sequence selected from the group consisting of: SEQ ID Nos. 50-98. In some embodiments, said third domain comprises a complementarity determining region (CDR2) comprising a sequence identical to or having one or more amino acid substitutions relative to a sequence selected from the group consisting of: SEQ ID Nos. 99-147. In some embodiments, said third domain comprises a complementarity determining region (CDR3) comprising a sequence identical to or having one or more amino acid substitutions relative to a sequence selected from the group consisting of: SEQ ID Nos. 148-196. In some embodiments, said third domain comprises a complementarity determining region (CDR1) comprising a sequence that is selected from the group consisting of: SEQ ID Nos. 50-98. In some embodiments, said third domain comprises a complementarity determining region (CDR2) comprising a sequence that is selected from the group consisting of: SEQ ID Nos. 99-147. In some embodiments, said third domain comprises a complementarity determining region (CDR3) comprising a sequence that is selected from the group consisting of: SEQ ID Nos. 148-196. In some embodiments, said third domain comprises the following formula:

$$f1\text{-}r1\text{-}f2\text{-}r2\text{-}f3\text{-}r3\text{-}f4$$

wherein, r1 is identical to or comprises one or more amino acid residue substitutions relative to a sequence selected from the group consisting of SEQ ID Nos. 50-98; r2 is identical to or comprises one or more amino acid residue substitutions relative to a sequence selected from the group consisting of SEQ ID Nos. 99-147; and r3 is identical to or comprises one or more amino acid residue substitutions relative to a sequence selected from the group consisting of SEQ ID Nos. 148-196; and wherein f1, f2, f3 and f4 are framework residues. In some embodiments, said third domain comprises a sequence that is at least about 75% identical to a sequence selected from the group consisting of SEQ ID Nos. 1-49. In some embodiments, said third domain comprises a sequence selected from the group consisting of SEQ ID Nos. 1-49. In some embodiments, said third-domain is the VHH domain, and wherein the VHH domain comprises the humanized sequence. In some embodiments, said linkers L1 and L2 are each independently selected from (GS)n (SEQ ID NO: 197), (GGS)n (SEQ ID NO: 198), (GGGS)n (SEQ ID NO: 199), (GGSG)n (SEQ ID NO: 200), (GGSGG)n (SEQ ID NO: 201), (GGGGS)n (SEQ ID NO: 202), (GGGGG)n, or (GGG)n, wherein n is 1, 2, 3, 4, 5, 6, 7, 8, 9, or 10. In some embodiments, said linkers L1 and L2 are each independently (GGGGSGGGGSGGGGS) (SEQ ID No. 314), (GGGGSGGGGSGGGGSGGGGS) (SEQ ID No. 315), or (GGGGSGGGS) (SEQ ID No. 246). In some embodiments, said domains are linked in the order H2N-(A)-(B)—(C)—COOH or H2N—(C)—(B)-(A)-COOH, H$_2$N-(A)-L1-(B)-L2-(C)—COOH, H$_2$N—(C)-L1-(B)-L2-(A)-COOH In some embodiments, said trispecific protein is less than about 80 kDa. In some embodiments, said trispecific protein is about 50 to about 75 kDa. In some embodiments, said trispecific protein is less than about 60 kDa. In some embodiments, said trispecific protein has an elimination half-time of at least about 50 hours. In some embodiments, said trispecific protein has an elimination half-time of at least about 100 hours. In some embodiments, said trispecific protein has increased tissue penetration as compared to an IgG to the same EGFR. In some embodiments, said second domain (B) binds a bulk serum protein. In some embodiments, said second domain (B) comprises a single domain antibody, a VHH domain, a scFv, a VH domain, a VL domain, a Fab, a Fab', a non-Ig domain, a ligand, a knottin, or a small molecule entity that specifically binds to the bulk serum protein. In some embodiments, said second domain (B) comprises the single domain antibody that specifically binds to the bulk serum protein. In some embodiments, said bulk serum protein comprises albumin, transferrin, IgG1, IgG2, IgG4, IgG3, IgA monomer, Factor XIII, Fibrinogen, IgE, pentameric IgM, or Igκ free light chain. In some embodiments, said bulk serum protein comprises the albumin. In some embodiments, said second domain (B) comprises a sequence that is at least about 75% identical to a sequence selected from the group consisting of SEQ ID Nos. 205-214. In some embodiments, said second domain (B) comprises a sequence that is at least about 75% identical to SEQ ID No. 210. In some embodiments, said first domain (A) comprises a single domain antibody, a VHH domain, a scFv, a VH domain, a VL domain, a Fab, a Fab', a non-Ig domain, a ligand, a knottin, or a small molecule entity that specifically binds to CD3. In some embodiments, said first domain (A) comprises a sequence that is at least about 75% identical to a sequence selected from the group consisting of SEQ ID Nos. 229-245. In some embodiments, said first domain (A) comprises a sequence that is at least 75% identical to SEQ ID No. 229.

One embodiment provides an EGFR binding protein comprising the following formula:

$$f1\text{-}r1\text{-}f2\text{-}r2\text{-}f3\text{-}r3\text{-}f4$$

wherein, r1 is a complementarity determining region 1 (CDR1) and is identical to or comprises one or more amino acid residue substitutions relative to a sequence selected from the group consisting of SEQ ID Nos. 50-98; r2 is a CDR2 and is identical to or comprises one or more amino acid residue substitutions relative to a sequence selected from the group consisting of SEQ ID Nos. 99-147; and r3 is a CDR3 and identical to or comprises one or more amino acid residue substitutions relative to a sequence selected from the group consisting of SEQ ID Nos. 148-196; and wherein f1, f2, f3 and f4 are framework residues. In some embodiments, the EGFR binding protein comprises a sequence that is at least about 75% identical to a sequence selected from the group consisting of SEQ ID Nos. 1-49.

One embodiment provides a pharmaceutical composition comprising (i) the EGFR binding trispecific protein according to any one of the preceding embodiments and (ii) a pharmaceutically acceptable carrier. One embodiment provides a process for the production of an EGFR binding trispecific protein according to any one of the preceding embodiments, said process comprising culturing a host transformed or transfected with a vector comprising a nucleic acid sequence encoding an EGFR binding trispecific protein according to any one of the preceding embodiments under conditions allowing the expression of the EGFR binding trispecific protein and recovering and purifying the produced protein from the culture. One embodiment provides a process for the production of an EGFR binding protein according to this disclosure, said process comprising culturing a host transformed or transfected with a vector comprising a nucleic acid sequence encoding an EGFR binding protein according to this disclosure under conditions allowing the expression of the EGFR binding protein and recovering and purifying the produced protein from the culture.

One embodiment provides a method for the treatment or amelioration of a proliferative disease, or a tumorous disease, comprising administration of an EGFR binding trispecific protein, an EGFR binding protein, or a pharmaceutical composition according to any one of the preceding embodiments, to a subject in need thereof. In some embodiments, said subject is human. In some embodiments, said method further comprises administration of an agent in combination with an EGFR binding trispecific protein, an EGFR binding protein, or a pharmaceutical composition according to any one of the preceding embodiments. In some embodiments are provided a method wherein the EGFR binding protein or the EGFR binding trispecific protein selectively binds to tumor cells expressing EGFR. In some embodiments are provided a method wherein said EGFR binding trispecific protein mediates T cell killing of tumor cells expressing EGFR. In some embodiments are provided a method wherein said tumorous disease comprises a solid tumor disease. In some embodiments are provided a method wherein the solid tumor disease comprises lung cancer, gastric cancer, ovarian cancer, or triple negative breast cancer. In some embodiments are provided a method wherein the solid tumor disease is metastatic.

One embodiment provides a method for the treatment or amelioration of a proliferative disease, or a tumorous disease, comprising administration of an EGFR binding trispecific protein comprising an EGFR binding domain comprising a sequence selected from the group consisting of SEQ ID Nos. 1-49. In some embodiments, the EGFR binding protein or the EGFR binding trispecific protein selectively binds to tumor cells expressing EGFR. In some embodiments, said EGFR binding trispecific protein directs T cell killing of tumor cells expressing EGFR. In some embodiments, said tumorous disease comprises a solid tumor disease. In some embodiments, said solid tumor disease comprises lung cancer, gastric cancer, ovarian cancer, or triple negative breast cancer. In some embodiments, said solid tumor disease is metastatic. In some embodiments, the method comprises administering the EGFR binding protein or the EGFR binding trispecific protein at a dose of up to 10 mg/kg. In some embodiments, the EGFR binding protein or the EGFR binding trispecific protein is administered once a week. In some embodiments, the EGFR binding protein or the EGFR binding trispecific protein is administered twice per week. In some embodiments, the EGFR binding protein or the EGFR binding trispecific protein is administered every other week. In some embodiments, the EGFR binding protein or the EGFR binding trispecific protein is administered every three weeks.

One embodiment provides an EGFR binding trispecific protein, comprising a sequence selected from the group consisting of SEQ ID Nos. 1-49. In some embodiments, said third domain comprises a CDR1 comprising a sequence as set forth in any one of SEQ ID Nos. 50-98. In some embodiments, said third domain comprises a CDR2 comprising a sequence as set forth in any one of SEQ ID Nos. 99-147. In some embodiments, said third domain comprises a CDR3 comprising a sequence as set forth in any one of SEQ ID Nos. 148-196.

One embodiment provides an EGFR binding trispecific protein comprising a sequence selected from a group consisting of SEQ ID Nos. 319-367.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
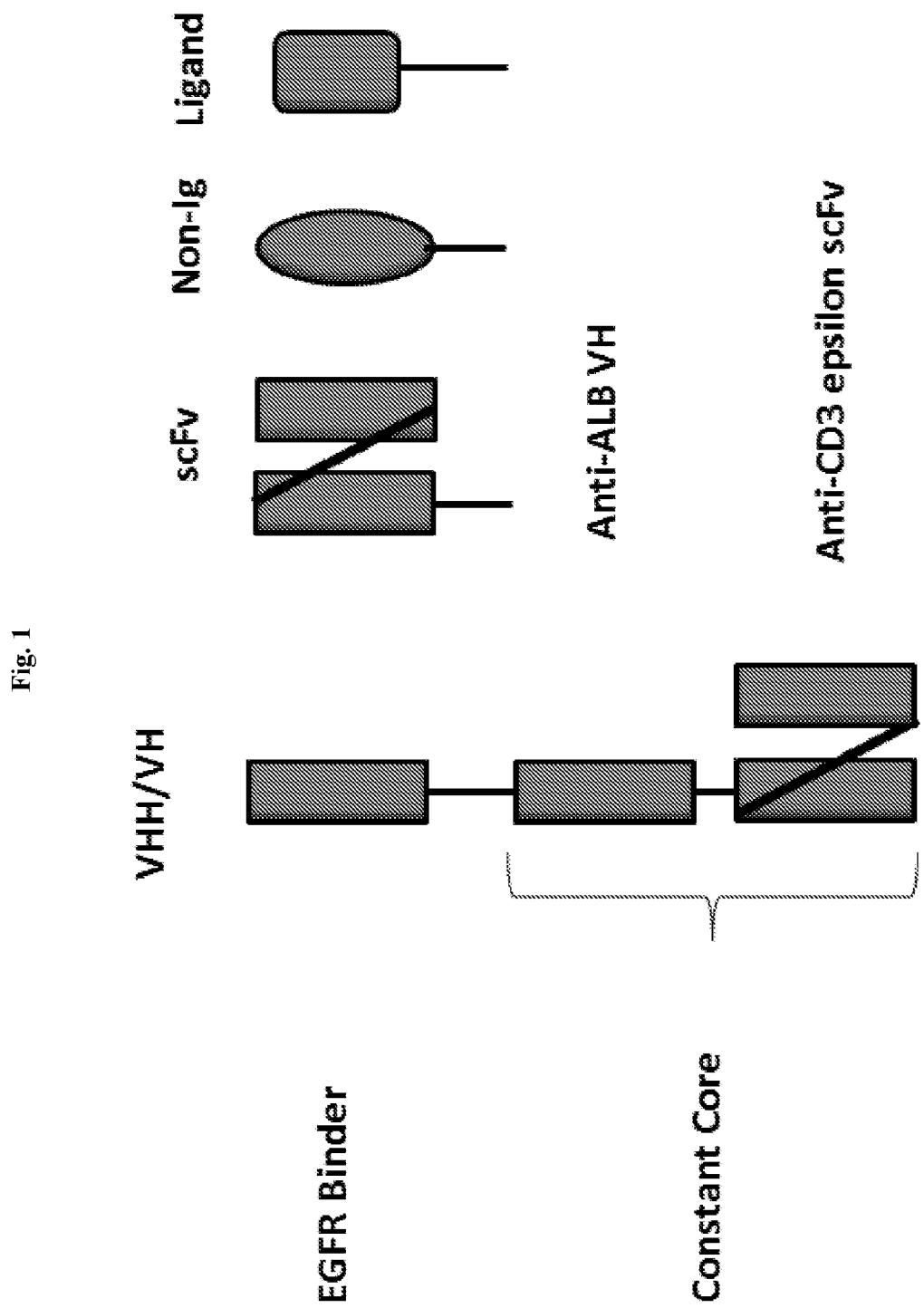
FIG. 1 illustrates the various domains of an exemplary EGFR targeting trispecific protein of this disclosure.
Figure 2:
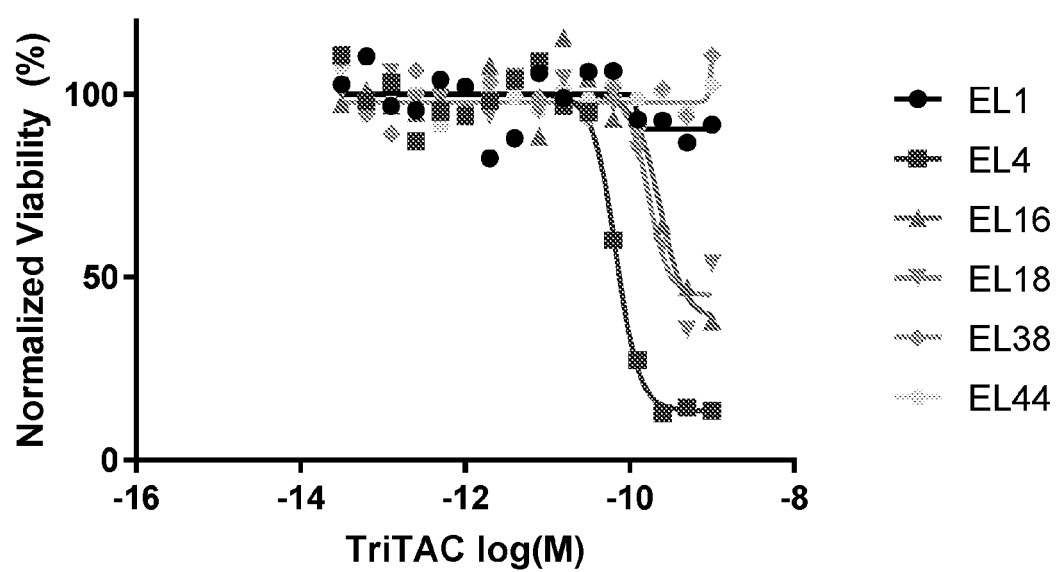
FIG. 2 illustrates results of a T cell dependent cellular cytotoxicity (TDCC) assay on HCT116 cells, using exemplary EGFR targeting trispecific proteins containing EGFR binding domains of this disclosure, EL1, EL4, EL16, EL18, EL38, and EL44.
Figure 3:
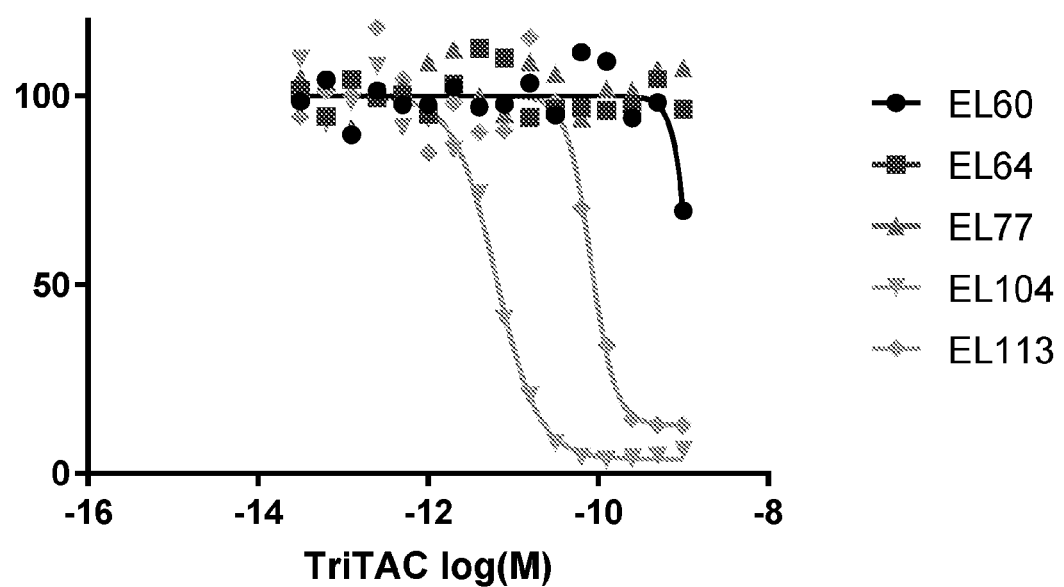
FIG. 3 illustrates results of a TDCC assay on HCT116 cells, using exemplary EGFR targeting trispecific proteins containing exemplary EGFR binding domains of this disclosure EL60, EL64, EL77, EL104, and EL 113.
Figure 4:
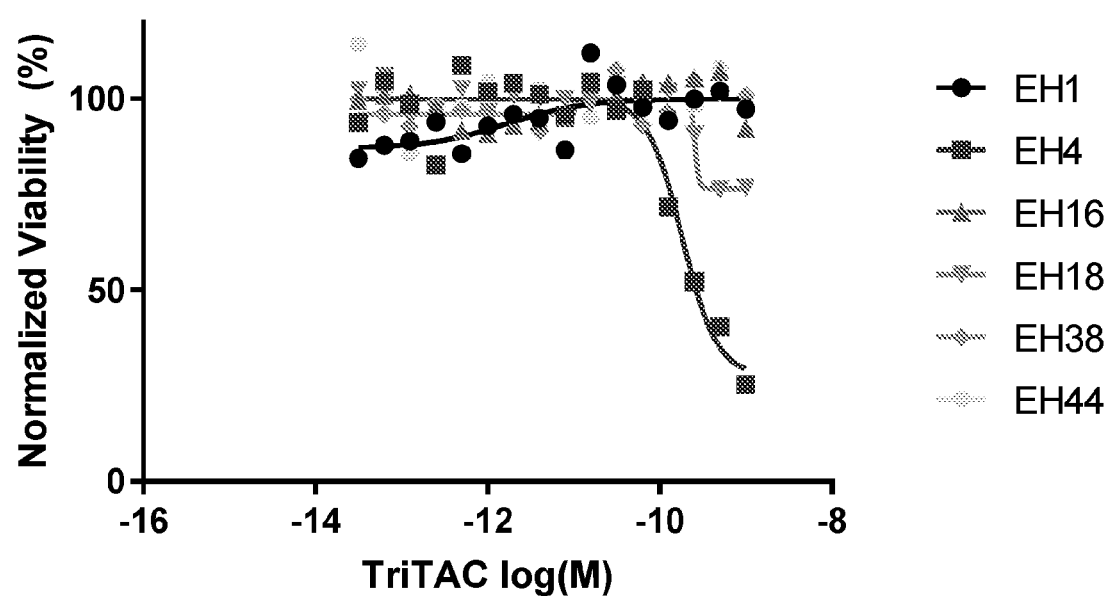
FIG. 4 illustrates results of a TDCC assay on HCT116 cells, using exemplary EGFR targeting trispecific proteins containing exemplary humanized EGFR binding domains of this disclosure EH1, EH4, EH16, EH18, EH38, and EH44.
Figure 5:
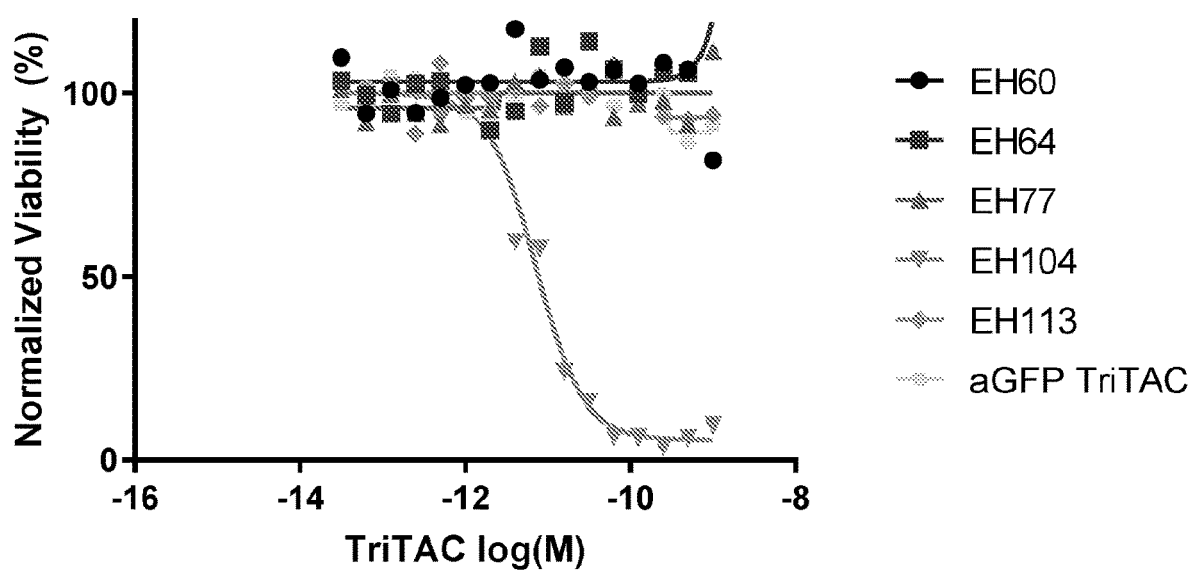
FIG. 5 illustrates results of a TDCC assay on HCT116 cells, using exemplary EGFR targeting trispecific proteins containing exemplary humanized EGFR binding domains of this disclosure EH60, EH64, EH77, EH104, EH113, and a control trispecific protein aGFP TriTAC™.

Described herein are trispecific proteins that target EGFR, pharmaceutical compositions thereof, as well as nucleic acids, recombinant expression vectors and host cells for making such proteins thereof. Also provided are methods of using the disclosed EGFR targeting trispecific proteins in the prevention, and/or treatment of diseases, conditions and disorders. The EGFR targeting trispecific proteins are capable of specifically binding to EGFR as well as CD3 and have a half-life extension domain, such as a domain binding to human albumin (ALB). FIG. 1 depicts one non-limiting example of a trispecific EGFR-binding protein.

Certain Definitions

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the given value. Where particular values are described in the application and claims, unless otherwise stated the term "about" should be assumed to mean an acceptable error range for the particular value.

The terms "individual," "patient," or "subject" are used interchangeably. None of the terms require or are limited to situation characterized by the supervision (e.g. constant or intermittent) of a health care worker (e.g. a doctor, a registered nurse, a nurse practitioner, a physician's assistant, an orderly, or a hospice worker).

An "antibody" typically refers to a Y-shaped tetrameric protein comprising two heavy (H) and two light (L) polypeptide chains held together by covalent disulfide bonds and non-covalent interactions. Human light chains comprise a variable domain (VL) and a constant domain (CL) wherein the constant domain may be readily classified as kappa or lambda based on amino acid sequence and gene loci. Each heavy chain comprises one variable domain (VH) and a constant region, which in the case of IgG, IgA, and IgD, comprises three domains termed CH1, CH2, and CH3 (IgM and IgE have a fourth domain, CH4). In IgG, IgA, and IgD classes the CH1 and CH2 domains are separated by a flexible hinge region, which is a proline and cysteine rich segment of variable length (generally from about 10 to about 60 amino acids in IgG). The variable domains in both the light and heavy chains are joined to the constant domains by a "J" region of about 12 or more amino acids and the heavy chain also has a "D" region of about 10 additional amino acids. Each class of antibody further comprises inter-chain and intra-chain disulfide bonds formed by paired cysteine residues. There are two types of native disulfide bridges or bonds in immunoglobulin molecules: interchain and intra-chain disulfide bonds. The location and number of interchain disulfide bonds vary according to the immunoglobulin class and species. Interchain disulfide bonds are located on the surface of the immunoglobulin, are accessible to solvent and are usually relatively easily reduced. In the human IgG1 isotype there are four interchain disulfide bonds, one from each heavy chain to the light chain and two between the heavy chains. The interchain disulfide bonds are not required for chain association. As is well known the cysteine rich IgG1 hinge region of the heavy chain has generally been held to consist of three parts: an upper hinge, a core hinge, and a lower hinge. Those skilled in the art will appreciate that that the IgG1 hinge region contain the cysteines in the heavy chain that comprise the interchain disulfide bonds (two heavy/heavy, two heavy/light), which provide structural flexibility that facilitates Fab movements. The interchain disulfide bond between the light and heavy chain of IgG1 are formed between C214 of the kappa or lambda light chain and C220 in the upper hinge region of the heavy chain. The interchain disulfide bonds between the heavy chains are at positions C226 and C229 (all numbered per the EU index according to Kabat, et al., infra.)

As used herein the term "antibody" includes polyclonal antibodies, multiclonal antibodies, monoclonal antibodies, chimeric antibodies, humanized and primatized antibodies, CDR grafted antibodies, human antibodies, recombinantly produced antibodies, intrabodies, multi specific antibodies, bispecific antibodies, monovalent antibodies, multivalent antibodies, anti-idiotypic antibodies, synthetic antibodies, including muteins and variants thereof, immunospecific antibody fragments such as Fd, Fab, F(ab')2, F(ab') fragments, single-chain fragments (e.g., ScFv and ScFvFc), disulfide-linked Fvs (sdFv), a Fd fragment consisting of the VH and CH1 domains, linear antibodies, single domain antibodies such as sdAb (VH, VL, or VHH domains); and derivatives thereof including Fc fusions and other modifications, and any other immunoreactive molecule so long as it comprises a domain having a binding site for preferential association or binding with a EGFR protein. Moreover, unless dictated otherwise by contextual constraints the term further comprises all classes of antibodies (i.e. IgA, IgD, IgE, IgG, and IgM) and all subclasses (i.e., IgG1, IgG2, IgG3, IgG4, IgA1, and IgA2). Heavy-chain constant domains that correspond to the different classes of antibodies are typically denoted by the corresponding lower case Greek letter alpha, delta, epsilon, gamma, and mu, respectively. Light chains of the antibodies from any vertebrate species can be assigned to one of two clearly distinct types, called kappa (kappa) and lambda (lambda), based on the amino acid sequences of their constant domains.

In some embodiments, the EGFR binding domain of the EGFR targeting trispecific proteins of this disclosure comprise a heavy chain only antibody, such as a VH or a VHH domain. In some embodiments, the EGFR binding domain of the EGFR targeting trispecific proteins of this disclosure comprise a heavy chain only single domain antibody. In some cases, the EGFR binding proteins comprise a heavy chain only antibody that is an engineered human VH domain. In some examples, the engineered human VH domain is produced by panning of phage display libraries. In some embodiments, the EGFR binding domain of the EGFR targeting trispecific proteins of this disclosure comprise a VHH. The term "VHH," as used herein, refers to single chain antibody binding domain devoid of light chain. In some cases, a VHH is derived from an antibody of the type that can be found in Camelidae or cartilaginous fish which are naturally devoid of light chains or to a synthetic and non-immunized VHH which can be constructed accordingly. Each heavy chain comprises a variable region encoded by V-, D- and J exons. A VHH, in some cases, is a natural VHH, such as a Camelid-derived VHH, or a recombinant protein comprising a heavy chain variable domain. In some embodiments, the VHH is derived from a species selected from the group consisting of camels, llamas, vicugnas, guanacos, and cartilaginous fish (such as, but not limited to, sharks). In another embodiment, the VHH is derived from an alpaca (such as, but not limited to, a Huacaya Alpaca or a Suri alpaca).

As used herein, "Variable region" or "variable domain" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain (VL) and the heavy-chain (VH) variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity. ScFv fragments (for single chain fragment variable), which in some cases are obtained by genetic engineering, associates in a single polypeptide chain, the VH and the VL region of an antibody, separated by a peptide linker.

In some embodiments of this disclosure, the EGFR binding domain, such as the EGFR binding domain of the EGFR targeting trispecific proteins comprise a single domain antibody, such as heavy chain only antibodies, such as VH or VHH domains, that comprise three CDRs. Such heavy chain only antibodies, in some embodiments, bind EGFR as a monomer with no dependency on dimerisation with a VL (light chain variable) region for optimal binding affinity. In some embodiments of this disclosure, the CD3 binding domain of the EGFR targeting trispecific proteins comprises an scFv. In some embodiments of this disclosure, the albumin binding domain of the EGFR targeting trispecific proteins comprise a heavy chain only antibody, such as a single domain antibody comprising a VH domain or a VHH domain, that comprises three CDRs.

The assignment of amino acids to each domain, framework region and CDR is, in some embodiments, in accordance with one of the numbering schemes provided by Kabat et al. (1991) Sequences of Proteins of Immunological Interest (5th Ed.), US Dept. of Health and Human Services, PHS, NIH, NIH Publication no. 91-3242; Chothia et al., 1987, PMID: 3681981; Chothia et al., 1989, PMID: 2687698; MacCallum et al., 1996, PMID: 8876650; or Dubel, Ed. (2007) Handbook of Therapeutic Antibodies, 3rd Ed., Wily-VCH Verlag GmbH and Co or AbM (Oxford Molecular/MSI Pharmacopia) unless otherwise noted. It is not intended that CDRs of the present disclosure necessarily correspond to the Kabat numbering convention.

"Variable domain residue numbering as in Kabat" or "amino acid position numbering as in Kabat," and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g., residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence.

The term "Framework" or "FR" residues (or regions) refer to variable domain residues other than the CDR or hypervariable region residues as herein defined. A "human consensus framework" is a framework which represents the most commonly occurring amino acid residue in a selection of human immunoglobulin VL or VH framework sequences.

The term "epitope," as used herein, refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

As used herein, the term "Percent (%) amino acid sequence identity" with respect to a sequence is defined as the percentage of amino acid residues in a candidate sequence that are identical with the amino acid residues in the specific sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer softwares such as EMBOSS MATCHER, EMBOSS WATER, EMBOSS STRETCHER, EMBOSS NEEDLE, EMBOSS LALIGN, BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

As used herein, "elimination half-time" is used in its ordinary sense, as is described in Goodman and Gillman's The Pharmaceutical Basis of Therapeutics 21-25 (Alfred Goodman Gilman, Louis S. Goodman, and Alfred Gilman, eds., 6th ed. 1980). Briefly, the term is meant to encompass a quantitative measure of the time course of drug elimination. The elimination of most drugs is exponential (i.e., follows first-order kinetics), since drug concentrations usually do not approach those required for saturation of the elimination process. The rate of an exponential process may be expressed by its rate constant, k, which expresses the fractional change per unit of time, or by its half-time, t½ the time required for 50% completion of the process. The units of these two constants are time−1 and time, respectively. A first-order rate constant and the half-time of the reaction are simply related (k×t½=0.693) and may be interchanged accordingly. Since first-order elimination kinetics dictates that a constant fraction of drug is lost per unit time, a plot of the log of drug concentration versus time is linear at all times following the initial distribution phase (i.e. after drug absorption and distribution are complete). The half-time for drug elimination can be accurately determined from such a graph.

As used herein, the term "binding affinity" refers to the affinity of the proteins described in the disclosure to their binding targets, and is expressed numerically using "Kd" values. If two or more proteins are indicated to have comparable binding affinities towards their binding targets, then the Kd values for binding of the respective proteins towards their binding targets, are within ±2-fold of each other. If two or more proteins are indicated to have comparable binding affinities towards single binding target, then the Kd values for binding of the respective proteins towards said single binding target, are within ±2-fold of each other. If a protein is indicated to bind two or more targets with comparable binding affinities, then the Kd values for binding of said protein to the two or more targets are within ±2-fold of each other. In general, a higher Kd value corresponds to a weaker binding. In some embodiments, the "Kd" is measured by a radiolabeled antigen binding assay (RIA) or surface plasmon resonance assays using a BIAcore™-2000 or a BIAcore™-3000 (BIAcore, Inc., Piscataway, N.J.). In certain embodiments, an "on-rate" or "rate of association" or "association rate" or "kon" and an "off-rate" or "rate of dissociation" or "dissociation rate" or "koff" are also determined with the surface plasmon resonance technique using a BIAcore™-2000 or a BIAcore™-3000 (BIAcore, Inc., Piscataway, N.J.). In additional embodiments, the "Kd", "kon", and "koff" are measured using the OCTET® Systems (Pall Life Sciences). In an exemplary method for measuring binding affinity using the OCTET® Systems, the ligand, e.g., biotinylated human, mouse or cynomolgus EGFR, is immobilized on the OCTET® streptavidin capillary sensor tip surface which streptavidin tips are then activated according to manufacturer's instructions using about 20-50 μg/ml human, mouse or cynomolgus EGFR protein. A solution of PBS/Casein is also introduced as a blocking agent. For association kinetic measurements, EGFR binding protein variants are introduced at a concentration ranging from about 10 ng/mL to about 100 μg/mL, about 50 ng/mL to about 5 μg/mL, or about 2 ng/mL to about 20 μg/mL. In some embodiments, the EGFR binding single domain proteins are used at a concentration ranging from about 2 ng/mL to about 20 μg/mL. Complete dissociation is observed in case of the negative control, assay buffer without the binding proteins. The kinetic parameters of the binding reactions are then determined using an appropriate tool, e.g., ForteBio software.

As used herein, in some embodiments, "treatment" or "treating" or "treated" refers to therapeutic treatment wherein the object is to slow (lessen) an undesired physiological condition, disorder or disease, or to obtain beneficial or desired clinical results. For the purposes described herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. In other embodiments, "treatment" or "treating" or "treated" refers to prophylactic measures, wherein the object is to delay onset of or reduce severity of an undesired physiological condition, disorder or disease, such as, for example is a person who is predisposed to a disease (e.g., an individual who carries a genetic marker for a disease such as breast cancer).

One embodiment provides an EGFR binding protein (also referred to herein as an EGFR binding domain, such as the EGFR binding domain of an EGFR trispecific antibody of this disclosure) that comprises a single domain antibody, comprising a CDR1 sequence comprising a sequence selected from the group consisting of SEQ ID Nos. 50-98, a CDR2 sequence comprising a sequence selected from the group consisting of SEQ ID Nos. 99-147, and a CDR3 sequence comprising a sequence selected from the group consisting of SEQ ID Nos. 148-196. It is contemplated that in some embodiments the EGFR binding protein of this disclosure is fairly small and no more than 25 kD, no more than 20 kDa, no more than 15 kDa, or no more than 10 kDa in some embodiments. In certain instances, the EGFR binding is 5 kDa or less if it is a peptide or a small molecule entity.

In some embodiments are provided EGFR targeting trispecific proteins (also referred to herein as EGFR targeting trispecific proteins, EGFR trispecific proteins, or EGFR TriTAC™), wherein the EGFR targeting trispecific proteins comprise a domain (A) which specifically binds to CD3, a domain (B) which specifically binds to a bulk serum protein, such as human serum albumin protein (ALB or HSA), and a domain (C) which specifically binds to EGFR (such as an EGFR binding single domain antibody as described herein). The three domains in EGFR targeting trispecific proteins are arranged in any order. Thus, it is contemplated that the domain order of the EGFR targeting trispecific proteins are:

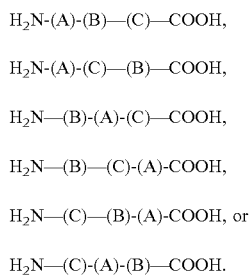

In some embodiments, the EGFR targeting trispecific proteins have a domain order of H₂N-(A)-(B)—(C)—COOH. In some embodiments, the EGFR targeting trispecific proteins have a domain order of H₂N-(A)-(C)—(B)—COOH. In some embodiments, the EGFR targeting trispecific proteins have a domain order of H₂N—(B)-(A)-(C)—COOH. In some embodiments, the EGFR targeting trispecific proteins have a domain order of H₂N—(B)—(C)-(A)-COOH. In some embodiments, the EGFR targeting trispecific proteins have a domain order of H₂N—(C)—(B)-(A)-COOH. In some embodiments, the EGFR targeting trispecific proteins have a domain order of H₂N—(C)-(A)-(B)—COOH.

In some embodiments, the EGFR targeting trispecific proteins have the HSA binding domain as the middle domain, such that the domain order is H₂N-(A)-(B)—(C)—COOH or H₂N—(C)—(B)-(A)-COOH. It is contemplated that in such embodiments where the bulk serum protein binding domain as the middle domain, the CD3 and EGFR binding domains are afforded additional flexibility to bind to their respective targets.

In some embodiments, the EGFR targeting trispecific proteins described herein comprise an EGFR binding domain, such as a polypeptide comprising a sequence selected from SEQ ID Nos. 1-49 and subsequences thereof. In some embodiments, the trispecific antigen binding protein comprises an EGFR binding domain, a polypeptide comprising a sequence that has at least 70%-95% or more homology to a sequence selected from SEQ ID Nos. 1-49. In some embodiments, the trispecific antigen binding protein comprises an EGFR binding domain, such as a polypeptide comprising a sequence that has at least 70%, 75%, 80%, 85%, 86%, 87%, 88%, 89%, 90%, 91%, 92%, 93%, 94%, 95%, or more homology to a sequence selected from SEQ ID Nos. 1-49.

In some embodiments, the EGFR targeting trispecific proteins described herein comprise an EGFR binding domain, such as a polypeptide comprising a sequence selected from SEQ ID Nos. 1-49 and subsequences thereof. In some embodiments, the trispecific antigen binding protein comprises an EGFR binding domain, a polypeptide comprising a sequence that has at least 70%-95% or more identity to a sequence selected from SEQ ID Nos. 1-49. In some embodiments, the trispecific antigen binding protein comprises an EGFR binding domain, such as a polypeptide comprising a sequence that has at least 70%, 75%, 80%, 85%, 86%, 87%, 88%, 89%, 90%, 91%, 92%, 93%, 94%, 95%, or more identity to a sequence selected from SEQ ID Nos. 1-49.

The EGFR targeting trispecific proteins described herein are designed to allow specific targeting of cells expressing EGFR by recruiting cytotoxic T cells. This improves efficacy compared to ADCC (antibody dependent cell-mediated cytotoxicity), which is using full length antibodies directed to a sole antigen and is not capable of directly recruiting cytotoxic T cells. In contrast, by engaging CD3 molecules expressed specifically on these cells, the EGFR targeting trispecific proteins can crosslink cytotoxic T cells with cells expressing EGFR in a highly specific fashion, thereby directing the cytotoxic potential of the T cell towards the target cell. The EGFR targeting trispecific proteins described herein engage cytotoxic T cells via binding to the surface-expressed CD3 proteins, which form part of the T-cell receptor (TCR). Simultaneous binding of several EGFR trispecific antigen-binding protein to CD3 and to EGFR expressed on the surface of particular cells causes T cell activation and mediates the subsequent lysis of the particular EGFR expressing cell. Thus, EGFR targeting trispecific proteins, in some embodiments, display strong, specific and efficient target cell killing. In some embodiments, the EGFR targeting trispecific proteins described herein stimulate target cell killing by cytotoxic T cells to eliminate pathogenic cells (e.g., tumor cells expressing EGFR). In some of such embodiments, cells are eliminated selectively, thereby reducing the potential for toxic side effects.

The EGFR targeting trispecific proteins described herein confer further therapeutic advantages over traditional monoclonal antibodies and other smaller bispecific molecules. Generally, the effectiveness of recombinant protein pharmaceuticals depends heavily on the intrinsic pharmacokinetics of the protein itself. One such benefit here is that the EGFR targeting trispecific proteins described herein have extended pharmacokinetic elimination half-time due to having a half-life extension domain such as a domain specific to HSA. In this respect, the EGFR targeting trispecific proteins described herein have an extended serum elimination half-time of about two, three, about five, about seven, about 10, about 12, or about 14 days in some embodiments. This contrasts to other binding proteins such as BiTE or DART molecules which have relatively much shorter elimination half-times. For example, the BiTE CD19×CD3 bispecific scFv-scFv fusion molecule requires continuous intravenous infusion (i.v.) drug delivery due to its short elimination half-time. The longer intrinsic half-times of the EGFR targeting trispecific proteins solve this issue thereby allowing for increased therapeutic potential such as low-dose pharmaceutical formulations, decreased periodic administration and/or novel pharmaceutical compositions.

The EGFR targeting trispecific proteins described herein also have an optimal size for enhanced tissue penetration and tissue distribution. Larger sizes limit or prevent penetration or distribution of the protein in the target tissues. The EGFR targeting trispecific proteins described herein avoid this by having a small size that allows enhanced tissue penetration and distribution. Accordingly, the EGFR targeting trispecific proteins described herein, in some embodiments have a size of about 50 kD to about 80 kD, about 50 kD to about 75 kD, about 50 kD to about 70 kD, or about 50 kD to about 65 kD. Thus, the size of the EGFR targeting trispecific proteins is advantageous over IgG antibodies which are about 150 kD and the BiTE and DART diabody molecules which are about 55 kD but are not half-life extended and therefore cleared quickly through the kidney.

In further embodiments, the EGFR targeting trispecific proteins described herein have an optimal size for enhanced tissue penetration and distribution. In these embodiments, the EGFR targeting trispecific proteins are constructed to be as small as possible, while retaining specificity toward its targets. Accordingly, in these embodiments, the EGFR targeting trispecific proteins described herein have a size of about 20 kD to about 40 kD or about 25 kD to about 35 kD to about 40 kD, to about 45 kD, to about 50 kD, to about 55 kD, to about 60 kD, to about 65 kD. In some embodiments, the EGFR targeting trispecific proteins described herein have a size of about 50 kD, 49, kD, 48 kD, 47 kD, 46 kD, 45 kD, 44 kD, 43 kD, 42 kD, 41 kD, 40 kD, about 39 kD, about 38 kD, about 37 kD, about 36 kD, about 35 kD, about 34 kD, about 33 kD, about 32 kD, about 31 kD, about 30 kD, about 29 kD, about 28 kD, about 27 kD, about 26 kD, about 25 kD, about 24 kD, about 23 kD, about 22 kD, about 21 kD, or about 20 kD. An exemplary approach to the small size is through the use of single domain antibody (sdAb) fragments for each of the domains. For example, a particular EGFR trispecific antigen-binding protein has an anti-CD3 sdAb, anti-ALB sdAb and an sdAb for EGFR. This reduces the size of the exemplary EGFR trispecific antigen-binding protein to under 60 kD. Thus in some embodiments, the domains of the EGFR targeting trispecific proteins are all single domain antibody (sdAb) fragments.

In other embodiments, the EGFR targeting trispecific proteins described herein comprise small molecule entity (SME) binders for ALB and/or the EGFR. SME binders are small molecules averaging about 500 to 2000 Da in size and are attached to the EGFR targeting trispecific proteins by known methods, such as sortase ligation or conjugation. In these instances, one of the domains of EGFR trispecific antigen-binding protein is a sortase recognition sequence, e.g., LPETG (SEQ ID No. 313). To attach an SME binder to EGFR trispecific antigen-binding protein with a sortase recognition sequence, the protein is incubated with a sortase and a SME binder whereby the sortase attaches the SME binder to the recognition sequence. Known SME binders include, but are not limited to quinazolines (e.g., gefitinib, erlotinib). EGFR. In yet other embodiments, the domain which binds to EGFR of EGFR targeting trispecific proteins described herein comprise a knottin peptide for binding EGFR. Knottins are disulfide-stabilized peptides with a cysteine knot scaffold and have average sizes about 3.5 kD. Knottins have been contemplated for binding to certain tumor molecules such as EGFR. In further embodiments, domain which binds to EGFR of EGFR targeting trispecific proteins described herein comprise a natural EGFR ligand.

Another feature of the EGFR targeting trispecific proteins described herein is that they are of a single-polypeptide design with flexible linkage of their domains. This allows for facile production and manufacturing of the EGFR targeting trispecific proteins as they can be encoded by single cDNA molecule to be easily incorporated into a vector. Further, because the EGFR targeting trispecific proteins described herein are a monomeric single polypeptide chain, there are no chain pairing issues or a requirement for dimerization. It is contemplated that the EGFR targeting trispecific proteins described herein have a reduced tendency to aggregate unlike other reported molecules such as bispecific proteins with Fc-gamma immunoglobulin domains.

In the EGFR targeting trispecific proteins described herein, the domains are linked by internal linkers L1 and L2, where L1 links the first and second domain of the EGFR targeting trispecific proteins and L2 links the second and third domains of the EGFR targeting trispecific proteins. Linkers L1 and L2 have an optimized length and/or amino acid composition. In some embodiments, linkers L1 and L2 are the same length and amino acid composition. In other embodiments, L1 and L2 are different. In certain embodiments, internal linkers L1 and/or L2 are "short," i.e., consist of 0, 1, 2, 3, 4, 5, 6, 7, 8, 9, 10, 11 or 12 amino acid residues. Thus, in certain instances, the internal linkers consist of about 12 or less amino acid residues. In the case of 0 amino acid residues, the internal linker is a peptide bond. In certain embodiments, internal linkers L1 and/or L2 are "long," i.e., consist of 15, 20 or 25 amino acid residues. In some embodiments, these internal linkers consist of about 3 to about 15, for example 8, 9 or 10 contiguous amino acid residues. Regarding the amino acid composition of the internal linkers L1 and L2, peptides are selected with properties that confer flexibility to the EGFR targeting trispecific proteins, do not interfere with the binding domains as well as resist cleavage from proteases. For example, glycine and serine residues generally provide protease resistance. Examples of internal linkers suitable for linking the domains in the EGFR targeting trispecific proteins include but are not limited to but are not limited to $(GS)_n$ (SEQ ID No. 197), $(GGS)_n$ (SEQ ID No. 198), $(GGGS)_n$ (SEQ ID No. 199), $(GGSG)_n$ (SEQ ID No. 200), (GGSGG), (SEQ ID No. 201), $(GGGGS)_n$ (SEQ ID No. 202), $(GGGGG)_n$ (SEQ ID No. 203), or $(GGG)_n$ (SEQ ID No. 204), wherein n is 1, 2, 3, 4, 5, 6, 7, 8, 9, or 10. In one embodiment, the internal linkers L1 and/or L2 independently are (GGGGSGGGGSGGGGS) (SEQ ID No. 314), (GGGGSGGGGSGGGGSGGGGS) (SEQ ID No. 315), or (GGGGSGGGS) (SEQ ID No. 246).

CD3 Binding Domain

The specificity of the response of T cells is mediated by the recognition of antigen (displayed in context of a major histocompatibility complex, MHC) by the TCR. As part of the TCR, CD3 is a protein complex that includes a CD3γ (gamma) chain, a CD3δ (delta) chain, and two CD3ε (epsilon) chains which are present on the cell surface. CD3 associates with the α (alpha) and β (beta) chains of the TCR as well as CD3 ζ (zeta) altogether to comprise the complete TCR. Clustering of CD3 on T cells, such as by immobilized anti-CD3 antibodies leads to T cell activation similar to the engagement of the T cell receptor but independent of its clone-typical specificity.

In one aspect, the EGFR targeting trispecific proteins described herein comprise a domain which specifically binds to CD3. In one aspect, the EGFR targeting trispecific proteins described herein comprise a domain which specifically binds to human CD3. In some embodiments, the EGFR targeting trispecific proteins described herein comprise a domain which specifically binds to CD3γ. In some embodiments, the EGFR targeting trispecific proteins described herein comprise a domain which specifically binds to CD3δ. In some embodiments, the EGFR targeting trispecific proteins described herein comprise a domain which specifically binds to CD3ε.

In further embodiments, the EGFR targeting trispecific proteins described herein comprise a domain which specifically binds to the TCR. In certain instances, the EGFR targeting trispecific proteins described herein comprise a domain which specifically binds the α chain of the TCR. In certain instances, the EGFR targeting trispecific proteins described herein comprise a domain which specifically binds the β chain of the TCR.

In certain embodiments, the CD3 binding domain of the EGFR targeting trispecific proteins described herein exhibit not only potent CD3 binding affinities with human CD3, but show also excellent crossreactivity with the respective cynomolgus monkey CD3 proteins. In some instances, the CD3 binding domain of the EGFR targeting trispecific proteins are cross-reactive with CD3 from cynomolgus monkey. In certain instances, human:cynomolgous $K_D$ ratios for CD3 are between 5 and 0.2.

In some embodiments, the CD3 binding domain of the EGFR trispecific antigen-binding protein can be any domain that binds to CD3 including but not limited to domains from a monoclonal antibody, a polyclonal antibody, a recombinant antibody, a human antibody, a humanized antibody. In some instances, it is beneficial for the CD3 binding domain to be derived from the same species in which the EGFR trispecific antigen-binding protein will ultimately be used in. For example, for use in humans, it may be beneficial for the CD3 binding domain of the EGFR trispecific antigen-binding protein to comprise human or humanized residues from the antigen binding domain of an antibody or antibody fragment.

Thus, in one aspect, the antigen-binding domain comprises a humanized or human antibody or an antibody fragment, or a murine antibody or antibody fragment. In one embodiment, the humanized or human anti-CD3 binding domain comprises one or more (e.g., all three) light chain complementary determining region 1 (LC CDR1), light chain complementary determining region 2 (LC CDR2), and light chain complementary determining region 3 (LC CDR3) of a humanized or human anti-CD3 binding domain described herein, and/or one or more (e.g., all three) heavy chain complementary determining region 1 (HC CDR1), heavy chain complementary determining region 2 (HC CDR2), and heavy chain complementary determining region 3 (HC CDR3) of a humanized or human anti-CD3 binding domain described herein, e.g., a humanized or human anti-CD3 binding domain comprising one or more, e.g., all three, LC CDRs and one or more, e.g., all three, HC CDRs.

In some embodiments, the humanized or human anti-CD3 binding domain comprises a humanized or human light chain variable region specific to CD3 where the light chain variable region specific to CD3 comprises human or non-human light chain CDRs in a human light chain framework region. In certain instances, the light chain framework region is a λ (lamda) light chain framework. In other instances, the light chain framework region is a κ (kappa) light chain framework.

In some embodiments, the humanized or human anti-CD3 binding domain comprises a humanized or human heavy chain variable region specific to CD3 where the heavy chain variable region specific to CD3 comprises human or non-human heavy chain CDRs in a human heavy chain framework region.

In certain instances, the complementary determining regions of the heavy chain and/or the light chain are derived from known anti-CD3 antibodies, such as, for example, muromonab-CD3 (OKT3), otelixizumab (TRX4), teplizumab (MGA031), visilizumab (Nuvion), SP34, TR-66 or X35-3, VIT3, BMA030 (BW264/56), CLB-T3/3, CRIS7, YTH12.5, F111-409, CLB-T3.4.2, TR-66, WT32, SPv-T3b, 11D8, XIII-141, XIII-46, XIII-87, 12F6, T3/RW2-8C8, T3/RW2-4B6, OKT3D, M-T301, SMC2, F101.01, UCHT-1 and WT-31.

In one embodiment, the CD3 binding domain is a single chain variable fragment (scFv) comprising a light chain and a heavy chain of an amino acid sequence provided herein. As used herein, "single chain variable fragment" or "scFv" refers to an antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single polypeptide chain, and wherein the scFv retains the specificity of the intact antibody from which it is derived. In an embodiment, the CD3 binding domain comprises: a light chain variable region comprising an amino acid sequence having at least one, two or three modifications (including insertion, deletion, or substitutions) but not more than 30, 20 or 10 modifications (including insertion, deletion, or substitutions) of an amino acid sequence of a light chain variable region provided herein, or a sequence with 95-99% identity with an amino acid sequence provided herein; a heavy chain variable region comprising an amino acid sequence having at least one, two or three modifications (including insertion, deletion, or substitutions) but not more than 30, 20 or 10 modifications (including insertion, deletion, or substitutions) of an amino acid sequence of a heavy chain variable region provided herein, or a sequence with 95-99% identity to an amino acid sequence provided herein, or a combination thereof. In some examples, the CD3 binding domain comprises a sequence selected from SEQ ID Nos. 229-245, or a sequence that is at least about 60%, about 70%, about 75%, about 80%, about 85%, about 90%, about 91%, about 92%, about 93%, about 94%, about 95%, about 96%, about 97%, about 98%, about 99%, or about 100% identity to a sequence selected from SEQ ID Nos. 229-245. In some examples, the anti-CD3 binding domain comprises three heavy chain CDRs (HC CDR1, HC CDR2, and HC CDR3), and three light chain CDRs (LC CDR1, LC CDR2, and LC CDR3). The heavy chain CDR1 (HC CDR1) of the CD3 binding domain comprises a sequence selected from SEQ ID Nos. 248-259, or a sequence comprising one or more modifications or substitutions in a sequence selected from SEQ ID Nos. 248-259, or at least about 80% to about 99%. The heavy chain CDR2 (HC CDR2) of the CD3 binding domain comprises a sequence selected from SEQ ID Nos. 260-269, or a sequence comprising one or more modifications or substitutions in a sequence selected from SEQ ID Nos. 260-269. The heavy chain CDR3 (HC CDR3) of the CD3 binding domain comprises a sequence selected from SEQ ID Nos. 270-279, or a sequence comprising one or more modifications or substitutions in a sequence selected from SEQ ID Nos. 270-279. The light chain CDR1 (LC CDR1) of the CD3 binding domain comprises a sequence selected from SEQ ID Nos. 280-292, or a sequence comprising one or more modifications or substitutions in a sequence selected from SEQ ID Nos. 280-292. The light chain CDR2 (LC CDR2) of the CD3 binding domain comprises a sequence selected from SEQ ID Nos. 293-305, or a sequence comprising one or more modifications or substitutions in a sequence selected from SEQ ID Nos. 293-305. The light chain CDR3 (LC CDR3) of the CD3 binding domain comprises a sequence selected from SEQ ID Nos. 306-312, or a sequence comprising one or more modifications or substitutions in a sequence selected from SEQ ID Nos. 306-312. In one embodiment, the humanized or human CD3 binding domain is a scFv, and a light chain variable region comprising an amino acid sequence described herein, is attached to a heavy chain variable region comprising an amino acid sequence described herein, via a scFv linker. The light chain variable region and heavy chain variable region of a scFv can be in any of the following orientations: light chain variable region-scFv linker-heavy chain variable region or heavy chain variable region-scFv linker-light chain variable region.

In some instances, scFvs which bind to CD3 are produced by linking VH and VL regions together using flexible polypeptide linkers. The scFv molecules comprise a scFv linker (e.g., a Ser-Gly linker) with an optimized length and/or amino acid composition. Accordingly, in some embodiments, the length of the scFv linker is such that the VH or VL domain can associate intermolecularly with the other variable domain to form the CD3 binding site. In certain embodiments, such scFv linkers are "short," i.e. consist of 0, 1, 2, 3, 4, 5, 6, 7, 8, 9, 10, 11 or 12 amino acid residues. Thus, in certain instances, the scFv linkers consist of about 12 or less amino acid residues. In the case of 0 amino acid residues, the scFv linker is a peptide bond. In some embodiments, these scFv linkers consist of about 3 to about 15, for example 8, 9 or 10 contiguous amino acid residues. Regarding the amino acid composition of the scFv linkers, peptides are selected that confer flexibility, do not interfere with the variable domains as well as allow interchain folding to bring the two variable domains together to form a functional CD3 binding site. For example, scFv linkers comprising glycine and serine residues generally provide protease resistance. In some embodiments, linkers in a scFv comprise glycine and serine residues. The amino acid sequence of the scFv linkers can be optimized, for example, by phage-display methods to improve the CD3 binding and production yield of the scFv. Examples of peptide scFv linkers suitable for linking a variable light domain and a variable heavy domain in a scFv include but are not limited to $(GS)_n$ (SEQ ID No. 197), $(GGS)_n$ (SEQ ID No. 198), $(GGGS)_n$ (SEQ ID No. 199), $(GGSG)_n$ (SEQ ID No. 200), $(GGSGG)_n$ (SEQ ID No. 201), $(GGGGS)_n$ (SEQ ID No. 202), $(GGGGG)_n$ (SEQ ID No. 203), or $(GGG)_n$ (SEQ ID No. 204), wherein n is 1, 2, 3, 4, 5, 6, 7, 8, 9, or 10. In one embodiment, the internal linkers L1 and/or L2 independently are $(GGGGS)_3$ (SEQ ID No. 314), $(GGGGS)_4$ (SEQ ID No. 315), or (GGGGSGGGS) (SEQ ID No. 246). Variation in the linker length may retain or enhance activity, giving rise to superior efficacy in activity studies.

In some embodiments, CD3 binding domain of EGFR targeting trispecific antigen-binding protein has an affinity to CD3 on CD3 expressing cells with a $K_D$ of 1000 nM or less, 500 nM or less, 200 nM or less, 100 nM or less, 80 nM or less, 50 nM or less, 20 nM or less, 10 nM or less, 5 nM or less, 1 nM or less, or 0.5 nM or less. In some embodiments, the CD3 binding domain of EGFR targeting trispecific antigen-binding protein has an affinity to CD3ε, γ, or δ with a $K_D$ of 1000 nM or less, 500 nM or less, 200 nM or less, 100 nM or less, 80 nM or less, 50 nM or less, 20 nM or less, 10 nM or less, 5 nM or less, 1 nM or less, or 0.5 nM or less. In further embodiments, CD3 binding domain of EGFR targeting trispecific antigen-binding protein has low affinity to CD3, i.e., about 100 nM or greater.

The affinity to bind to CD3 can be determined, for example, by the ability of the EGFR targeting trispecific antigen-binding protein itself or its CD3 binding domain to bind to CD3 coated on an assay plate; displayed on a microbial cell surface; in solution; etc. The binding activity of the EGFR targeting trispecific antigen-binding protein itself or its CD3 binding domain of the present disclosure to CD3 can be assayed by immobilizing the ligand (e.g., CD3) or the EGFR targeting trispecific antigen-binding protein itself or its CD3 binding domain, to a bead, substrate, cell, etc. Agents can be added in an appropriate buffer and the binding partners incubated for a period of time at a given temperature. After washes to remove unbound material, the bound protein can be released with, for example, SDS, buffers with a high pH, and the like and analyzed, for example, by Surface Plasmon Resonance (SPR).

In some embodiments, CD3 binding domain of EGFR trispecific antigen-binding protein has an affinity to CD3 on CD3 expressing cells with a $K_D$ of 1000 nM or less, 500 nM or less, 200 nM or less, 100 nM or less, 80 nM or less, 50 nM or less, 20 nM or less, 10 nM or less, 5 nM or less, 1 nM or less, or 0.5 nM or less. In some embodiments, the CD3 binding domain of EGFR trispecific antigen-binding protein has an affinity to CD3ε, γ, or δ with a $K_D$ of 1000 nM or less, 500 nM or less, 200 nM or less, 100 nM or less, 80 nM or less, 50 nM or less, 20 nM or less, 10 nM or less, 5 nM or less, 1 nM or less, or 0.5 nM or less. In further embodiments, CD3 binding domain of EGFR trispecific antigen-binding protein has low affinity to CD3, i.e., about 100 nM or greater.

The affinity to bind to CD3 can be determined, for example, by the ability of the EGFR trispecific antigen-binding protein itself or its CD3 binding domain to bind to CD3 coated on an assay plate; displayed on a microbial cell surface; in solution; etc. The binding activity of the EGFR trispecific antigen-binding protein itself or its CD3 binding domain of the present disclosure to CD3 can be assayed by immobilizing the ligand (e.g., CD3) or the EGFR trispecific antigen-binding protein itself or its CD3 binding domain, to a bead, substrate, cell, etc. Agents can be added in an appropriate buffer and the binding partners incubated for a period of time at a given temperature. After washes to remove unbound material, the bound protein can be released with, for example, SDS, buffers with a high pH, and the like and analyzed, for example, by Surface Plasmon Resonance (SPR).

Half-Life Extension Domain

Contemplated herein are domains which extend the half-life of an antigen-binding domain. Such domains are contemplated to include but are not limited to Albumin binding domains, Fc domains, small molecules, and other half-life extension domains known in the art.

Human albumin (ALB) (molecular mass 67 kDa) is the most abundant protein in plasma, present at about 50 mg/ml (600 µM), and has a half-life of around 20 days in humans. ALB serves to maintain plasma pH, contributes to colloidal blood pressure, functions as carrier of many metabolites and fatty acids, and serves as a major drug transport protein in plasma.

Noncovalent association with albumin extends the elimination half-time of short lived proteins. For example, a recombinant fusion of an albumin binding domain to a Fab fragment resulted in an in vivo clearance of 25- and 58-fold and a half-life extension of 26- and 37-fold when administered intravenously to mice and rabbits respectively as compared to the administration of the Fab fragment alone. In another example, when insulin is acylated with fatty acids to promote association with albumin, a protracted effect was observed when injected subcutaneously in rabbits or pigs. Together, these studies demonstrate a linkage between albumin binding and prolonged action.

In one aspect, the EGFR targeting trispecific proteins described herein comprise a half-life extension domain, for example a domain which specifically binds to ALB (also referred to herein as HSA). In some embodiments, the ALB binding domain of the EGFR targeting trispecific antigen-binding protein can be any domain that binds to ALB including but not limited to domains from a monoclonal antibody, a polyclonal antibody, a recombinant antibody, a human antibody, a humanized antibody. In some embodiments, the ALB binding domain is a single chain variable fragments (scFv), single-domain antibody such as a heavy chain variable domain (VH), a light chain variable domain (VL) and a variable domain (VHH) of camelid derived single domain antibody, peptide, ligand or small molecule entity specific for HSA. In certain embodiments, the HSA binding domain is a single-domain antibody. In other embodiments, the HSA binding domain is a peptide. In further embodiments, the HSA binding domain is a small molecule. It is contemplated that in some embodiments the HSA binding domain of EGFR trispecific antigen-binding protein is fairly small and no more than 25 kD, no more than 20 kDa, no more than 15 kDa, or no more than 10 kDa in some embodiments. In certain instances, the ALB binding is 5 kDa or less if it is a peptide or small molecule entity.

The half-life extension domain of EGFR targeting trispecific antigen-binding protein provides for altered pharmacodynamics and pharmacokinetics of the EGFR targeting trispecific antigen-binding protein itself. As above, the half-life extension domain extends the elimination half-time. The half-life extension domain also alters pharmacodynamic properties including alteration of tissue distribution, penetration, and diffusion of the trispecific antigen-binding protein. In some embodiments, the half-life extension domain provides for improved tissue (including tumor) targeting, tissue distribution, tissue penetration, diffusion within the tissue, and enhanced efficacy as compared with a protein without a half-life extension domain. In one embodiment, therapeutic methods effectively and efficiently utilize a reduced amount of the trispecific antigen-binding protein, resulting in reduced side effects, such as reduced non-tumor cell cytotoxicity.

Further, the binding affinity of the half-life extension domain can be selected so as to target a specific elimination half-time in a particular trispecific antigen-binding protein. Thus, in some embodiments, the half-life extension domain has a high binding affinity. In other embodiments, the half-life extension domain has a medium binding affinity. In yet other embodiments, the half-life extension domain has a low or marginal binding affinity. Exemplary binding affinities include KD concentrations at 10 nM or less (high), between 10 nM and 100 nM (medium), and greater than 100 nM (low). As above, binding affinities to ALB are determined by known methods such as Surface Plasmon Resonance (SPR). In some embodiments, ALB binding domains described herein comprise a single domain antibody.

In some embodiments, the half-life extension domain comprises a sequence selected from SEQ ID Nos. 205-214, or a sequence that is at least about 70%, about 75%, about 80%, about 85%, about 90%, about 95%, about 96%, about 97%, about 98%, about 99%, or 100% identical to a sequence selected from SEQ ID Nos. 205-214. In some examples, the half-life extension comprises three heavy chain CDRs (HC CDR1, HC CDR2, and HC CDR3), and three light chain CDRs (LC CDR1, LC CDR2, and LC CDR3). In some examples, the half-life extension comprises three heavy chain CDRs (HC CDR1, HC CDR2, and HC CDR3), or three light chain CDRs. The heavy chain CDR1 (HC CDR1) of the half-life extension domain, in some embodiments, comprises a sequence selected from SEQ ID Nos. 215 and 218-220, or a sequence comprising one or more modifications or substitutions in a sequence selected from SEQ ID Nos. 215 and 218-220, or at least about 80% to about 99%. The heavy chain CDR2 (HC CDR2) of the half-life extension domain, in some embodiments, comprises a sequence selected from SEQ ID Nos. 216 and 221-226, or a sequence comprising one or more modifications or substitutions in a sequence selected from SEQ ID Nos. 216 and 221-226. The heavy chain CDR3 (HC CDR3) of the CD3 binding domain comprises a sequence selected from SEQ ID Nos. 217 and 227-228, or a sequence comprising one or more modifications or substitutions in a sequence selected from SEQ ID Nos. 217 and 227-228.

EGFR Binding Domain

Epidermal growth factor receptor (EGFR, also known as HER1 or ErbB1) is a member of the ErbB/HER family of type 1 receptor tyrosine kinases (RTKs). Other members of this family include ErbB2 (HER2 or Neu), ErbB3 (HER3) and ErbB4 (HER4). Known ligands for EGFR include epidermal growth factor (EGF) and transforming growth factor alpha (TGF-alpha). Ligand binding to EGFR is known to induce tyrosine phosphorylation and receptor dimerization with other ErbB family members.

RTKs such as EGFR function to allow cells to respond to diverse external stimuli. However, aberrant activation and/or overexpression of EGFR is associated with the development and progression of several human cancers. Accordingly, EGFR is a target for anti-cancer therapies. Approved drugs targeting EGFR include small molecule inhibitors such as gefitinib (Iressa®) and erlotinib (Tarceva®), and anti-EGFR antibodies such as cetuximab (Erbitux®) and panitumumab (Vectibix®). Anti-EGFR antibodies are mentioned in, e.g., U.S. Pat. Nos. 4,943,533, 5,844,093, 7,060,808, 7,247,301, 7,595,378, 7,723,484, and 7,939,072. There is still a need for having available further options for the treatment of diseases related to the overexpression of EGFR, including, but not limited to, renal cell carcinoma, pancreatic carcinoma, breast cancer, head and neck cancer, prostate cancer, malignant gliomas, osteosarcoma, colorectal cancer, gastric cancer (e.g., gastric cancer with MET amplification), malignant mesothelioma, multiple myeloma, ovarian cancer, small cell lung cancer, non-small cell lung cancer (e.g., EGFR-dependent non-small cell lung cancer), synovial sarcoma, thyroid cancer, or melanoma. The present disclosure provides, in certain embodiments, EGFR binding proteins, EGFR targeting trispecific proteins containing EGFR binding domains which specifically bind to EGFR on the surface of tumor target cells.

The design of the EGFR targeting trispecific proteins described herein allows the binding domain to EGFR to be flexible in that the binding domain to EGFR can be any type of binding domain, including but not limited to, domains from a monoclonal antibody, a polyclonal antibody, a recombinant antibody, a human antibody, a humanized antibody. In some embodiments, the binding domain to EGFR is a single chain variable fragments (scFv), single-domain antibody such as a heavy chain variable domain (VH), a light chain variable domain (VL) and a variable domain (VHH) of camelid derived single domain antibody. In other embodiments, the binding domain to EGFR is a non-Ig binding domain, i.e., antibody mimetic, such as anticalins, affilins, affibody molecules, affimers, affitins, alphabodies, avimers, DARPins, fynomers, kunitz domain peptides, and monobodies. In further embodiments, the binding domain to EGFR is a ligand or peptide that binds to or associates with EGFR. In yet further embodiments, the binding domain to EGFR is a knottin. In yet further embodiments, the binding domain to EGFR is a small molecular entity.

In some embodiments, the EGFR binding domain is an anti-EGFR antibody or an antibody variant. As used herein, the term "antibody variant" refers to variants and derivatives of an antibody described herein. In certain embodiments, amino acid sequence variants of the anti-EGFR antibodies described herein are contemplated. For example, in certain embodiments amino acid sequence variants of anti-EGFR antibodies described herein are contemplated to improve the binding affinity and/or other biological properties of the antibodies. Exemplary method for preparing amino acid variants include, but are not limited to, introducing appropriate modifications into the nucleotide sequence encoding the antibody, or by peptide synthesis. Such modifications include, for example, deletions from, and/or insertions into and/or substitutions of residues within the amino acid sequences of the antibody.

Any combination of deletion, insertion, and substitution can be made to arrive at the final construct, provided that the final construct possesses the desired characteristics, e.g., antigen-binding. In certain embodiments, antibody variants having one or more amino acid substitutions are provided. Sites of interest for substitution mutagenesis include the CDRs and framework regions. Examples of such substitutions are described below. Amino acid substitutions may be introduced into an antibody of interest and the products screened for a desired activity, e.g., retained/improved antigen binding, decreased immunogenicity, or improved T-cell mediated cytotoxicity (TDCC). Both conservative and non-conservative amino acid substitutions are contemplated for preparing the antibody variants.

In another example of a substitution to create a variant anti-EGFR antibody, one or more hypervariable region residues of a parent antibody are substituted. In general, variants are then selected based on improvements in desired properties compared to a parent antibody, for example, increased affinity, reduced affinity, reduced immunogenicity, increased pH dependence of binding.

In some embodiments, the EGFR binding domain of the EGFR targeting trispecific protein is a single domain antibody such as a heavy chain variable domain (VH), a variable domain (VHH) of a llama derived sdAb, a peptide, a ligand or a small molecule entity specific for EGFR. In some embodiments, the EGFR binding domain of the EGFR targeting trispecific protein described herein is any domain that binds to EGFR including but not limited to domains from a monoclonal antibody, a polyclonal antibody, a recombinant antibody, a human antibody, a humanized antibody. In certain embodiments, the EGFR binding domain is a single-domain antibody. In other embodiments, the EGFR binding domain is a peptide. In further embodiments, the EGFR binding domain is a small molecule.

Generally, it should be noted that the term single domain antibody as used herein in its broadest sense is not limited to a specific biological source or to a specific method of preparation. Single domain antibodies are antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, goat, rabbit, bovine. For example, in some embodiments, the single domain antibodies of the disclosure are obtained: (1) by isolating the VHH domain of a naturally occurring heavy chain antibody; (2) by expression of a nucleotide sequence encoding a naturally occurring VHH domain; (3) by "humanization" of a naturally occurring VHH domain or by expression of a nucleic acid encoding a such humanized VHH domain; (4) by "camelization" of a naturally occurring VH domain from any animal species, and in particular from a species of mammal, such as from a human being, or by expression of a nucleic acid encoding such a camelized VH domain; (5) by "camelisation" of a "domain antibody" or "Dab," or by expression of a nucleic acid encoding such a camelized VH domain; (6) by using synthetic or semi-synthetic techniques for preparing proteins, polypeptides or other amino acid sequences; (7) by preparing a nucleic acid encoding a single domain antibody using techniques for nucleic acid synthesis known in the field, followed by expression of the nucleic acid thus obtained; and/or (8) by any combination of one or more of the foregoing.

In one embodiment, a single domain antibody corresponds to the VHH domains of naturally occurring heavy chain antibodies directed against EGFR. As further described herein, such VHH sequences can generally be generated or obtained by suitably immunizing a species of Llama with EGFR, (i.e., so as to raise an immune response and/or heavy chain antibodies directed against EGFR), by obtaining a suitable biological sample from said Llama (such as a blood sample, serum sample or sample of B-cells), and by generating VHH sequences directed against EGFR, starting from said sample, using any suitable technique known in the field.

In another embodiment, such naturally occurring VHH domains against EGFR, are obtained from naïve libraries of Camelid VHH sequences, for example by screening such a library using EGFR, or at least one part, fragment, antigenic determinant or epitope thereof using one or more screening techniques known in the field. Such libraries and techniques are for example described in WO 99/37681, WO 01/90190, WO 03/025020 and WO 03/035694 Alternatively, improved synthetic or semi-synthetic libraries derived from naïve VHH libraries are used, such as VHH libraries obtained from naïve VHH libraries by techniques such as random mutagenesis and/or CDR shuffling, as for example described in WO 00/43507

In a further embodiment, yet another technique for obtaining VHH sequences directed against EGFR, involves suitably immunizing a transgenic mammal that is capable of expressing heavy chain antibodies (i.e., so as to raise an immune response and/or heavy chain antibodies directed against EGFR), obtaining a suitable biological sample from said transgenic mammal (such as a blood sample, serum sample or sample of B-cells), and then generating VHH sequences directed against EGFR, starting from said sample, using any suitable technique known in the field. For example, for this purpose, the heavy chain antibody-expressing rats or mice and the further methods and techniques described in WO 02/085945 and in WO 04/049794 can be used.

In some embodiments, the EGFR binding domain of this disclosure binds to a protein comprising the sequence of SEQ ID No. 316 (UniProt Accession No. Q504U8). In some embodiments, the EGFR binding domain binds to a protein comprising a truncated sequence compared to SEQ ID No. 316. In some embodiments, the EGFR binding domain binds to a protein comprising the sequence of SEQ ID No. 317 (UniProt Accession No. Q01279). In some embodiments, the EGFR binding domain binds to a protein comprising a truncated sequence compared to SEQ ID No. 317. In some embodiments, the EGFR binding domain binds to a protein comprising the sequence of SEQ ID No. 318 (UniProt Accession No. A0A2K5WK39). In some embodiments, the EGFR binding domain binds to a protein comprising a truncated sequence compared to SEQ ID No. 318.

In some embodiments, the EGFR binding domains disclosed herein recognize full-length EGFR. In certain instances, the EGFR binding domains disclosed herein recognize an epitope within EGFR, such as, in some cases the EGFR targeting trispecific proteins interact with one or more amino acids found within the extracellular domain of human EGFR (e.g., within extracellular domain I, II, III, and/or IV). The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids located within the extracellular domain of EGFR. Alternatively, the epitope may consist of a plurality of non-contiguous amino acids (or amino acid sequences) located within the extracellular domain of EGFR.

In some embodiments, the EGFR binding proteins of this disclosure binds to the full length EGFR protein or to a fragment thereof, such as epitope containing fragments within the full length EGFR protein, as described above. In some cases, the epitope containing fragment comprises antigenic or immunogenic fragments and derivatives thereof of the EGFR protein. Epitope containing fragments, including antigenic or immunogenic fragments, are, in some embodiments, 12 amino acids or more, e.g., 20 amino acids or more, 50 or 100 amino acids or more. The EGFR fragments, in some embodiments, comprises 95% or more of the length of the full protein, 90% or more, 75% or 50% or 25% or 10% or more of the length of the full protein. In some embodiments, the epitope-containing fragments of EGFR including antigenic or immunogenic fragments are capable of eliciting a relevant immune response in a patient. Derivatives of EGFR include, in some embodiments, variants on the sequence in which one or more (e.g., 1-20 such as 15 amino acids, or up to 20% such as up to 10% or 5% or 1% by number of amino acids based on the total length of the protein) deletions, insertions or substitutions have been made to the EGFR sequence provided in SEQ ID No. 316, 317, or 318.

In some embodiments, substitutions comprise conservative substitutions. Derivatives and variants of, in some examples, have essentially the same biological function as the protein from which they are derived. For instance, derivatives and variants of EGFR are, in some cases, comparably antigenic or immunogenic to the protein from which they are derived, have either the ligand-binding activity, or the active receptor-complex forming ability, or preferably both, of the protein from which they are derived, and have the same tissue distribution as EGFR.

In some embodiments, the EGFR binding protein specifically binds EGFR with equivalent or better affinity as that of a reference EGFR binding protein, and the EGFR binding protein in such embodiments comprises an affinity matured EGFR binding molecule, and is derived from the EGFR binding parental molecule, comprising one or more amino acid mutations (e.g., a stabilizing mutation, a destabilizing mutation) with respect to the EGFR binding parental molecule. In some embodiments, the affinity matured EGFR binding molecule has superior stability with respect to selected destabilizing agents, as that of a reference EGFR binding parental molecule. In some embodiments, the affinity matured EGFR binding molecule is identified in a process comprising panning of one or more pre-candidate EGFR binding molecules derived from one or more EGFR binding parental molecule, expressed in a phage display library, against a EGFR protein, such as a human EGFR protein. The pre-candidate EGFR binding molecule comprises, in some embodiments, amino acid substitutions in the variable regions, CDRs, or framework residues, relative to a parental molecule.

As used herein, "Phage display" refers to a technique by which variant polypeptides are displayed as fusion proteins to at least a portion of a coat protein on the surface of phage, e.g., filamentous phage, particles. A utility of phage display lies in the fact that large libraries of randomized protein variants can be rapidly and efficiently selected for those sequences that bind to a target molecule with high affinity. Display of peptide and protein libraries on phage has been used for screening millions of polypeptides for ones with specific binding properties. Polyvalent phage display methods have been used for displaying small random peptides and small proteins through fusions to either gene III or gene VIII of filamentous phage. Wells and Lowman, Curr. Opin. Struct. Biol, 3:355-362 (1992), and references cited therein. In monovalent phage display, a protein or peptide library is fused to a gene III or a portion thereof, and expressed at low levels in the presence of wild type gene III protein so that phage particles display one copy or none of the fusion proteins. Avidity effects are reduced relative to polyvalent phage so that selection is on the basis of intrinsic ligand affinity, and phagemid vectors are used, which simplify DNA manipulations. Lowman and Wells, Methods: A companion to Methods in Enzymology, 3:205-0216 (1991).

In some embodiments, the panning comprises using varying binding times and concentrations to identify EGFR binding molecules with increased or decreased on-rates, from pre-candidate EGFR binding molecules. In some embodiments, the panning comprises using varying wash times to identify EGFR binding molecules with increased or decreased off-rates, from pre-candidate EGFR molecules. In some embodiments, the panning comprises using both varying binding times and varying wash times. In some embodiments, one or more stabilizing mutations are combined to increase the stability of the affinity matured EGFR binding molecule, for example, by shuffling to create a second-stage combinatorial library from such mutants and conducting a second round of panning followed by a binding selection.

In some embodiments, the affinity matured EGFR binding molecule comprises an equivalent or better affinity to a EGFR protein (such as human EGFR protein) as that of a EGFR binding parental molecule, but that has reduced cross reactivity, or in some embodiments, increased cross reactivity, with selected substances, such as ligands, proteins, antigens, or the like, other than the EGFR epitope for which the EGFR binding parental molecule is specific, or is designed to be specific for. In regard to the latter, an affinity matured EGFR binding molecule, in some embodiments, is more successfully tested in animal models if the affinity matured EGFR binding molecule is reacted with both human EGFR and the corresponding target of the animal model, e.g. mouse EGFR or cynomolgus EGFR. In some embodiments, the parental EGFR binding molecule binds to human EGFR with an affinity of about 10 nM or less, and to cynomolgus EGFR with an affinity of about 15 nM or less. In some embodiments, the affinity matured EGFR binding molecule, identified after one round of panning, binds to human EGFR with an affinity of about 5 nM or less, and to cynomolgus EGFR with an affinity of about 7.5 nM or less. In some embodiments, the affinity matured EGFR binding molecule, identified after two rounds of panning, binds to human EGFR with an affinity of about 2.5 nM or less, and to cynomolgus EGFR with an affinity of about 3.5 nM or less.

In some embodiments, the EGFR binding protein comprises an antigen-specific binding domain polypeptide that specifically bind to targets, such as targets on diseased cellSs, or targets on other cells that support the diseased state, such as targets on stromal cells that support tumor growth or targets on immune cells that support disease-mediated immunosuppression. In some examples, the antigen-specific binding domain includes antibodies, single chain antibodies, Fabs, Fv, T-cell receptor binding domains, ligand binding domains, receptor binding domains, domain antibodies, single domain antibodies, minibodies, NANOBODY® molecules, peptibodies, or various other antibody mimics (such as affimers, affitins, alphabodies, atrimers, CTLA4-based molecules, adnectins, anticalins, Kunitz domain-based proteins, avimers, knottins, fynomers, darpins, affibodies, affilins, monobodies and armadillo repeat protein-based proteins).

In some embodiments, an anti-EGFR single domain antibody of the EGFR targeting trispecific protein comprises a single domain antibody with an amino acid sequence that corresponds to the amino acid sequence of a naturally occurring VHH domain, but that has been "humanized," i.e., by replacing one or more amino acid residues in the amino acid sequence of said naturally occurring VHH sequence (and in particular in the framework sequences) by one or more of the amino acid residues that occur at the corresponding position(s) in a VH domain from a conventional 4-chain antibody from a human being (e.g., as indicated above). This can be performed in a manner known in the field, which will be clear to the skilled person, for example on the basis of the further description herein. Again, it should be noted that such humanized anti-EGFR single domain antibodies of the disclosure are obtained in any suitable manner known per se (i.e., as indicated under points (1)-(8) above) and thus are not strictly limited to polypeptides that have been obtained using a polypeptide that comprises a naturally occurring VHH domain as a starting material. In some additional embodiments, a single domain anti-EGFR antibody, as described herein, comprises a single domain antibody with an amino acid sequence that corresponds to the amino acid sequence of a naturally occurring VH domain, but that has been "camelized" i.e., by replacing one or more amino acid residues in the amino acid sequence of a naturally occurring VH domain from a conventional 4-chain antibody by one or more of the amino acid residues that occur at the corresponding position(s) in a VHH domain of a heavy chain antibody. Such "camelizing" substitutions are preferably inserted at amino acid positions that form and/or are present at the VH-VL interface, and/or at the so-called Camelidae hallmark residues (see for example WO 94/04678 and Davies and Riechmann (1994 and 1996)). Preferably, the VH sequence that is used as a starting material or starting point for generating or designing the camelized single domain is preferably a VH sequence from a mammal, more preferably the VH sequence of a human being, such as a VH3 sequence. However, it should be noted that such camelized anti-EGFR single domain antibodies of the disclosure, in certain embodiments, are obtained in any suitable manner known in the field (i.e., as indicated under points (1)-(8) above) and thus are not strictly limited to polypeptides that have been obtained using a polypeptide that comprises a naturally occurring VH domain as a starting material. For example, as further described herein, both "humanization" and "camelization" is performed by providing a nucleotide sequence that encodes a naturally occurring VHH domain or VH domain, respectively, and then changing, one or more codons in said nucleotide sequence in such a way that the new nucleotide sequence encodes a "humanized" or "camelized" single domain antibody, respectively. This nucleic acid can then be expressed, so as to provide a desired anti-EGFR single domain antibody of the disclosure. Alternatively, in other embodiments, based on the amino acid sequence of a naturally occurring VHH domain or VH domain, respectively, the amino acid sequence of the desired humanized or camelized anti-EGFR single domain antibody of the disclosure, respectively, are designed and then synthesized de novo using known techniques for peptide synthesis. In some embodiments, based on the amino acid sequence or nucleotide sequence of a naturally occurring VHH domain or VH domain, respectively, a nucleotide sequence encoding the desired humanized or camelized anti-EGFR single domain antibody of the disclosure, respectively, is designed and then synthesized de novo using known techniques for nucleic acid synthesis, after which the nucleic acid thus obtained is expressed in using known expression techniques, so as to provide the desired anti-EGFR single domain antibody of the disclosure.

Other suitable methods and techniques for obtaining the anti-EGFR single domain antibody of the disclosure and/or nucleic acids encoding the same, starting from naturally occurring VH sequences or VHH sequences for example comprises combining one or more parts of one or more naturally occurring VH sequences (such as one or more framework (FR) sequences and/or complementarity determining region (CDR) sequences), one or more parts of one or more naturally occurring VHH sequences (such as one or more FR sequences or CDR sequences), and/or one or more synthetic or semi-synthetic sequences, in a suitable manner, so as to provide an anti-EGFR single domain antibody of the disclosure or a nucleotide sequence or nucleic acid encoding the same.

In some embodiments, the EGFR binding domain is an anti-EGFR specific antibody comprising a heavy chain variable complementarity determining region CDR1, a heavy chain variable CDR2, a heavy chain variable CDR3, a light chain variable CDR1, a light chain variable CDR2, and a light chain variable CDR3. In some embodiments, the EGFR binding domain comprises any domain that binds to EGFR including but not limited to domains from a monoclonal antibody, a polyclonal antibody, a recombinant antibody, a human antibody, a humanized antibody, or antigen binding fragments such as single domain antibodies (sdAb), Fab, Fab', F(ab)2, and Fv fragments, fragments comprised of one or more CDRs, single-chain antibodies (e.g., single chain Fv fragments (scFv)), disulfide stabilized (dsFv) Fv fragments, heteroconjugate antibodies (e.g., bispecific antibodies), pFv fragments, heavy chain monomers or dimers, light chain monomers or dimers, and dimers consisting of one heavy chain and one light chain. In some embodiments, the EGFR binding domain is a single domain antibody. In some embodiments, the anti-EGFR single domain antibody comprises heavy chain variable complementarity determining regions (CDR), CDR1, CDR2, and CDR3.

In some embodiments, the EGFR binding domain is a polypeptide comprising an amino acid sequence that is comprised of four framework regions/sequences (f1-f4) interrupted by three complementarity determining regions/sequences, as represented by the formula: f1-r1-f2-r2-f3-r3-f4, wherein r1, r2, and r3 are complementarity determining regions CDR1, CDR2, and CDR3, respectively, and f1, f2, f3, and f4 are framework residues. The framework residues of the EGFR binding protein of the present disclosure comprise, for example, 75, 76, 77, 78, 79, 80, 81, 82, 83, 84, 85, 86, 87, 88, 89, 90, 91, 92, 93, or 94 amino acid residues, and the complementarity determining regions comprise, for example, 24, 25, 26, 27, 28, 29, 30, 31, 32, 33, 34, 35, or 36 amino acid residues. In some embodiments, the EGFR binding domain comprises an amino acid sequence selected from SEQ ID Nos. 1-49.

In some embodiments, the EGFR binding domains described herein comprise a polypeptide having a sequence selected from SEQ ID Nos. 1-49, subsequences thereof, and variants thereof. In some embodiments, the EGFR binding protein comprises at least 70%-95% or more homology to a sequence selected from SEQ ID Nos. 1-49, subsequences thereof, and variants thereof. In some embodiments, the EGFR binding protein comprises at least 70%, 75%, 80%, 85%, 90%, 95%, 96%, 97%, 98%, 99%, or more homology to a sequence selected from SEQ ID Nos. 1-49, subsequences thereof, and variants thereof. In some embodiments, the EGFR binding protein comprises at least 70%-95% or more identity to a sequence selected from SEQ ID Nos. 1-49, subsequences thereof, and variants thereof. In some embodiments, the EGFR binding protein comprises at least 70%, 75%, 80%, 85%, 90%, 95%, 96%, 97%, 98%, 99% or more identity to a sequence selected from SEQ ID Nos. 1-49, subsequences thereof, and variants thereof.

In some embodiments, the CDR1 comprises the amino acid sequence as set forth in any one of SEQ ID Nos. 50-98 or a variant having one, two, three, four, five, six, seven, eight, nine, or ten amino acid substitutions in any one of SEQ ID Nos. 50-98. In some embodiments, the CDR2 comprises a sequence as set forth in any one of SEQ ID Nos. 99-147 or a variant having one, two, three, four, five, six, seven, eight, nine, or ten amino acid substitutions in any one of SEQ ID Nos. 99-147. In some embodiments, the CDR3 comprises a sequence as set forth in any one of SEQ ID Nos. 148-196 or a variant having one, two, three, four, five, six, seven, eight, nine, or ten amino acid substitutions in any one of SEQ ID Nos. 148-196.

In various embodiments, the EGFR binding domain of the present disclosure is at least about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to an amino acid sequence selected from SEQ ID Nos. 1-49.

In various embodiments, a complementarity determining region of the EGFR binding domain of the present disclosure is at least about 10%, about 20%, about 30%, about 40%, about 50%, about 60%, about 70%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to an amino acid sequence set forth in any one of SEQ ID Nos. 50-98.

In various embodiments, a complementarity determining region of the EGFR binding domain of the present disclosure is at least about 10%, about 20%, about 30%, about 40%, about 50%, about 60%, about 70%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to an amino acid sequence set forth in any one of SEQ ID Nos. 99-147.

In various embodiments, a complementarity determining region of the EGFR binding domain of the present disclosure is at least about 10%, about 20%, about 30%, about 40%, about 50%, about 60%, about 70%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to an amino acid sequence set forth in any one of SEQ ID Nos. 148-196.

In various embodiments, an EGFR targeting trispecific protein of the present disclosure is at least about 10%, about 20%, about 30%, about 40%, about 50%, about 60%, about 70%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to an amino acid sequence set forth in any one of SEQ ID Nos. 319-367. In various embodiments, an EGFR targeting trispecific protein of the present disclosure is at least about 10%, about 20%, about 30%, about 40%, about 50%, about 60%, about 70%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identical to an amino acid sequence set forth in any one of SEQ ID Nos. 358 and SEQ ID No. 363.

In some embodiments, the EGFR binding domain is cross-reactive with human cynomolgus and mouse EGFR. In some embodiments, the EGFR binding domain is specific for human EGFR. In certain embodiments, the EGFR binding domains disclosed herein bind to human EGFR with a human Kd (hKd). In certain embodiments, the EGFR binding domains disclosed herein bind to cynomolgus EGFR with a cyno Kd (cKd). In certain embodiments, the EGFR binding domains disclosed herein bind to cynomolgus EGFR with a mouse Kd (mKd). In certain embodiments, the EGFR binding domains disclosed herein bind to both cynomolgus EGFR and a human EGFR, with a cyno Kd (cKd) and a human Kd (hKd), respectively. In certain embodiments, the EGFR binding domains disclosed herein bind to cynomolgus EGFR, mouse EGFR, and a human EGFR, with a cyno Kd (cKd), mouse Kd (mKd), and a human Kd (hKd), respectively. In some embodiments, the EGFR binding protein binds to human, mouse and cynomolgus EGFR with comparable binding affinities (i.e., hKd, mKd and cKd values do not differ by more than ±10%). In some embodiments, the hKd, mKd and the cKd range from about 0.1 nM to about 500 nM. In some embodiments, the hKd, mKd and the cKd range from about 0.1 nM to about 450 nM. In some embodiments, the hKd, mKd and the cKd range from about 0.1 nM to about 400 nM. In some embodiments, the hKd, mKd and the cKd range from about 0.1 nM to about 350 nM. In some embodiments, the hKd, mKd and the cKd range from about 0.1 nM to about 300 nM. In some embodiments, the hKd, mKd and the cKd range from about 0.1 nM to about 250 nM. In some embodiments, the hKd, mKd and the cKd range from about 0.1 nM to about 200 nM. In some embodiments, the hKd, mKd and the cKd range from about 0.1 nM to about 150 nM. In some embodiments, the hKd, mKd and the cKd range from about 0.1 nM to about 100 nM. In some embodiments, the hKd, mKd and the cKd range from about 0.1 nM to about 90 nM. In some embodiments, the hKd, mKd and the cKd range from about 0.2 nM to about 80 nM. In some embodiments, the hKd, mKd and the cKd range from about 0.3 nM to about 70 nM. In some embodiments, the hKd, mKd and the cKd range from about 0.4 nM to about 50 nM. In some embodiments, the hKd, mKd and the cKd range from about 0.5 nM to about 30 nM. In some embodiments, the hKd, mKd and the cKd range from about 0.6 nM to about 10 nM. In some embodiments, the hKd, mKd and the cKd range from about 0.7 nM to about 8 nM. In some embodiments, the hKd, mKd and the cKd range from about 0.8 nM to about 6 nM. In some embodiments, the hKd, mKd and the cKd range from about 0.9 nM to about 4 nM. In some embodiments, the hKd, mKd and the cKd range from about 1 nM to about 2 nM.

In some embodiments, any of the foregoing EGFR binding domains (e.g., anti-EGFR single domain antibodies of SEQ ID Nos. 1-49) are affinity peptide tagged for ease of purification. In some embodiments, the affinity peptide tag is six consecutive histidine residues, also referred to as 6×-his (SEQ ID No. 247).

In certain embodiments, the EGFR binding domains of the present disclosure preferentially bind membrane bound EGFR over soluble EGFR Membrane bound EGFR refers to the presence of EGFR in or on the cell membrane surface of a cell that expresses EGFR. Soluble EGFR refers to EGFR that is no longer on in or on the cell membrane surface of a cell that expresses or expressed EGFR. In certain instances, the soluble EGFR is present in the blood and/or lymphatic circulation in a subject. In one embodiment, the EGFR binding domains bind membrane-bound EGFR at least 5 fold, 10 fold, 15 fold, 20 fold, 25 fold, 30 fold, 40 fold, 50 fold, 100 fold, 500 fold, or 1000 fold greater than soluble EGFR. In one embodiment, the EGFR targeting trispecific antigen binding proteins of the present disclosure preferentially bind membrane-bound EGFR 30 fold greater than soluble EGFR. Determining the preferential binding of an antigen binding protein to membrane bound EGFR over soluble EGFR can be readily determined using binding assays. It is contemplated that in some embodiments the EGFR binding protein is fairly small and no more than 25 kDa, no more than 20 kDa, no more than 15 kDa, or no more than 10 kDa in some embodiments. In certain instances, the EGFR binding protein is 5 kDa or less if it is a peptide or small molecule entity.

In other embodiments, the EGFR binding proteins described herein comprise small molecule entity (SME) binders for EGFR. SME binders are small molecules averaging about 500 to 2000 Da in size and are attached to the EGFR binding proteins by known methods, such as sortase ligation or conjugation. In these instances, the EGFR binding protein comprises a domain comprising a sortase recognition sequence, e.g., LPETG (SEQ ID No. 208). To attach a SME binder to EGFR binding protein comprising a sortase recognition sequence, the protein is incubated with a sortase and a SME binder whereby the sortase attaches the SME binder to the recognition sequence. In yet other embodiments, the EGFR binding proteins described herein comprise a knottin peptide for binding EGFR. Knottins are disufide-stabilized peptides with a cysteine knot scaffold and have average sizes about 3.5 kDa. Knottins have been contemplated for binding to certain tumor molecules such as EGFR. In further embodiments, the EGFR binding proteins described herein comprise a natural EGFR ligand.

In some embodiments, the EGFR binding protein comprises more than one domain and are of a single-polypeptide design with flexible linkage of the domains. This allows for facile production and manufacturing of the EGFR binding proteins as they can be encoded by single cDNA molecule to be easily incorporated into a vector. Further, in some embodiments where the EGFR binding proteins described herein are a monomeric single polypeptide chain, there are no chain pairing issues or a requirement for dimerization. It is contemplated that, in such embodiments, the EGFR binding proteins described herein have a reduced tendency to aggregate.

In the EGFR binding proteins comprising more than one domain, the domains are linked by one or more internal linker. In certain embodiments, the internal linkers are "short," i.e., consist of 0, 1, 2, 3, 4, 5, 6, 7, 8, 9, 10, 11 or 12 amino acid residues. Thus, in certain instances, the internal linkers consist of about 12 or less amino acid residues. In the case of 0 amino acid residues, the internal linker is a peptide bond. In certain embodiments, the internal linkers are "long," i.e., consist of 15, 20 or 25 amino acid residues. In some embodiments, the internal linkers consist of about 3 to about 15, for example 8, 9 or 10 contiguous amino acid residues. Regarding the amino acid composition of the internal linkers, peptides are selected with properties that confer flexibility to the EGFR binding proteins, do not interfere with the binding domains as well as resist cleavage from proteases. For example, glycine and senile residues generally provide protease resistance. Examples of internal linkers suitable for linking the domains in the EGFR binding proteins include but are not limited to $(GS)_n$ (SEQ ID No. 197), $(GGS)_n$ (SEQ ID No. 198), $(GGGS)_n$ (SEQ ID No. 199), $(GGSG)_n$ (SEQ ID No. 200), $(GGSGG)_n$ (SEQ ID No. 201), $(GGGGS)_n$ (SEQ ID No. 202), $(GGGGG)_n$ (SEQ ID No. 203), or $(GGG)_n$ (SEQ ID No. 204), wherein n is 1, 2, 3, 4, 5, 6, 7, 8, 9, or 10. In one embodiment, the linker is (GGGGSGGGGSGGGGSGGGGS)(SEQ ID No. 315), (GGGGSGGGGSGGGGS) (SEQ ID No. 314), or (GGGGSGGGS) (SEQ ID No. 246).

In some cases, where the EGFR binding protein comprises more than one domain, the domains within the EGFR binding proteins are conjugated using an enzymatic site-specific conjugation method which involves the use of a mammalian or bacterial transglutaminase enzyme. Microbial transglutaminases (mTGs) are versatile tools in modern research and biotechnology. The availability of large quantities of relatively pure enzymes, ease of use, and lack of regulation by calcium and guanosine-5'-triphosphate (GTP) has propelled mTG to be the main cross-linking enzyme used in both the food industry and biotechnology. Currently, mTGs are used in many applications to attach proteins and peptides to small molecules, polymers, surfaces, DNA, as well as to other proteins. See, e.g., Pavel Strp, Veracity of microbial transglutaminase, Bioconjugate Chem. 25, 5, 855-862).

In some examples are provided EGFR binding proteins comprising more than one domain, wherein one of the domains comprises an acceptor glutamine in a constant region, which can then be conjugated to another domain via a lysine-based linker (e.g., any primary amine chain which is a substrate for TGase, e.g. comprising an alkylamine, oxoamine) wherein the conjugation occurs exclusively on one or more acceptor glutamine residues present in the targeting moiety outside of the antigen combining site (e.g., outside a variable region, in a constant region). Conjugation thus does not occur on a glutamine, e.g. an at least partly surface exposed glutamine, within the variable region. The EGFR binding protein, in some examples, is formed by reacting one of the domains with a lysine-based linker in the presence of a TGase.

In some embodiments, where one or more domains within the EGFR binding proteins are directly joined, a hybrid vector is made where the DNA encoding the directly joined domains are themselves directly ligated to each other. In some embodiments, where linkers are used, a hybrid vector is made where the DNA encoding one domain is ligated to the DNA encoding one end of a linker moiety and the DNA encoding another domain is ligated to the other end of the linker moiety.

In some embodiments, the EGFR binding protein is a single chain variable fragments (scFv), single-domain antibody such as a heavy chain variable domain (VH), a light chain variable domain (VL) and a variable domain (VHH) of camelid derived single domain antibody. In other embodiments, the EGFR binding protein is a non-Ig binding domain, i.e., an antibody mimetic, such as anticalins, affilins, affibody molecules, affimers, affitins, alphabodies, avimers, DARPins, fynomers, kunitz domain peptides, and monobodies. In further embodiments, the EGFR binding protein is a ligand or peptide that binds to or associates with EGFR. In yet further embodiments, the EGFR binding protein is a knottin. In yet further embodiments, the binding domain to EGFR is a small molecular entity.

In some embodiments, the EGFR binding proteins as set forth above are fused to an Fc region from any species, including but not limited to, human immunoglobulin, such as human IgG1, a human IgG2, a human IgG3, human IgG4, to generate Fc-fusion proteins. In some embodiments, the Fc-fusion proteins of this disclosure have extended half-life compared to an otherwise identical EGFR binding protein. In some embodiments, the Fc-fusion EGFR binding proteins of this disclosure contain inter alia one or more additional amino acid residue substitutions, mutations and/or modifications, e.g., in the Fc region, which result in a binding protein with preferred characteristics including, but not limited to: altered pharmacokinetics, extended serum half-life.

In some embodiments, such Fc-fused EGFR binding proteins provide extended half-lives in a mammal, such as in a human, of greater than 5 days, greater than 10 days, greater than 15 days, greater than 20 days, greater than 25 days, greater than 30 days, greater than 35 days, greater than 40 days, greater than 45 days, greater than 2 months, greater than 3 months, greater than 4 months, or greater than 5 months. The increased half-life, in some cases, results in a higher serum titer which thus reduces the frequency of the administration of the EGFR binding proteins and/or reduces the concentration of the antibodies to be administered. Binding to human FcRn in vivo and serum half-life of human FcRn high affinity binding polypeptides is assayed, in some examples, in transgenic mice or transfected human cell lines expressing human FcRn, or in primates to which the polypeptides with a variant Fc region are administered.

The EGFR binding proteins, in some cases, are differentially modified during or after production, e.g., by glycosylation, acetylation, phosphorylation, amidation, derivatization by known protecting/blocking groups, proteolytic cleavage, linkage to an antibody molecule or other cellular ligand, etc. Any of numerous chemical modifications are carried out by techniques, including but not limited, to specific chemical cleavage by cyanogen bromide, trypsin, chymotrypsin, papain, V8 protease, NaBH4, acetylation, formylation, oxidation, reduction, metabolic synthesis in the presence of tunicamycin, etc.

Various post-translational modifications of the EGFR binding proteins also encompassed by the disclosure include, for example, N-linked or O-linked carbohydrate chains, processing of N-terminal or C-terminal ends, attachment of chemical moieties to the amino acid backbone, chemical modifications of N-linked or O-linked carbohydrate chains, and addition or deletion of an N-terminal methionine residue as a result of prokaryotic host cell expression. Moreover, the EGFR binding proteins are, in some cases, modified with a detectable label, such as an enzymatic, fluorescent, radioisotopic or affinity label to allow for detection and isolation of the modulator.

In some embodiments, the EGFR binding proteins of the disclosure are monovalent or multivalent bivalent, trivalent, etc.). As used herein, the term "valency" refers to the number of potential target binding sites associated with an antibody. Each target binding site specifically binds one target molecule or specific position or locus on a target molecule. When an antibody is monovalent, each binding site of the molecule will specifically bind to a single antigen position or epitope. When an antibody comprises more than one target binding site (multivalent), each target binding site may specifically bind the same or different molecules (e.g., may bind to different ligands or different antigens, or different epitopes or positions on the same antigen).

Integration into Chimeric Antigen Receptors (CAR)

The EGFR targeting trispecific antigen binding proteins of the present disclosure can, in certain examples, be incorporated into a chimeric antigen receptor (CAR). An engineered immune effector cell, e.g., a T cell or NK cell, can be used to express a CAR that includes an anti-EGFR targeting trispecific protein containing an anti-EGFR single domain antibody as described herein. In one embodiment, the CAR including an anti-EGFR targeting trispecific protein as described herein is connected to a transmembrane domain via a hinge region, and further a costimulatory domain, e.g., a functional signaling domain obtained from OX40, CD27, CD28, CD5, ICAM-1, LFA-1 (CD11a/CD18), ICOS (CD278), or 4-1BB. In some embodiments, the CAR further comprises a sequence encoding an intracellular signaling domain, such as 4-1BB and/or CD3 zeta.

Tumor Growth Reduction Properties

In certain embodiments, the EGFR targeting trispecific proteins of the disclosure reduce the growth of tumor cells in vivo when administered to a subject who has tumor cells that express EGFR. Measurement of the reduction of the growth of tumor cells can be determined by multiple different methodologies, such as tumor volume measured by microCT, PET, caliper etc. Non-limiting examples include direct measurement of tumor dimension, measurement of excised tumor mass and comparison to control subjects, measurement via imaging techniques (e.g., CT or MRI) that may or may not use isotopes or luminescent molecules (e.g., luciferase) for enhanced analysis, and the like. In specific embodiments, administration of the trispecific proteins of the disclosure results in a reduction of in vivo growth of tumor cells as compared to a control antigen binding agent by at least about 10%, 20%, 30%, 40%, 50%, 60%, 70%, 80%, 90% or 100%, with an about 100% reduction in tumor growth indicating a complete response and disappearance of the tumor. In further embodiments, administration of the trispecific proteins of the disclosure results in a reduction of in vivo growth of tumor cells as compared to a control antigen binding agent by about 50-100%, about 75-100% or about 90-100%. In further embodiments, administration of the trispecific proteins of the disclosure results in a reduction of in vivo growth of tumor cells as compared to a control antigen binding agent by about 50-60%, about 60-70%, about 70-80%, about 80-90%, or about 90-100%.

EGFR Trispecific Protein Modifications

The EGFR targeting trispecific proteins described herein encompass derivatives or analogs in which (i) an amino acid is substituted with an amino acid residue that is not one encoded by the genetic code, (ii) the mature polypeptide is fused with another compound such as polyethylene glycol, or (iii) additional amino acids are fused to the protein, such as a leader or secretory sequence or a sequence for purification of the protein.

Typical modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Modifications are made anywhere in EGFR targeting trispecific proteins described herein, including the peptide backbone, the amino acid side-chains, and the amino or carboxyl termini. Certain common peptide modifications that are useful for modification of EGFR targeting trispecific proteins include glycosylation, lipid attachment, sulfation, gamma-carboxylation of glutamic acid residues, hydroxylation, blockage of the amino or carboxyl group in a polypeptide, or both, by a covalent modification, and ADP-ribosylation. In some embodiments, derivatives of the EGFR targeting trispecific proteins as described herein comprise immunoreactive modulator derivatives and antigen binding molecules comprising one or more modifications.

Polynucleotides Encoding EGFR Targeting Trispecific Proteins

Also provided, in some embodiments, are polynucleotide molecules encoding an anti-EGFR trispecific binding protein described herein. In some embodiments, the polynucleotide molecules are provided as a DNA construct. In other embodiments, the polynucleotide molecules are provided as a messenger RNA transcript.

The polynucleotide molecules are constructed by known methods such as by combining the genes encoding the three binding domains either separated by peptide linkers or, in other embodiments, directly linked by a peptide bond, into a single genetic construct operably linked to a suitable promoter, and optionally a suitable transcription terminator, and expressing it in bacteria or other appropriate expression system such as, for example CHO cells. In the embodiments where the EGFR binding domain is a small molecule, the polynucleotides contain genes encoding the CD3 binding domain and the half-life extension domain. In the embodiments where the half-life extension domain is a small molecule, the polynucleotides contain genes encoding the domains that bind to CD3 and EGFR. Depending on the vector system and host utilized, any number of suitable transcription and translation elements, including constitutive and inducible promoters, may be used. The promoter is selected such that it drives the expression of the polynucleotide in the respective host cell.

In some embodiments, the polynucleotide is inserted into a vector, preferably an expression vector, which represents a further embodiment. This recombinant vector can be constructed according to known methods. Vectors of particular interest include plasmids, phagemids, phage derivatives, virii (e.g., retroviruses, adenoviruses, adeno-associated viruses, herpes viruses, lentiviruses, and the like), and cosmids.

A variety of expression vector/host systems may be utilized to contain and express the polynucleotide encoding the polypeptide of the described trispecific antigen-binding protein. Examples of expression vectors for expression in *E. coli* are pSKK (Le Gall et al., J Immunol Methods. (2004) 285(1):111-27) or pcDNA5 (Invitrogen) for expression in mammalian cells.

Thus, the EGFR targeting trispecific proteins as described herein, in some embodiments, are produced by introducing a vector encoding the protein as described above into a host cell and culturing said host cell under conditions whereby the protein domains are expressed, may be isolated and, optionally, further purified.

Pharmaceutical Compositions

Also provided, in some embodiments, are pharmaceutical compositions comprising an EGFR binding protein or an anti-EGFR trispecific binding protein described herein, a vector comprising the polynucleotide encoding the polypeptide of the EGFR binding protein, or the EGFR targeting trispecific proteins or a host cell transformed by such a vector and at least one pharmaceutically acceptable carrier. The term "pharmaceutically acceptable carrier" includes, but is not limited to, any carrier that does not interfere with the effectiveness of the biological activity of the ingredients and that is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at a suitable dose. Preferably, the compositions are sterile. These compositions may also contain adjuvants such as preservative, emulsifying agents and dispersing agents. Prevention of the action of microorganisms may be ensured by the inclusion of various antibacterial and antifungal agents. A further embodiment provides one or more of the above described EGFR binding proteins or the EGFR targeting trispecific proteins packaged in lyophilized form, or packaged in an aqueous medium.

In some embodiments of the pharmaceutical compositions, the EGFR binding proteins or the EGFR targeting trispecific proteins described herein are encapsulated in nanoparticles. In some embodiments, the nanoparticles are fullerenes, liquid crystals, liposome, quantum dots, superparamagnetic nanoparticles, dendrimers, or nanorods. In other embodiments of the pharmaceutical compositions, the EGFR binding protein or the EGFR trispecific antigen-binding protein is attached to liposomes. In some instances, EGFR binding protein or the EGFR trispecific antigen-binding protein are conjugated to the surface of liposomes. In some instances, the EGFR binding protein or the EGFR trispecific antigen-binding protein are encapsulated within the shell of a liposome. In some instances, the liposome is a cationic liposome.

The EGFR binding protein or the EGFR targeting trispecific proteins described herein are contemplated for use as a medicament. Administration is effected by different ways, e.g., by intravenous, intraperitoneal, subcutaneous, intramuscular, topical or intradermal administration. In some embodiments, the route of administration depends on the kind of therapy and the kind of compound contained in the pharmaceutical composition. The dosage regimen will be determined by the attending physician and other clinical factors. Dosages for any one patient depends on many factors, including the patient's size, body surface area, age, sex, the particular compound to be administered, time and route of administration, the kind of therapy, general health and other drugs being administered concurrently. An "effective dose" refers to amounts of the active ingredient that are sufficient to affect the course and the severity of the disease, leading to the reduction or remission of such pathology and may be determined using known methods.

In some embodiments, the EGFR binding proteins or the EGFR targeting trispecific proteins of this disclosure are administered at a dosage of up to 10 mg/kg at a frequency of once a week. In some cases, the dosage ranges from about 1 ng/kg to about 10 mg/kg. In some embodiments, the dose is from about 1 ng/kg to about 10 ng/kg, about 5 ng/kg to about 15 ng/kg, about 12 ng/kg to about 20 ng/kg, about 18 ng/kg to about 30 ng/kg, about 25 ng/kg to about 50 ng/kg, about 35 ng/kg to about 60 ng/kg, about 45 ng/kg to about 70 ng/kg, about 65 ng/kg to about 85 ng/kg, about 80 ng/kg to about 1 µg/kg, about 0.5 µg/kg to about 5 µg/kg, about 2 µg/kg to about 10 µg/kg, about 7 µg/kg to about 15 µg/kg, about 12 µg/kg to about 25 µg/kg, about 20 µg/kg to about 50 µg/kg, about 35 µg/kg to about 70 µg/kg, about 45 µg/kg to about 80 µg/kg, about 65 µg/kg to about 90 µg/kg, about 85 µg/kg to about 0.1 mg/kg, about 0.095 mg/kg to about 10 mg/kg. In some cases, the dosage is about 0.1 mg/kg to about 0.2 mg/kg; about 0.25 mg/kg to about 0.5 mg/kg, about 0.45 mg/kg to about 1 mg/kg, about 0.75 mg/kg to about 3 mg/kg, about 2.5 mg/kg to about 4 mg/kg, about 3.5 mg/kg to about 5 mg/kg, about 4.5 mg/kg to about 6 mg/kg, about 5.5 mg/kg to about 7 mg/kg, about 6.5 mg/kg to about 8 mg/kg, about 7.5 mg/kg to about 9 mg/kg, or about 8.5 mg/kg to about 10 mg/kg. The frequency of administration, in some embodiments, is about less than daily, every other day, less than once a day, twice a week, weekly, once in 7 days, once in two weeks, once in two weeks, once in three weeks, once in four weeks, or once a month. In some cases, the frequency of administration is weekly. In some cases, the frequency of administration is weekly and the dosage is up to 10 mg/kg. In some cases, duration of administration is from about 1 day to about 4 weeks or longer.

Methods of Treatment

Also provided herein, in some embodiments, are methods and uses for stimulating the immune system of an individual in need thereof comprising administration of an anti-EGFR binding protein or an anti-EGFR targeting trispecific protein as described herein. In some instances, the administration of an anti-EGFR binding protein or an anti-EGFR targeting trispecific protein described herein induces and/or sustains cytotoxicity towards a cell expressing a target antigen. In some instances, the cell expressing a target antigen is a cancer or tumor cell, a virally infected cell, a bacterially infected cell, an autoreactive T or B cell, damaged red blood cells, arterial plaques, or fibrotic tissue.

Also provided herein are methods and uses for a treatment of a disease, disorder or condition associated with a target antigen comprising administering to an individual in need thereof an anti-EGFR binding protein or an anti-EGFR targeting trispecific protein described herein. Diseases, disorders or conditions associated with a target antigen include, but are not limited to, viral infection, bacterial infection, auto-immune disease, transplant rejection, atherosclerosis, or fibrosis. In other embodiments, the disease, disorder or condition associated with a target antigen is a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease. In one embodiment, the disease, disorder or condition associated with a target antigen is cancer. Cancers that can be treated, prevented, or managed by the EGFR binding proteins or EGFR targeting trispecific proteins of the present disclosure, and methods of using them, include but are not limited to cancers of an epithelial cell origin. Examples of such cancers include the following: leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to ductal carcinoma, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, prostatic intraepithelial neoplasia, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

The EGFR binding protein or the EGFR targeting trispecific proteins of the disclosure are also useful in the treatment or prevention of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Burkitt's lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xeroderma pigmentosum, keratoactanthoma, seminoma, thyroid follicular cancer and teratocarcinoma. It is also contemplated that cancers caused by aberrations in apoptosis would also be treated by the methods and compositions of the disclosure. Such cancers may include but not be limited to follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented in the skin, lung, colon, breast, prostate, bladder, kidney, pancreas, ovary, or uterus. In other specific embodiments, sarcoma, melanoma, or leukemia is treated or prevented.

In some embodiments, the EGFR binding proteins or the EGFR targeting tri specific proteins of the present disclosure are administered to treat a neoplastic condition. Neoplastic conditions, in some embodiments, are benign or malignant; solid tumors or other blood neoplasia; and, in some embodiments, are selected from the group including, but not limited to: adrenal gland tumors, AIDS-associated cancers, alveolar soft part sarcoma, astrocytic tumors, autonomic ganglia tumors, bladder cancer (squamous cell carcinoma and transitional cell carcinoma), blastocoelic disorders, bone cancer (adamantinoma, aneurismal bone cysts, osteochondroma, osteosarcoma), brain and spinal cord cancers, metastatic brain tumors, breast cancer including triple negative breast cancer, carotid body tumors, cervical cancer, chondrosarcoma, chordoma, chromophobe renal cell carcinoma, clear cell carcinoma, colon cancer, colorectal cancer, cutaneous benign fibrous histiocytomas, desmoplastic small round cell tumors, ependymomas, epithelial disorders, Ewing's tumors, extraskeletal myxoid chondrosarcoma, fibrogenesis imperfecta ossium, fibrous dysplasia of the bone, gallbladder and bile duct cancers, gastric cancer, gastrointestinal, gestational trophoblastic disease, germ cell tumors, glandular disorders, head and neck cancers, hypothalamic, intestinal cancer, islet cell tumors, Kaposi's Sarcoma, kidney cancer (nephroblastoma, papillary renal cell carcinoma), leukemias, lipoma/benign lipomatous tumors, liposarcoma/malignant lipomatous tumors, liver cancer (hepatoblastoma, hepatocellular carcinoma), lymphomas, lung cancers (small cell carcinoma, adenocarcinoma, squamous cell carcinoma, large cell carcinoma etc.), macrophagal disorders, medulloblastoma, melanoma, meningiomas, multiple endocrine neoplasia, multiple myeloma, myelodysplastic syndrome, neuroblastoma, neuroendocrine tumors, ovarian cancer, pancreatic cancers, papillary thyroid carcinomas, parathyroid tumors, pediatric cancers, peripheral nerve sheath tumors, phaeochromocytoma, pituitary tumors, prostate cancer, posterious unveal melanoma, rare hematologic disorders, renal metastatic cancer, rhabdoid tumor, rhabdomysarcoma, sarcomas, skin cancer, soft-tissue sarcomas, squamous cell cancer, stomach cancer, stromal disorders, synovial sarcoma, testicular cancer, thymic carcinoma, thymoma, thyroid metastatic cancer, and uterine cancers (carcinoma of the cervix, endometrial carcinoma, and leiomyoma).

In certain embodiments the EGFR binding proteins or the EGFR targeting trispecific proteins of the present disclosure are used as a front line therapy and administered to subjects who have not previously been treated for the cancerous condition. In other embodiments the EGFR binding proteins or the EGFR targeting trispecific proteins of the present disclosure are used to treat subjects that have previously been treated (with an EGFR binding protein or trispecific protein of this disclosure or with other anti-cancer agent) and have relapsed or determined to be refractory to the previous treatment. In some embodiments the EGFR binding proteins or the EGFR targeting trispecific proteins of the present disclosure are used to treat subjects that have recurrent tumors.

In some aspects, the EGFR binding proteins or the EGFR targeting trispecific proteins of the present disclosure are administered to treat a proliferative disorder comprising a solid tumor including, but not limited to, adrenal, liver, kidney, bladder, breast, gastric, ovarian, cervical, uterine, esophageal, colorectal, prostate, pancreatic, lung (both small cell and non-small cell), thyroid, carcinomas, sarcomas, glioblastomas and various head and neck tumors.

In some embodiments, the EGFR binding proteins or the EGFR targeting trispecific proteins of the present disclosure are administered to a subject suffering from melanoma. In some embodiments, the EGFR binding proteins or the EGFR targeting trispecific proteins of the present disclosure are used to diagnose, monitor, treat or prevent melanoma. The term "melanoma," as used herein, includes all types of melanoma including, but not limited to, primary melanoma, malignant melanoma, cutaneous melanoma, extracutaneous melanoma, superficial spreading melanoma, polypoid melanoma, melanocarcinomas, melanoepitheliomas, melanosarcomas, melanoma in situ, nodular malignant melanoma, lentigo maligna melanoma, lentiginous melanoma, lentiginous malignant melanoma, mucosal lentiginous melanoma, mucosal melanoma, acral lentiginous melanoma, soft tissue melanoma, ocular melanoma, invasive melanoma, familial atypical mole and melanoma (FAM-M) syndrome, desmoplastic malignant melanoma or uveal melanoma.

EGFR is an effective tumor marker that is expressed on a number of different cancers and has been found to be associated with cancer stem cells. Thus, in some embodiments where the EGFR binding proteins or the EGFR targeting trispecific proteins of the disclosure are incorporated in a chimeric antigen receptor expressed on lymphocytes, the resulting "EGFR sensitized lymphocytes" (e.g., natural killer cells or T cells that immunospecifically recognize a EGFR determinant) are able to effectively mount an immune response directed to aberrant EGFR positive cells including cancer stem cells. This ability to effectively eliminate tumorigenic "seed" cells is often critical in reducing the possibility of tumor recurrence or metastasis. In some embodiments, such EGFR sensitized lymphocytes are used in combination with other therapeutic agents or as part of a maintenance regimen following standard of care treatments.

More generally a chimeric antigen receptor is an artificially constructed hybrid protein or polypeptide containing or comprising an antigen binding domain of an antibody linked to a signaling domain (e.g., T-cell signaling or T-cell activation domains). In some embodiments, CARs comprising the EGFR binding protein or the EGFR targeting trispecific proteins of the present disclosure have the ability to redirect the specificity and reactivity of sensitized lymphocytes (e.g., T-cells) toward EGFR positive target cells in a non-MHC-restricted manner by exploiting the antigen-binding properties of antibodies or antigen binding fragments thereof. The non-MHC-restricted antigen recognition gives T-cells expressing EGFR CARs the ability to recognize tumorigenic EGFR independent of antigen processing, thus bypassing a major mechanism of tumor escape. Moreover, when expressed in T-cells, CARs advantageously do not dimerize with endogenous T cell receptor (TCR) alpha and beta chains.

In selected aspects the EGFR binding proteins or the EGFR targeting trispecific proteins of the disclosure is incorporated into a chimeric antigen receptor (CAR) and the EGFR CAR is administered in a CAR based therapy effective at treating lung cancer, including the following subtypes: small cell lung cancer, non-small cell lung cancer (e.g., squamous cell non-small cell lung cancer or squamous cell small cell lung cancer) and large cell neuroendocrine carcinoma (LCNEC).

In some embodiments, the EGFR sensitive lymphocytes are administered to patients exhibiting limited stage disease or extensive stage disease. In other embodiments the disclosed EGFR binding proteins or the EGFR targeting trispecific proteins are administered to refractory patients (i.e., those whose disease recurs during or shortly after completing a course of initial therapy); sensitive patients (i.e., those whose relapse is longer than 2-3 months after primary therapy); or patients exhibiting resistance to a platinum based agent (e.g., carboplatin, cisplatin, oxaliplatin) and/or a taxane (e.g., docetaxel, paclitaxel, larotaxel or cabazitaxel). In another embodiment the disclosed EGFR CAR treatments are effective at treating ovarian cancer, including ovarian-serous carcinoma and ovarian-papillary serous carcinoma.

In another embodiment the EGFR binding proteins of the disclosure, the EGFR targeting trispecific proteins, the EGFR CAR, or the EGFR sensitized lymphocytes, or any combination thereof are used in maintenance therapy to reduce or eliminate the chance of tumor recurrence following the initial presentation of the disease. In some cases, the disorder has been treated and the initial tumor mass eliminated, reduced or otherwise ameliorated so the patient is asymptomatic or in remission. At such time the subject is administered pharmaceutically effective amounts of the disclosed the EGFR binding proteins of the disclosure, the EGFR targeting trispecific proteins, the EGFR CAR, or the EGFR sensitized lymphocytes, or any combination thereof one or more times regardless of if there is little or no indication of disease using standard diagnostic procedures. In some embodiments, the EGFR binding proteins or the EGFR targeting trispecific proteins of the disclosure, the EGFR CAR, or the EGFR sensitized lymphocytes, or any combination thereof is administered on a regular schedule over a period of time, such as weekly, every two weeks, monthly, every six weeks, every two months, every three months every six months or annually, for example, to reduce the potential of disease recurrence. Moreover such treatments are in some embodiments continued for a period of weeks, months, years or even indefinitely depending on the patient response and clinical and diagnostic parameters.

In yet another embodiment, the EGFR binding proteins or the EGFR targeting trispecific proteins of the disclosure, the EGFR CAR, or the EGFR sensitized lymphocytes, or any combination thereof are used to prophylactically or as an adjuvant therapy to prevent or reduce the possibility of tumor metastasis following a debulking procedure. As used in the present disclosure a "debulking procedure," means any procedure, technique or method that eliminates, reduces, treats or ameliorates a tumor or tumor proliferation. Exemplary debulking procedures include, but are not limited to, surgery, radiation treatments (i.e., beam radiation), chemotherapy, immunotherapy or ablation. In some embodiments, at appropriate times, the EGFR binding proteins or the EGFR targeting trispecific proteins of the disclosure, the EGFR CAR, or the EGFR sensitized lymphocytes, or any combination thereof are administered as suggested by clinical, diagnostic or theranostic procedures to reduce tumor metastasis. In some embodiments, the dosing regimen is accompanied by appropriate diagnostic or monitoring techniques that allow it to be modified.

Yet other embodiments of the disclosure comprise administering the EGFR binding protein or the EGFR targeting trispecific proteins of the disclosure, the EGFR CAR, or the EGFR sensitized lymphocytes, or any combination thereof to subjects that are asymptomatic but at risk of developing a proliferative disorder. That is, in some embodiments, the EGFR binding protein or the EGFR targeting trispecific proteins of the disclosure, the EGFR CAR, or the EGFR sensitized lymphocytes, or any combination thereof are used in preventative sense and given to patients that have been examined or tested and have one or more noted risk factors (e.g., genomic indications, family history, in vivo or in vitro test results, etc.) but have not developed neoplasia. In such cases those skilled in the art would be able to determine an effective dosing regimen through empirical observation or through accepted clinical practices.

In some embodiments of the methods described herein, the EGFR binding proteins or the EGFR targeting trispecific proteins as described herein are administered in combination with an agent for treatment of the particular disease, disorder or condition. Agents include but are not limited to, therapies involving antibodies, small molecules (e.g., chemotherapeutics), hormones (steroidal, peptide, and the like), radiotherapies (γ-rays, X-rays, and/or the directed delivery of radioisotopes, microwaves, UV radiation and the like), gene therapies (e.g., antisense, retroviral therapy and the like) and other immunotherapies. In some embodiments, an EGFR targeting trispecific protein as described herein is administered in combination with anti-diarrheal agents, anti-emetic agents, analgesics, opioids and/or non-steroidal anti-inflammatory agents. In some embodiments, an EGFR binding proteins or an EGFR targeting trispecific protein as described herein is administered in combination with anti-cancer agents. Non-limiting examples of anti-cancer agents that can be used in the various embodiments of the disclosure, including pharmaceutical compositions and dosage forms and kits of the disclosure, include: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alpha-2a; interferon alpha-2b; interferon alpha-n1 interferon alpha-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinzolidine sulfate; vinzolidine sulfate; vorozole; zeniplatin; zinostatin; zorubicin hydrochloride. Other examples of anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-I receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; HMG-CoA reductase inhibitor (such as but not limited to, Lovastatin, Pravastatin, Fluvastatin, Statin, Simvastatin, and Atorvastatin); loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; Vitaxin®; vorozole; zanoterone; zeniplatin; zilascorb; and zinostatin stimalamer. Additional anti-cancer drugs are 5-fluorouracil and leucovorin. These two agents are particularly useful when used in methods employing thalidomide and a topoisomerase inhibitor. In some embodiments, an EGFR binding protein or an EGFR targeting trispecific protein of the present disclosure is used in combination with gemcitabine.

In some embodiments, the EGFR targeting trispecific protein as described herein is administered before, during, or after surgery.

Methods of Detection of EGFR Expression and Diagnosis of EGFR Associated Cancer

According to another embodiment of the disclosure, kits for detecting expression of EGFR in vitro or in vivo are provided. The kits include the foregoing EGFR targeting trispecific proteins (e.g., a trispecific protein containing a labeled anti-EGFR single domain antibody or antigen binding fragments thereof), and one or more compounds for detecting the label. In some embodiments, the label is selected from the group consisting of a fluorescent label, an enzyme label, a radioactive label, a nuclear magnetic resonance active label, a luminescent label, and a chromophore label.

In some cases, EGFR expression is detected in a biological sample. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. A biological sample is typically obtained from a mammal, such as a human or non-human primate.

In one embodiment, provided is a method of determining if a subject has cancer by contacting a sample from the subject with an anti-EGFR binding protein (such as an anti-EGFR single domain antibody) as disclosed herein; and detecting binding of the single domain antibody to the sample. An increase in binding of the antibody to the sample as compared to binding of the antibody to a control sample identifies the subject as having cancer.

In another embodiment, provided is a method of confirming a diagnosis of cancer in a subject by contacting a sample from a subject diagnosed with cancer with an anti-EGFR single domain antibody as disclosed herein; and detecting binding of the antibody to the sample. An increase in binding of the antibody to the sample as compared to binding of the antibody to a control sample confirms the diagnosis of cancer in the subject.

In some examples of the disclosed methods, an EGFR single domain antibody of the trispecific protein is directly labeled.

In some examples, the methods further include contacting a second antibody that specifically binds the anti-EGFR single domain antibody with the sample; and detecting the binding of the second antibody. An increase in binding of the second antibody to the sample as compared to binding of the second antibody to a control sample detects cancer in the subject or confirms the diagnosis of cancer in the subject.

In some cases, the cancer is mesothelioma, prostate cancer, lung cancer, stomach cancer, squamous cell carcinoma, pancreatic cancer, cholangiocarcinoma, triple negative breast cancer or ovarian cancer, or any other type of cancer that expresses EGFR.

In some examples, the control sample is a sample from a subject without cancer. In particular examples, the sample is a blood or tissue sample.

In some cases, the antibody that binds (for example specifically binds) EGFR is directly labeled with a detectable label. In another embodiment, the antibody that binds (for example, specifically binds) EGFR (the first antibody) is unlabeled and a second antibody or other molecule that can bind the antibody that specifically binds EGFR is labeled. A second antibody is chosen such that it is able to specifically bind the specific species and class of the first antibody. For example, if the first antibody is a llama IgG, then the secondary antibody may be an anti-llama-IgG. Other molecules that can bind to antibodies include, without limitation, Protein A and Protein G, both of which are available commercially. Suitable labels for the antibody or secondary antibody are described above, and include various enzymes, prosthetic groups, fluorescent materials, luminescent materials, magnetic agents and radioactive materials.

Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include 125I, 131I, 35S or 3H.

In an alternative embodiment, EGFR can be assayed in a biological sample by a competition immunoassay utilizing EGFR standards labeled with a detectable substance and an unlabeled antibody that specifically binds EGFR. In this assay, the biological sample, the labeled EGFR standards and the antibody that specifically bind EGFR are combined and the amount of labeled EGFR standard bound to the unlabeled antibody is determined. The amount of EGFR in the biological sample is inversely proportional to the amount of labeled EGFR standard bound to the antibody that specifically binds EGFR.

The immunoassays and method disclosed herein can be used for a number of purposes. In one embodiment, an antibody that specifically binds EGFR may be used to detect the production of EGFR in cells in cell culture. In another embodiment, the antibody can be used to detect the amount of EGFR in a biological sample, such as a tissue sample, or a blood or serum sample. In some examples, the EGFR is cell-surface EGFR. In other examples, the EGFR is soluble EGFR (e.g., EGFR in a cell culture supernatant or soluble EGFR in a body fluid sample, such as a blood or serum sample).

In one embodiment, a kit is provided for detecting EGFR in a biological sample, such as a blood sample or tissue sample. For example, to confirm a cancer diagnosis in a subject, a biopsy can be performed to obtain a tissue sample for histological examination. Alternatively, a blood sample can be obtained to detect the presence of soluble EGFR protein or fragment. Kits for detecting a polypeptide will typically comprise a single domain antibody, according to the present disclosure, that specifically binds EGFR. In some embodiments, an antibody fragment, such as an scFv fragment, a VH domain, or a Fab is included in the kit. In a further embodiment, the antibody is labeled (for example, with a fluorescent, radioactive, or an enzymatic label).

In one embodiment, a kit includes instructional materials disclosing means of use of an antibody that binds EGFR (such as an EGFR binding protein or an EGFR targeting trispecific protein). The instructional materials may be written, in an electronic form (such as a computer diskette or compact disk), may be visual (such as video files), or provided through an electronic network, for example, over the internet, World Wide Web, an intranet, or other network. The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting EGFR in a biological sample generally includes the steps of contacting the biological sample with an antibody which specifically reacts, under immunologically reactive conditions, to a EGFR polypeptide. The antibody is allowed to specifically bind under immunologically reactive conditions to form an immune complex, and the presence of the immune complex (bound antibody) is detected directly or indirectly.

Methods of determining the presence or absence of a cell surface marker are well known in the art. For example, the antibodies can be conjugated to other compounds including, but not limited to, enzymes, magnetic beads, colloidal magnetic beads, haptens, fluorochromes, metal compounds, radioactive compounds or drugs. The antibodies can also be utilized in immunoassays such as but not limited to radio-immunoassays (RIAs), ELISA, or immunohistochemical assays. The antibodies can also be used for fluorescence activated cell sorting (FACS). FACS employs a plurality of color channels, low angle and obtuse light-scattering detection channels, and impedance channels, among other more sophisticated levels of detection, to separate or sort cells (see U.S. Pat. No. 5,061,620). Any of the single domain antibodies that bind EGFR, as disclosed herein, can be used in these assays. Thus, the antibodies can be used in a conventional immunoassay, including, without limitation, an ELISA, an RIA, FACS, tissue immunohistochemistry, Western blot or immunoprecipitation.

EXAMPLES

Example 1: Screening of Phage Display Library for Identification of EGFR Binding Domains Llamas were immunized with purified EGFR protein expressed in 293 cells. A phage display library for expression of heavy chain variable antibody domains was constructed from circulating B cells (see van der Linden, de Geus, Stok, Bos, van Wassenaar, Verrips, and Frenken. 2000. J Immunol Methods 240:185-195). Phage clones were screening for binding to EGFR by expressing the clones in E. coli, preparing periplasmic extracts, and screening the clones for EGFR binding activity by ELISA. Thirty-eight unique heavy chain only sequences were identified that produced a signal in the ELISA screening (SEQ ID Nos. 1 to 38). The CDR1, CDR2, and CDR3 sequences for these heavy variable domains were, respectively, SEQ ID Nos. 50 to 87, SEQ ID Nos. 99 to 136, and SEQ ID Nos. 148 to 185.

Example 2: Humanization of EGFR Binding Heavy Chain Only Single Domain Antibodies and T Cell Dependent Cellular Cytotoxicity Assay Eleven llama anti-EGFR heavy chain only single domain antibodies from Example 1 were humanized (SEQ ID Nos. 39 to 49). The CDR1, CDR2, and CDR3 sequences for these heavy variable domains are, respectively, SEQ ID Nos. 88 to 98, SEQ ID Nos. 137 to 147, and SEQ ID Nos. 186 to 196.

The 11 humanized anti-EGFR sequences, along with their 11 parental llama anti-EGFR sequences, were cloned into trispecific (also referred to herein as TriTAC™) expression constructs with a signal domain followed by an anti-EGFR domain followed by a GGGGSGGGS (SEQ ID No. 246) linker followed by anti-human albumin single domain antibody 10G (SEQ ID No. 210) followed by a GGGGSGGGS (SEQ ID No. 246) linker followed by anti-human CD3 antibody 2B2 (SEQ ID No. 229) followed by a HHHHHH (SEQ ID No. 247) tag.

The anti-EGFR TriTAC™ constructs were transfected into EXPI293™ cells. These anti-EGFR TriTAC™ proteins were engineered with a protein A binding site, and the amount of anti-EGFR TriTAC™ protein in the conditioned media from the transfected EXPI293™ cells was quantitated by using an Octet instrument with protein A tips using a TriTAC™ protein of similar molecular weight to the EGFR TriTAC™ proteins as a standard.

The conditioned media were tested in a T-cell dependent cellular cytotoxicity assay (see Nazarian A A, Archibeque I L, Nguyen Y H, Wang P, Sinclair A M, Powers D A. 2015. J Biomol Screen. 20:519-27). In this assay, luciferase labelled HCT116 cells were combined with purified human T cells and a titration of EGFR TriTAC™ proteins. The titration was based on the quantitation described in the previous paragraph. If an EGFR TriTAC™ protein directs T cells to kill the EGFR-expression HCT116 cells, then the viability of the HCT116 cells, as determined by running a luciferase assay at 48 hours after starting the experiment, was expected to decrease. The results are shown in FIGS. 2-5, which provide have graphs of representative TDCC data, and $EC_{50}$ values from the TDCC assay are listed in Table 1. The EGFR TriTAC™ proteins with TDCC activity had $EC_{50}$ values ranging from 6.3 pM to 183 nM. In some cases, the humanized version of a binder did not have activity whereas the llama binder did have activity, as exemplified by the comparison of EL16 and EL18 to EH16 and EH18. It is contemplated that the lack of activity could signify that the humanization process requires refinement to generate a humanized molecule with TDCC activity similar to the parental llama sequence. In some cases, neither the llama nor the equivalent humanized EGFR binder had activity in the TDCC assay. It is contemplated that this lack of activity does not conclusively show these binders lack TDCC activity but could be caused by a different complication, for example, differential glycosylation of EGFR in HCT116 cells. A negative control for the TDCC assays was a TriTAC™ protein targeting GFP (FIG. 5), which did not direct the T cells to kills the HCT116 cells.

TABLE 1

Activity of Anti-EGFR TriTAC ™ molecules in DMS153 TDCC Assays.

| EGFR binder | $K_D$ (M) |
| --- | --- |
| EL1 | n/d |
| EL4 | 6.82E−11 |
| EL16 | 2.33E−10 |
| EL18 | 1.69E−10 |
| EL38 | n/d |
| EL44 | n/d |
| EL60 | n/d |
| EL64 | n/d |
| EL77 | n/d |
| EL104 | 6.33E−12 |
| EL113 | 8.23E−11 |
| EH1 | n/d |
| EH4 | 1.83E−10 |
| EH16 | n/d |
| EH18 | n/d |
| EH38 | n/d |
| EH44 | n/d |
| EH60 | n/d |
| EH64 | n/d |
| EH77 | n/d |
| EH104 | 7.15E−12 |
| EH113 | n/d | n/d means an $EC_{50}$ value was not possible to determine with these assay data.

Using the same conditioned media used in the TDCC assay, the binding affinities of the anti-EGFR TriTAC™ molecules for human, cynomolgus, and mouse EGFR proteins were measured using biotinylated EGFR proteins and an Octet instrument with streptavidin tips. The $K_D$ measurements were made using a single 80 nM concentration of TriTAC™ protein, which allowed for rank ordering potency. These measured relative affinities are listed in Table 2. Some TriTAC™ proteins did not bind the biotinylated immobilized EGFR in this assay, but other bound with Kd values ranging from 4 nM to 112 nM for human EGFR, 4 nM to 92 nM for cynomolgus EGFR, and 16 nM to 63 nM for mouse EGFR. It is contemplated that lack of binding in this assay could happen because, for example, biotinylation of EGFR could have happened at a recognition site of an anti-EGFR binder, and thus lack of binding does not demonstrate a molecule is unable to bind EGFR.

TABLE 2

Binding Affinities of Anti-EGFR TriTAC ™ molecules for Human, Cynomolgus, and Mouse EGFR Protein.

| EGFR binder | $K_D$ human EGFR (nM) | $K_D$ cynomolgus EGFR (nM) | $K_D$ mouse EGFR (nM) |
| --- | --- | --- | --- |
| EL4 | 54 | 59 | 49 |
| EL16 | 112 | 73 | n/b |
| EL18 | 49 | 44 | 63 |
| EL104 | 4 | 4 | 13 |
| EL113 | 15 | 15 | 59 |
| EH4 | 61 | 70 | 59 |
| EH104 | 5 | 6 | 16 |
| EH113 | 93 | 92 | l/b | l/b means low binding and a $K_D$ value could not be calculated, n/b means no binding with detected in this assay.

Example 3: An Exemplary Anti-EGFR TriTAC™ Directs T Cells to Kill EGFR Expressing Ovarian Cancer Cells A human T-cell dependent cellular cytotoxicity (TDCC) assay is used to measure the ability of T cell engagers, including trispecific molecules, to direct T cells to kill tumor cells (see Nazarian et al. 2015. J Biomol Screen. 20:519-27). The Caov3 cells used in this assay are engineered to express luciferase. T cells from 5 different healthy and target cancer cells Caov3 are mixed together and varying amounts of an exemplary EGFR targeting trispecific molecule of this disclosure is added and the mixture is incubated for 48 hours at 37° C. Caov3 cells and T cells are also incubated for 48 hours at 37° C. with a control trispecific molecule which targets GFP. After 48 hours, the remaining viable tumor cells are quantified by a luminescence assay.

It is observed that the exemplary anti-EGFR TriTAC™ molecule is able to direct the T cells from all 5 healthy donors to kill the target cancer cells Caov3, whereas the control TriTAC™ molecule is not able to direct the T cells from any of the 5 health donors to kill the Caov3 cells.

Example 4: Xenograft Tumor Model

An EGFR targeting trispecific protein of this disclosure is evaluated in a xenograft model. In order to determine efficacy of the exemplary EGFR targeting trispecific molecule in vivo, multiple xenograft tumor models are used. Examples of common tumor cell lines for use in xenograft tumor studies include A549 (non-small cell lung carcinoma) cells, DU-145 (prostate) cells, MCF-7 (breast) cells, Colo 205 (colon) cells, 3T3/]GF-IR (mouse fibroblast) cells, NCI H441 cells, HEP G2 (hepatoma) cells, MDA MB 231 (breast) cells, HT-29 (colon) cells, MDA-MB-435s (breast) cells, U266 cells, SH-SYSY cells, Sk-Mel-2 cells, NCI-H929, RPM18226, and A431 cells. Immune-deficient NOD/scid mice are sub-lethally irradiated (2 Gy) and subcutaneously inoculated with $1 \times 10^6$ tumor cells (e.g., NCI H441 cells) into their right dorsal flank. When tumors reach 100 to 200 mm³, animals are allocated into 3 treatment groups. Groups 2 and 3 are intraperitoneally injected with $1.5 \times 10^7$ activated human T-cells. Three days later, animals from Group 3 are subsequently treated with the exemplary EGFR targeting trispecific antigen-binding protein of. Groups 1 and 2 are only treated with vehicle. Body weight and tumor volume are determined for 30 days, beginning at least 5 days post treatment with the exemplary EGFR targeting trispecific protein.

It is expected that animals treated with the exemplary EGFR targeting trispecific protein have a statistically significant delay in tumor growth in comparison to the respective vehicle-treated control group.

Example 5: Proof-of-Concept Clinical Trial Protocol for Administration of the EGFR Trispecific Antigen-Binding Protein of Example 1 to Ovarian Cancer Patients This is a Phase I/II clinical trial for studying an exemplary EGFR trispecific antigen-binding protein of this disclosure as a treatment for triple negative breast cancer.

Study Outcomes

Primary: Maximum tolerated dose of the exemplary EGFR targeting trispecific protein.

Secondary: To determine whether in vitro response of the exemplary EGFR targeting trispecific proteins associated with clinical response Phase I The maximum tolerated dose (MTD) will be determined in the phase I section of the trial.

1.1 The maximum tolerated dose (MTD) will be determined in the phase I section of the trial.

1.2 Patients who fulfill eligibility criteria will be entered into the trial to EGFR targeting trispecific proteins of the previous examples.

1.3 The goal is to identify the highest dose of EGFR targeting trispecific proteins of the previous examples that can be administered safely without severe or unmanageable side effects in participants. The dose given will depend on the number of participants who have been enrolled in the study prior and how well the dose was tolerated. Not all participants will receive the same dose.

Phase II 2.1 A subsequent phase II section will be treated at the MTD with a goal of determining if therapy with therapy of the exemplary EGFR targeting trispecific protein results in at least a 20% response rate.

Primary Outcome for the Phase II—To determine if therapy of EGFR targeting trispecific protein results in at least 20% of patients achieving a clinical response (blast response, minor response, partial response, or complete response)

Eligibility

Histologically confirmed triple negative breast cancer, showing at least one of the following:

High grade or metaplastic morphology, may have medullary features;

Geographic necrosis, pushing borders, stromal lymphocytic response, increased mitotic count;

Secretory breast carcinomas with ETV6-NTRK3 fusion gene solid growth pattern, high nuclear grade, marked lymphocytic infiltrate and geographic necrosis.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

| SEQ. ID NO. | Name | Sequence |
|---|---|---|
| 1 | EL1 | QVQLQESGGGLVQAGGSLRLSCAASGSIAYIYTMDWYRQAPGKQRELVATSTRDGNVD YAESVKGRFTISRDNAKNTVYLQMNSLKPEDTAVYYCNADLRTAVDLIRANYWGQGTQ VTVSS |
| 2 | EL104 | QVQLQESGGGLVQAGDSLRLSCVVSGRTDSWYVMGWFRQAPGKDREFVAGVSWSYGNT YYADSVKGRFTASRDNAKNTAYLQMNSLNAEDTAVYYCAARVSREVIPTRWDLYNYWG QGTQVTVSS |
| 3 | EL106 | QVQLQESGGGSVQPGGSLRVSCVVSRTIISINAMTWYHQAPGKRRELVAIITSGGETN YADSVKGRFTISRDNAKNTAYLQMNNLKPEDTGVYYCNVVPPLGSWGQGTQVTVSS |
| 4 | EL113 | QVQLQESGGGRVQAGGSLRLSCSASARTLRLYAVGWFRQAPGKEREFVAGIGRSERTY YTDSVKGRFTLSRDNAKNTVFLEMNDLEPEDTAVYFCALTFQTTDMVDVPTTQHEYDY WGRGTQVTVSS |
| 5 | EL12 | QVQLQESGGGLVQAGGSLRLSCAASGSIAYIYTMDWYRQAPGKQRELVATSTHDGNTD YADSVKGRFTISRDNVKNTVYLQMNSLKPEDTAVYYCNADLRTAVDLIRANYWGQGTQ VTVSS |
| 6 | EL120 | QVQLQESGGGLVQPGGSLRLSCAASGSIAYIYTMDWYRQAPGKQRELVATSTRDGNTD YADSVKGRFTISRDNAKDTVYLQMNSLKPEDTAVYYCNADLRTAVDLIRANYWGQGTQ VTVSS |
| 7 | EL133 | QVQLQESGGGLVQAGGSLTLSCAASGRYQMAWFRQAPEKEREFVGTISSGDSTWYTNS VKGRFAISRDSARNTVYLQMNDLKPEDTAIYYCAAALYYRDSRRAADYPYWGQGTQVT VSS |
| 8 | EL138 | QVQLQESGGGRVQAGESLRLSCSTSTRTLKLYAVGWFRQAPGKERDFVAGIGRSERIY YIDSVKGRFTLSRDNAKNTVFLEMNDLEPEDTAVYFCAATFQTSDNVGVPTVQHEYDY WGQGTQVTVSS |
| 9 | EL147 | QVQLQESGGGLVQAGGSLRLSCAASGSIAYIYTMDWYRQAPGKQRELVATSTHDGNTD YADSVKGRFTISRDNAKNTVTLQMNSLKPEDTAVYYCNADLRTAVDLIRANYWGQGTQ VTVSS |
| 10 | EL148 | QVQLQESGGGLVQAGGSLRLSCAASGSIAYIYTMDWYRQAPGKQRELVATFTRDGNTD YADSVKGRFTISRDNAKNTVYLQMNSLKPEDTAVYYCNTDLRTAVDLIRANYWGQGTQ VTVSS |
| 11 | EL15 | QVQLQESGGGLVQAGGSLRLSCAASGSIAYIYTMDWYRQAPGKQRELVATSTHDGNTD YADSLKGRFTISRDNAKNTVYLQMNSLKPEDTAVYYCNADLRTAVDLIRANYWGQGTQ VTVSS |
| 12 | EL153 | QVQLQESGGGSVQAGGSLRLSCAASGRYQMAWFRQAPEKEREFVGTISSGDSTWYTNS LKGRFAISRDSARDTVYLQMNDLKPEDTAVYYCAAALYYRDSRRAADYPYWGQGTQVT VSS |
| 13 | EL16 | QVQLQESGGGLVQTGGSLRLSCAVSGSIVTINAMTWYRQAPGKRRELVAIITSGGETN YADSVKGRFTISRDNAKNTAHLQMNSLNPEDTGVYYCNVVPPLGSWGQGTQVTVSS |
| 14 | EL162 | QVQLQESGGGLVQTGGSLRLSCAVSRSIVSIKSMTWYRQAPGKRRELVALITSGGETN YSDSVKGRFTISRDNAKNTVYLQMNSLKPEDTGVYYCNVVPPLGSWGQGTQVTVSS |
| 15 | EL165 | QVQLQESGGGLVETGGSLRLSCAGSGSTFRHHAMAWFRQTPGKEREFVSAINDHGDRT KYLDSVRGRFTISRDNTDNMVYLQMTDLRPEDTANYSCAAGPLVDYLETTPLVYTYWG HGTQVTVSS |
| 16 | EL17 | QVQLQESGGGLVQAGGSLRLSCAASGSIAYIYTMDWYRQAPGKQRELVATSTHDGNTD YADSVKGRFTISRDNAKNTVYLQMNSLKPEDTAVYYCNADLRTAVDLIRANYWGQGTQ VTVSS |

| SEQ. ID NO. | Name | Sequence |
|---|---|---|
| 17 | EL171 | QVQLQESGGGSVQAGGSLTLSCAASGSIAYIYTMDWYRQAPGKQRELVATSTHDGNTD YADSVKGRFTISRDNAKNTVYLQMNSLKPEDTAVYYCNADLRTAVDLIRANYWGQGTQ VTVSS |
| 18 | EL172 | QVQLQESGGGLVQPGGSLRLSCTASVSIFSVNAVDWYRQSPGKERELVAIMTSDGSTN YGDSVKGRFTISRDNAKNTVYLQMNNLKPEDTAVYYCNTVPPRYWGQGTQVTVSS |
| 19 | EL176 | QVQLQESGGGLVQPGGSLRLSCAASGSIAYIYTMDWYRQAPGKQRELVATSTRDGNID YADSVKGRFTISRDSAKNTVYLQMSSLKPEDTAVYYCNADLRTAVDLIRANYWGQGTQ VTVSS |
| 20 | EL178 | QVQLQESGGGLVQAGGSLTLSCAASGRYQLAWFRQAPEKVREFVGTISSGDSTWYTNS VKGRFAISRDSARNTVYLQMNDLKPEDTAVYYCAAALYYRDSRRAADYPYWGQGTQVT VSS |
| 21 | EL18 | QVQLQESGGGSVQAGGSLRLSCAASGRYHMAWFRQAPEKEREFVGTISSGDSTWYTNS VKGRFAISRDSARNTAYLQMNDLKPEDTAVYYCAAALYYGDSRRAADYPYWGQGTQVT VSS |
| 22 | EL187 | QVQLQESGGGSVQAGGSLRLSCAASGSIAYIYTMDWYRQAPGKQRELVATSTHDGNTD YTDSVKGRFTISRDNAKNTVYLQMNSLKPEDTAVYYCNADLRTAVDLIRANYWGQGTQ VTVSS |
| 23 | EL27 | QVQLQESGGGLVQAGGSLRLSCAASGSIAYIYTMDWYRQTPGKQRELVATSTRDANTD YAGSVKGRFTISRDNAKDTVYLQMNSLKPEDTAVYYCHADLRTAVDLIRANYWGQGTQ VTVSS |
| 24 | EL30 | QVQLQESGGGLVQAGGSLRLSCAASGRYNMAWFRQAPEKEREFVGTITSADSTWYTNS VKGRFAITQDSARNTVYLQMNDLKPEDTAVYYCAAALYYGDSRRAADYPYWGQGTQVT VSS |
| 25 | EL33 | QVQLQESGGGLVQPGGSLRLSCAASGRYQMAWFRQAPEKEREFVGTISSGDSTWYTNS VKGRFAISRDSARTTVYLQMNDLKPEDTAVYYCAAALYYRDSWRAADYPYWGQGTQVT VSS |
| 26 | EL35 | QVQLQESGGGLVQPGESLRLSCAATGRYHLAWFRQAPEKEREFVGTITSADSTWYTNS VKGRFAITRDSARNTVYLQMNDLKPEDTAVYYCAAALYYGDSRRAADYPYWGQGTQVT VSS |
| 27 | EL4 | QVQLQESGGGLVQAGGSLKLSCADSGRSFSNYIMGWFRQAPGKEREFVAGLGWSPGNT YYADSVKGRFTISRDNAKNMVYLQMNSLNPEDTAVYYCAARRGDVIYTTPWNYVYWGQ GTQVTVSS |
| 28 | EL40 | QVQLQESGGGLVQAGGSLRLSCAASGSIAYIYTMDWYRQAPGKQRELVATSTHDGNTD YADSVKGRFTISRDNAKNTVYLQMNSLKPEDTAVYYCNADLRTPVDLIRANYWGQGTQ VTVSS |
| 29 | EL43 | QVQLQESGGGLVQAGGSLRLSCAAPGRYQMAWFRQAPEKEREFVGTISSGDSTWYTNS VKGRFAISRDSARNTVYLQMNDLKSEDTAVYYCAAALYYRDSRRAIDYPYWGQGTQVT VSS |
| 30 | EL44 | QVQLQESGGGSVQAGGSLRLSCAASGLTFSSYAMAWFRQAPGKQRELVARITSGGTTD YADSVKGRFTISRDNAKNTMYLQMNSLKPEDTAVYYCAADLTYRNLLLKLPHYWGQGT QVTVSS |
| 31 | EL51 | QVQLQESGGGLVQAGGSLRLSCAASGNIAYIYTMDWYRQAPGKQRELVATSTHDGSTD YADSVKGRFTISRDNAKNTVYLQMNSLKPEDTAVYYCNADLRTPVDLIRANYWGQGTQ VTVSS |
| 32 | EL56 | QVQLQESGGGLVQPGGSLRLSCAASGSIAYIYTMDWYRQAPGKQRELVATSTWDGNTD YADSVKGRFTISRDNAKNTVYLQMNSLKPEDTAVYYCNADLRTAVDLIRANYWGQGTQ VTVSS |
| 33 | EL6 | QVQLQESGGGLVQAGGSLRLSCAASGSIAYIYTMDWYRQAPGKQRELVATSTHDGNTD YADSVKGRFTISRDNAKNTVYLQMSSLKPDDTAVYYCNADLRTAVDLIRANYWGQGTQ VTVSS |
| 34 | EL64 | QVQLQESGGGLVQAGESLSLSCAASGNDFVITDMHWYRQAPGKQREWVATITRFATTN YADSVKGRFTISRDNAKNTYLQMNSLKPDDTAVYYCKAIGLRGVPDVNRQFEVWGQG TQVTVSS |
| 35 | EL77 | QVQLQESGGGLVQAGGSLRLSCAASGAIAYIYGMGWYRQAPGNQRELVAAISSGGSTD YADSVKGRFTISRDNAKNTVYLQMSSLKPEDTAVYYCNADVRTSRNLVRSDYWGQGTQ VTVSS |

-continued

| SEQ. ID NO. | Name | Sequence |
|---|---|---|
| 36 | EL79 | QVQLQESGGGLVQAGGSLRLSCAASGRYHTAWFRQAPEKEREFVGTISSGDSTWYTNSVKGRFAISRDSARNTVYLQMNDLKPEDTAVYYCAAALYYGDSRRAGDYPYWGQGTQVTVSS |
| 37 | EL83 | QVQLQESGGGLVQAGGSLRLSCAASGNIAYIYTMNWYRQAPGKQRELVATSTHAGNTDYADSVKGRFTISRDNAKNTVYLQMNSLKPEDTAVYYCNVDLRTAVDLIRANYWGQGTQVTVSS |
| 38 | EL88 | QVQLQESGGGLVQPGGSLRLSCAASGNIAYIYTMGWYRQAPGKQRELVATSTHDGNSDYADSVKGRFTISRDNAKNTVYLQMNTLKPDDTAVYYCNADLRTPVDRIRGNFWGQGTQVTVSS |
| 39 | EH1 | EVQLLESGGGLVQPGGSLTLSCAASGSIAYIYTMDWYRQAPGKQRELVATSTRDGNVDYADSVKGRFTISRDNSKNTLYLQMNSLRAEDTAVYYCNADLRTAVDLIRANYWGLGTQVTVSS |
| 40 | EH104 | EVQLLESGGGLVQPGGSLTLSCAASGRTDSWYVMGWFRQAPGKDREFVAGVSWSYGNTYYADSVKGRFTISRDNSKNTLYLQMNSLRAEDTAVYYCAARVSREVIPTRWDLYNYWGLGTQVTVSS |
| 41 | EH113 | EVQLLESGGGLVQPGGSLTLSCAASARTLRLYAVGWFRQAPGKEREFVAGIGRSERTYYTDSVKGRFTISRDNSKNTLYLQMNSLRAEDTAVYYCALTFQTTDMVDVPTTQHEYDYWGLGTQVTVSS |
| 42 | EH16 | EVQLLESGGGLVQPGGSLTLSCAASGSIVTINAMTWYRQAPGKRRELVAIITSGGETNYADSVKGRFTISRDNSKNTLYLQMNSLRAEDTAVYYCNVVPPLGSWGLGTQVTVSS |
| 43 | EH18 | EVQLLESGGGLVQPGGSLTLSCAASGRYHMAWFRQAPGKEREFVGTISSGDSTWYTNSVKGRFTISRDNSKNTLYLQMNSLRAEDTAVYYCAAALYYGDSRRAADYPYWGLGTQVTVSS |
| 44 | EH38 | EVQLLESGGGLVQPGGSLTLSCAASGSTFRHHAMAWFRQTPGKEREFVSAINDHGDRTKYLDSVKGRFTISRDNSKNTLYLQMNSLRAEDTAVYYCAAGPLVDYLETTPLVYTYWGLGTQVTVSS |
| 45 | EH4 | EVQLLESGGGLVQPGGSLTLSCAASGRSFSNYIMGWFRQAPGKEREFVAGLGWSPGNTYYADSVKGRFTISRDNSKNTLYLQMNSLRAEDTAVYYCAARRGDVIYTTPWNYVYWGLGTQVTVSS |
| 46 | EH44 | EVQLLESGGGLVQPGGSLTLSCAASGLTFSSYAMAWFRQAPGKQRELVARITSGGTTDYADSVKGRFTISRDNSKNTLYLQMNSLRAEDTAVYYCAADLTYRNLLLKLPHYWGLGTQVTVSS |
| 47 | EH60 | EVQLLESGGGLVQPGGSLTLSCAASVSIFSVNAVDWYRQSPGKERELVAIMTSDGSTNYDDSVKGRFTISRDNSKNTLYLQMNSLRAEDTAVYYCNTVPPRYWGLGTQVTVSS |
| 48 | EH64 | EVQLLESGGGLVQPGGSLTLSCAASGNDFVITDMHWYRQAPGKREWVATITRFATTNYADSVKGRFTISRDNSKNTLYLQMNSLRAEDTAVYYCKAIGLRGVPDVNRQFEVWGLGTQVTVSS |
| 49 | EH77 | EVQLLESGGGLVQPGGSLTLSCAASGAIAYIYGMGWYRQAPGKQRELVAAISSGGSTDYADSVKGRFTISRDNSKNTLYLQMNSLRAEDTAVYYCNADVRTSRNLVRSDYWGLGTQVTVSS |

| SEQ. ID NO. | Name | CDR1 Sequence |
|---|---|---|
| 50 | EL1 | GSIAYIYTMD |
| 51 | EL104 | GRTDSWYVMG |
| 52 | EL106 | RTIISINAMT |
| 53 | EL113 | ARTLRLYAVG |
| 54 | EL12 | GSIAYIYTMD |
| 55 | EL120 | GSIAYIYTMD |
| 56 | EL133 | GRYQMA |
| 57 | EL138 | TRTLKLYAVG |
| 58 | EL147 | GSIAYIYTMD |
| 59 | EL148 | GSIAYIYTMD |
| 60 | EL15 | GSIAYIYTMD |
| 61 | EL153 | GRYQMA |
| 62 | EL16 | GSIVTINAMT |
| 63 | EL162 | RSIVSIKSMT |
| 64 | EL165 | GSTFRHHAMA |

| SEQ. ID NO. | Name | CDR1 Sequence |
|---|---|---|
| 65 | EL17 | GSIAYIYTMD |
| 66 | EL171 | GSIAYIYTMD |
| 67 | EL172 | VSIFSVNAVD |
| 68 | EL176 | GSIAYIYTMD |
| 69 | EL178 | GRYQLA |
| 70 | EL18 | GRYHMA |
| 71 | EL187 | GSIAYIYTMD |
| 72 | EL27 | GSIAYIYTMD |
| 73 | EL30 | GRYNMA |
| 74 | EL33 | GRYQMA |
| 75 | EL35 | GRYHLA |
| 76 | EL4 | GRSFSNYIMG |
| 77 | EL40 | GSIAYIYTMD |
| 78 | EL43 | GRYQMA |
| 79 | EL44 | GLTFSSYAMA |
| 80 | EL51 | GNIAYIYTMD |
| 81 | EL56 | GSIAYIYTMD |
| 82 | EL6 | GSIAYIYTMD |
| 83 | EL64 | GNDFVITDMH |
| 84 | EL77 | GAIAYIYGMG |
| 85 | EL79 | GRYHTA |
| 86 | EL83 | GNIAYIYTMN |
| 87 | EL88 | GNIAYIYTMG |
| 88 | EH1 | GSIAYIYTMD |
| 89 | EH104 | GRTDSWYVMG |
| 90 | EH113 | ARTLRLYAVG |
| 91 | EH16 | GSIVTINAMT |
| 92 | EH18 | GRYHMA |
| 93 | EH38 | GSTFRHHAMA |
| 94 | EH4 | GRSFSNYIMG |
| 95 | EH44 | GLTFSSYAMA |
| 96 | EH60 | VSIFSVNAVD |
| 97 | EH64 | GNDFVITDMH |
| 98 | EH77 | GAIAYIYGMG |

| SEQ. ID NO. | Name | CDR2 Sequence |
|---|---|---|
| 99 | EL1 | TSTRDGNVDYAESVKG |
| 100 | EL104 | VSWSYGNTYYADSVKG |
| 101 | EL106 | IITSGGETNYADSVKG |
| 102 | EL113 | GIGRSERTYYTDSVKG |
| 103 | EL12 | TSTHDGNTDYADSVKG |
| 104 | EL120 | TSTRDGNTDYADSVKG |
| 105 | EL133 | TISSGDSTWYTNSVKG |
| 106 | EL138 | GIGRSERIYYIDSVKG |
| 107 | EL147 | TSTHDGNTDYADSVKG |
| 108 | EL148 | TFTRDGNTDYADSVKG |
| 109 | EL15 | TSTHDGNTDYADSLKG |
| 110 | EL153 | TISSGDSTWYTNSLKG |
| 111 | EL16 | IITSGGETNYADSVKG |
| 112 | EL162 | LITSGGETNYSDSVKG |
| 113 | EL165 | AINDHGDRTKYLDSVRG |
| 114 | EL17 | TSTHDGNTDYADSVKG |
| 115 | EL171 | TSTHDGNTDYADSVKG |
| 116 | EL172 | IMTSDGSTNYGDSVKG |
| 117 | EL176 | TSTRDGNIDYADSVKG |
| 118 | EL178 | TISSGDSTWYTNSVKG |
| 119 | EL18 | TISSGDSTWYTNSVKG |
| 120 | EL187 | TSTHDGNTDYTDSVKG |
| 121 | EL27 | TSTRDANTDYAGSVKG |
| 122 | EL30 | TITSADSTWYTNSVKG |
| 123 | EL33 | TISSGDSTWYTNSVKG |
| 124 | EL35 | TITSADSTWYTNSVKG |
| 125 | EL4 | GLGWSPGNTYYADSVKG |
| 126 | EL40 | TSTHDGNTDYADSVKG |
| 127 | EL43 | TISSGDSTWYTNSVKG |
| 128 | EL44 | RITSGGTTDYADSVKG |
| 129 | EL51 | TSTHDGSTDYADSVKG |
| 130 | EL56 | TSTWDGNTDYADSVKG |
| 131 | EL6 | TSTHDGNTDYADSVKG |
| 132 | EL64 | TITRFATTNYADSVKG |
| 133 | EL77 | AISSGGSTDYADSVKG |
| 134 | EL79 | TISSGDSTWYTNSVKG |
| 135 | EL83 | TSTHAGNTDYADSVKG |
| 136 | EL88 | TSTHDGNSDYADSVKG |
| 137 | EH1 | TSTRDGNVDYADSVKG |

| SEQ. ID NO. | Name | CDR2 Sequence |
|---|---|---|
| 138 | EH104 | GVSWSYGNTYYADSVKG |
| 139 | EH113 | GIGRSERTYYTDSVKG |
| 140 | EH16 | IITSGGETNYADSVKG |
| 141 | EH18 | TISSGDSTWYTNSVKG |
| 142 | EH38 | AINDHGDRTKYLDSVKG |
| 143 | EH4 | GLGWSPGNTYYADSVKG |
| 144 | EH44 | RITSGGTTDYADSVKG |
| 145 | EH60 | IMTSDGSTNYDDSVKG |
| 146 | EH64 | TITRFATTNYADSVKG |
| 147 | EH77 | AISSGGSTDYADSVKG |

| SEQ. ID NO. | Name | CDR3 Sequence |
|---|---|---|
| 148 | EL1 | DLRTAVDLIRANY |
| 149 | EL104 | RVSREVIPTRWDLYNY |
| 150 | EL106 | VPPLGS |
| 151 | EL113 | TFQTTDMVDVPTTQHEYDY |
| 152 | EL12 | DLRTAVDLIRANY |
| 153 | EL120 | DLRTAVDLIRANY |
| 154 | EL133 | ALYYRDSRRAADYPY |
| 155 | EL138 | TFQTSDNVGVPTVQHEYDY |
| 156 | EL147 | DLRTAVDLIRANY |
| 157 | EL148 | DLRTAVDLIRANY |
| 158 | EL15 | DLRTAVDLIRANY |
| 159 | EL153 | ALYYRDSRRAADYPY |
| 160 | EL16 | VPPLGS |
| 161 | EL162 | VPPLGS |
| 162 | EL165 | GPLVDYLETTPLVYTY |
| 163 | EL17 | DLRTAVDLIRANY |
| 164 | EL171 | DLRTAVDLIRANY |
| 165 | EL172 | VPPRY |
| 166 | EL176 | DLRTAVDLIRANY |
| 167 | EL178 | ALYYRDSRRAADYPY |
| 168 | EL18 | ALYYGDSRRAADYPY |
| 169 | EL187 | DLRTAVDLIRANY |
| 170 | EL27 | DLRTAVDLIRANY |
| 171 | EL30 | ALYYGDSRRAADYPY |
| 172 | EL33 | ALYYRDSWRAADYPY |

| SEQ. ID NO. | Name | CDR3 Sequence |
|---|---|---|
| 173 | EL35 | ALYYGDSRRAADYPY |
| 174 | EL4 | RRGDVIYTTPWNYVY |
| 175 | EL40 | DLRTPVDLIRANY |
| 176 | EL43 | ALYYRDSRRAIDYPY |
| 177 | EL44 | DLTYRNLLLKLPHY |
| 178 | EL51 | DLRTPVDLIRANY |
| 179 | EL56 | DLRTAVDLIRANY |
| 180 | EL6 | DLRTAVDLIRANY |
| 181 | EL64 | IGLRGVPDVNRQFEV |
| 182 | EL77 | DVRTSRNLVRSDY |
| 183 | EL79 | ALYYGDSRRAGDYPY |
| 184 | EL83 | DLRTAVDLIRANY |
| 185 | EL88 | DLRTPVDRIRGNF |
| 186 | EH1 | DLRTAVDLIRANY |
| 187 | EH104 | RVSREVIPTRWDLYNY |
| 188 | EH113 | TFQTTDMVDVPTTQHEYDY |
| 189 | EH16 | VPPIGS |
| 190 | EH18 | ALYYGDSRRAADYPY |
| 191 | EH38 | GPLVDYLETTPLVYTY |
| 192 | EH4 | RRGDVIYTTPWNYVY |
| 193 | EH44 | DLTYRNLLLKLPHY |
| 194 | EH60 | VPPRY |
| 195 | EH64 | IGLRGVPDVNRQFEV |
| 196 | EH77 | DVRTSRNLVRSDY |

| SEQ ID NO: | Description | AA Sequence |
|---|---|---|
| 197 | Linker | $(GS)_n$ |
| 198 | Linker | $(GGS)_n$ |
| 199 | Linker | $(GGGS)_n$ |
| 200 | Linker | $(GGSG)_n$ |
| 201 | Linker | $(GGSGG)_n$ |
| 202 | Linker | $(GGGGS)_n$ |
| 203 | Linker | $(GGGGG)_n$ |
| 204 | Linker | $(GGG)_n$ |

| SEQ ID NO: | Description | AA Sequence |
|---|---|---|
| 205 | Anti-HSA sdAb clone 6C | EVQLVESGGGLVQPGNSLRLSCAASGFTFSRFGMSWVRQAPGKGLEWVSS ISGSGSDTLYADSVKGRFTISRDNAKTTLYLQMNSLRPEDTAVYYCTIGG SLSRSSQGTLVTVSS |
| 206 | Anti-HSA sdAb clone 7A | EVQLVESGGGLVQPGNSLRLSCAASGFTFSKFGMSWVRQAPGKGLEWVSS ISGSGADTLYADSLKGRFTISRDNAKTTLYLQMNSLRPEDTAVYYCTIGG SLSKSSQGTLVTVSS |
| 207 | Anti-HSA sdAb clone 7G | EVQLVESGGGLVQPGNSLRLSCAASGFTYSSFGMSWVRQAPGKGLEWVSS ISGSGSDTLYADSVKGRFTISRDNAKTTLYLQMNSLRPEDTAVYYCTIGG SLSKSSQGTLVTVSS |
| 208 | Anti-HSA sdAb clone 8H | EVQLVESGGGLVQPGNSLRLSCAASGFTFSKFGMSWVRQAPGKGLEWVSS ISGSGTDTLYADSVKGRFTISRDNAKTTLYLQMNSLRPEDTAVYYCTIGG SLSRSSQGTLVTVSS |
| 209 | Anti-HSA sdAb clone 9A | EVQLVESGGGLVQPGNSLRLSCAASGFTFSRFGMSWVRQAPGKGLEWVSS ISGSGSDTLYADSVKGRFTISRDNAKTTLYLQMNSLRPEDTAVYYCTIGG SLSKSSQGTLVTVSS |
| 210 | Anti-HSA sdAb clone 10G | EVQLVESGGGLVQPGNSLRLSCAASGFTFSKFGMSWVRQAPGKGLEWVSS ISGSGRDTLYADSVKGRFTISRDNAKTTLYLQMNSLRPEDTAVYYCTIGG SLSVSSQGTLVTVSS |
| 211 | wt anti-HSA | EVQLVESGGGLVQPGNSLRLSCAASGFTFSSFGMSWVRQAPGKGLEWVSS ISGSGSDTLYADSVKGRFTISRDNAKTTLYLQMNSLRPEDTAVYYCTIGG SLSRSSQGTLVTVSS |
| 212 | Anti-HSA sdAb clone 6CE | EVQLVESGGGLVQPGNSLRLSCAASGFTFSRFGMSWVRQAPGKGLEWVSS ISGSGSDTLYAESVKGRFTISRDNAKTTLYLQMNSLRPEDTAVYYCTIGG SLSRSSQGTLVTVSS |
| 213 | Anti-HSA sdAb clone 8HE | EVQLVESGGGLVQPGNSLRLSCAASGFTFSKFGMSWVRQAPGKGLEWVSS ISGSGTDTLYAESVKGRFTISRDNAKTTLYLQMNSLRPEDTAVYYCTIGG SLSRSSQGTLVTVSS |
| 214 | Anti-HSA sdAb clone 10GE | EVQLVESGGGLVQPGNSLRLSCAASGFTFSKFGMSWVRQAPGKGLEWVSS ISGSGRDTLYAESVKGRFTISRDNAKTTLYLQMNSLRPEDTAVYYCTIGG SLSVSSQGTLVTVSS |
| 215 | wt anti-HSA CDR1 | GFTFSSFGMS |
| 216 | wt anti-HSA CDR2 | SISGSGSDTLYADSVK |
| 217 | wt anti-HSACDR3 | GGSLSR |
| 218 | CDR1 variant 1 | GFTFSRFGMS |
| 219 | CDR1 variant 2 | GFTFSKFGMS |
| 220 | CDR1 variant 3 | GFTYSSFGMS |
| 221 | CDR2 variant 1 | SISGSGADTLYADSLK |
| 222 | CDR2 variant 2 | SISGSGTDTLYADSVK |
| 223 | CDR2 variant 3 | SISGSGRDTLYADSVK |
| 224 | CDR2 variant 4 | SISGSGSDTLYAESVK |
| 225 | CDR2 variant 5 | SISGSGTDTLYAESVK |
| 226 | CDR2 variant 6 | SISGSGRDTLYAESVK |
| 227 | CDR3 variant 1 | GGSLSK |
| 228 | CDR3 variant 2 | GGSLSV |

| SEQ ID NO: | Description | AA Sequence |
|---|---|---|
| 229 | Anti-CD3, clone 2B2 | EVQLVESGGGLVQPGGSLKLSCAASGFTFNKYAINWVRQAPGKGLEWVAR<br>IRSKYNNYATYYADQVKDRFTISRDDSKNTAYLQMNNLKTEDTAVYYCVR<br>HANFGNSYISYWAYWGQGTLVTVSSGGGGSGGGGSGGGGSQTVVTQEPSL<br>TVSPGGTVTLTCASSTGAVTSGNYPNWVQQKPGQAPRGLIGGTKFLVPGT<br>PARFSGSLLGGKAALTLSGVQPEDEAEYYCTLWYSNRWVFGGGTKLTVL |
| 230 | Anti-CD3, clone 9F2 | EVQLVESGGGLVQPGGSLKLSCAASGFEFNKYAMNWVRQAPGKGLEWVAR<br>IRSKYNKYATYYADSVKDRFTISRDDSKNTAYLQMNNLKTEDTAVYYCVR<br>HGNFGNSYISYWAYWGQGTLVTVSSGGGGSGGGGSGGGGSQTVVTQEPSL<br>TVSPGGTVTLTCGSSFGAVTSGNYPNWVQQKPGQAPRGLIGGTKFLAPGT<br>PARFSGSLLGGKAALTLSGVQPEDEAEYYCVLWYDNRWVFGGGTKLTVL |
| 231 | Anti-CD3, clone 5A2 | EVQLVESGGGLVQPGGSLKLSCAASGFTFNKYAMNWVRQAPGKGLEWVAR<br>IRSKYNNYATYYADSVKDRFTISRDDSKNTAYLQMNNLKTEDTAVYYCVR<br>HGNFGNSHISYWAYWGQGTLVTVSSGGGGSGGGGSGGGGSQTVVTQEPSL<br>TVSPGGTVTLTCGSSTGYVTSGNYPNWVQQKPGQAPRGLIGGTSFLAPGT<br>PARFSGSLLGGKAALTLSGVQPEDEAEYYCVLWYSNRWIFGGGTKLTVL |
| 232 | Anti-CD3, clone 6A2 | EVQLVESGGGLVQPGGSLKLSCAASGFMFNKYAMNWVRQAPGKGLEWVAR<br>IRSKSNNYATYYADSVKDRFTISRDDSKNTAYLQMNNLKTEDTAVYYCVR<br>HGNFGNSYISYWATWGQGTLVTVSSGGGGSGGGGSGGGGSQTVVTQEPSL<br>TVSPGGTVTLTCGSSFGAVTSGNYPNWVQQKPGQAPRGLIGGTKLLAPGT<br>PARFSGSLLGGKAALTLSGVQPEDEAEYYCVLWYSNSWVFGGGTKLTVL |
| 233 | Anti-CD3, clone 2D2 | EVQLVESGGGLVQPGGSLKLSCAASGFTFNTYAMNWVRQAPGKGLEWVAR<br>IRSKYNNYATYYKDSVKDRFTISRDDSKNTAYLQMNNLKTEDTAVYYCVR<br>HGNFGNSPISYWAYWGQGTLVTVSSGGGGSGGGGSGGGGSQTVVTQEPSL<br>TVSPGGTVTLTCGSSTGAVVSGNYPNWVQQKPGQAPRGLIGGTEFLAPGT<br>PARFSGSLLGGKAALTLSGVQPEDEAEYYCVLWYSNRWVFGGGTKLTVL |
| 234 | Anti-CD3, clone 3F2 | EVQLVESGGGLVQPGGSLKLSCAASGFTYNKYAMNWVRQAPGKGLEWVAR<br>IRSKYNNYATYYADEVKDRFTISRDDSKNTAYLQMNNLKTEDTAVYYCVR<br>HGNFGNSPISYWAYWGQGTLVTVSSGGGGSGGGGSGGGGSQTVVTQEPSL<br>TVSPGGTVTLTCGSSKGAVTSGNYPNWVQQKPGQAPRGLIGGTKELAPGT<br>PARFSGSLLGGKAALTLSGVQPEDEAEYYCTLWYSNRVFGGGTKLTVL |
| 235 | Anti-CD3, clone 1A2 | EVQLVESGGGLVQPGGSLKLSCAASGNTFNKYAMNWVRQAPGKGLEWVAR<br>IRSKYNNYETYYADSVKDRFTISRDDSKNTAYLQMNNLKTEDTAVYYCVR<br>HTNFGNSYISYWAYWGQGTLVTVSSGGGGSGGGGSGGGGSQTVVTQEPSL<br>TVSPGGTVTLTCGSSTGAVSGYYPNWVQQKPGQAPRGLIGGTYFLAPGT<br>PARFSGSLLGGKAALTLSGVQPEDEAEYYCVLWYSNRWVFGGGTKLTVL |
| 236 | Anti-CD3, clone 1C2 | EVQLVESGGGLVQPGGSLKLSCAASGFTFNNYAMNWVRQAPGKGLEWVAR<br>IRSKYNNYATYYADAVKDRFTISRDDSKNTAYLQMNNLKTEDTAVYYCVR<br>HGNFGNSQISYWAYWGQGTLVTVSSGGGGSGGGGSGGGGSQTVVTQEPSL<br>TVSPGGTVTLTCGSSTGAVTDGNYPNWVQQKPGQAPRGLIGGIKFLAPGT<br>PARFSGSLLGGKAALTLSGVQPEDEAEYYCVLWYSNRWVFGGGTKLTVL |
| 237 | Anti-CD3, clone 2E4 | EVQLVESGGGLVQPGGSLKLSCAASGFTFNKYAVNWVRQAPGKGLEWVAR<br>IRSKYNNYATYYADSVKDRFTISRDDSKNTAYLQMNNLKTEDTAVYYCVR<br>HGNFGNSYISYWAYWGQGTLVTVSSGGGGSGGGGSGGGGSQTVVTQEPSL<br>TVSPGGTVTLTCGESTGAVTSGNYPNWVQQKPGQAPRGLIGGTKILAPGT<br>PARFSGSLLGGKAALTLSGVQPEDEAEYYCVLWYSNRWVFGGGTKLTVL |
| 238 | Anti-CD3, clone 10E4 | EVQLVESGGGLVQPGGSLKLSCAASGFTFNKYPMNWVRQAPGKGLEWVAR<br>IRSKYNNYATYYADSVKDRFTISRDDSKNTAYLQMNNLKNEDTAVYYCVR<br>HGNFNNSYISYWAYWGQGTLVTVSSGGGGSGGGGSGGGGSQTVVTQEPSL<br>TVSPGGTVTLTCGSSTGAVTKGNYPNWVQQKPGQAPRGLIGGTKMLAPGT<br>PARFSGSLLGGKAALTLSGVQPEDEAEYYCALWYSNRWVFGGGTKLTVL |
| 239 | Anti-CD3, clone 2H2 | EVQLVESGGGLVQPGGSLKLSCAASGFTFNGYAMNWVRQAPGKGLEWVAR<br>IRSKYNNYATYYADEVKDRFTISRDDSKNTAYLQMNNLKTEDTAVYYCVR<br>HGNFGNSPISYWAYWGQGTLVTVSSGGGGSGGGGSGGGGSQTVVTQFPSL<br>TVSPGGTVTLTCGSSTGAVVSGNYPNWVQQKPGQAPRGLIGGTEFLAPGT<br>PARFSGSLLGGKAALTLSGVQPEDEAEYYCVLWYSNRWVFGGGTKLTVL |
| 240 | Anti-CD3, clone 2A4 | EVQLVESGGGLVQPGGSLKLSCAASGNTFNKYAMNWVRQAPGKGLEWVAR<br>IRSKYNNYATYYADSVKDRFTISRDDSKNTAYLQMNNLKTEDTAVYYCVR<br>HGNFGDSYISYWAYWGQGTLVTVSSGGGGSGGGGSGGGGSQTVVTQFPSL<br>TVSPGGTVTLTCGSSTGAVTHGNYPNWVQQKPGQAPRGLIGGTKVLAPGT<br>PARFSGSLLGGKAALTLSGVQPEDEAEYYCVLWYSNRWVFGGGTKLTVL |
| 241 | Anti-CD3, clone 10B2 | EVQLVESGGGLVQPGGSLKLSCAASGFTFNNYAMNWVRQAPGKGLEWVAR<br>IRSGYNNYATYYADSVKDRFTISRDDSKNTAYLQMNNLKTEDTAVYYCVR<br>HGNFGNSYISYWAYWGQGTLVTVSSGGGGSGGGGSGGGGSQTVVTQEPSL<br>TVSPGGTVTLTCGSYTGAVTSGNYPNWVQQKPGQAPRGLIGGTKFNAPGT<br>PARFSGSLLGGKAALTLSGVQPEDEAEYYCVLWYANRWVFGGGTKLTVL |

| SEQ ID NO: | Description | AA Sequence |
|---|---|---|
| 242 | Anti-CD3, clone 1G4 | EVQLVESGGGLVQPGGSLKLSCAASGFEFNKYAMNWVRQAPGKGLEWVAR<br>IRSKYNNYETYYADSVKDRFTISRDDSKNTAYLQMNNLKTEDTAVYYCVR<br>HGNFGNSLISYWAYWGQGTLVTVSSGGGGSGGGGSGGGGSQTVVTQEPSL<br>TVSPGGTVTLTCGSSSGAVTSGNYPNWVQQKPGQAPRGLIGGTKFGAPGT<br>PARFSGSLLGGKAALTLSGVQPEDEAEYYCVLWYSNRWVFGGGTKLTVL |
| 243 | wt anti-CD3 | EVQLVESGGGLVQPGGSLKLSCAASGFTFNKYAMNWVRQAPGKGLEWVAR<br>IRSKYNNYATYYADSVKDRFTISRDDSKNTAYLQMNNLKTEDTAVYYCVR<br>HGNFGNSYISYWAYWGQGTLVTVSSGGGGSGGGGSGGGGSQTVVTQEPSL<br>TVSPGGTVTLTCGSSTGAVTSGNYPNWVQQKPGQAPRGLIGGTKFLAPGT<br>PARFSGSLLGGKAALTLSGVQPEDEAEYYCVLWYSNRWVFGGGTKLTVL |
| 244 | Anti-CD3, clone 2G5 | EVQLVESGGGLVQPGGSLKLSCAASGFTFNKYALNWVRQAPGKGLEWVAR<br>IRSKYNNYATEYADSVKDRFTISRDDSKNTAYLQMNNLKTEDTAVYYCVR<br>HGNFGNSPISYWAYWGQGTLVTVSSGGGGSGGGGSGGGGSQTVVTQEPSL<br>TVSPGGTVTLTCGSSTGAVTSGNYPNWVQQKPGQAPRGLIGGTNFLAPGT<br>PERFSGSLLGGKAALTLSGVQPEDEAEYYCVLWYSNRWAFGGGTKLTVL |
| 245 | Anti-CD3, clone 8A5 | EVQLVESGGGLVQPGGSLKLSCAASGFTFNEYAMNWVRQAPGKGLEWVAR<br>IRSKYNNYATYYADDVKDRFTISRDDSKNTAYLQMNNLKTEDTAVYYCVR<br>HGNFGNSGISYWAYWGQGTLVTVSSGGGGSGGGGSGGGGSQTVVTQEPSL<br>TVSPGGTVTLTCGSSTGAVTVGNYPNWVQQKPGQAPRGLIGGTEFLAPGT<br>PARFSGSLLGGKAALTLSGVQPEDEAEYYCVLWYSNRWVFGGGTKLTVL |

| SEQ ID NO: | Description | AA Sequence |
|---|---|---|
| 246 | Linker | GGGGSGGGS |
| 247 | Histidine tag | HHHHHH |

CD3 Binding Domain CDR Sequences

| SEQ ID NO: | CD3 Binding Domain CDR | Sequence |
|---|---|---|
| 248 | HC CDR1 variant 1 | GNTFNKYAMN |
| 249 | HC CDR1 variant 2 | GFEFNKYAMN |
| 250 | HC CDR1 variant 3 | GFMFNKYAMN |
| 251 | HC CDR1 variant 4 | GFTYNKYAMN |
| 252 | HC CDR1 variant 5 | GFTFNNYAMN |
| 253 | HC CDR1 variant 6 | GFTFNGYAMN |
| 254 | HC CDR1 variant 7 | GFTFNTYAMN |
| 255 | HC CDR1 variant 8 | GFTFNEYAMN |
| 256 | HC CDR1 variant 9 | GFTFNKYPMN |
| 257 | HC CDR1 variant 10 | GFTFNKYAVN |
| 258 | HC CDR1 variant 11 | GFTFNKYAIN |
| 259 | HC CDR1 variant 12 | GFTFNKYALN |
| 260 | HC CDR2 variant 1 | RIRSGYNNYATYYADSVK |
| 261 | HC CDR2 variant 2 | RIRSKSNNYATYYADSVK |
| 262 | HC CDR2 variant 3 | RIRSKYNKYATYYADSVK |
| 263 | HC CDR2 variant 4 | RIRSKYNNYETYYADSVK |
| 264 | HC CDR2 variant 5 | RIRSKYNNYATEYADSVK |
| 265 | HC CDR2 variant 6 | RIRSKYNNYATYYKDSVK |
| 266 | HC CDR2 variant 7 | RIRSKYNNYATYYADEVK |
| 267 | HC CDR2 variant 8 | RIRSKYNNYATYYADAVK |
| 268 | HC CDR2 variant 9 | RIRSKYNNYATYYADQVK |
| 269 | HC CDR2 variant 10 | RIRSKYNNYATYYADDVK |
| 270 | HC CDR3 variant 1 | HANFGNSYISYWAY |
| 271 | HC CDR3 variant 2 | HTNFGNSYISYWAY |
| 272 | HC CDR3 variant 3 | HGNFNNSYISYWAY |
| 273 | HC CDR3 variant 4 | HGNFGDSYISYWAY |

-continued

| SEQ ID NO: | CD3 Binding Domain CDR | Sequence |
|---|---|---|
| 274 | HC CDR3 variant 5 | HGNFGNSHISYWAY |
| 275 | HC CDR3 variant 6 | HGNFGNSPISYWAY |
| 276 | HC CDR3 variant 7 | HGNFGNSQISYWAY |
| 277 | HC CDR3 variant 8 | HGNFGNSLISYWAY |
| 278 | HC CDR3 variant 9 | HGNFGNSGISYWAY |
| 279 | HC CDR3 variant 10 | HGNFGNSYISYWAT |
| 280 | LC CDR1 variant 1 | ASSTGAVTSGNYPN |
| 281 | LC CDR1 variant 2 | GESTGAVTSGNYPN |
| 282 | LC CDR1 variant 3 | GSYTGAVTSGNYPN |
| 283 | LC CDR1 variant 4 | GSSFGAVTSGNYPN |
| 284 | LC CDR1 variant 5 | GSSKGAVTSGNYPN |
| 285 | LC CDR1 variant 6 | GSSSGAVTSGNYPN |
| 286 | LC CDR1 variant 7 | GSSTGYVTSGNYPN |
| 287 | LC CDR1 variant 8 | GSSTGAVVSGNYPN |
| 288 | LC CDR1 variant 9 | GSSTGAVTDGNYPN |
| 289 | LC CDR1 variant 10 | GSSTGAVTKGNYPN |
| 290 | LC CDR1 variant 11 | GSSTGAVTHGNYPN |
| 291 | LC CDR1 variant 12 | GSSTGAVTVGNYPN |
| 292 | LC CDR1 variant 13 | GSSTGAVTSGYYPN |
| 293 | LC CDR2 variant 1 | GIKFLAP |
| 294 | LC CDR2 variant 2 | GTEFLAP |

-continued

| SEQ ID NO: | CD3 Binding Domain CDR | Sequence |
|---|---|---|
| 295 | LC CDR2 variant 3 | GTYFLAP |
| 296 | LC CDR2 variant 4 | GTSFLAP |
| 297 | LC CDR2 variant 5 | GTNFLAP |
| 298 | LC CDR2 variant 6 | GTKLLAP |
| 299 | LC CDR2 variant 7 | GTKELAP |
| 300 | LC CDR2 variant 8 | GTKILAP |
| 301 | LC CDR2 variant 9 | GTKMLAP |
| 302 | LC CDR2 variant 10 | GTKVLAP |
| 303 | LC CDR2 variant 11 | GTKFNAP |
| 304 | LC CDR2 variant 12 | GTKFGAP |
| 305 | LC CDR2 variant 13 | GTKFLVP |
| 306 | LC CDR3 variant 1 | TLWYSNRWV |
| 307 | LC CDR3 variant 2 | ALWYSNRWV |
| 308 | LC CDR3 variant 3 | VLWYDNRWV |
| 309 | LC CDR3 variant 4 | VLWYANRWV |
| 310 | LC CDR3 variant 5 | VLWYSNSWV |
| 311 | LC CDR3 variant 6 | VLWYSNRWI |
| 312 | LC CDR3 variant 7 | VLWYSNRWA |

| SEQ ID NO: | Description | Sequence |
|---|---|---|
| 313 | Sortase | LPETG |

| SEQ ID NO: | Description | AA Sequence |
|---|---|---|
| 314 | Linker | GGGGSGGGGSGGGGS |
| 315 | Linker | GGGGSGGGGSGGGGSGGGGS |
| 316 | EGFR-human | >tr\|Q504U8\|Q504U8_HUMAN Receptor protein-tyrosine kinase OS = Homo sapiens OX = 9606 GN = EGFR PE = 1 SV = 1 MRPSGTAGAALLALLAALCPASRALEEKKVCQGTSNKLTQLGTFEDHFLS LQRMFNNCEVVLGNLEITYVQRNYDLSFLKTIQEVAGYVLIALNTVERIP LENLQIIRGNMYYENSYALAVLSNYDANKTGLKELPMRNLQGQKCDPSCP NGSCWGAGEENCQKLTKIICAQQCSGRCRGKSPSDCCHNQCAAGCTGPRE SDCLVCRKFRDEATCKDTCPPLMLYNPTTYQMDVNPEGKYSFGATCVKKC PRNYVVTDHGSCVRACGADSYEMEEDGVRKCKKCEGPCRKVCNGIGIGEF KDSLSINATNIKHFKNCTSISGDLHILPVAFRGDSFTHTPPLDPQELDIL KTVKEITGFLLIQAWPENRTDLHAFENLEIIRGRTKQHGQFSLAVVSLNI TSLGLRSLKEISDGDVIISGNKNLCYANTINWKKLFGTSGQKTKIISNRG ENSCKATGQVCHALCSPEGCWGPEPRDCVSCRNVSRGRECVDKCNLLEGE PREFVENSECIQCHPECLPQAMNITCTGRGPDNCIQCAHYIDGPHCVKTC RAGVMGENNTLVWKYADAGHVCHLCHPNCTYGCTGPGLEGCPTNGPKIPS IATGMVGALLLLLVVALGIGLFMRRRHIVRKRTLRRLLQERELVEPLTPS GEAPNQALLRILKETEFKKIKVLGSGAFGTVYKGLWIPEGEKVKIPVAIK ELREATSPKANKEILDEAYVMASVDNPHVCRLLGICLTSTVQLITQLMPF GCLLDYVREHKDNIGSQYLLNWCVQIAKGMNYLEDRRLVHRDLAARNVLV KTPQHVKITDFGLAKLLGAEEKEYHAEGGKVPIKWMALESILHRIYTHQS DVWSYGVTVWELMTFGSKPYDGIPASEISSILEKGERLPQPPICTIDVYM IMVKCWMIDADSRPKFRELIIEFSKMARDPQRYLVIQGDERMHLPSPTDS NFYRALMDEEDMDDVVDADEYLIPQQGFFSSPSTSRTPLLSSLSATSNNS TVACIDRNGLQSCPIKEDSFLQRYSSDPTGALTEDSIDDTFLPVPGEWLV WKQSCSSTSSTHSAAASLQCPSQVLPPASPEGETVADLQTQ |
| 317 | EGFR_Mouse | >sp\|Q01279\|EGFR_MOUSE Epidermal growth factor receptor OS = Mus musculus OX = 10090 GN = Egfr PE = 1 S = 1 MRPSGTARTTLLVLLTALCAAGGALEEKKVCQGTSNRLTQLGTFEDHFLS LQRMYNNCEVVLGNLEITYVQRNYDLSFLKTIQEVAGYVLIALNTVERIP LENLQIIRGNALYENTYALAILSNYGTNRTGLRELPMRNLQEILIGAVRF SNNPILCNMDTIQWRDIVQNVFMSNMSMDLQSHPSSCPKCDPSCPNGSCW GGGEENCQKLTKIICAQQCSHRCRGRSPSDCCHNQCAAGCTGPRESDCLV CQKFQDEATCKDTCPPLMLYNPTTYQMDVNPEGKYSFGATCVKKCPRNYV VTDHGSCVRACGPDYYEVEEDGIRKCKKCDGPCRKVCNGIGIGEFKDTLS INATNIKHFKYCTAISGDLHILPVAFKGDSFTRTPPLDPRELEILKTVKE ITGFLLIQAWPDNWTDLHAFENLEIIRGRTKQHGQFSLAVVGLNITSLGL RSLKEISDGDVIISGNRNLCYANTINWKKLFGTPNQKTKIMNNRAEKDCK AVNHVCNPLCSSEGCWGPEPRDCVSCQNVSRGRECVEKCNILEGEPREFV ENSECIQCHPECLPQAMNITCTGRGPDNCIQCAHYIDGPHCVKTCPAGIM GENNTLVWKYADANNVCHLCHANCTYGCAGPGLQGCEVWPSGPKIPSIAT GIVGGLLFIVVVALGIGLFMRRHIVRKRTLRRLLQERELVEPLTPSGEA PNQAHLRILKETEFKKIKVLGSGAFGTVYKGLWIPEGEKVKIPVAIKELR EATSPKANKEILDEAYVMASVDNPHVCRLLGICLTSTVQLITQLMPYGCL LDYVREHKDNIGSQYLLNWCVQIAKGMNYLEDRRLVHRDLAARNVLVKTP QHVKITDFGLAKLLGAEEKEYHAEGGKVPIKWMALESILHRIYTHQSDVW SYGVTVWELMTFGSKPYDGIPASDISSILEKGERLPQPPICTIDVYMIMV KCWMIDADSRPKFRELILEFSKMARDPQRYLVIQGDERMHLPSPTDSNFY RALMDEEDMEDVVDADEYLIPQQGFFNSPSTSRTPLLSSLSATSNNSTVA CINRNGSCRVKEDAFLQRYSSDPTGAVTEDNIDDAFLPVPEYVNQSVPKR RAGSVQNPVYHNQPLHPAPGRDLHYQNPHSNAVGNPEYLNTAQPTCLSSG FNSPALWIQKGSHQMSLDNPDYQQDFFPKETKPNGIFKGPTAENAEYLRV APPSSEFIGA |
| 318 | FGFR_Cynomolgus | >tr\|A0A2K5WK39\|A0A2K5WK39_MACFA Receptor protein-tyrosine kinase OS = Macaca fascicularis OX = 9541 GN = EGFR PE = 3 SV = 1 MRPSGTAGAALLALLAALCPASRALEEKKVCQGTSNKLTQLGTFEDHFLS LQRMENNCEVVLGNLEITYVQRNYDLSFLKTIQEVAGYVLIALNTVERIP LENLQIIRGNMYYENSYALAVLSNYDANKTGLKELPMRNLQEILHGAVRF SNNPALCNVESIQWRDIVSSEFLSNMSMDFQNHLGSCQKCDPSCPNGSCW GAGEENCQKLTKIICAQQCSGRCRGKSPSDCCHNQCAAGCTGPRESDCLV CRKFRDEATCKDTCPPLMLYNPTTYQMDVNPEGKYSFGATCVKKCPRNYV VTDHGSCVRACGADSYEMEEDGVRKCKKCEGPCRKVCNGIGIGEFKDTLS INATNIKHFKNCTSISGDLHILPVAFRGDSFTHTPPLDPQELDILKTVKE ITGFLLIQAWPENRTDLHAFENLEIIRGRTKQHGQFSLAVVSLNITSLGL RSLKEISDGDVIISGNKNLCYANTINWKKLFGTSSQKTKIISNRGENSCK ATGQVCHALCSPEGCWGPEPRDCVSCQNVSRGRECVDKCNILEGEPREFV ENSECIQCHPECLPQVMNITCTGRGPDNCIQCAHYIDGPHCVKTCPAGVM GENNTLVWKYADAGHVCHLCHPNCTYGCTGPGLEGCARNGPKIPSIATGM VGALLLLLVVALGIGLFMRRHIVRKRTLRRLLQERELVEPLTPSGEAPN QALLRILKETEFKKIKVLGSGAFGTVYKGLWIPEGEKVKIPVAIKELREA TSPKANKEILDEAYVMASVDNPHVCRLLGICLTSTVQLITQLMPFGCLLD YVREHKDNIGSQYLLNWCVQIAKGMNYLEDRRLVHRDLAARNVLVKTPQH |

| SEQ ID NO: | Description | AA Sequence |
|---|---|---|
| | | VKITDFGLAKLLGAFEKEYHAEGGKVPIKWMALESILHRIYTHQSDVWSY<br>GVTVWELMTFGSKPYDGIPASEISSILEKGERLPQPPICTIDVYMIMVKC<br>WMIDADSRPKFRELIIEFSKMARDPQRYLVIQGDERMHLPSPTDSNFYRA<br>LMDEEDMDDVVDADEYLIPQQGFFSSPSTSRTPLLSSLSATSNNSTVACI<br>DRNGLQSCPIKEDSFLQRYSSDPTGALTEDSIDDTFLPVPEYINQSVPKR<br>RAGSVQNPVYHNQPLNPAPSRDPHYQDPHSTAVGNPEYLNTVQPTCVNST<br>FDSPAHWAQKGSHQISLDNPDYQQDFFPKEAKPNGIFKGSTAENAEYLRV<br>APQSSEFIGA |

| SEQ. ID NO. | Name | Sequence |
|---|---|---|
| 319 | Exemplary EL1 TriTAC sequence | QVQLQESGGGLVQAGGSLRLSCAASGSIAYIYTMDWYRQAPGKQRELV<br>ATSTRDGNVDYAESVKGRFTISRDNAKNTVYLQMNSLKPEDTAVYYCN<br>ADLRTAVDLIRANYWGQGTQVTVSSGGGGSGGGGSEVQLVESGGGLVQP<br>GNSLRLSCAASGFTFSKFGMSWVRQAPGKGLEWVSSISGSGRDTLYAD<br>SVKGRFTISRDNAKTTLYLQMNSLRPEDTAVYYCTIGGSLSVSSQGTL<br>VTVSSGGGGSGGGGSEVQLVESGGGLVQPGGSLKLSCAASGFTFNKYAI<br>NWVRQAPGKGLEWVARIRSKYNNYATYYADQVKDRFTISRDDSKNTAY<br>LQMNNLKTEDTAVYYCVRHANFGNSYISYWAYWGQGTLVTVSSGGGGS<br>GGGGSGGGGSQTVVTQEPSLTVSPGGTVTLTCASSTGAVTSGNYPNWV<br>QQKPGQAPRGLIGGTKELVPGTPARFSGSLLGGKAALTLSGVQPEDEA<br>EYYCTLWYSNRWVFGGGTKLTVLHHHHHH** |
| 320 | Exemplary EL104 TriTAC sequence | QVQLQESGGGLVQAGDSLRLSCVVSGRTDSWYVMGWERQAPGKDREFV<br>AGVSWSYGNTYYADSVKGRFTASRDNAKNTAYLQMNSLNAEDTAVYYC<br>AARVSREVIPTRWDLYNYWGQGTQVTVSSGGGGSGGGGSEVQLVESGGG<br>LVQPGNSLRLSCAASGFTFSKFGMSWVRQAPGKGLEWVSSISGSGRDT<br>LYADSVKGRFTISRDNAKTTLYLQMNSLRPEDTAVYYCTIGGSLSVSS<br>QGTLVTVSSGGGGSGGGGSEVQLVESGGGLVQPGGSLKLSCAASGFTFN<br>KYAINWVRQAPGKGLEWVARIRSKYNNYATYYADQVKDRFTISRDDSK<br>NTAYLQMNNLKTEDTAVYYCVRHANEGNSYISYWAYWGQGTLVTVSSG<br>GGGSGGGGSGGGGSQTVVTQEPSLTVSPGGTVTLTCASSTGAVTSGNY<br>PNWVQQKPGQAPRGLIGGTKFLVPGTPARFSGSLLGGKAALTLSGVQP<br>EDEAEYYCTLWYSNRWVFGGGTKLTVLHHHHHH** |
| 321 | Exemplary EL106 TriTAC sequence | QVQLQESGGGSVQPGGSLRVSCVVSRTIISINAMTWYHQAPGKRRELV<br>AIITSGGETNYADSVKGRFTISRDNAKNTAYLQMNNLKPEDTGVYYCN<br>VVPPLGSWGQGTQVTVSSGGGGSGGGGSEVQLVESGGGLVQPGNSLRLS<br>CAASGFTFSKFGMSWVRQAPGKGLEWVSSISGSGRDTLYADSVKGRFT<br>ISRDNAKTTLYLQMNSLRPEDTAVYYCTIGGSLSVSSQGTLVTVSSGG<br>GGSGGGGSEVQLVESGGGLVQPGGSLKLSCAASGFTFNKYAINWVRQAP<br>GKGLEWVARIRSKYNNYATYYADQVKDRFTISRDDSKNTAYLQMNNLK<br>TEDTAVYYCVRHANFGNSYISYWAYWGQGTLVTVSSGGGGSGGGGSGG<br>GGSQTVVTQEPSLTVSPGGTVTLTCASSTGAVTSGNYPNWVQQKPGQA<br>PRGLIGGTKFLVPGTPARFSGSLLGGKAALTLSGVQPEDEAEYYCTLW<br>YSNRWVFGGGTKLTVLHHHHHH** |
| 322 | Exemplary EL113 TriTAC sequence | QVQLQESGGGRVQAGGSLRLSCSASARTLRLYAVGWFRQAPGKEREFV<br>AGIGRSERTYYTDSVKGRFTLSRDNAKNTVFLEMNDLEPEDTAVYFCA<br>LTFQTTDMVDVPTTQHEYDYWGRGTQVTVSSGGGGSGGGGSEVQLVESG<br>GGLVQPGNSLRLSCAASGFTFSKFGMSWVRQAPGKGLEWVSSISGSGR<br>DTLYADSVKGRFTISRDNAKTTLYLQMNSLRPEDTAVYYCTIGGSLSV<br>SSQGTLVTVSSGGGGSGGGGSEVQLVESGGGLVQPGGSLKLSCAASGFT<br>FNKYAINWVRQAPGKGLEWVARIRSKYNNYATYYADQVKDRFTISRDD<br>SKNTAYLQMNNLKTEDTAVYYCVRHANFGNSYISYWAYWGQGTLVTVS<br>SGGGGSGGGGSGGGGSQTVVTQEPSLTVSPGGTVTLTCASSTGAVTSG<br>NYPNWVQQKPGQAPRGLIGGTKFLVPGTPARFSGSLLGGKAALTLSGV<br>QPEDEAEYYCTLWYSNRWVFGGGTKLTVLHHHHHH** |
| 323 | Exemplary EL12 TriTAC sequence | QVQLQESGGGLVQAGGSLRLSCAASGSIAYIYTMDWYRQAPGKQRELV<br>ATSTHDGNITYADSVKGRFTISRDNVKNTVYLQMNSLKPEDTAVYYCN<br>ADLRTAVDLIRANYWGQGTQVTVSSGGGGSGGGGSEVQLVESGGGLVQP<br>GNSLRLSCAASGFTFSKFGMSWVRQAPGKGLEWVSSISGSGRDTLYAD<br>SVKGRFTISRDNAKTTLYLQMNSLRPEDTAVYYCTIGGSLSVSSQGTL<br>VTVSSGGGGSGGGGSEVQLVESGGGLVQPGGSLKLSCAASGFTFNKYAI<br>NWVRQAPGKGLEWVARIRSKYNNYATYYADQVKDRFTISRDDSKNTAY<br>LQMNNLKTEDTAVYYCVRHANFGNSYISYWAYWGQGTLVTVSSGGGGS<br>GGGGSGGGGSQTVVTQEPSLTVSPGGTVTLTCASSTGAVTSGNYPNWV<br>QQKPGQAPRGLIGGTKFLVPGTPARFSGSLLGGKAALTLSGVQPEDEA<br>EYYCTLWYSNRWVFGGGTKLTVLHHHHHH** |

| SEQ. ID NO. | Name | Sequence |
|---|---|---|
| 324 | Exemplary EL120 TriTAC sequence | QVQLQESGGGLVQPGGSLRLSCAASGSIAYIYTMDWYRQAPGKQRELV ATSTRDGNITYADSVKGRFTISRDNAKDTVYLQMNSLKPEDTAVYYCN ADLRTAVDLIRANYWGQGTQVTVSSGGGGSGGGSEVQLVESGGGLVQP GNSLRLSCAASGFTFSKFGMSWVRQAPGKGLEWVSSISGSGRDTLYAD SVKGRFTISRDNAKTTLYLQMNSLRPEDTAVYYCTIGGSLSVSSQGTL VTVSSGGGGSGGGSEVQLVESGGGLVQPGGSLKLSCAASGFTFNKYAI NWVRQAPGKGLEWVARIRSKYNNYATYYADQVKDRFTISRDDSKNTAY LQMNNLKTEDTAVYYCVRHANFGNSYISYWAYWGQGTLVTVSSGGGGS GGGGSGGGGSQTVVTQEPSLTVSPGGTVTLTCASSTGAVTSGNYPNWV QQKPGQAPRGLIGGTKFLVPGTPARFSGSLLGGKAALTLSGVQPEDEA EYYCTLWYSNRWVFGGGTKLTVLHHHHHH** |
| 325 | Exemplary EL133 TriTAC sequence | QVQLQESGGGLVQAGGSLTLSCAASGRYQMAWFRQAPEKEREFVGTIS SGDSTWYTNSVKGRFAISRDSARNTVYLQMNDLKPEDTAIYYCAAALY YRDSRRAADYPYWGQGTQVTVSSGGGGSGGGSEVQLVESGGGLVQPGN SLRLSCAASGFTFSKFGMSWVRQAPGKGLEWVSSISGSGRDTLYADSV KGRFTISRDNAKTTLYLQMNSLRPEDTAVYYCTIGGSLSVSSQGTLVT VSSGGGGSGGGSEVQLVESGGGLVQPGGSLKLSCAASGFTFNKYAINW VRQAPGKGLEWVARIRSKYNNYATYYADQVKDRFTISRDDSKNTAYLQ MNNLKTEDTAVYYCVRHANFGNSYISYWAYWGQGTLVTVSSGGGGSGG GGSGGGGSQTVVTQEPSLTVSPGGTVTLICASSTGAVTSGNYPNWVQQ KPGQAPRGLIGGTKFLVPGTPARFSGSLLGGKAALTLSGVQPEDEAEY YCTLWYSNRWVFGGGTKLTVLHHHHHH** |
| 326 | Exemplary EL138 TriTAC sequence | QVQLQESGGGRVQAGESLRLSCSTSTRTLKLYAVGWFRQAPGKERDFV AGIGRSERIYYIDSVKGRFTLSRDNKNTVFLEMNDLEPEDTAVYFCA ATFQTSDNVGVPTVQHEYDYWGQGTQVTVSSGGGGSGGGSEVQLVESG GGLVQPGNSLRLSCAASGETFSKFGMSWVRQAPGKGLEWVSSISGSGR DTLYADSVKGRFTISRDNAKTTLYLQMNSLRPEDTAVYYCTIGGSLSV SSQGTLVTVSSGGGGSGGGSEVQLVESGGGLVQPGGSLKLSCAASGFT FNKYAINWVRQAPGKGLEWVARIRSKYNNYATYYADQVKDRFTISRDD SKNTAYLQMNNLKTEDTAVYYCVRHANFGNSYISYWAYWGQGTLVTVS SGGGGSGGGGSGGGSQTVVTQEPSLTVSPGGTVTLICASSTGAVTSG NYPNWVQQKPGQAPRGLIGGTKFLVPGTPARFSGSLLGGKAALTLSGV QPEDEAEYYCTLWYSNRWVFGGGTKLTVLHHHHHH** |
| 327 | Exemplary EL147 TriTAC sequence | QVQLQESGGGLVQAGGSLRLSCAASGSIAYIYTMDWYRQAPGKQRELV ATSTHDGNIDYADSVKGRFTISRDNAKNIVTLQMNSLKPEDTAVYYCN ADLRTAVDLIRANYWGQGTQVTVSSGGGGSGGGSEVQLVESGGGLVQP GNSLRLSCAASGFTFSKFGMSWVRQAPGKGLEWVSSISGSGRDTLYAD SVKGRFTISRDNAKTTLYLQMNSLRPEDTAVYYCTIGGSLSVSSQGTL VTVSSGGGGSGGGSEVQLVESGGGLVQPGGSLKLSCAASGFTENKYAI NWVRQAPGKGLEWVARIRSKYNNYATYYADQVKDRFTISRDDSKNTAY LQMNNLKTEDTAVYYCVRHANFGNSYISYWAYWGQGTLVTVSSGGGGS GGGGSGGGGSQTVVTQEPSLTVSPGGTVTLICASSTGAVTSGNYPNWV QQKPGQAPRGLIGGTKFLVPGTPARFSGSLLGGKAALTLSGVQPEDEA EYYCTLWYSNRWVFGGGTKLTVLHHHHHH** |
| 328 | Exemplary EL148 TriTAC sequence | QVQLQESGGGLVQAGGSLRLSCAASGSIAYIYTMDWYRQAPGKQRELV ATFTRDGNIDYADSVKGRFTISRDNAKNTVYLQMNSLKPEDTAVYYCN TDLRTAVDLIRANYWGQGTQVTVSSGGGGSGGGSEVQLVESGGGLVQP GNSLRLSCAASGFTFSKFGMSWVRQAPGKGLEWVSSISGSGRDTLYAD SVKGRFTISRDNAKTTLYLQMNSLRPEDTAVYYCTIGGSLSVSSQGTL VTVSSGGGGSGGGSEVQLVESGGGLVQPGGSLKLSCAASGFTFNKYAI NWVRQAPGKGLEWVARIRSKYNNYATYYADQVKDRFTISRDDSKNTAY LQMNNLKTEDTAVYYCVRHANFGNSYISYWAYWGQGTLVTVSSGGGGS GGGGSGGGGSQTVVTQEPSLTVSPGGTVTLICASSTGAVTSGNYPNWV QQKPGQAPRGLIGGTKFLVPGTPARFSGSLLGGKAALTLSGVQPEDEA EYYCTLWYSNRWVFGGGTKLTVLHHHHHH** |
| 329 | Exemplary EL15 TriTAC sequence | QVQLQESGGGLVQAGGSLRLSCAASGSIAYIYTMDWYRQAPGKQRELV ATSTHDGNITYADSLKGRFTISRDNAKNTVYLQMNSLKPEDTAVYYCN ADLRTAVDLIRANYWGQGTQVTVSSGGGGSGGGSEVQLVESGGGLVQP GNSLRLSCAASGFTFSKFGMSWVRQAPGKGLEWVSSISGSGRDTLYAD SVKGRFTISRDNAKTTLYLQMNSLRPEDTAVYYCTIGGSLSVSSQGTL VTVSSGGGGSGGGSEVQLVESGGGLVQPGGSLKLSCAASGFTENKYAI NWVRQAPGKGLEWVARIRSKYNNYATYYADQVKDRFTISRDDSKNTAY LQMNNLKTEDTAVYYCVRHANFGNSYISYWAYWGQGTLVTVSSGGGGS GGGGSGGGGSQTVVTQEPSLTVSPGGTVTLTCASSTGAVTSGNYPNWV QQKPGQAPRGLIGGTKFLVPGTPARFSGSLLGGKAALTLSGVQPEDEA EYYCTLWYSNRWVFGGGTKLTVLHHHHHH** |
| 330 | Exemplary EL153 TriTAC sequence | QVQLQESGGGSVQAGGSLRLSCAASGRYQMAWFRQAPEKEREFVGTIS SGDSTWYTNSLKGRFAISRDSARDTVYLQMNDLKPEDTAVYYCAAALY YRDSRRAADYPYWGQGTQVTVSSGGGGSGGGSEVQLVESGGGLVQPGN |

| SEQ. ID NO. | Name | Sequence |
|---|---|---|
| | | SLRLSCAASGFTFSKFGMSWVRQAPGKGLEMVSSISGSGRDTLYADSV<br>KGRFTISRDNAKTTLYLQMNSLRPEDTAVYYCTIGGSLSVSSQGTLVT<br>VSSGGGGSGGGSEVQLVESGGGLVQPGGSLKLSCAASGFTFNKYAINW<br>VRQAPGKGLEWVARIRSKYNNYATYYADQVKDRFTISRDDSKNTAYLQ<br>MNNLKTEDTAVYYCVRHANFGNSYISYWAYWGQGTLVTVSSGGGGSGG<br>GGSGGGGSQTVVTQEPSLTVSPGGTVTLTCASSTGAVTSGNYPNWVQQ<br>KPGQAPRGLIGGTKFLVPGTPARFSGSLLGGKAALTLSGVQPEDEAEY<br>YCTLWYSNRWVFGGGTKLTVLHHHHHH** |
| 331 | Exemplary EL16 TriTAC sequence | QVQLQESGGGLVQTGGSLRLSCAVSGSIVTINAMTWYRQAPGKRRELV<br>AIITSGGETNYADSVKGRFTISRDNAKNTAHLQMNSLNPEDTGVYYCN<br>VVPPLGSWGQGTQVTVSSGGGGSGGGSEVQLVESGGGLVQPGNSLRLS<br>CAASGFTFSKFGMSWVRQAPGKGLEWVSSISGSGRDTLYADSVKGRFT<br>ISRDNAKTTLYLQMNSLRPEDTAVYYCTIGGSLSVSSQGTLVTVSSGG<br>GGSGGGGSEVQLVESGGGLVQPGGSLKLSCAASGFTFNKYAINWVRQAP<br>GKGLEWVARIRSKYNNYATYYADQVKDRFTISRDDSKNTAYLQMNNLK<br>TEDTAVYYCVRHANFGNSYISYWAYWGQGTLVTVSSGGGGSGGGGSGG<br>GGSQTVVTQEPSLTVSPGGTVTLTCASSTGAVTSGNYPNWVQQKPGQA<br>PRGLIGGTKFLVPGTPARFSGSLLGGKAALTLSGVQPEDEAEYYCTLW<br>YSNRWVFGGGTKLTVLHHHHHH** |
| 332 | Exemplary EL162 TriTAC sequence | QVQLQESGGGLVQTGGSLRLSCAVSRSIVSIKSMTWYRQAPGKRRELV<br>ALITSGGETNYSDSVKGRFTISRDNAKNTVYLQMNSLKPEDTGVYYCN<br>VVPPLGSWGQGTQVTVSSGGGGSGGGSEVQLVESGGGLVQPGNSLRLS<br>CAASGFTFSKFGMSWVRQAPGKGLEWVSSISGSGRDTLYADSVKGRFT<br>ISRDNAKTTLYLQMNSLRPEDTAVYYCTIGGSLSVSSQGTLVTVSSGG<br>GGSGGGGSEVQLVESGGGLVQPGGSLKLSCAASGFTENKYAINWVRQAP<br>GKGLEWVARIRSKYNNYATYYADQVKDRFTISRDDSKNTAYLQMNNLK<br>TEDTAVYYCVRHANFGNSYISYWAYWGQGTLVTVSSGGGGSGGGGSGG<br>GGSQTVVTQEPSLTVSPGGTVTLTCASSTGAVTSGNYPNWVQQKPGQA<br>PRGLIGGTKFLVPGTPARFSGSLLGGKAALTLSGVQPEDEAEYYCTLW<br>YSNRWVFGGGTKLTVLHHHHHH** |
| 333 | Exemplary EL165 TriTAC sequence | QVQLQESGGGLVETGGSLRLSCAGSGSTFRHHAMAWFRQTPGKEREFV<br>SAINDHGDRTKYLDSVRGRFTISRDNIDNMVYLQMTDLRPEDTANYSC<br>AAGPLVDYLETTPLVYTYWGHGTQVTVSSGGGGSGGGSEVQLVESGGG<br>LVQPGNSLRLSCAASGFTFSKFGMSWVRQAPGKGLEWVSSISGSGRDT<br>LYADSVKGRFTISRDNAKTTLYLQMNSLRPEDTAVYYCTIGGSLSVSS<br>QGTLVTVSSGGGGSGGGGSEVQLVESGGGLVQPGGSLKLSCAASGFTFN<br>KYAINWVRQAPGKGLEWVARIRSKYNNYATYYADQVKDRFTISRDDSK<br>NTAYLQMNNLKTEDTAVYYCVRHANFGNSYISYWAYWGQGTLVTVSSG<br>GGGSGGGGSGGGGSQTVVTQEPSLTVSPGGTVTLTCASSTGAVTSGNY<br>PNWVQQKPGQAPRGLIGGTKFLVPGTPARFSGSLLGGKAALTLSGVQP<br>EDEAEYYCTLWYSNRWVFGGGTKLTVLHHHHHH** |
| 334 | Exemplary EL17 TriTAC sequence | QVQLQESGGGLVQAGGSLRLSCAASGSIAYIYTMDWYRQAPGKQRELV<br>ATSTHDGNITYADSVKGRFTISRDNAKNTVYLQMNSLKPEDTAVYYCN<br>ADLRTAVDLIRANYWGQGTQVTVSSGGGGSGGGSEVQLVESGGGLVQP<br>GNSLRLSCAASGFTFSKFGMSWVRQAPGKGLEWVSSISGSGRDTLYAD<br>SVKGRFTISRDNAKTTLYLQMNSLRPEDTAVYYCTIGGSLSVSSQGTL<br>VTVSSGGGGSGGGSEVQLVESGGGLVQPGGSLKLSCAASGFTFNKYAI<br>NWVRQAPGKGLEWVARIRSKYNNYATYYADQVKDRFTISRDDSKNTAY<br>LQMNNLKTEDTAVYYCVRHANFGNSYISYWAYWGQGTLVTVSSGGGGS<br>GGGGSGGGGSQTVVTQEPSLTVSPGGTVTLTCASSTGAVTSGNYPNWV<br>QQKPGQAPRGLIGGTKFLVPGTPARFSGSLLGGKAALTLSGVQPEDEA<br>EYYCTLWYSNRWVFGGGTKLTVLHHHHHH** |
| 335 | Exemplary EL171 TriTAC sequence | QVQLQESGGGSVQAGGSLTLSCAASGSIAYIYTMDWYRQAPGKQRELV<br>ATSTHDGNITYADSVKGRFTISRDNAKNTVYLQMNSLKPEDTAVYYCN<br>ADLRTAVDLIRANYWGQGTQVTVSSGGGGSGGGSEVQLVESGGGLVQP<br>GNSLRLSCAASGFTFSKFGMSWVRQAPGKGLEWVSSISGSGRDTLYAD<br>SVKGRFTISRDNAKTTLYLQMNSLRPEDTAVYYCTIGGSLSVSSQGTL<br>VTVSSGGGGSGGGSEVQLVESGGGLVQPGGSLKLSCAASGFTENKYAI<br>NWVRQAPGKGLEWVARIRSKYNNYATYYADQVKDRFTISRDDSKNTAY<br>LQMNNLKTEDTAVYYCVRHANFGNSYISYWAYWGQGTLVTVSSGGGGS<br>GGGGSGGGGSQTVVTQEPSLTVSPGGTVTLTCASSTGAVTSGNYPNWV<br>QQKPGQAPRGLIGGTKFLVPGTPARFSGSLLGGKAALTLSGVQPEDEA<br>EYYCTLWYSNRWVFGGGTKLTVLHHHHHH** |
| 336 | Exemplary EL172 TriTAC sequence | QVQLQESGGGLVQPGGSLRLSCTASVSIFSVNAVDWYRQSPGKERELV<br>AIMTSDGSTNYGDSVKGRFTISRDNAKNTVYLQMNNLKPEDTAVYYCN<br>TVPPRYWGQGTQVTVSSGGGGSGGGSEVQLVESGGGLVQPGNSLRLSC<br>AASGFTESKFGMSWVRQAPGKGLEWVSSISGSGRDTLYADSVKGRFTI<br>SRDNAKTTLYLQMNSLRPEDTAVYYCTIGGSLSVSSQGTLVTVSSGGG<br>GSGGGSEVQLVESGGGLVQPGGSLKLSCAASGFTENKYAINWVRQAPG<br>KGLEWVARIRSKYNNYATYYADQVKDRFTISRDDSKNTAYLQMNNLKT |

| SEQ. ID NO. | Name | Sequence |
|---|---|---|
| | | EDTAVYYCVRHANFGNSYISYWAYWGQGTLVTVSSGGGGSGGGGSGGG<br>GSQTVVTQEPSLTVSPGGTVTLICASSTGAVTSGNYPNWVQQKPGQAP<br>RGLIGGTKFLVPGTPARFSGSLLGGKAALTLSGVQPEDEAEYYCTLWY<br>SNRWVFGGGTKLTVLHHHHHH** |
| 337 | Exemplary EL176 TriTAC sequence | QVQLQESGGGLVQPGGSLRLSCAASGSIAYIYTMDWYRQAPGKQRELV<br>ATSTRDGNIDYADSVKGRFTISRDSAKNTVYLQMSSLKPEDTAVYYCN<br>ADLRTAVDLIRANYWGQGTQVTVSSGGGGSGGGGSEVQLVESGGGLVQP<br>GNSLRLSCAASGFTESKFGMSWVRQAPGKGLEWVSSISGSGRDTLYAD<br>SVKGRFTISRDNAKTTLYLQMNSLRPEDTAVYYCTIGGSLSVSSQGTL<br>VTVSSGGGGSGGGGSEVQLVESGGGLVQPGGSLKLSCAASGFTENKYAI<br>NWVRQAPGKGLEWVARIRSKYNNYATYYADQVKDRFTISRDDSKNTAY<br>LQMNNLKTEDTAVYYCVRHANFGNSYISYWAYWGQGTLVTVSSGGGGS<br>GGGGSGGGGSQTVVTQEPSLTVSPGGTVTLICASSTGAVTSGNYPNWV<br>QQKPGQAPRGLIGGTKFLVPGTPARFSGSLLGGKAALTLSGVQPEDEA<br>EYYCTLWYSNRWVFGGGTKLTVLHHHHHH** |
| 338 | Exemplary EL178 TriTAC sequence | QVQLQESGGGLVQAGGSLTLSCAASGRYQLAWFRQAPEKVREFVGTIS<br>SGDSTWYTNSVKGRFAISRDSARNTVYLQMNDLKPEDTAVYYCAAALY<br>YRDSRRAADYPYWGQGTQVTVSSGGGGSGGGGSEVQLVESGGGLVQPGN<br>SLRLSCAASGFTESKFGMSWVRQAPGKGLEWVSSISGSGRDTLYADSV<br>KGRFTISRDNAKTTLYLQMNSLRPEDTAVYYCTIGGSLSVSSQGTLVT<br>VSSGGGGSGGGGSEVQLVESGGGLVQPGGSLKLSCAASGFTENKYAINW<br>VRQAPGKGLEWVARIRSKYNNYATYYADQVKDRFTISRDDSKNTAYLQ<br>MNNLKTEDTAVYYCVRHANFGNSYISYWAYWGQGTLVTVSSGGGGSGG<br>GGSGGGGSQTVVTQEPSLTVSPGGTVTLICASSTGAVTSGNYPNWVQQ<br>KPGQAPRGLIGGTKFLVPGTPARFSGSLLGGKAALTLSGVQPEDEAEY<br>YCTLWYSNRWVFGGGTKLTVLHHHHHH** |
| 339 | Exemplary EL18 TriTAC sequence | QVQLQESGGGSVQAGGSLRLSCAASGRYHMAWFRQAPEKEREFVGTIS<br>SGDSTWYTNSVKGRFAISRDSARNTVYLQMNDLKPEDTAVYYCAAALY<br>YGDSRRAADYPYWGQGTQVTVSSGGGGSGGGGSEVQLVESGGGLVQPGN<br>SLRLSCAASGFTFSKFGMSWVRQAPGKGLEWVSSISGSGRDTLYADSV<br>KGRFTISRDNAKTTLYLQMNSLRPEDTAVYYCTIGGSLSVSSQGTLVT<br>VSSGGGGSGGGGSEVQLVESGGGLVQPGGSLKLSCAASGFTFNKYAINW<br>VRQAPGKGLEWVARIRSKYNNYATYYADQVKDRFTISRDDSKNTAYLQ<br>MNNLKTEDTAVYYCVRHANFGNSYISYWAYWGQGTLVTVSSGGGGSGG<br>GGSGGGGSQTVVTQEPSLTVSPGGTVTLTCASSTGAVTSGNYPNWVQQ<br>KPGQAPRGLIGGTKFLVPGTPARFSGSLLGGKAALTLSGVQPEDEAEY<br>YCTLWYSNRWVFGGGTKLTVLHHHHHH** |
| 340 | Exemplary EL187 TriTAC sequence | QVQLQESGGGSVQAGGSLRLSCAASGSIAYIYTMDWYRQAPGKQRELV<br>ATSTHDGNITYTDSVKGRFTISRDNAKNTVYLQMNSLKPEDTAVYYCN<br>ADLRTAVDLIRANYWGQGTQVTVSSGGGGSGGGGSEVQLVESGGGLVQP<br>GNSLRLSCAASGFTFSKFGMSWVRQAPGKGLEWVSSISGSGRDTLYAD<br>SVKGRFTISRDNAKTTLYLQMNSLRPEDTAVYYCTIGGSLSVSSQGTL<br>VTVSSGGGGSGGGGSEVQLVESGGGLVQPGGSLKLSCAASGFTFNKYAI<br>NWVRQAPGKGLEWVARIRSKYNNYATYYADQVKDRFTISRDDSKNTAY<br>LQMNNLKTEDTAVYYCVRHANFGNSYISYWAYWGQGTLVTVSSGGGGS<br>GGGGSGGGGSQTVVTQEPSLTVSPGGTVTLTCASSTGAVTSGNYPNWV<br>QQKPGQAPRGLIGGTKFLVPGTPARFSGSLLGGKAALTLSGVQPEDEA<br>EYYCTLWYSNRWVFGGGTKLTVLHHHHHH** |
| 341 | Exemplary EL27 TriTAC sequence | QVQLQESGGGLVQAGGSLRLSCAASGSIAYIYTMDWYRQTPGKQRELV<br>ATSTRDANTDYAGSVKGRFTISRDNAKDTVYLQMNSLKPEDTAVYYCH<br>ADLRTAVDLIRANYWGQGTQVTVSSGGGGSGGGGSEVQLVESGGGLVQP<br>GNSLRLSCAASGFTFSKFGMSWVRQAPGKGLEWVSSISGSGRDTLYAD<br>SVKGRFTISRDNAKTTLYLQMNSLRPEDTAVYYCTIGGSLSVSSQGTL<br>VTVSSGGGGSGGGGSEVQLVESGGGLVQPGGSLKLSCAASGFTFNKYAI<br>NWVRQAPGKGLEWVARIRSKYNNYATYYADQVKDRFTISRDDSKNTAY<br>LQMNNLKTEDTAVYYCVRHANFGNSYISYWAYWGQGTLVTVSSGGGGS<br>GGGGSGGGGSQTVVTQEPSLTVSPGGTVTLTCASSTGAVTSGNYPNWV<br>QQKPGQAPRGLIGGTKFLVPGTPARFSGSLLGGKAALTLSGVQPEDEA<br>EYYCTLWYSNRWVFGGGTKLTVLHHHHHH** |
| 342 | Exemplary EL30 TriTAC sequence | QVQLQESGGGLVQAGGSLRLSCAASGRYNMAWFRQAPEKEREFVGTIT<br>SADSTWYTNSVKGRFAITQDSARNTVYLQMNDLKPEDTAVYYCAAALY<br>YGDSRRAADYPYWGQGTQVTVSSGGGGSGGGGSEVQLVESGGGLVQPGN<br>SLRLSCAASGFTFSKFGMSWVRQAPGKGLEWVSSISGSGRDTLYADSV<br>KGRFTISRDNAKTTLYLQMNSLRPEDTAVYYCTIGGSLSVSSQGTLVT<br>VSSGGGGSGGGGSEVQLVESGGGLVQPGGSLKLSCAASGFTFNKYAINW<br>VRQAPGKGLEWVARIRSKYNNYATYYADQVKDRFTISRDDSKNTAYLQ<br>MNNLKTEDTAVYYCVRHANFGNSYISYWAYWGQGTLVTVSSGGGGSGG<br>GGSGGGGSQTVVTQEPSLTVSPGGTVTLTCASSTGAVTSGNYPNWVQQ<br>KPGQAPRGLIGGTKFLVPGTPARFSGSLLGGKAALTLSGVQPEDEAEY<br>YCTLWYSNRWVFGGGTKLTVLHHHHHH** |

| SEQ. ID NO. | Name | Sequence |
|---|---|---|
| 343 | Exemplary EL33 TriTAC sequence | QVQLQESGGGLVQPGGSLRLSCAASGRYQMAWFRQAPEKEREFVGTIS<br>SGDSTWYTNSVKGRFAISRDSARTTVYLQMNDLKPEDTAVYYCAAALY<br>YRDSWRAADYPYWGQGTQVTVSSGGGGSGGGSEVQLVESGGGLVQPGN<br>SLRLSCAASGFTFSKFGMSWVRQAPGKGLEWVSSISGSGRDTLYADSV<br>KGRFTISRDNAKTTLYLQMNSLRPEDTAVYYCTIGGSLSVSSQGTLVT<br>VSSGGGGSGGGSEVQLVESGGGLVQPGGSLKLSCAASGFTFNKYAINW<br>VRQAPGKGLEWVARIRSKYNNYATYYADQVKDRFTISRDDSKNTAYLQ<br>MNNLKTEDTAVYYCVRHANFGNSYISYWAYWGQGTLVTVSSGGGGSGG<br>GGSGGGGSQTVVTQEPSLTVSPGGTVTLTCASSTGAVTSGNYPNWVQQ<br>KPGQAPRGLIGGTKFLVPGTPARFSGSLLGGKAALTLSGVQPEDEAEY<br>YCTLWYSNRWVFGGGTKLTVLHHHHHH** |
| 344 | Exemplary EL35 TriTAC sequence | QVQLQESGGGLVQPGESLRLSCAATGRYHLAWFRQAPEKEREFVGTIT<br>SADSTWYTNSVKGRFAITRDSARNTVYLQMNDLKPEDTAVYYCAAALY<br>YGDSRRAADYPYWGQGTQVTVSSGGGGSGGGSEVQLVESGGGLVQPGN<br>SLRLSCAASGFTFSKFGMSWVRQAPGKGLEMVSSISGSGRDTLYADSV<br>KGRFTISRDNAKTTLYLQMNSLRPEDTAVYYCTIGGSLSVSSQGTLVT<br>VSSGGGGSGGGSEVQLVESGGGLVQPGGSLKLSCAASGFTFNKYAINW<br>VRQAPGKGLEWVARIRSKYNNYATYYADQVKDRFTISRDDSKNTAYLQ<br>MNNLKTEDTAVYYCVRHANFGNSYISYWAYWGQGTLVTVSSGGGGSGG<br>GGSGGGGSQTVVTQEPSLTVSPGGIVTLICASSTGAVTSGNYPNWVQQ<br>KPGQAPRGLIGGTKFLVPGTPARFSGSLLGGKAALTLSGVQPEDEAEY<br>YCTLWYSNRWVFGGGTKLTVLHHHHHH** |
| 345 | Exemplary EL4 TriTAC sequence | QVQLQESGGGLVQAGGSLKLSCADSGRSFSNYIMGWFRQAPGKEREFV<br>AGLGWSPGNTYYADSVKGRFTISRDNAKNMVYLQMNVYLQMNSLKPEDTAVYYC<br>AARRGDVIYTTPWNYVYWGQGTQVTVSSGGGGSGGGSEVQLVESGGGL<br>VQPGNSLRLSCAASGFTFSKFGMSWVRQAPGKGLEWVSSISGSGRDTL<br>YADSVKGRFTISRDNAKTTLYLQMNSLRPEDTAVYYCTIGGSLSVSSQ<br>GTLVTVSSGGGGSGGGSEVQLVESGGGLVQPGGSLKLSCAASGFTFNK<br>YAINWVRQAPGKGLEWVARIRSKYNNYATYYADQVKDRFTISRDDSKN<br>TAYLQMNNLKTEDTAVYYCVRHANFGNSYISYWAYWGQGTLVTVSSGG<br>GGSGGGGSGGGGSQTVVTQEPSLTVSPGGTVTLTCASSTGAVTSGNYP<br>NWVQQKPGQAPRGLIGGTKFLVPGTPARFSGSLLGGKAALTLSGVQPE<br>DEAEYYCTLWYSNRWVFGGGTKLTVLHHHHHH** |
| 346 | Exemplary EL40 TriTAC sequence | QVQLQESGGGLVQAGGSLRLSCAASGSIAYIYTMDWYRQAPGKQRELV<br>ATSTHDGNITYADSVKGRFTISRDNAKNTVYLQMNSLKPEDTAVYYCN<br>ADLRTPVDLIRANYWGQGTQVTVSSGGGGSGGGSEVQLVESGGGLVQP<br>GNSLRLSCAASGFTFSKFGMSWVRQAPGKGLEWVSSISGSGRDTLYAD<br>SVKGRFTISRDNAKTTLYLQMNSLRPEDTAVYYCTIGGSLSVSSQGTL<br>VTVSSGGGGSGGGSEVQLVESGGGLVQPGGSLKLSCAASGFTENKYAI<br>NWVRQAPGKGLEWVARIRSKYNNYATYYADQVKDRFTISRDDSKNTAY<br>LQMNNLKTEDTAVYYCVRHANFGNSYISYWAYWGQGTLVTVSSGGGGS<br>GGGGSGGGGSQTVVTQEPSLTVSPGGTVTLTCASSTGAVTSGNYPNWV<br>QQKPGQAPRGLIGGTKFLVPGTPARFSGSLLGGKAALTLSGVQPEDEA<br>EYYCTLWYSNRWVFGGGTKLTVLHHHHHH** |
| 347 | Exemplary EL43 TriTAC sequence | QVQLQESGGGSVQAGGSLRLSCAAPGRYQMAWFRQAPEKEREFVGTIS<br>SGDSTWYTNSVKGRFAISRDSARNTVYLQMNDLKSEDTAVYYCAAALY<br>YRDSRRAIDYPYWGQGTQVTVSSGGGGSGGGSEVQLVESGGGLVQPGN<br>SLRLSCAASGFTFSKFGMSWVRQAPGKGLEWVSSISGSGRDTLYADSV<br>KGRFTISRDNAKTTLYLQMNSLRPEDTAVYYCTIGGSLSVSSQGTLVT<br>VSSGGGGSGGGSEVQLVESGGGLVQPGGSLKLSCAASGFTFNKYAINW<br>VRQAPGKGLEWVARIRSKYNNYATYYADQVKDRFTISRDDSKNTAYLQ<br>MNNLKTEDTAVYYCVRHANFGNSYISYWAYWGQGTLVTVSSGGGGSGG<br>GGSGGGGSQTVVTQEPSLTVSPGGTVTLTCASSTGAVTSGNYPNWVQQ<br>KPGQAPRGLIGGTKFLVPGTPARFSGSLLGGKAALTLSGVQPEDEAEY<br>YCTLWYSNRWVFGGGTKLTVLHHHHHH** |
| 348 | Exemplary EL44 TriTAC sequence | QVQLQESGGGSVQAGGSLRLSCAASGLTFSSYAMAWFRQAPGKQRELV<br>ARITSGGTTDYADSVKGRFTISRDNAKNTMYLQMNSLKPEDTAVYYCA<br>ADLTYRNLLLKLPHYWGQGTQVTVSSGGGGSGGGSEVQLVESGGGLVQ<br>PGNSLRLSCAASGFTFSKFGMSWVRQAPGKGLEWVSSISGSGRDTLYA<br>DSVKGRFTISRDNAKTTLYLQMNSLRPEDTAVYYCTIGGSLSVSSQGT<br>LVTVSSGGGGSGGGSEVQLVESGGGLVQPGGSLKLSCAASGFTFNKYA<br>INWVRQAPGKGLEWVARIRSKYNNYATYYADQVKDRFTISRDDSKNTA<br>YLQMNNLKTEDTAVYYCVRHANFGNSYISYWAYWGQGTLVTVSSGGGG<br>SGGGGSGGGGSQTVVTQEPSLTVSPGGTVTLTCASSTGAVTSGNYPNW<br>VQQKPGQAPRGLIGGTKFLVPGTPARFSGSLLGGKAALTLSGVQPEDE<br>AEYYCTLWYSNRWVFGGGTKLTVLHHHHHH** |
| 349 | Exemplary EL51 TriTAC sequence | QVQLQESGGGLVQAGGSLRLSCAASGNIAYIYTMDWYRQAPGKQRELV<br>ATSTHDGSTDYADSVKGRFTISRDNAKNTVYLQMNSLKPEDTAVYYCN<br>ADLRTPVDLIRANYWGQGTQVTVSSGGGGSGGGSEVQLVESGGGLVQP |

| SEQ. ID NO. | Name | Sequence |
|---|---|---|
| | | GNSLRLSCAASGFTFSKFGMSWVRQAPGKGLEWVSSISGSGRDTLYAD SVKGRFTISRDNAKTTLYLQMNSLRPEDTAVYYCTIGGSLSVSSQGTL VTVSSGGGGSGGGSEVQLVESGGGLVQPGGSLKLSCAASGFTENKYAI NWVRQAPGKGLEWVARIRSKYNNYATYYADQVKDRFTISRDDSKNTAY LQMNNLKTEDTAVYYCVRHANFGNSYISYWAYWGQGTLVTVSSGGGGS GGGGSGGGSQTVVTQEPSLTVSPGGTVTLTCASSTGAVTSGNYPNWV QQKPGQAPRGLIGGTKFLVPGTPARFSGSLLGGKAALTLSGVQPEDEA EYYCTLWYSNRWVFGGGTKLTVLHHHHHH** |
| 350 | Exemplary EL56 TriTAC sequence | QVQLQESGGGLVQPGGSLRLSCAASGSIAYIYTMDWYRQAPGKQRELV ATSTWDGNITYADSVKGRFTISRDNAKNTVYLQMNSLKPEDTAVYYCN ADLRTAVDLIRANYWGQGTQVTVSSGGGGSGGGSEVQLVESGGGLVQP GNSLRLSCAASGFTFSKFGMSWVRQAPGKGLEWVSSISGSGRDTLYAD SVKGRFTISRDNAKTTLYLQMNSLRPEDTAVYYCTIGGSLSVSSQGTL VTVSSGGGGSGGGSEVQLVESGGGLVQPGGSLKLSCAASGFTFNKYAI NWVRQAPGKGLEWVARIRSKYNNYATYYADQVKDRFTISRDDSKNTAY LQMNNLKTEDTAVYYCVRHANEGNSYISYWAYWGQGTLVTVSSGGGGS GGGGSGGGSQTVVTQEPSLTVSPGGTVTLTCASSTGAVTSGNYPNWV QQKPGQAPRGLIGGTKFLVPGTPARFSGSLLGGKAALTLSGVQPEDEA EYYCTLWYSNRWVFGGGTKLTVLHHHHHH** |
| 351 | Exemplary EL6 TriTAC sequence | QVQLQESGGGLVQAGGSLRLSCAASGSIAYIYTMDWYRQAPGKQRELV ATSTHDGNITYADSVKGRFTISRDNAKNTVYLQMSSLKPDDTAVYYCN ADLRTAVDLIRANYWGQGTQVTVSSGGGGSGGGSEVQLVESGGGLVQP GNSLRLSCAASGFTFSKFGMSWVRQAPGKGLEWVSSISGSGRDTLYAD SVKGRFTISRDNAKTTLYLQMNSLRPEDTAVYYCTIGGSLSVSSQGTL VTVSSGGGGSGGGSEVQLVESGGGLVQPGGSLKLSCAASGFTFNKYAI NWVRQAPGKGLEWVARIRSKYNNYATYYADQVKDRFTISRDDSKNTAY LQMNNLKTEDTAVYYCVRHANFGNSYISYWAYWGQGTLVTVSSGGGGS GGGGSGGGSQTVVTQEPSLTVSPGGTVTLTCASSTGAVTSGNYPNWV QQKPGQAPRGLIGGTKFLVPGTPARFSGSLLGGKAALTLSGVQPEDEA EYYCTLWYSNRWVFGGGTKLTVLHHHHHH** |
| 352 | Exemplary EL64 TriTAC sequence | QVQLQESGGGLVQAGESLSLSCAASGNDFVITDMHWYRQAPGKQREWV ATITRFATTNYADSVKGRFTISRDNAKNTWYLQMNSLKPDDTAVYYCK AIGLRGVPDVNRQFEVWGQGTQVTVSSGGGGSGGGSEVQLVESGGGLV QPGNSLRLSCAASGFTFSKFGMSWVRQAPGKGLEWVSSISGSGRDTLY ADSVKGRFTISRDNAKTTLYLQMNSLRPEDTAVYYCTIGGSLSVSSQG TLVTVSSGGGGSGGGSEVQLVESGGGLVQPGGSLKLSCAASGFTENKY AINWVRQAPGKGLEWVARIRSKYNNYATYYADQVKDRFTISRDDSKNT AYLQMNNLKTEDTAVYYCVRHANFGNSYISYWAYWGQGTLVTVSSGGG GSGGGGSGGGSQTVVTQEPSLTVSPGGTVTLTCASSTGAVTSGNYPN WVQQKPGQAPRGLIGGTKFLVPGTPARFSGSLLGGKAALTLSGVQPED EAEYYCTLWYSNRWVFGGGTKLTVLHHHHHH** |
| 353 | Exemplary EL77 TriTAC sequence | QVQLQESGGGLVQAGGSLRLSCAASGAIAYIYGMGWYRQAPGNQRELV AAISSGGSTDYADSVKGRFTISRDNAKNTVYLQMSSLKPEDTAVYYCN ADVRTSRNLVRSDYWGQGTQVTVSSGGGGSGGGSEVQLVESGGGLVQP GNSLRLSCAASGFTFSKFGMSWVRQAPGKGLEWVSSISGSGRDTLYAD SVKGRFTISRDNAKTTLYLQMNSLRPEDTAVYYCTIGGSLSVSSQGTL VTVSSGGGGSGGGSEVQLVESGGGLVQPGGSLKLSCAASGFTFNKYAI NWVRQAPGKGLEWVARIRSKYNNYATYYADQVKDRFTISRDDSKNTAY LQMNNLKTEDTAVYYCVRHANFGNSYISYWAYWGQGTLVTVSSGGGGS GGGGSGGGSQTVVTQEPSLTVSPGGTVTLTCASSTGAVTSGNYPNWV QQKPGQAPRGLIGGTKFLVPGTPARFSGSLLGGKAALTLSGVQPEDEA EYYCTLWYSNRWVFGGGTKLTVLHHHHHH** |
| 354 | Exemplary EL79 TriTAC sequence | QVQLQESGGGLVQAGGSLRLSCAASGRYHTAWFRQAPEKEREFVGTIS SGDSTWYTNSVKGRFAISRDSARNTVYLQMNDLKPEDTAVYYCAAALY YGDSRRAGDYPYWGQGTQVTVSSGGGGSGGGSEVQLVESGGGLVQPGN SLRLSCAASGFTFSKFGMSWVRQAPGKGLEMVSSISGSGRDTLYADSV KGRFTISRDNAKTTLYLQMNSLRPEDTAVYYCTIGGSLSVSSQGTLVT VSSGGGGSGGGSEVQLVESGGGLVQPGGSLKLSCAASGFTFNKYAINW VRQAPGKGLEWVARIRSKYNNYATYYADQVKDRFTISRDDSKNTAYLQ MNNLKTEDTAVYYCVRHANFGNSYISYWAYWGQGTLVTVSSGGGGSGG GGSGGGSQTVVTQEPSLTVSPGGTVTLICASSTGAVTSGNYPNWVQQ KPGQAPRGLIGGTKFLVPGTPARFSGSLLGGKAALTLSGVQPEDEAEY YCTLWYSNRWVFGGGTKLTVLHHHHHH** |
| 355 | Exemplary EL83 TriTAC sequence | QVQLQESGGGLVQAGGSLRLSCAASGNIAYIYTMNWYRQAPGKQRELV ATSTHAGNITYADSVKGRFTISRDNAKNTVYLQMNSLKPEDTAVYYCN VDLRTAVDLIRANYWGQGTQVTVSSGGGGSGGGSEVQLVESGGGLVQP GNSLRLSCAASGFTFSKFGMSWVRQAPGKGLEWVSSISGSGRDTLYAD SVKGRFTISRDNAKTTLYLQMNSLRPEDTAVYYCTIGGSLSVSSQGTL VTVSSGGGGSGGGSEVQLVESGGGLVQPGGSLKLSCAASGFTFNKYAI NWVRQAPGKGLEWVARIRSKYNNYATYYADQVKDRFTISRDDSKNTAY |

| SEQ. ID NO. | Name | Sequence |
|---|---|---|
| | | LQMNNLKTEDTAVYYCVRHANFGNSYISYWAYWGQGTLVTVSSGGGGS GGGGSGGGGSQTVVTQEPSLTVSPGGTVTLTCASSTGAVTSGNYPNWV QQKPGQAPRGLIGGTKFLVPGTPARFSGSLLGGKAALTLSGVQPEDEA EYYCTLWYSNRWVFGGGTKLTVLHHHHHH** |
| 356 | Exemplary EL88 TriTAC sequence | QVQLQESGGGLVQPGGSLRLSCAASGNIAYIYTMGWYRQAPGKQRELV ATSTHDGNSDYADSVKGRFTISRDNAKNTVYLQMNTLKPDDTAVYYCN ADLRTPVDRIRGNFWGQGTQVTVSSGGGGSGGGGSEVQLVESGGGLVQP GNSLRLSCAASGFTFSKFGMSWVRQAPGKGLEWVSSISGSGRDTLYAD SVKGRFTISRDNAKTTLYLQMNSLRPEDTAVYYCTIGGSLSVSSQGTL VTVSSGGGGSGGGGSEVQLVESGGGLVQPGGSLKLSCAASGFTENKYAI NWVRQAPGKGLEWVARIRSKYNNYATYYADQVKDRFTISRDDSKNTAY LQMNNLKTEDTAVYYCVRHANFGNSYISYWAYWGQGTLVTVSSGGGGS GGGGSGGGGSQTVVTQEPSLTVSPGGTVTLTCASSTGAVTSGNYPNWV QQKPGQAPRGLIGGTKFLVPGTPARFSGSLLGGKAALTLSGVQPEDEA EYYCTLWYSNRWVFGGGTKLTVLHHHHHH** |
| 357 | Exemplary EH1 TriTAC sequence | EVQLLESGGGLVQPGGSLTLSCAASGSIAYIYTMDWYRQAPGKQRELV ATSTRDGNVDYADSVKGRFTISRDNAKNTLYLQMNSLRAEDTAVYYCN ADLRTAVDLIRANYWGLGTQVTVSSGGGGSGGGGSEVQLVESGGGLVQP GNSLRLSCAASGFTFSKEGMSWVRQAPGKGLEWVSSISGSGRDTLYAD SVKGRFTISRDNAKTTLYLQMNSLRPEDTAVYYCTIGGSLSVSSQGTL VTVSSGGGGSGGGGSEVQLVESGGGLVQPGGSLKLSCAASGFTENKYAI NWVRQAPGKGLEWVARIRSKYNNYATYYADQVKDRFTISRDDSKNTAY LQMNNLKTEDTAVYYCVRHANFGNSYISYWAYWGQGTLVTVSSGGGGS GGGGSGGGGSQTVVTQEPSLTVSPGGTVTLICASSTGAVTSGNYPNWV QQKPGQAPRGLIGGTKFLVPGTPARFSGSLLGGKAALTLSGVQPEDEA EYYCTLWYSNRWVFGGGTKLTVLHHHHHH** |
| 358 | Exemplary EH104 TriTAC sequence | EVQLLESGGGLVQPGGSLTLSCAASGRTDSWYVMGWFRQAPGKDREFV AGVSWSYGNTYYADSVKGRFTISRDNKNTLYLQMNSLRAEDTAVYYC AARVSREVIPTRWDLYNYWGLGTQVTVSSGGGGSGGGGSEVQLVESGGG LVQPGNSLRLSCAASGFTESKFGMSWVRQAPGKGLEWVSSISGSGRDT LYADSVKGRFTISRDNAKTTLYLQMNSLRPEDTAVYYCTIGGSLSVSS QGTLVTVSSGGGGSGGGGSEVQLVESGGGLVQPGGSLKLSCAASGFTFN KYAINWVRQAPGKGLEWVARIRSKYNNYATYYADQVKDRFTISRDDSK NTAYLQMNNLKTEDTAVYYCVRHANFGNSYISYWAYWGQGTLVTVSSG GGGSGGGGSGGGGSQTVVTQEPSLTVSPGGTVTLTCASSTGAVTSGNY PNWVQQKPGQAPRGLIGGTKFLVPGTPARFSGSLLGGKAALTLSGVQP EDEAEYYCTLWYSNRWVFGGGTKLTVLHHHHHH** |
| 359 | Exemplary EH113 TriTAC sequence | EVQLLESGGGLVQPGGSLTLSCAASARTLRLYAVGWFRQAPGKEREFV AGIGRSERTYYTDSVKGRFTISRDNSKNTLYLQMNSLRAEDTAVYYCA LTFQTTDMVDVPTTQHEYDYWGLGTQVTVSSGGGGSGGGGSEVQLVESG GGLVQPGNSLRLSCAASGFTFSKFGMSWVRQAPGKGLEWVSSISGSGR DTLYADSVKGRFTISRDNAKTTLYLQMNSLRPEDTAVYYCTIGGSLSV SSQGTLVTVSSGGGGSGGGGSEVQLVESGGGLVQPGGSLKLSCAASGFT FNKYAINWVRQAPGKGLEWVARIRSKYNNYATYYADQVKDRFTISRDD SKNTAYLQMNNLKTEDTAVYYCVRHANFGNSYISYWAYWGQGTLVTVS SGGGGSGGGGSGGGGSQTVVTQEPSLTVSPGGTVTLTCASSTGAVTSG NYPNWVQQKPGQAPRGLIGGTKFLVPGTPARFSGSLLGGKAALTLSGV QPEDEAEYYCTLWYSNRWVFGGGTKLTVLHHHHHH** |
| 360 | Exemplary EH16 TriTAC sequence | EVQLLESGGGLVQPGGSLTLSCAASGSIVTINAMTWYRQAPGKRRELV AIITSGGETNYADSVKGRFTISRDNSKNTLYLQMNSLRAEDTAVYYCN VVPPLGSWGLGTQVTVSSGGGGSGGGGSEVQLVESGGGLVQPGNSLRLS CAASGFTFSKFGMSWVRQAPGKGLEWVSSISGSGRDTLYADSVKGRFT ISRDNAKTTLYLQMNSLRPEDTAVYYCTIGGSLSVSSQGTLVTVSSGG GGSGGGGSEVQLVESGGGLVQPGGSLKLSCAASGFTFNKYAINWVRQAP GKGLEWVARIRSKYNNYATYYADQVKDRFTISRDDSKNTAYLQMNNLK TEDTAVYYCVRHANFGNSYISYWAYWGQGTLVTVSSGGGGSGGGGSGG GGSQTVVTQEPSLTVSPGGTVTLTCASSTGAVTSGNYPNWVQQKPGQA PRGLIGGTKFLVPGTPARFSGSLLGGKAALTLSGVQPEDEAEYYCTLW YSNRWVFGGGTKLTVLHHHHHH** |
| 361 | Exemplary EH18 TriTAC sequence | EVQLLESGGGLVQPGGSLTLSCAASGRYHMAWFRQAPGKEREFVGTIS SGDSTWYTNSVKGRFTISRDNSKNTLYLQMNSLRAEDTAVYYCAAALY YGDSRRAADYPYWGLGTQVTVSSGGGGSGGGGSEVQLVESGGGLVQPGN SLRLSCAASGFTFSKFGMSWVRQAPGKGLEWVSSISGSGRDTLYADSV KGRFTISRDNAKTTLYLQMNSLRPEDTAVYYCTIGGSLSVSSQGTLVT VSSGGGGSGGGGSEVQLVESGGGLVQPGGSLKLSCAASGFTFNKYAINW VRQAPGKGLEWVARIRSKYNNYATYYADQVKDRFTISRDDSKNTAYLQ MNNLKTEDTAVYYCVRHANFGNSYISYWAYWGQGTLVTVSSGGGGSGG GGSGGGGSQTVVTQEPSLTVSPGGIVTLICASSTGAVTSGNYPNWVQQ KPGQAPRGLIGGTKFLVPGTPARFSGSLLGGKAALTLSGVQPEDEAEY YCTLWYSNRWVFGGGTKLTVLHHHHHH** |

| SEQ. ID NO. | Name | Sequence |
|---|---|---|
| 362 | Exemplary EH38 TriTAC sequence | EVQLLESGGGLVQPGGSLTLSCAASGSTFRHHAMAWFRQTPGKEREFV SAINDHGDRTKYLDSVKGRFTISRDNSKNTLYLQMNSLRAEDTAVYYC AAGPLVDYLETTPLVYTYWGLGTQVTVSSGGGGSGGGGSEVQLVESGGG LVQPGNSLRLSCAASGFTFSKFGMSWVRQAPGKGLEWVSSISGSGRDT LYADSVKGRFTISRDNAKTTLYLQMNSLRPEDTAVYYCTIGGSLSVSS QGTLVTVSSGGGGSGGGGSEVQLVESGGGLVQPGGSLKLSCAASGFTFN KYAINWVRQAPGKGLEWVARIRSKYNNYATYYADQVKDRFTISRDDSK NTAYLQMNNLKTEDTAVYYCVRHANFGNSYISYWAYWGQGTLVTVSSG GGGSGGGGSGGGGSQTVVTQEPSLTVSPGGTVTLTCASSTGAVTSGNY PNWVQQKPGQAPRGLIGGTKFLVPGTPARFSGSLLGGKAALTLSGVQP EDEAEYYCTLWYSNRWVFGGGTKLTVLHHHHHH** |
| 363 | Exemplary EH4 TriTAC sequence | EVQLLESGGGLVQPGGSLTLSCAASGRSFSNYIMGWFRQAPGKEREFV AGLGWSPGNTYYADSVKGRFTISRDNSKNTLYLQMNSLRAEDTAVYYC AARRGDVIYTTPWNYVYWGLGTQVTVSSGGGGSGGGGSEVQLVESGGGL VQPGNSLRLSCAASGFTFSKFGMSWVRQAPGKGLEWVSSISGSGRDTL YADSVKGRFTISRDNAKTTLYLQMNSLRPEDTAVYYCTIGGSLSVSSQ GTLVTVSSGGGGSGGGGSEVQLVESGGGLVQPGGSLKLSCAASGFTFNK YAINWVRQAPGKGLEWVARIRSKYNNYATYYADQVKDRFTISRDDSKN TAYLQMNNLKTEDTAVYYCVRHANFGNSYISYWAYWGQGTLVTVSSGG GGSGGGGSGGGGSQTVVTQEPSLTVSPGGTVTLTCASSTGAVTSGNYP NWVQQKPGQAPRGLIGGTKFLVPGTPARFSGSLLGGKAALTLSGVQPE DEAEYYCTLWYSNRWVFGGGTKLTVLHHHHHH** |
| 364 | Exemplary EH44 TriTAC sequence | EVQLLESGGGLVQPGGSLTLSCAASGLIFSSYAMAWFRQAPGKQRELV ARITSGGITDYADSVKGRFTISRDNSKNTLYLQMNSLRAEDTAVYYCA ADLTYRNLLLKLPHYWGLGTQVTVSSGGGGSGGGGSEVQLVESGGGLVQ PGNSLRLSCAASGFTFSKFGMSWVRQAPGKGLEWVSSISGSGRDTLYA DSVKGRFTISRDNAKTTLYLQMNSLRPEDTAVYYCTIGGSLSVSSQGT LVTVSSGGGGSGGGGSEVQLVESGGGLVQPGGSLKLSCAASGFTFNKYA INWVRQAPGKGLEWVARIRSKYNNYATYYADQVKDRFTISRDDSKNTA YLQMNNLKTEDTAVYYCVRHANFGNSYISYWAYWGQGTLVTVSSGGGG SGGGGSGGGGSQTVVTQEPSLTVSPGGTVTLTCASSTGAVTSGNYPNW VQQKPGQAPRGLIGGTKFLVPGTPARFSGSLLGGKAALTLSGVQPEDE AEYYCTLWYSNRWVFGGGTKLTVLHHHHHH** |
| 365 | Exemplary EH60 TriTAC sequence | EVQLLESGGGLVQPGGSLTLSCAASVSIFSVNAVDWYRQSPGKERELV AIMTSDGSTNYDDSVKGRFTISRDNSKNTLYLQMNSLRAEDTAVYYCN TVPPRYWGLGTQVTVSSGGGGSGGGGSEVQLVESGGGLVQPGNSLRLSC AASGFTFSKFGMSWVRQAPGKGLEWVSSISGSGRDTLYADSVKGRFTI SRDNAKTTLYLQMNSLRPEDTAVYYCTIGGSLSVSSQGTLVTVSSGGG GSGGGGSEVQLVESGGGLVQPGGSLKLSCAASGFTFNKYAINWVRQAPG KGLEWVARIRSKYNNYATYYADQVKDRFTISRDDSKNTAYLQMNNLKT EDTAVYYCVRHANFGNSYISYWAYWGQGTLVTVSSGGGGSGGGGSGGGG GSQTVVTQEPSLTVSPGGTVTLICASSTGAVTSGNYPNWVQQKPGQAP RGLIGGTKFLVPGTPARFSGSLLGGKAALTLSGVQPEDEAEYYCTLWY SNRWVFGGGTKLTVLHHHHHH** |
| 366 | Exemplary EH64 TriTAC sequence | EVQLLESGGGLVQPGGSLTLSCAASGNDFVITDMHWYRQAPGKQREWV ATITRFATTNYADSVKGRFTISRDNSKNTLYLQMNSLRAEDTAVYYCK AIGLRGVPDVNRQFEVWGLGTQVTVSSGGGGSGGGGSEVQLVESGGGLV QPGNSLRLSCAASGFTFSKFGMSWVRQAPGKGLEWVSSISGSGRDTLY ADSVKGRFTISRDNAKTTLYLQMNSLRPEDTAVYYCTIGGSLSVSSQG TLVTVSSGGGGSGGGGSEVQLVESGGGLVQPGGSLKLSCAASGETFNKY AINWVRQAPGKGLEWVARIRSKYNNYATYYADQVKDRFTISRDDSKNT AYLQMNNLKTEDTAVYYCVRHANFGNSYISYWAYWGQGTLVTVSSGGG GSGGGGSGGGGSQTVVTQEPSLTVSPGGTVTLTCASSTGAVTSGNYPN WVQQKPGQAPRGLIGGTKFLVPGTPARFSGSLLGGKAALTLSGVQPED EAEYYCTLWYSNRWVFGGGTKLTVLHHHHHH** |
| 367 | Exemplary EH77 TriTAC sequence | EVQLLESGGGLVQPGGSLTLSCAASGAIAYIYGMGWYRQAPGKQRELV AAISSGGSTDYADSVKGRFTISRDNSKNTLYLQMNSLRAEDTAVYYCN ADVRTSRNLVRSDYWGLGTQVTVSSGGGGSGGGGSEVQLVESGGGLVQP GNSLRLSCAASGFTFSKFGMSWVRQAPGKGLEWVSSISGSGRDTLYAD SVKGRFTISRDNAKTTLYLQMNSLRPEDTAVYYCTIGGSLSVSSQGTL VTVSSGGGGSGGGGSEVQLVESGGGLVQPGGSLKLSCAASGFTENKYAI NWVRQAPGKGLEWVARIRSKYNNYATYYADQVKDRFTISRDDSKNTAY LQMNNLKTEDTAVYYCVRHANFGNSYISYWAYWGQGTLVTVSSGGGGS GGGGSGGGGSQTVVTQEPSLTVSPGGTVTLICASSTGAVTSGNYPNWV QQKPGQAPRGLIGGTKFLVPGTPARFSGSLLGGKAALTLSGVQPEDEA EYYCTLWYSNRWVFGGGTKLTVLHHHHHH** |

What is claimed is:

1. An EGFR binding protein comprising a complementarity determining region 1 (CDR1), a complementarity determining region 2 (CDR2) and a complementarity determining region 3 (CDR3), wherein:
   (a) the CDR1 comprises an amino acid sequence of SEQ ID No. 76, the CDR2 comprises an amino acid sequence of SEQ ID No. 125, and the CDR3 comprises an amino acid sequence of SEQ ID No. 174;
   (b) the CDR1 comprises an amino acid sequence of SEQ ID No. 62, the CDR2 comprises an amino acid sequence of SEQ ID No. 111, and the CDR3 comprises an amino acid sequence of SEQ ID No. 160;
   (c) the CDR1 comprises an amino acid sequence of SEQ ID No. 70, the CDR2 comprises an amino acid sequence of SEQ ID No. 119, and the CDR3 comprises an amino acid sequence of SEQ ID No. 168;
   (d) the CDR1 comprises an amino acid sequence of SEQ ID No. 51, the CDR2 comprises an amino acid sequence of SEQ ID No. 100, and the CDR3 comprises an amino acid sequence of SEQ ID No. 149;
   (e) the CDR1 comprises an amino acid sequence of SEQ ID No. 53, the CDR2 comprises an amino acid sequence of SEQ ID No. 102, and the CDR3 comprises an amino acid sequence of SEQ ID No. 151;
   (f) the CDR1 comprises an amino acid sequence of SEQ ID No. 94, the CDR2 comprises an amino acid sequence of SEQ ID No. 143, and the CDR3 comprises an amino acid sequence of SEQ ID No. 192;
   (g) the CDR1 comprises an amino acid sequence of SEQ ID No. 89, the CDR2 comprises an amino acid sequence of SEQ ID No. 138, and the CDR3 comprises an amino acid sequence of SEQ ID No. 187; or
   (h) the CDR1 comprises an amino acid sequence of SEQ ID No. 90, the CDR2 comprises an amino acid sequence of SEQ ID No. 139, and the CDR3 comprises an amino acid sequence of SEQ ID No. 188.

2. The EGFR binding protein of claim 1, wherein the CDR1 comprises an amino acid sequence of SEQ ID No. 76, wherein the CDR2 comprises an amino acid sequence of SEQ ID No. 125, and wherein the CDR3 comprises an amino acid sequence of SEQ ID No. 174.

3. The EGFR binding protein of claim 1, wherein the CDR1 comprises an amino acid sequence of SEQ ID No. 62, wherein the CDR2 comprises an amino acid sequence of SEQ ID No. 111, and wherein the CDR3 comprises an amino acid sequence of SEQ ID No. 160.

4. The EGFR binding protein of claim 1, wherein the CDR1 comprises an amino acid sequence of SEQ ID No. 70, wherein the CDR2 comprises an amino acid sequence of SEQ ID No. 119, and wherein the CDR3 comprises an amino acid sequence of SEQ ID No. 168.

5. The EGFR binding protein of claim 1, wherein the CDR1 comprises an amino acid sequence of SEQ ID No. 51, wherein the CDR2 comprises an amino acid sequence of SEQ ID No. 100, and wherein the CDR3 comprises an amino acid sequence of SEQ ID No. 149.

6. The EGFR binding protein of claim 1, wherein the CDR1 comprises an amino acid sequence of SEQ ID No. 53, wherein the CDR2 comprises an amino acid sequence of SEQ ID No. 102, and wherein the CDR3 comprises an amino acid sequence of SEQ ID No. 151.

7. The EGFR binding protein of claim 1, wherein the CDR1 comprises an amino acid sequence of SEQ ID No. 94, wherein the CDR2 comprises an amino acid sequence of SEQ ID No. 143, and wherein the CDR3 comprises an amino acid sequence of SEQ ID No. 192.

8. The EGFR binding protein of claim 1, wherein the CDR1 comprises an amino acid sequence of SEQ ID No. 89, wherein the CDR2 comprises an amino acid sequence of SEQ ID No. 138, and wherein the CDR3 comprises an amino acid sequence of SEQ ID No. 187.

9. The EGFR binding protein of claim 1, wherein the CDR1 comprises an amino acid sequence of SEQ ID No. 90, wherein the CDR2 comprises an amino acid sequence of SEQ ID No. 139, and wherein the CDR3 comprises an amino acid sequence of SEQ ID No. 188.

10. The EGFR binding protein of claim 1, wherein the EGFR binding protein comprises an amino acid sequence of SEQ ID No. 2.

11. The EGFR binding protein of claim 1, wherein the EGFR binding protein comprises an amino acid sequence of SEQ ID No. 4.

12. The EGFR binding protein of claim 1, wherein the EGFR binding protein comprises an amino acid sequence of SEQ ID No. 13.

13. The EGFR binding protein of claim 1, wherein the EGFR binding protein comprises an amino acid sequence of SEQ ID No. 21.

14. The EGFR binding protein of claim 1, wherein the EGFR binding protein comprises an amino acid sequence of SEQ ID No. 27.

15. The EGFR binding protein of claim 1, wherein the EGFR binding protein comprises an amino acid sequence of SEQ ID No. 40.

16. The EGFR binding protein of claim 1, wherein the EGFR binding protein comprises an amino acid sequence of SEQ ID No. 41.

17. The EGFR binding protein of claim 1, wherein the EGFR binding protein comprises an amino acid sequence of SEQ ID No. 45.

18. A polynucleotide encoding the EGFR binding protein of claim 1.

19. A vector comprising the polynucleotide of claim 18.

20. A host cell comprising the vector of claim 19.

21. A pharmaceutical composition comprising the EGFR binding protein of claim 1 and at least one pharmaceutically acceptable carrier.

22. A process for the production of an EGFR binding protein, said process comprising culturing a host cell of claim 20 under conditions allowing the expression of the EGFR binding protein and recovering and purifying the produced EGFR binding protein from the culture.

23. An EGFR binding trispecific protein, wherein said protein comprises:
  (a) a first domain which specifically binds to human CD3,
  (b) a second domain which is a half-life extension domain; and
  (c) a third domain which is the EGFR binding protein of claim 1.

24. A polynucleotide encoding the EGFR binding trispecific protein of claim 23.

25. A vector comprising the polynucleotide of claim 24.

26. A host cell comprising the vector of claim 25.

27. A pharmaceutical composition comprising the EGFR binding trispecific protein of claim 23 and at least one pharmaceutically acceptable carrier.

28. A process for the production of an EGFR binding trispecific protein, said process comprising culturing a host cell of claim 26 under conditions allowing the expression of the EGFR binding trispecific protein and recovering and purifying the produced EGFR binding trispecific protein from the culture.

29. A method for the treatment or amelioration of a proliferative disease, or a tumorous disease, comprising administration of the EGFR binding trispecific protein of claim 23 to a subject in need thereof.

* * * * *